US010300058B2

(12) United States Patent
Wu

(10) Patent No.: US 10,300,058 B2
(45) Date of Patent: May 28, 2019

(54) TYROSINE KINASE INHIBITOR AND USES THEREOF

(71) Applicant: Xuanzhu Pharma Co., Ltd., Jinan (CN)

(72) Inventor: Frank Wu, Jinan (CN)

(73) Assignee: Xuanzhu Pharma Co., Ltd., Jinan, Shandong (CN)

(*) Notice: Subject to any disclaimer, the term of this patent is extended or adjusted under 35 U.S.C. 154(b) by 5 days.

(21) Appl. No.: 15/304,708

(22) PCT Filed: Apr. 20, 2015

(86) PCT No.: PCT/CN2015/076988
§ 371 (c)(1),
(2) Date: Oct. 17, 2016

(87) PCT Pub. No.: WO2015/158310
PCT Pub. Date: Oct. 22, 2015

(65) Prior Publication Data
US 2017/0112833 A1   Apr. 27, 2017

(30) Foreign Application Priority Data

Apr. 18, 2014 (CN) .......................... 2014 1 0158807

(51) Int. Cl.
| | | |
|---|---|---|
| *A61K 31/506* | (2006.01) | |
| *C07D 403/12* | (2006.01) | |
| *C07D 401/14* | (2006.01) | |
| *C07D 401/12* | (2006.01) | |
| *C07D 487/04* | (2006.01) | |
| *C07D 487/08* | (2006.01) | |
| *C07D 213/74* | (2006.01) | |
| *C07D 239/48* | (2006.01) | |
| *C07D 403/04* | (2006.01) | |
| *C07D 405/14* | (2006.01) | |
| *C07D 451/02* | (2006.01) | |
| *C07D 487/10* | (2006.01) | |
| *A61K 31/4545* | (2006.01) | |
| *A61K 31/496* | (2006.01) | |
| *A61K 31/505* | (2006.01) | |
| *A61K 31/5377* | (2006.01) | |
| *A61K 45/06* | (2006.01) | |

(52) U.S. Cl.
CPC ........ *A61K 31/506* (2013.01); *A61K 31/4545* (2013.01); *A61K 31/496* (2013.01); *A61K 31/505* (2013.01); *A61K 31/5377* (2013.01); *A61K 45/06* (2013.01); *C07D 213/74* (2013.01); *C07D 239/48* (2013.01); *C07D 401/12* (2013.01); *C07D 401/14* (2013.01); *C07D 403/04* (2013.01); *C07D 403/12* (2013.01); *C07D 405/14* (2013.01); *C07D 451/02* (2013.01); *C07D 487/04* (2013.01); *C07D 487/08* (2013.01); *C07D 487/10* (2013.01)

(58) Field of Classification Search
CPC .............. A61K 31/506; A61K 31/4545; A61K 31/496; A61K 31/505; A61K 31/5377; A61K 45/06; C07D 213/74; C07D 239/48; C07D 401/12; C07D 401/14; C07D 403/04; C07D 403/12; C07D 405/14; C07D 451/02; C07D 487/04; C07D 487/08; C07D 487/10
USPC .......................................................... 514/7.5
See application file for complete search history.

(56) References Cited

U.S. PATENT DOCUMENTS

| | | |
|---|---|---|
| 8,993,585 B2 | 3/2015 | Singh et al. |
| 9,296,737 B2 | 3/2016 | Singh et al. |
| 9,409,921 B2 | 8/2016 | Singh et al. |
| 2005/0256111 A1 | 11/2005 | Kath et al. |
| 2014/0024620 A1 | 1/2014 | Dalgarno et al. |

FOREIGN PATENT DOCUMENTS

| | | |
|---|---|---|
| CN | 101903357 A | 12/2010 |
| CN | 102083800 A | 6/2011 |
| CN | 102740847 A | 10/2012 |
| CN | 103153064 A | 6/2013 |
| WO | WO 2006/074057 A3 | 7/2006 |
| WO | WO 2008/005538 A2 | 1/2008 |
| WO | WO 2008/045978 A1 | 4/2008 |
| WO | WO 2009/017838 A3 | 2/2009 |
| WO | WO 2012/061299 A1 | 5/2012 |
| WO | WO 2012/064706 A1 | 5/2012 |

OTHER PUBLICATIONS

Chkhikvadze et al Khimiya Geterotsiklicheskih Soedinenii, 1969, 1, 138-44; CAPLUS abstract (Year: 1969).*
International Search Report for Application No. PCT/CN2015/076988 dated Jul. 23, 2015, 13 pages.
English language abstract for CN 101903357 extracted from espacenet.com database on Oct. 24, 2016, 1 page.
English language abstract for CN 102083800 extracted from espacenet.com database on Oct. 24, 2016, 2 pages.
English language abstract for CN 102740847 extracted from espacenet.com database on Oct. 24, 2016, 1 page.

(Continued)

*Primary Examiner* — Yevgeny Valenrod
(74) *Attorney, Agent, or Firm* — Howard & Howard Attorneys PLLC

(57) ABSTRACT

Disclosed is a compound of Formula (I) or a pharmaceutically acceptable salt, ester, or solvate thereof, or their stereoisomers, which can be used as tyrosine kinase inhibitor. Also disclosed is a method for preparing the compound, a pharmaceutical composition and a kit comprising the compound, and uses of the compound. The compound can be used as tyrosine kinase inhibitor, or can be used to reduce or inhibit activity of EGFR or mutant thereof, such as EGFR mutant comprising T790M mutation, in a cell, or to treat and/or prevent a disease associated with overactivity of EGFR, such as cancer.

16 Claims, No Drawings

Specification includes a Sequence Listing.

(56) References Cited

OTHER PUBLICATIONS

English language abstract for CN 103153064 extracted from espacenet.com database on Oct. 24, 2016, 1 page.

Aliagas-Martin, I. et al., "A Class of 2,4-Bisanilinopyrimidine Aurora A Inhibitors with Unusually High Selectivity Against Aurora B", J. Med. Chem., No. 52, vol. 10, Apr. 29, 2009, pp. 3300-3307.

Walker, D.P. et al., "Trifluoromethylpyrimidine-based Inhibitors of Proline Rich Tyrosine Kinase 2 (PYK2): Structure-Activity Relationships and Strategies for the Elimination of Reactive Metabolite Formation", Bioorganic & Medicinal Chemistry Letters, No. 18, Nol. 23, Oct. 11, 2008, p. 6075.

Walter, A.O. et al., "Discovery of a Mutant-Selective Covalent Inhibitor of EGFR that Overcomes T790M-Mediated Resistance of NSCLC", Cancer Discov., No. 3, vol. 12, Dec. 31, 2013, pp. 1404-1415.

Yang, E.H. et al., "New Pyrimidine Derivatives Possessing ALK Inhibitory Activities", Bull. Korean Chem. Soc., No. 34, vol. 10, Dec. 31, 2013, p. 3130.

* cited by examiner

TYROSINE KINASE INHIBITOR AND USES THEREOF

CROSS-REFERENCE TO RELATED APPLICATIONS

This application is the National Stage of International Patent Application No. PCT/CN2015/076988, filed on Apr. 20, 2015, which claims priority to and all the advantages of Chinese Patent Application No. 201410158807.8, filed on Apr. 18, 2014, the content of which is incorporated herein by reference.

1. Technical Field

The invention belongs to the technical field of medicines. Particularly, the invention relates to a new compound or a pharmaceutically acceptable salt, ester, or solvate thereof, or their stereoisomers, which can be used as tyrosine kinase inhibitor, a pharmaceutical composition and a kit comprising the compound or a pharmaceutically acceptable salt, ester, or solvate thereof, and/or their stereoisomers, a method for preparing the compound or a pharmaceutically acceptable salt, ester, or solvate thereof, or their stereoisomers, and uses of the compound or a pharmaceutically acceptable salt, ester, or solvate thereof, or their stereoisomers. For example, the compound according to the invention can be used as tyrosine kinase inhibitor, or can be used to reduce or inhibit activity of EGFR or mutant thereof (such as EGFR mutant comprising T790M mutation) in a cell, or to treat and/or prevent a disease associated with overactivity of EGFR (e.g., cancerous disease, such as lung cancer), particularly the disease having drug resistance caused by EGFR mutation (e.g., T790M mutation of EGFR) (e.g., cancerous disease, such as lung cancer).

2. Background Art

Cancer, also called malignant tumor, has been a serious threat to human health and life. In 2004, about 7.4 million people died of cancer globally. In 2008, the National Third Investigation on Cause of Death was performed in China. The results show that in the last 30 years, deaths caused by cancer increased by about 80%, and nearly 2 million people died of cancer every year. The situation is severe.

Lung cancer is one of the common types of malignant tumors in clinic, and its incidence and mortality rank first among malignant tumors. From histopathology, lung cancer can be classified into two types: small cell lung cancer (SCLC) and non-small cell lung cancer (NSCLC). NSCLC includes lung cancer other than SCLC, such as squamous cell cancer, adenocarcinoma and large cell carcinoma, and accounts for 80-85% of lung cancer. Since 70% of patients are in advanced stage when diagnosed with NSCLC, they can hardly be cured by surgery or radiotherapy. Moreover, although more than 50% of patients in early stage received active treatment such as surgery, radiotherapy and adjuvant chemotherapy, local recurrence and distant metastasis still occur. Therefore, chemotherapy-based systemic therapy is of important significance for the treatment of NSCLC.

In recent years, with the deep development of signal transduction pathway of tumor cells, a small molecule tyrosine kinase inhibitor (TKI) targeting epidermal growth factor receptor (EGFR), as a targeted drug, achieves good result in the treatment of NSCLC. EGFR, a transmembrane protein, is a member of the receptor tyrosine kinase family (ERBB), including four subtypes: EGFR (ERBB1 or HER-1), HER-2 (ERBB2), HER-3 (ERBB3) and HER-4 (ERBB4); and plays an important role in tumor transformation and proliferation. FDA has quickly approved two reversible single-targeted small molecule EGFR TKIs one after another, i.e., Gefitinib (Iressa) and Erlotinib (Tarcewa), which are used to treat advanced NSCLC for which first-line treatment failed. In 2013, FDA further approved the first unreversible multi-targeted EGFR TKI, Afatinib, so as to better treat NSCLC.

The commercially available EGFR TKIs are only sensitive to NSCLC patients with EGFR mutation, wherein more than 90% of EGFR mutations are deletion in Exon 19 and L858R mutation in Exon 21, commonly found in female, non-smoker in Asian. In the early phage of using EGFR TKI in patients, the therapeutic effect is significant, progression-free survival (PFS) prolongs, objective response rate (ORR) increases, and quality of life is greatly improved. However, most of patients show resistance to these drugs 10 months after treatment on average. In addition, the existing EGFR TKI can act on wild-type EGFR, resulting in side effects such as erythra and diarrhea, which restricts its application in clinic. Therefore, there is a need to develop EGFR TKIs that have higher selectivity and reduce or avoid drug resistance, so as to better treat NSCLC.

Among patients showing drug resistance, 50% of the patients comprise T790M mutation in Exon 20, and only less than 5% of the pateints comprise other mutations (such as D761Y, L747S, T845A); 20% of the patients having drug resistance caused by amplification of MET tumor gene, half of which also comprise T790M mutation. This indicates that T790M mutation is the main reason for resistance to EGFR TKI in tumor cells. T790M mutation refers to substitution of Thr with Met at EGFR 790 position; its mechanism of causing drug-resistance is not known yet. The possible mechanism may be that since Met takes a bigger space than Thr, it forms steric hindrance and changes the affinity of EGFR kinase to ATP; and therefore small-molecule drugs of EGFR-TKI cannot effectively block EGFR activation signal, thereby losing the ability of killing tumor cells and generating drug resistance.

So far, there are not EGFR TKI drugs against T790M mutation in the market yet. WO2012061299A1 (publication date: 2012 May 10) discloses a drug CO-1686, developed by Avila Therapeutics Company and in phase III clinical trial. The drug is against T790M mutation, is used in the treatment of EGFR TKI-resistant NSCLC, can selectively inhibit mutant EGFR, and has a high safety. It has been confirmed in clinic to some extent. CO-1686 has the following structure:

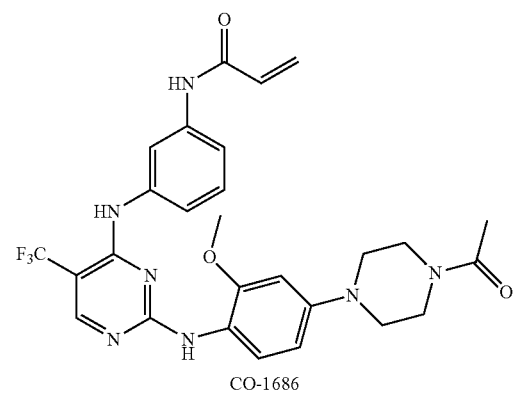 [SMILES: C=CC(=O)Nc1cccc(Nc2nc(Nc3ccc(N4CCN(C(C)=O)CC4)cc3OC)ncc2C(F)(F)F)c1]

CO-1686

A compound for use as a medicament is required to have not only good activity and safety, but also good physical-chemical properties (such as solubility, stability, and peameability). Therefore, it is of important significance for the treatment of NSCLC to develop EGFR TKIs of different structures against T790M mutation, so that they have higher selectivity, higher pharmacological activity, higher safety or better physical-chemical properties.

3. Contents of Invention

One of the technical problems to be solved by the invention is to provide a new compound which can be used as tyrosine kinase inhibitor, and can be used to reduce or inhibit activity of EGFR or mutant thereof (e.g., EGFR mutant comprising T790M mutation) in a cell, and/or to treat and/or prevent a disease associated with overactivity of EGFR (e.g., cancerous disease, such as lung cancer), particularly the disease having drug resistance caused by EGFR mutation (e.g., T790M mutation of EGFR) (e.g., cancerous disease, such as lung cancer).

The technical solutions according to the invention are as follows.

Solution 1. A compound of Formula (I), or a pharmaceutically acceptable salt, ester, or solvate thereof, or their stereoisomers:

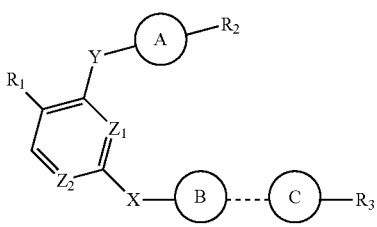
(I)

wherein $Z_1$ and $Z_2$ are independently selected from N or $CR_4$; and at least one of $Z_1$ and $Z_2$ is N;

X is selected from O, S, $C(R_5R_{5'})$ or $NR_5$, or is absent;

Y is selected from O, S, $C(R_5R_{5'})$ or $NR_5$;

Ring A is selected from 6-8 membered aryl, 5-8 membered heteroaryl, 3-8 membered heterocyclyl or 3-8 membered cycloalkyl, each of which is optionally substituted by a substituent, wherein the substituent is selected from hydrogen atom, halogen atom, hydroxyl, amino, cyano, C1-6alkyl, C1-6alkoxy, halo-C1-6alkyl, halo-C1-6alkoxy, C1-6alkylcarbonyl, C1-6alkylcarbonyloxy, C1-6alkylamino, di-C1-6alkylamino, C1-6alkylsulfonylamino, C1-6alkylsulfonyl or 3-8 membered cycloalkyl;

Ring B and Ring C are independently absent, or 3-14 membered ring structure optionally substituted by a substituent; or Ring B and Ring C are fused to form 3-14 membered N-containing fused heterocyclyl optionally substituted by a substituent, wherein the substituent is selected from hydrogen atom, halogen atom, hydroxyl, amino, cyano, C1-6alkyl, C1-6alkoxy, halo-C1-6alkyl, halo-C1-6alkoxy, C1-6alkylcarbonyl, C1-6alkylcarbonyloxy, C1-6alkylamino, di-C1-6alkylamino, C1-6alkylsulfonylamino, C1-6alkylsulfonyloxy, C1-6alkylsulfonyl, C1-6alkylsulfonyl C1-6alkoxy, 3-8 membered cycloalkyl or 3-8 membered heterocyclyl;

R1 is selected from halogen atom, cyano, hydroxyl, amino, C1-6alkyl, halo-C1-6alkyl, C1-6alkoxy, C1-6alkylcarbonyl, C1-6alkylsulfonyl or nitro;

R2 is selected from hydrogen atom, —N(R6)(R7), —N(R6)C(O)(R7), —N(R6)S(O)(R7), —N(R6)SO2(R7), C2-6alkenyl, C2-6alkynyl, C1-6alkyl, halo-C1-6alkyl, C1-6alkoxy, 3-8 membered cycloalkyl, 6-8 membered aryl, 5-8 membered heteroaryl or 3-8 membered heterocyclyl;

R3 is hydrogen atom; or R3 is C1-6alkyl, C1-6alkoxy, —C(O)—R8, 3-8 membered heterocyclyl, 6-8 membered aryl or 5-8 membered heteroaryl, each of which is optionally substituted by a substituent, wherein the substituent is selected from hydrogen atom, halogen atom, hydroxyl, amino, nitro, C1-6alkyl or C1-6alkylsulfonyl;

R4, R5 and R5' are independently selected from hydrogen atom, halogen atom, hydroxyl, amino, cyano, nitro, C1-6alkyl, halo-C1-6alkyl, C1-6alkoxy or 3-8 membered cycloalkyl;

R6 and R7 are independently selected from hydrogen atom, C1-6alkyl, halo-C1-6alkyl, C1-6alkoxy, C2-6alkenyl, C2-6alkynyl, 3-8 membered cycloalkyl or 3-8 membered heterocyclyl;

R8 is selected from hydrogen atom, C1-6alkyl, halo-C1-6alkyl, C1-6alkoxy, 3-8 membered cycloalkyl optionally substituted by a substituent or 3-8 membered heterocyclyl optionally substituted by a substituent, wherein the substituent is selected from hydrogen atom, halogen atom, hydroxyl, amino, cyano, C1-6alkoxy or C1-6alkyl.

In some preferred embodiments, the 3-14 membered ring structure is selected from 6-8 membered aryl, 6-14 membered fused aryl, 3-8 membered cycloalkyl, 3-14 membered fused cyclyl, 3-14 membered spirocyclyl, 3-14 membered bridged cyclyl, 3-10 membered heterocyclyl, 3-14 membered fused heterocyclyl, 3-14 membered spiroheterocyclyl, 3-14 membered bridged heterocyclyl, 5-8 membered heteroaryl, 5-14 membered fused heteroaryl.

In some preferred embodiments, when Ring A is phenyl, Ring B is phenyl, and Ring B is linked to Ring C via a chemical bond, Ring C is not piperazinyl or morpholinyl.

Solution 2. The compound, or a pharmaceutically acceptable salt, ester, or solvate thereof, or their stereoisomers according to Solution 1, wherein Z1 and Z2 are independently selected from N or CR4; and at least one of Z1 and Z2 is N;

X is selected from C(R5R5') or NR5, or is absent;

Y is selected from C(R5R5') or NR5;

Ring A is selected from 6-8 membered aryl, 5-6 membered heteroaryl, 3-8 membered heterocyclyl or 3-8 membered cycloalkyl, each of which is optionally substituted by a substituent, wherein the substituent is selected from hydrogen atom, halogen atom, hydroxyl, amino, cyano, C1-6alkyl, C1-6alkoxy, halo-C1-6alkyl, halo-C1-6alkoxy or 3-8 membered cycloalkyl;

Ring B and Ring C are independently absent, or 3-10 membered ring structure optionally substituted by a substituent; or Ring B and Ring C are fused to form 3-10 membered N-containing fused heterocyclyl optionally substituted by a substituent, wherein the substituent is selected from hydrogen atom, halogen atom, hydroxyl, amino, cyano, C1-6alkyl, C1-6 alkoxy, halo-C1-6 alkyl, halo-C1-6alkoxy, C1-6alkylsulfonyl, C1-6alkylsulfonyloxy, C1-6alkylsulfonyl C1-6alkoxy, 3-6 membered cycloalkyl or 3-6 membered heterocyclyl;

R1 is selected from halogen atom, cyano, hydroxyl, amino, C1-6alkyl, halo-C1-6alkyl or C1-6alkoxy;

R2 is selected from hydrogen atom, —N(R6)(R7), —N(R6)C(O)(R7), C2-6alkenyl, C2-6alkynyl, C1-6alkyl, 3-6 membered cycloalkyl, 6-8 membered aryl, 5-8 membered heteroaryl or 3-6 membered heterocyclyl;

R3 is hydrogen atom; or R3 is C1-6alkyl, C1-6alkoxy or —C(O)—R8, each of which is optionally substituted by a substituent, wherein the substituent is selected from hydrogen atom, halogen atom, amino, nitro, C1-6alkyl or C1-6alkylsulfonyl;

R4, R5, and R5' are independently selected from hydrogen atom, halogen atom, C1-6alkyl, halo-C1-6alkyl, C1-6alkoxy or 3-8 membered cycloalkyl;

R6 and R7 are independently selected from hydrogen atom, C1-6alkyl, halo-C1-6alkyl, C2-6alkenyl or C2-6alkynyl;

R8 is selected from hydrogen atom, C1-6alkyl, halo-C1-6alkyl, C1-6alkoxy, or 3-8 membered cycloalkyl optionally substituted by a substituent, wherein the substituent is selected from hydrogen atom, halogen atom, hydroxyl, amino, cyano, C1-6alkoxy or C1-6alkyl.

In some preferred embodiments, the 3-10 membered ring structure is selected from 6-8 membered aryl, 6-10 membered fused aryl, 3-8 membered cycloalkyl, 3-10 membered fused cyclyl, 3-10 membered spirocyclyl, 3-10 membered bridged cyclyl, 3-10 membered heterocyclyl (e.g., 3-10 membered N-containing heterocyclyl, 3-10 membered O-containing heterocyclyl), 3-10 membered fused heterocyclyl (e.g., 3-10 membered N-containing fused heterocyclyl), 3-10 membered spiroheterocyclyl, 3-10 membered bridged heterocyclyl, 5-8 membered heteroaryl or 5-10 membered fused heteroaryl.

In some preferred embodiments, when Ring A is phenyl, Ring B is phenyl, and Ring B is linked to Ring C via a chemical bond, Ring C is not piperazinyl or morpholinyl.

Solution 3. The compound, or a pharmaceutically acceptable salt, ester, or solvate thereof, or their stereoisomers according to Solution 2, wherein Z1 and Z2 are independently selected from N or CH; and at least one of Z1 and Z2 is N;

X is NR5 or absent;

Y is NR5;

Ring A is selected from 6-8 membered aryl, 5-6 membered heteroaryl or 3-6 membered heterocyclyl, each of which is optionally substituted by a substituent, wherein the substituent is selected from hydrogen atom, halogen atom, cyano, C1-4alkyl, C1-4alkoxy or halo-C1-4alkyl;

Ring B and Ring C are independently absent, or 6-8 membered aryl, 5-6 membered heteroaryl, 5-10 membered N-containing heterocyclyl, 6-11 membered fused heterocyclyl, 7-10 membered spiroheterocyclyl or 7-9 membered bridged heterocyclyl, each of which is optionally substituted by a substituent, or Ring B and Ring C are fused to form 9-10 membered N-containing fused heterocyclyl optionally substituted by a substituent, wherein the substituent is selected from hydrogen atom, halogen atom, cyano, C1-4alkyl, C1-4alkoxy, halo-C1-4alkyl, halo-C1-4alkoxy, C1-4alkylsulfonyl, C1-4alkylsulfonyloxy, C1-4alkylsulfonyl C1-4alkoxy, 3-6 membered cycloalkyl or 3-6 membered O-containing heterocyclyl;

R1 is selected from halo-C1-4alkyl or C1-4alkoxy;

R2 is selected from hydrogen atom, —N(R6)(R7), —N(R6)C(O)(R7), C2-4alkenyl, C2-4alkynyl, C1-4alkyl, 3-6 membered cycloalkyl, 6-8 membered aryl, 5-8 membered heteroaryl or 3-6 membered heterocyclyl;

R3 is hydrogen atom; or R3 is C1-4alkyl, C1-4alkoxy or —C(O)—R8, each of which is optionally substituted by a substituent, wherein the substituent is selected from hydrogen atom, halogen atom, amino, nitro, C1-4alkyl or C1-4alkylsulfonyl;

R5 is selected from hydrogen atom, halogen atom, C1-4alkyl or 3-6 membered cycloalkyl;

R6 and R7 are independently selected from hydrogen atom, C1-4alkyl, halo-C1-4alkyl, C2-4alkenyl or C2-4alkynyl;

R8 is selected from hydrogen atom, C1-4alkyl or C1-4alkoxy.

In some preferred embodiments, when Ring A is phenyl, Ring B is phenyl, and Ring B is linked to Ring C via a chemical bond, Ring C is not piperazinyl or morpholinyl.

Solution 4. The compound, or a pharmaceutically acceptable salt, ester, or solvate thereof, or their stereoisomers according to Solution 3, wherein Z1 is N; Z2 is N;

X is NR5 or absent;

Y is NR5;

Ring A is selected from phenyl or pyridyl, each of which is optionally substituted by a substituent, wherein the substituent is selected from hydrogen atom, halogen atom, cyano, C1-4alkyl, C1-4alkoxy or halo-C1-4alkyl;

Ring B and Ring C are independently absent, or phenyl, 5-6 membered heteroaryl, 5-6 membered N-containing heterocyclyl, 7-10 membered N-containing fused heterocyclyl, 7-9 membered spiroheterocyclyl or 8 membered bridged heterocyclyl, each of which is optionally substituted by a substituent, wherein the substituent is selected from hydrogen atom, halogen atom, cyano, C1-4alkyl, C1-4alkoxy, halo-C1-4alkyl, halo-C1-4alkoxy, C1-4alkylsulfonyl, C1-4alkylsulfonyloxy, C1-4alkylsulfonyl C1-4alkoxy or 3-6 membered O-containing heterocyclyl; and when Ring A is phenyl and Ring B is phenyl, Ring C is not piperazinyl or morpholinyl;

R1 is selected from halo-methyl or halo-ethyl;

R2 is selected from hydrogen atom, —N(R6)(R7), —N(R6)C(O)(R7), C1-4alkyl or 3-6 membered cycloalkyl;

R3 is hydrogen atom; or R3 is C1-4alkyl, C1-4alkoxy or —C(O)—R8, each of which is optionally substituted by a substituent, wherein the substituent is selected from hydrogen atom, halogen atom or C1-4alkyl or C1-4alkylsulfonyl;

R5 is selected from hydrogen atom, halogen atom or C1-4alkyl;

R6 and R7 are independently selected from hydrogen atom, C1-4alkyl, halo-C1-4alkyl or C2-4alkenyl;

R8 is selected from hydrogen atom, methyl, ethyl or methoxyl.

Solution 5. The compound, or a pharmaceutically acceptable salt, ester, or solvate thereof, or their stereoisomers according to Solution 4, wherein Z1 is N; Z2 is N;

X and Y are independently NH;

Ring A is selected from phenyl or pyridyl, each of which is optionally substituted by a substituent, wherein the substituent is selected from fluorine atom, chlorine atom, methyl, ethyl or trifluoromethyl;

Ring B is phenyl optionally substituted by a substituent, wherein the substituent is selected from fluorine atom, chlorine atom, methyl, ethyl, methoxyl, ethoxyl, trifluoromethyl, trifluoromethoxyl, methylsulfonylpropoxy or ethylsulfonylpropoxy;

Ring C is absent, or azetidinyl, pyrrolidinyl, dihydropyrrolyl, imidazolidinyl, thiazolidinyl, oxazolidinyl, piperidyl, piperidin-one-yl, piperazinyl, tetrahydropyridyl, tetrahydropyridin-one-yl, dihydropiperidin-one-yl, 2-azaspiro[3.5]nonyl, 8-azabicyclo[3.2.1]octyl, octahydrocyclopenta[c]pyrrolyl, 2,7-diazaspiro[3.5]nonyl, 2,6-diazaspiro[3.3]heptyl, 2-azaspiro[3.3]heptyl, 3,8-diazabicyclo[3.2.1]octyl or hexahydropyrrolo[3,4-c]pyrrolyl, each of which is optionally substituted by a substituent, wherein the substituent is selected from fluorine atom, chlorine atom, methyl, ethyl, methoxyl, trifluoromethyl, methyl sulfonyl, oxetanyl, tetrahydrofuranyl, piperidyl, piperazinyl or morpholinyl, and when Ring A is phenyl and Ring B is phenyl, Ring C is not piperazinyl or morpholinyl;

R1 is trifluoromethyl;

R2 is —NHC(O)CH=CH2;

R3 is selected from hydrogen atom, methyl, ethyl, trifluoromethyl, methoxyl, 2-fluoroethyl, acetyl, propionyl, 3-fluoropropionyl or 3-methylsulfonylpropoxy.

Solution 6. The compound, or a pharmaceutically acceptable salt, ester, or solvate thereof, or their stereoisomers according to Solution 5, wherein Ring A is selected from phenyl or pyridyl, each of which is optionally substituted by a substituent, wherein the substituent is selected from fluorine atom, chlorine atom, methyl, ethyl or trifluoromethyl;

Ring B is phenyl optionally substituted by a substituent, wherein the substituent is selected from fluorine atom, chlorine atom, methyl, ethyl, methoxyl, ethoxyl, trifluoromethyl, trifluoromethoxyl, methylsulfonylpropoxy or ethylsulfonylpropoxy;

Ring C is absent, or azetidinyl, pyrrolidinyl, dihydropyrrolyl, imidazolidinyl, thiazolidinyl, oxazolidinyl, piperidyl, piperidin-one-yl, piperazinyl, tetrahydropyridyl, tetrahydropyridin-one-yl or dihydropiperidin-one-yl, each of which is optionally substituted by a substituent, wherein the substituent is selected from fluorine atom, chlorine atom, methyl, ethyl, methoxyl, trifluoromethyl, oxetanyl, tetrahydrofuranyl or morpholinyl, and when Ring A is phenyl and Ring B is phenyl, Ring C is not piperazinyl or morpholinyl.

Solution 7. The compound, or a pharmaceutically acceptable salt, ester, or solvate thereof, or their stereoisomers according to Solution 3, wherein Z1 is N, Z2 is CH; or Z1 is CH, Z2 is N;

X is NR5 or absent;

Y is NR5;

Ring A is selected from phenyl or pyridyl, each of which is optionally substituted by a substituent, wherein the substituent is selected from hydrogen atom, halogen atom, cyano, C1-4alkyl, C1-4alkoxy or halo-C1-4alkyl;

Ring B and Ring C are independently absent, or phenyl, 5-6 membered heteroaryl, 5-6 membered N-containing heterocyclyl, 7-10 membered N-containing fused heterocyclyl, 7-9 membered spiroheterocyclyl or 8 membered bridged heterocyclyl, each of which is optionally substituted by a substituent, wherein the substituent is selected from hydrogen atom, halogen atom, cyano, C1-4alkyl, C1-4alkoxy, halo-C1-4alkyl, halo-C1-4alkoxy, C1-4alkylsulfonyl, C1-4alkylsulfonyloxy, C1-4alkylsulfonyl C1-4alkoxy or 3-6 membered O-containing heterocyclyl, and when Ring A is phenyl and Ring B is phenyl, Ring C is not piperazinyl or morpholinyl;

R1 is selected from halo-methyl or halo-ethyl;

R2 is selected from hydrogen atom, —N(R6)(R7), —N(R6)C(O)(R7), C1-4alkyl or 3-6 membered cycloalkyl;

R3 is hydrogen atom; or R3 is C1-4alkyl, C1-4alkoxy or —C(O)—R8, each of which is optionally substituted by a substituent, wherein the substituent is selected from hydrogen atom, halogen atom, C1-4alkyl or C1-4alkylsulfonyl;

R5 is selected from hydrogen atom, halogen atom or C1-4alkyl;

R6 and R7 are independently selected from hydrogen atom, C1-4alkyl, halo-C1-4alkyl or C2-4alkenyl;

R8 is selected from hydrogen atom, methyl, ethyl or methoxyl.

Solution 8. The compound, or a pharmaceutically acceptable salt, ester, or solvate thereof, or their stereoisomers according to Solution 7, wherein Z1 is N, Z2 is CH, or Z1 is CH, Z2 is N;

X is NR5 or absent;

Y is NR5;

Ring A is selected from phenyl or pyridyl, each of which is optionally substituted by a substituent, wherein the substituent is selected from fluorine atom, chlorine atom, methyl, ethyl or trifluoromethyl;

Ring B is phenyl optionally substituted by a substituent, wherein the substituent is selected from fluorine atom, chlorine atom, methyl, ethyl, methoxyl, ethoxyl, trifluoromethyl, trifluoromethoxyl, methylsulfonylpropoxy or ethylsulfonylpropoxy;

Ring C is absent, or azetidinyl, pyrrolidinyl, dihydropyrrolyl, imidazolidinyl, thiazolidinyl, oxazolidinyl, piperidyl, piperidin-one-yl, piperazinyl, tetrahydropyridyl, tetrahydropyridin-one-yl, dihydropiperidin-one-yl, 2-azaspiro[3.5]nonyl, 8-azabicyclo[3.2.1]octyl, octahydrocyclopenta[c]pyrrolyl, 2,7-diazaspiro[3.5]nonyl, 2,6-diazaspiro[3.3]heptyl, 2-azaspiro[3.3]heptyl, 3,8-diazabicyclo[3.2.1]octyl or hexahydropyrrolo[3,4-c]pyrrolyl, each of which is optionally substituted by a substituent, wherein the substituent is selected from fluorine atom, chlorine atom, methyl, ethyl, methoxyl, trifluoromethyl, methyl sulfonyl, oxetanyl, tetrahydrofuranyl, piperidyl, piperazinyl or morpholinyl, and when Ring A is phenyl and Ring B is phenyl, Ring C is not piperazinyl or morpholinyl;

R1 is trifluoromethyl;

R2 is —NHC(O)CH=CH2;

R3 is selected from hydrogen atom, methyl, ethyl, trifluoromethyl, methoxyl, 2-fluoroethyl, acetyl, propionyl, 3-fluoropropionyl or 3-methylsulfonylpropoxy.

Solution 9. The compound, or a pharmaceutically acceptable salt, ester, or solvate thereof, or their stereoisomers according to Solution 3, wherein Z1 and Z2 are independently selected from N or CH; and at least one of Z1 and Z2 is N;

X is NR5 or absent;

Y is NR5;

Ring A is selected from 6-8 membered aryl or 5-6 membered heteroaryl, each of which is optionally substituted by a substituent, wherein the substituent is selected from hydrogen atom, halogen atom, cyano, C1-4alkyl, C1-4alkoxy or halo-C1-4alkyl;

Ring B and Ring C are fused to form benzo-5 membered N-containing heterocyclyl or benzo-6 membered N-containing heterocyclyl, each of which is optionally substituted by a substituent, wherein the substituent is selected from hydrogen atom, halogen atom, cyano, C1-4alkyl, C1-4alkoxy, halo-C1-4alkyl, halo-C1-4alkoxy, C1-4alkylsulfonyl, C1-4alkylsulfonyloxy, C1-4 alkylsulfonyl C1-4 alkoxy, 3-6 membered cycloalkyl or 3-6 membered O-containing heterocyclyl;

R1 is selected from halo-C1-4alkyl or C1-4alkoxy;

R2 is selected from hydrogen atom, —N(R6)(R7), —N(R6)C(O)(R7), C2-4alkenyl, C2-4alkynyl, C1-4alkyl, 3-6 membered cycloalkyl, 6-8 membered aryl, 5-8 membered heteroaryl or 3-6 membered heterocyclyl;

R3 is hydrogen atom; or R3 is C1-4alkyl, C1-4alkoxy or —C(O)—R8, each of which is optionally substituted by a substituent, wherein the substituent is selected from hydrogen atom, halogen atom, amino, nitro, C1-4alkyl or C1-4alkylsulfonyl;

R5 is selected from hydrogen atom, halogen atom, C1-4alkyl or 3-6 membered cycloalkyl;

R6 and R7 are independently selected from hydrogen atom, C1-4alkyl, halo-C1-4alkyl, C2-4alkenyl or C2-4alkynyl;

R8 is selected from hydrogen atom, C1-4alkyl or C1-4alkoxy.

Solution 10. The compound, or a pharmaceutically acceptable salt, ester, or solvate thereof, or their stereoisomers according to Solution 9, wherein Z1 and Z2 are independently N;

X is NH or absent; Y is NH;

Ring A selected from phenyl, pyrrolyl, furanyl, thienyl, imidazolyl, pyrazolyl, thiazolyl, isothiazolyl, oxazolyl, isoxazolyl, pyridyl or pyrimidinyl, each of which is optionally substituted by a substituent, wherein the substituent is selected from fluorine atom, chlorine atom, methyl or ethyl;

Ring B and Ring C are fused to form indolyl, dihydroindolyl, benzo-pyrrolidinyl, benzo-dihydropyrrolyl, isoindolyl, dihydroisoindolyl, indazolyl, dihydroindazolyl, benzo-dihydropyrazolyl, benzo-oxazolidinyl, benzo-thiazolidinyl, benzo-imidazolidinyl, benzo-imidazolyl, benzo-dihydroimidazolyl, 1,2,3,4-tetrahydroisoquinolyl or 1,2,3,4-tetrahydroquinolyl, each of which is optionally substituted by a substituent, wherein the substituent is selected from methoxyl, methyl or ethyl;

R1 is trifluoromethyl;

R2 is —NHC(O)CH=CH2;

R3 is selected from hydrogen atom, methyl, ethyl, methoxyl or acetyl.

Solution 11. The compound, or a pharmaceutically acceptable salt, ester, or solvate thereof, or their stereoisomers according to Solution 1, wherein the compound is selected from:

| Compound | Structural formula |
|---|---|
| 1 | |
| 2 | |
| 3 | |
| 4 | |
| 5 | |
| 6 | |

| Compound | Structural formula |
|---|---|
| 7 | 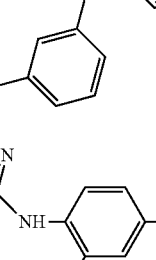 |
| 8 | |
| 9 | |
| 10 | |
| Compound | Structural formula |
|---|---|
| 10-1 | 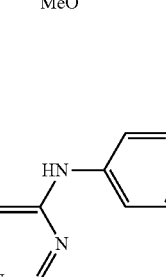 |
| 11 | |
| 12 | |
| 13 | |

| Com-pound | Structural formula |
|---|---|
| 14 | 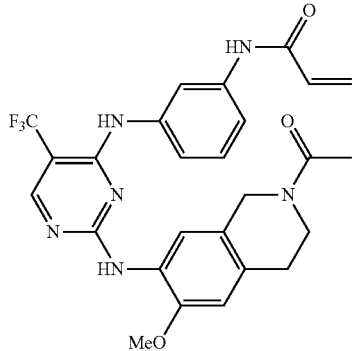 [SMILES: C=CC(=O)Nc1cccc(Nc2nc(Nc3cc4c(cc3OC)CCN(C(C)=O)C4)ncc2C(F)(F)F)c1] |
| 15 | 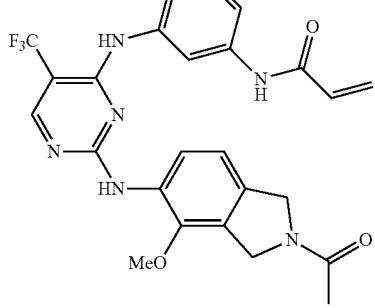 |
| 16 | 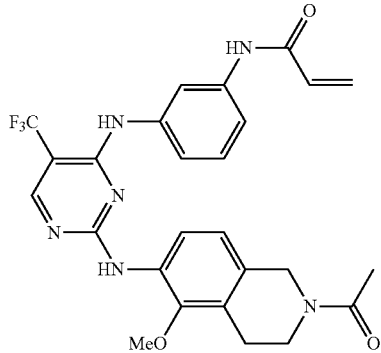 [SMILES: C=CC(=O)Nc1cccc(Nc2nc(Nc3ccc4c(c3OC)CCN(C(C)=O)C4)ncc2C(F)(F)F)c1] |
| 17 | 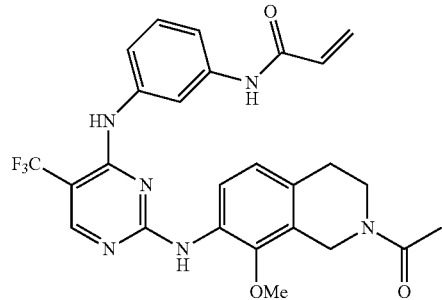 [SMILES: C=CC(=O)Nc1cccc(Nc2nc(Nc3ccc4c(c3OC)CN(C(C)=O)CC4)ncc2C(F)(F)F)c1] |
| Com-pound | Structural formula |
|---|---|
| 18 | 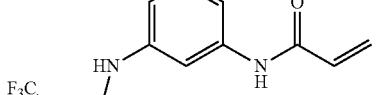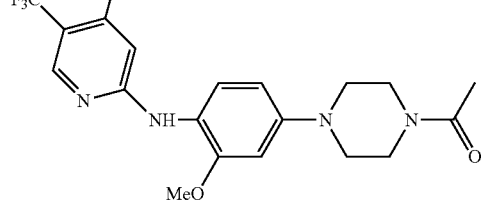 |
| 19 | 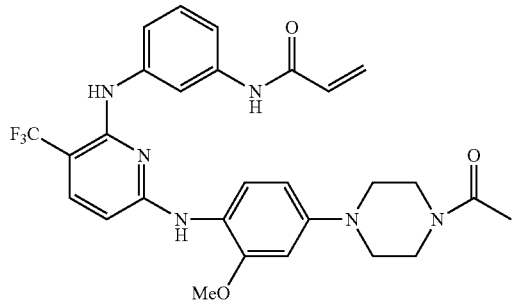 [SMILES: C=CC(=O)Nc1cccc(Nc2nc(Nc3ccc(N4CCN(C(C)=O)CC4)cc3OC)ccc2C(F)(F)F)c1] |
| 20 | 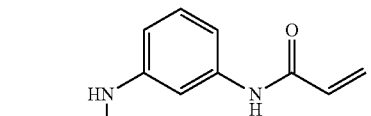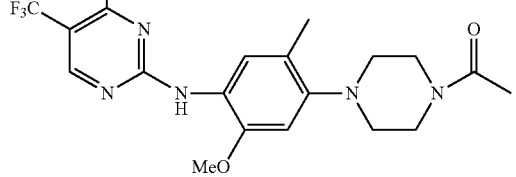 |
| 21 | 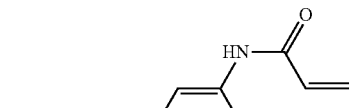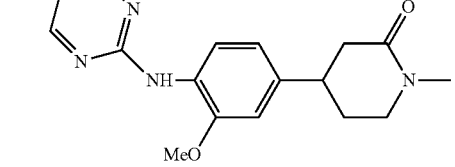 |

| Compound | Structural formula |
|---|---|
| 22 | 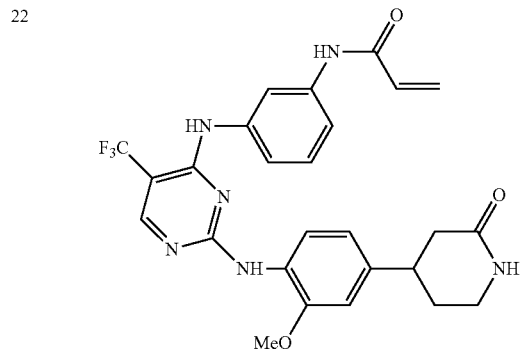 |
| 23 | 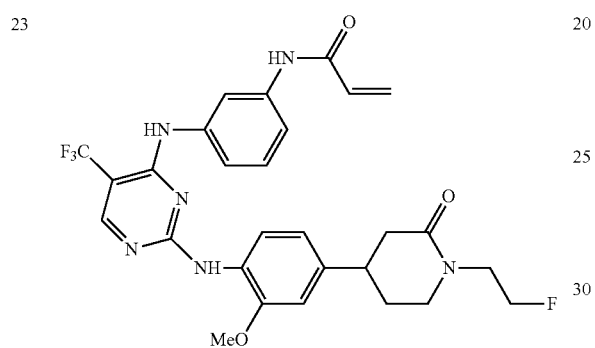 |
| 24 | 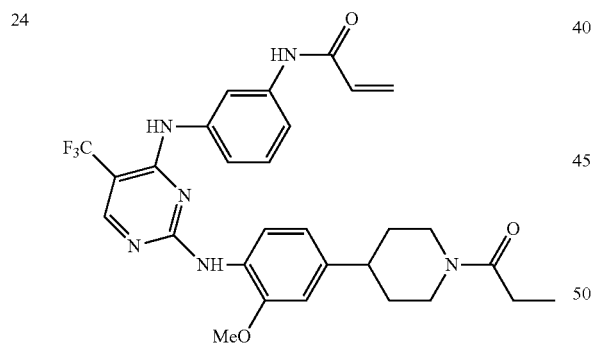 |
| 25 | 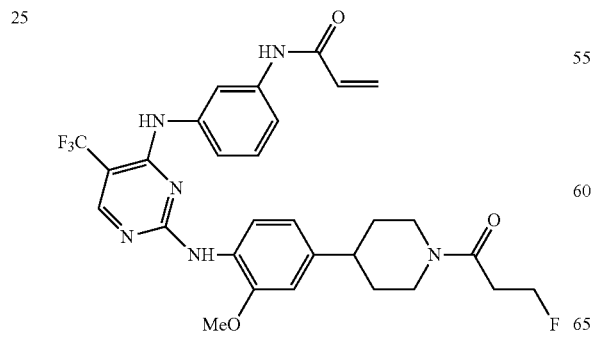 |
| 26 | 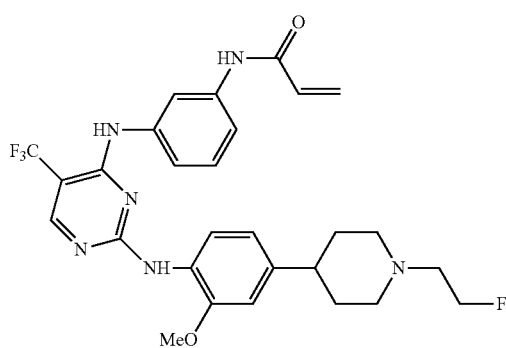 [SMILES: C=CC(=O)Nc1cccc(Nc2nc(Nc3ccc(C4CCN(CCF)CC4)cc3OC)ncc2C(F)(F)F)c1] |
| 27 | 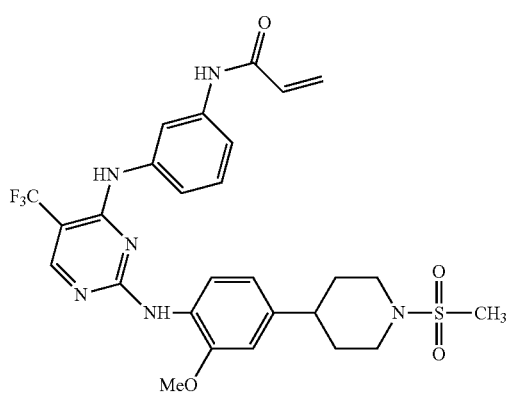 [SMILES: C=CC(=O)Nc1cccc(Nc2nc(Nc3ccc(C4CCN(S(C)(=O)=O)CC4)cc3OC)ncc2C(F)(F)F)c1] |
| 28 | 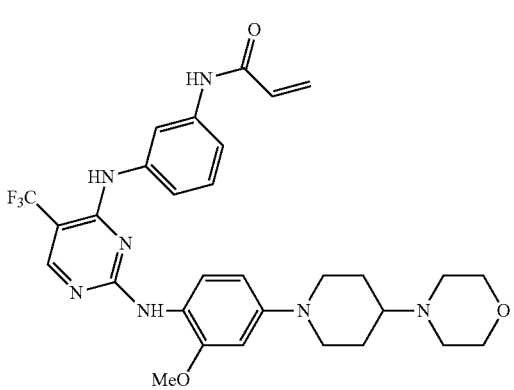 [SMILES: C=CC(=O)Nc1cccc(Nc2nc(Nc3ccc(N4CCC(N5CCOCC5)CC4)cc3OC)ncc2C(F)(F)F)c1] |
| 29 | 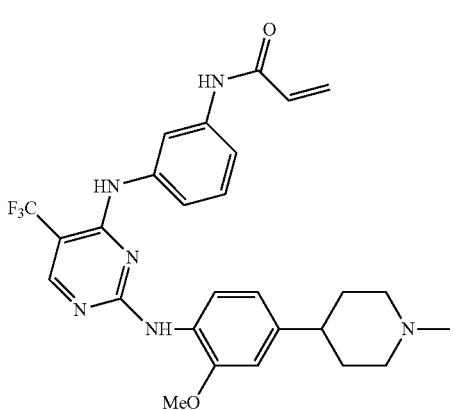 [SMILES: C=CC(=O)Nc1cccc(Nc2nc(Nc3ccc(C4CCN(C)CC4)cc3OC)ncc2C(F)(F)F)c1] |

| Compound | Structural formula |
|---|---|
| 30 | 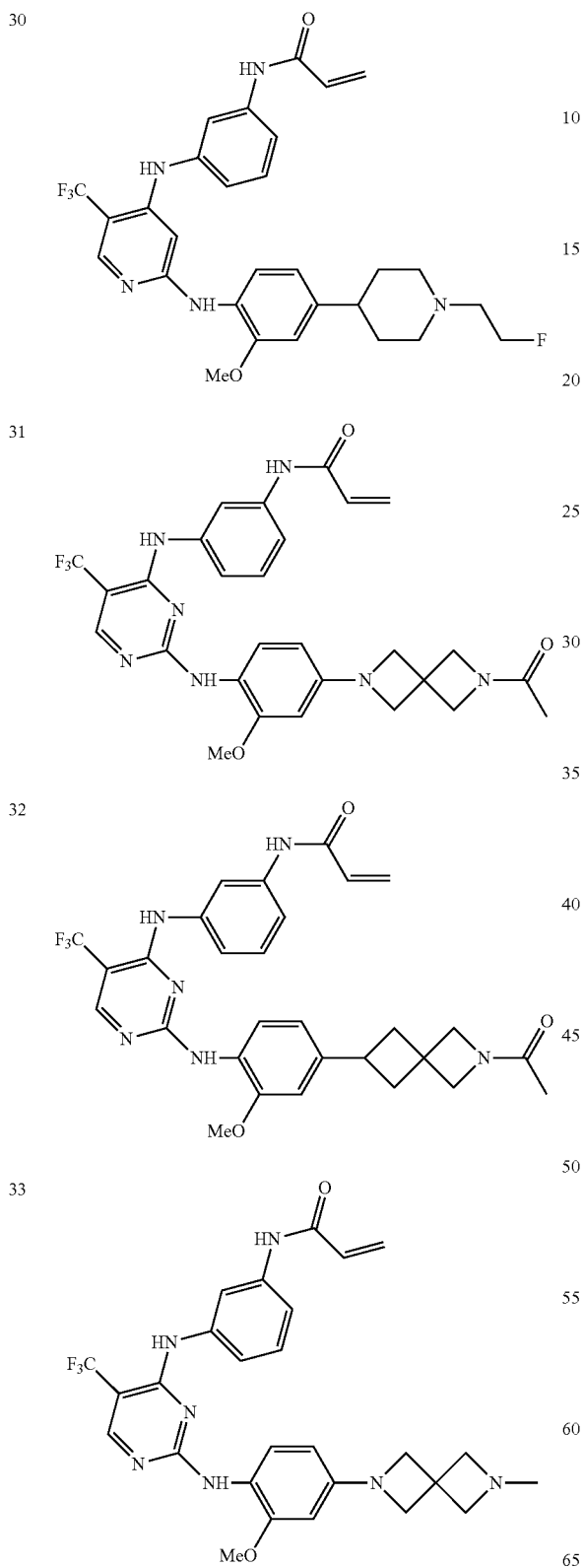 |
| 31 | |
| 32 | |
| 33 | |
| Compound | Structural formula |
|---|---|
| 34 | 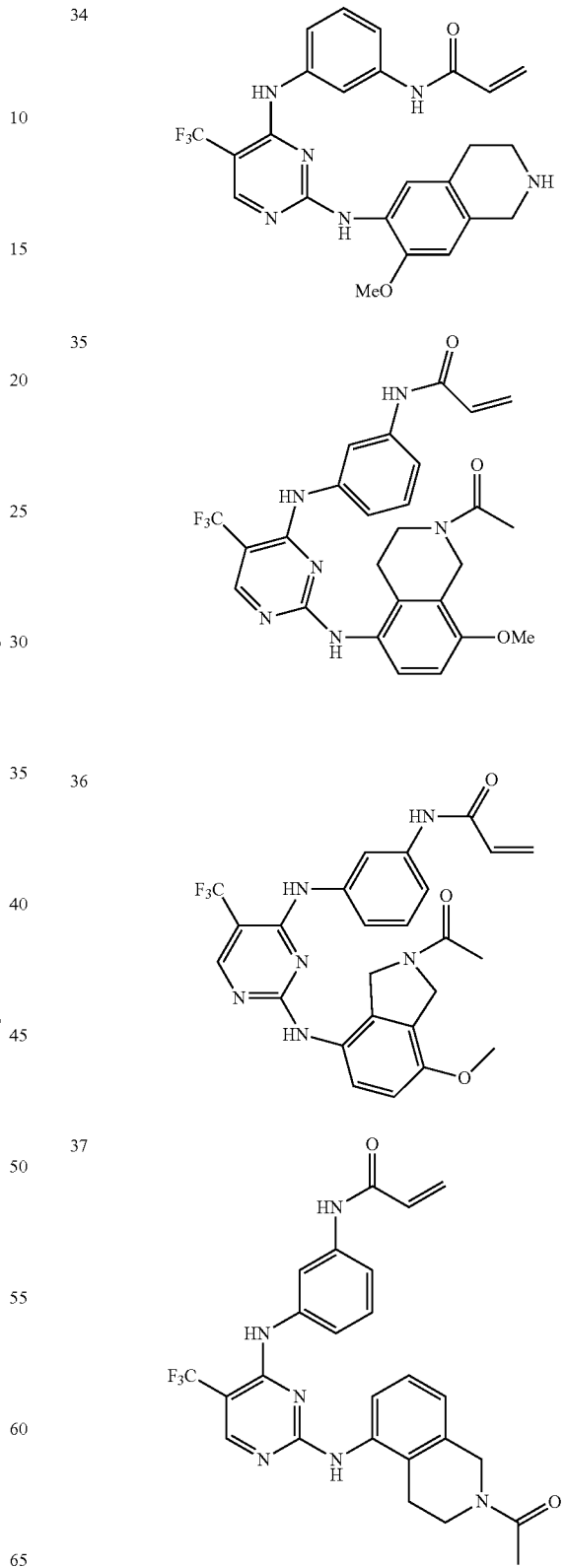 |
| 35 | |
| 36 | |
| 37 | |

| Compound | Structural formula |
|---|---|
| 38 | (structure) |
| 39 | (structure) |
| 40 | (structure) |
| 41 | (structure) |
| 42 | (structure) |
| 43 | (structure) |
| 44 | (structure) |

| Compound | Structural formula |
|---|---|
| 9-1 | (structure shown) |

The invention also relates to uses of the disclosed compounds. Therefore, the invention also relates to the following exemplary technical solutions.

Solution 12. A pharmaceutical composition, comprising the compound, or a pharmaceutically acceptable salt, ester, or solvate thereof, or their stereoisomers according to any one of Solutions 1-11.

In some preferred embodiments, the pharmaceutical composition further comprises one or more second therapeutic agents. In some preferred embodiments, the second therapeutic agent is selected from: DNA replication inhibitors (e.g., topoisomerase inhibitors and alkylating agents), mitotic inhibitors, angiogenesis inhibitors, growth factor inhibitors, antibodies, antimetabolites, antitumor hormone drugs, platinum drugs, immunosuppressors, and additional tyrosine kinase inhibitors. In some preferred embodiments, the second therapeutic agent is selected from: methotrexate, capecitabine, gemcitabine, doxifluridine, pemetrexed disodium, pazopanib, imatinib, erlotinib, lapatinib, gefitinib, vandetanib, herceptin, bevacizumab, rituximab, trastuzumab, paclitaxel, vinorelbine, docetaxel, doxorubicin, hydroxycamptothecine, mitomycin, epirubicin, pirarubicin, letrozole, tamoxifen, fulvestrant, triptorelin, flutamide, leuprorelin, anastrozole, ifosfamide, busulfan, cyclophosphamide, carmustine, nimustine, semustine, mechlorethamine, melphalan, chlorambucil, carboplatin, cisplatin, oxaliplatin, lobaplatin, camptothecin, topotecan, everolimus, sirolimus, temsirolimus, 6-mercaptopurine, 6-thioguanine, azathioprine, actinomycin D, daunorubicin, adriamycin, mitoxantrone, bleomycin, mithramycin or aminoglutethimide.

In some preferred embodiments, the pharmaceutical composition further comprises one or more pharmaceutically acceptable carriers and/or diluents.

Solution 13. Use of the compound, or a pharmaceutically acceptable salt, ester, or solvate thereof, or their stereoisomers according to any one of Solutions 1-11 for the manufacture of a medicament for the treatment and/or prevention of a disease associated with overactivity of EGFR in a subject.

In some preferred embodiments, the disease is hyperproliferative disease, e.g., cancer and noncancerous disease. In some preferred embodiments, the cancer is selected from: esophageal cancer (e.g., esophageal adenocarcinoma and esophageal squamous cancer), brain tumor, lung cancer (e.g., small cell lung cancer and non-small cell lung cancer), squamous cell cancer, bladder cancer, gastric cancer, ovarian cancer, peritoneal cancer, pancreatic cancer, breast cancer, head and neck cancer, cervical cancer, endometrial cancer, colorectal cancer, liver cancer, renal cancer, solid tumor, non-Hodgkin's lymphoma, central nervous system tumor (e.g., neuroglioma, glioblastoma multiforme, glioma or sarcoma), prostatic cancer and thyroid cancer. In some preferred embodiments, the noncancerous disease is benign hyperplasia of skin or prostate. In some preferred embodiments, the disease is chronic obstructive pulmonary disease.

In some preferred embodiments, the overactivity of EGFR is resulted from overexpression of EGFR. In some preferred embodiments, the disease (e.g., cancerous disease) has drug resistance caused by EGFR mutant. In some preferred embodiments, the EGFR mutant comprises one or more of the following mutations: T790M mutation, L858R mutation, and d746-750 mutation. In some preferred embodiments, the EGFR mutant comprises T790M mutation. In some preferred embodiments, the EGFR mutant comprises T790M mutation and L858R mutation. In some preferred embodiments, the EGFR mutant comprises T790M mutation and d746-750 mutation. In some preferred embodiments, the EGFR mutant comprises T790M mutation, L858R mutation, and d746-750 mutation.

In some preferred embodiments, the subject is mammal, such as bovine, equine, caprid, suidae, canine, feline, rodent, and primate; wherein the particularly preferred subject is human.

In some preferred embodiments, the medicament further comprises one or more second therapeutic agents. In some preferred embodiments, the second therapeutic agent is selected from: DNA replication inhibitors (e.g., topoisomerase inhibitors and alkylating agents), mitotic inhibitors, angiogenesis inhibitors, growth factor inhibitors, antibodies, antimetabolites, antitumor hormone drugs, platinum drugs, immunosuppressors, and additional tyrosine kinase inhibitors. In some preferred embodiments, the second therapeutic agent is selected from: methotrexate, capecitabine, gemcitabine, doxifluridine, pemetrexed disodium, pazopanib, imatinib, erlotinib, lapatinib, gefitinib, vandetanib, herceptin, bevacizumab, rituximab, trastuzumab, paclitaxel, vinorelbine, docetaxel, doxorubicin, hydroxycamptothecine, mitomycin, epirubicin, pirarubicin, letrozole, tamoxifen, fulvestrant, triptorelin, flutamide, leuprorelin, anastrozole, ifosfamide, busulfan, cyclophosphamide, carmustine, nimustine, semustine, mechlorethamine, melphalan, chlorambucil, carboplatin, cisplatin, oxaliplatin, lobaplatin, camptothecin, topotecan, everolimus, sirolimus, temsirolimus, 6-mercaptopurine, 6-thioguanine, azathioprine, actinomycin D, daunorubicin, adriamycin, mitoxantrone, bleomycin, mithramycin or aminoglutethimide.

Solution 14. A method for treating and/or preventing a disease associated with overactivity of EGFR in a subject, comprising administering to the subject in need thereof a therapeutically and/or prophylactically effective amount of the compound, or a pharmaceutically acceptable salt, ester, or solvate thereof, or their stereoisomers according to any one of Solution 1-11, or the pharmaceutical composition according to Solution 12.

In some preferred embodiments, the disease is hyperproliferative disease, e.g., cancer and noncancerous disease. In some preferred embodiments, the cancer is selected from: esophageal cancer (e.g., esophageal adenocarcinoma and esophageal squamous cancer), brain tumor, lung cancer (e.g., small cell lung cancer and non-small cell lung cancer), squamous cell cancer, bladder cancer, gastric cancer, ovarian cancer, peritoneal cancer, pancreatic cancer, breast cancer, head and neck cancer, cervical cancer, endometrial cancer, colorectal cancer, liver cancer, renal cancer, solid tumor, non-Hodgkin's lymphoma, central nervous system tumor (e.g., neuroglioma, glioblastoma multiforme, glioma or sarcoma), prostatic cancer and thyroid cancer. In some preferred embodiments, the noncancerous disease is benign hyperplasia of skin or prostate. In some preferred embodiments, the disease is chronic obstructive pulmonary disease.

In some preferred embodiments, the overactivity of EGFR is resulted from overexpression of EGFR. In some preferred embodiments, the disease (e.g., cancerous disease) has drug resistance caused by EGFR mutant. In some preferred embodiments, the EGFR mutant comprises one or more of the following mutations: T790M mutation, L858R mutation, and d746-750 mutation. In some preferred embodiments, the EGFR mutant comprises T790M mutation. In some preferred embodiments, the EGFR mutant comprises T790M mutation and L858R mutation. In some preferred embodiments, the EGFR mutant comprises T790M mutation and d746-750 mutation. In some preferred embodiments, the EGFR mutant comprises T790M mutation, L858R mutation, and d746-750 mutation.

In some preferred embodiments, the subject is mammal, such as bovine, equine, caprid, suidae, canine, feline, rodent, and primate; wherein the particularly preferred subject is human.

In some preferred embodiments, the method further comprises administering to the subject one or more second therapeutic agents. In some preferred embodiments, the second therapeutic agent is selected from: DNA replication inhibitors (e.g., topoisomerase inhibitors and alkylating agents), mitotic inhibitors, angiogenesis inhibitors, growth factor inhibitors, antibodies, antimetabolites, antitumor hormone drugs, platinum drugs, immunosuppressors, and additional tyrosine kinase inhibitors. In some preferred embodiments, the second therapeutic agent is selected from: methotrexate, capecitabine, gemcitabine, doxifluridine, pemetrexed disodium, pazopanib, imatinib, erlotinib, lapatinib, gefitinib, vandetanib, herceptin, bevacizumab, rituximab, trastuzumab, paclitaxel, vinorelbine, docetaxel, doxorubicin, hydroxycamptothecine, mitomycin, epirubicin, pirarubicin, letrozole, tamoxifen, fulvestrant, triptorelin, flutamide, leuprorelin, anastrozole, ifosfamide, busulfan, cyclophosphamide, carmustine, nimustine, semustine, mechlorethamine, melphalan, chlorambucil, carboplatin, cisplatin, oxaliplatin, lobaplatin, camptothecin, topotecan, everolimus, sirolimus, temsirolimus, 6-mercaptopurine, 6-thioguanine, azathioprine, actinomycin D, daunorubicin, adriamycin, mitoxantrone, bleomycin, mithramycin or aminoglutethimide. In some preferred embodiments, the second therapeutic agent is administered before, at the same time or after administration of the compound, or a pharmaceutically acceptable salt, ester, or solvate thereof, or their stereoisomers, or the pharmaceutical composition.

Solution 15. The compound, or a pharmaceutically acceptable salt, ester, or solvate thereof, or their stereoisomers according to any one of Solutions 1-11, for use in the treatment and/or prevention of a disease associated with overactivity of EGFR in a subject.

In some preferred embodiments, the disease is hyperproliferative disease, e.g., cancer and noncancerous disease. In some preferred embodiments, the cancer is selected from: esophageal cancer (e.g., esophageal adenocarcinoma and esophageal squamous cancer), brain tumor, lung cancer (e.g., small cell lung cancer and non-small cell lung cancer), squamous cell cancer, bladder cancer, gastric cancer, ovarian cancer, peritoneal cancer, pancreatic cancer, breast cancer, head and neck cancer, cervical cancer, endometrial cancer, colorectal cancer, liver cancer, renal cancer, solid tumor, non-Hodgkin's lymphoma, central nervous system tumor (e.g., neuroglioma, glioblastoma multiforme, glioma or sarcoma), prostatic cancer and thyroid cancer. In some preferred embodiments, the noncancerous disease is benign hyperplasia of skin or prostate. In some preferred embodiments, the disease is chronic obstructive pulmonary disease.

In some preferred embodiments, the overactivity of EGFR is resulted from overexpression of EGFR. In some preferred embodiments, the disease (e.g., cancerous disease) has drug resistance caused by EGFR mutant. In some preferred embodiments, the EGFR mutant comprises one or more of the following mutations: T790M mutation, L858R mutation, and d746-750 mutation. In some preferred embodiments, the EGFR mutant comprises T790M mutation. In some preferred embodiments, the EGFR mutant comprises T790M mutation and L858R mutation. In some preferred embodiments, the EGFR mutant comprises T790M mutation and d746-750 mutation. In some preferred embodiments, the EGFR mutant comprises T790M mutation, L858R mutation, and d746-750 mutation.

In some preferred embodiments, the subject is mammal, such as bovine, equine, caprid, suidae, canine, feline, rodent, and primate; wherein the particularly preferred subject is human.

In some preferred embodiments, the compound, or a pharmaceutically acceptable salt, ester, or solvate thereof, or their stereoisomers is used in combination with one or more second therapeutic agents. In some preferred embodiments, the second therapeutic agent is selected from: DNA replication inhibitors (e.g., topoisomerase inhibitors and alkylating agents), mitotic inhibitors, angiogenesis inhibitors, growth factor inhibitors, antibodies, antimetabolites, antitumor hormone drugs, platinum drugs, immunosuppressors, and additional tyrosine kinase inhibitors. In some preferred embodiments, the second therapeutic agent is selected from: methotrexate, capecitabine, gemcitabine, doxifluridine, pemetrexed disodium, pazopanib, imatinib, erlotinib, lapatinib, gefitinib, vandetanib, herceptin, bevacizumab, rituximab, trastuzumab, paclitaxel, vinorelbine, docetaxel, doxorubicin, hydroxycamptothecine, mitomycin, epirubicin, pirarubicin, letrozole, tamoxifen, fulvestrant, triptorelin, flutamide, leuprorelin, anastrozole, ifosfamide, busulfan, cyclophosphamide, carmustine, nimustine, semustine, mechlorethamine, melphalan, chlorambucil, carboplatin, cisplatin, oxaliplatin, lobaplatin, camptothecin, topotecan, everolimus, sirolimus, temsirolimus, 6-mercaptopurine, 6-thioguanine, azathioprine, actinomycin D, daunorubicin, adriamycin, mitoxantrone, bleomycin, mithramycin or aminoglutethimide. In some preferred embodiments, the second therapeutic agent is administered before, at the same time or after administration of the compound, or a pharmaceutically acceptable salt, ester, or solvate thereof, or their stereoisomers, or the pharmaceutical composition.

Solution 16. Use of the compound, or a pharmaceutically acceptable salt, ester, or solvate thereof, or their stereoisomers according to any one of Solution 1-11 for the manufacture of a formulation, which is used as tyrosine kinase inhibitor, or is used to reduce or inhibit activity of EGFR or mutant thereof in a cell.

In some preferred embodiments, the formulation is administered in vivo or in vitro. In some preferred embodiments, the formulation is administered to a subject (e.g., mammal, such as bovine, equine, caprid, suidae, canine, feline, rodent, and primate; e.g., human), to reduce or inhibit activity of EGFR or mutant thereof in the cell of the subject.

In some preferred embodiments, the formulation is administered to an in vitro cell (e.g., a cell line or a cell from a subject such as a cancer cell), to reduce or inhibit activity of EGFR or mutant thereof in the in vitro cell.

In some preferred embodiments, the EGFR mutant comprises one or more of the following mutations: T790M mutation, L858R mutation, and d746-750 mutation. In some preferred embodiments, the EGFR mutant comprises T790M mutation. In some preferred embodiments, the EGFR mutant comprises T790M mutation and L858R mutation. In some preferred embodiments, the EGFR mutant comprises T790M mutation and d746-750 mutation. In some preferred embodiments, the EGFR mutant comprises T790M mutation, L858R mutation, and d746-750 mutation.

In some preferred embodiments, the cell is selected from esophageal cancer cell (e.g., esophageal adenocarcinoma cell and esophageal squamous cancer cell), brain tumor cell, lung cancer cell (e.g., small cell lung cancer cell and non-small cell lung cancer cell), squamous cell cancer cell, bladder cancer cell, gastric cancer cell, ovarian cancer cell, peritoneal cancer cell, pancreatic cancer cell, breast cancer cell, head and neck cancer cell, cervical cancer cell, endometrial cancer cell, colorectal cancer cell, liver cancer cell, renal cancer cell, solid tumor cell, non-Hodgkin's lymphoma cell, central nervous system tumor cell (e.g., neuroglioma cell, glioblastoma multiforme cell, glioma cell or sarcoma cell), prostatic cancer cell and thyroid cancer cell.

In some preferred embodiments, the cell is the primary cell from the subject or culture thereof, or an established cell line. In some preferred embodiments, the subject is mammal, such as bovine, equine, caprid, suidae, canine, feline, rodent, and primate; wherein the particularly preferred subject is human.

Solution 17. A method for reducing or inhibiting activity of EGFR or mutant thereof in a cell, comprising administering to the cell an effective amount of the compound, or a pharmaceutically acceptable salt, ester, or solvate thereof, or their stereoisomers according to any one of Solutions 1-11.

In some preferred embodiments, the method is carried out in vivo or in vitro. In some preferred embodiments, the method is carry out in vivo, for example, is applied to a subject (e.g., mammal, such as bovine, equine, caprid, suidae, canine, feline, rodent, and primate; e.g., human), to reduce or inhibit activity of EGFR or mutant thereof in the cell of the subject. In some preferred embodiments, the method is carried out in vitro, for example is applied to an in vitro cell (e.g., a cell line or a cell from a subject such as a cancer cell), to reduce or inhibit activity of EGFR or mutant thereof in the in vitro cell.

In some preferred embodiments, the EGFR mutant comprises one or more of the following mutations: T790M mutation, L858R mutation, and d746-750 mutation. In some preferred embodiments, the EGFR mutant comprises T790M mutation. In some preferred embodiments, the EGFR mutant comprises T790M mutation and L858R mutation. In some preferred embodiments, the EGFR mutant comprises T790M mutation and d746-750 mutation. In some preferred embodiments, the EGFR mutant comprises T790M mutation, L858R mutation, and d746-750 mutation.

In some preferred embodiments, the cell is selected from esophageal cancer cell (e.g., esophageal adenocarcinoma cell and esophageal squamous cancer cell), brain tumor cell, lung cancer cell (e.g., small cell lung cancer cell and non-small cell lung cancer cell), squamous cell cancer cell, bladder cancer cell, gastric cancer cell, ovarian cancer cell, peritoneal cancer cell, pancreatic cancer cell, breast cancer cell, head and neck cancer cell, cervical cancer cell, endometrial cancer cell, colorectal cancer cell, liver cancer cell, renal cancer cell, solid tumor cell, non-Hodgkin's lymphoma cell, central nervous system tumor cell (e.g., neuroglioma cell, glioblastoma multiforme cell, glioma cell or sarcoma cell), prostatic cancer cell and thyroid cancer cell.

In some preferred embodiments, the cell is the primary cell from the subject or culture thereof, or an established cell line. In some preferred embodiments, the subject is mammal, such as bovine, equine, caprid, suidae, canine, feline, rodent, and primate; wherein the particularly preferred subject is human.

Solution 18. The compound, or a pharmaceutically acceptable salt, ester, or solvate thereof, or their stereoisomers according to any one of Solutions 1-11, for use in reducing or inhibiting activity of EGFR or mutant thereof in a cell.

In some preferred embodiments, the compound, or a pharmaceutically acceptable salt, ester, or solvate thereof, or their stereoisomers is administered in vivo or in vitro. In some preferred embodiments, the compound, or a pharmaceutically acceptable salt, ester, or solvate thereof, or their stereoisomers is administered to a subject (e.g., mammal, such as bovine, equine, caprid, suidae, canine, feline, rodent, and primate; e.g., human), to reduce or inhibit activity of EGFR or mutant thereof in the cell of the subject. In some preferred embodiments, the compound, or a pharmaceutically acceptable salt, ester, or solvate thereof, or their stereoisomers is administered to an in vitro cell (e.g., a cell line or a cell from a subject such as a cancer cell), to reduce or inhibit activity of EGFR or mutant thereof in the in vitro cell.

In some preferred embodiments, the EGFR mutant comprises one or more of the following mutations: T790M mutation, L858R mutation, and d746-750 mutation. In some preferred embodiments, the EGFR mutant comprises T790M mutation. In some preferred embodiments, the EGFR mutant comprises T790M mutation and L858R mutation. In some preferred embodiments, the EGFR mutant comprises T790M mutation and d746-750 mutation. In some preferred embodiments, the EGFR mutant comprises T790M mutation, L858R mutation, and d746-750 mutation.

In some preferred embodiments, the cell is selected from esophageal cancer cell (e.g., esophageal adenocarcinoma cell and esophageal squamous cancer cell), brain tumor cell, lung cancer cell (e.g., small cell lung cancer cell and non-small cell lung cancer cell), squamous cell cancer cell, bladder cancer cell, gastric cancer cell, ovarian cancer cell, peritoneal cancer cell, pancreatic cancer cell, breast cancer cell, head and neck cancer cell, cervical cancer cell, endometrial cancer cell, colorectal cancer cell, liver cancer cell, renal cancer cell, solid tumor cell, non-Hodgkin's lymphoma cell, central nervous system tumor cell (e.g., neuroglioma cell, glioblastoma multiforme cell, glioma cell or sarcoma cell), prostatic cancer cell and thyroid cancer cell.

In some preferred embodiments, the cell is the primary cell from the subject or culture thereof, or an established cell line. In some preferred embodiments, the subject is mammal, such as bovine, equine, caprid, suidae, canine, feline, rodent, and primate; wherein the particularly preferred subject is human.

Solution 19. A kit comprising the compound, or a pharmaceutically acceptable salt, ester, or solvate thereof, or their stereoisomers according to any one of Solutions 1-11, and optionally, instructions.

In some preferred embodiments, the kit is used to reduce or inhibit activity of EGFR or mutant thereof in a cell. In some preferred embodiments, the EGFR mutant comprises one or more of the following mutations: T790M mutation, L858R mutation, and d746-750 mutation. In some preferred embodiments, the EGFR mutant comprises T790M mutation. In some preferred embodiments, the EGFR mutant comprises T790M mutation and L858R mutation. In some preferred embodiments, the EGFR mutant comprises T790M mutation and d746-750 mutation. In some preferred embodiments, the EGFR mutant comprises T790M mutation, L858R mutation, and d746-750 mutation.

In some preferred embodiments, the cell is selected from esophageal cancer cell (e.g., esophageal adenocarcinoma cell and esophageal squamous cancer cell), brain tumor cell, lung cancer cell (e.g., small cell lung cancer cell and non-small cell lung cancer cell), squamous cell cancer cell, bladder cancer cell, gastric cancer cell, ovarian cancer cell, peritoneal cancer cell, pancreatic cancer cell, breast cancer cell, head and neck cancer cell, cervical cancer cell, endometrial cancer cell, colorectal cancer cell, liver cancer cell, renal cancer cell, solid tumor cell, non-Hodgkin's lymphoma cell, central nervous system tumor cell (e.g., neuroglioma cell, glioblastoma multiforme cell, glioma cell or sarcoma cell), prostatic cancer cell and thyroid cancer cell. In some preferred embodiments, the cell is the primary cell from the subject or culture thereof, or an established cell line. In some preferred embodiments, the subject is mammal, such as bovine, equine, caprid, suidae, canine, feline, rodent, and primate; wherein the particularly preferred subject is human.

Detailed Contents of Invention

In the description and claims of the present application, the compounds are named according to their formulae, and if the name and the formula for the same compound are not consistent with each other, the formula shall prevail.

In the present application, unless otherwise specified, the scientific and technical terms used herein have the meanings as generally understood by a person skilled in the art. However, in order to understand the invention better, definitions and explanations are provided for a part of terms. In addition, if the definitions and explanations of the terms provided in the present application are different from the meanings generally understood by a person skilled in the art, the definitions and explanations of the terms provided in the present application shall prevail.

The term "halo-" used herein refers to substitution by "halogen atom", and the term "halogen atom" refers to fluorine atom, chlorine atom, bromine atom, iodine atom, etc.

As used in the present application, in the compounds according to the invention (e.g., a compound of Formula (I)), solid line represents chemical bond, dotted line "----" represents presence or absence of chemical bond. For example, the dotted line "----" between Ring B and Ring C represents: (1) there is a chemical bond between Ring B and Ring C, i.e., they are linked via a chemical bond; or (2) there is no chemical bond between Ring B and Ring C, i.e., they are fused to form a fused cyclyl (e.g., a 3-14 membered N-containing fused heterocyclyl optionally substituted by a substituent).

The term "C1-6alkyl" used herein refers to linear or branched alkyl containing 1 to 6 carbon atoms, including, e.g., "C1-4alkyl", "C1-3alkyl" etc. Its examples include, but are not limited to: methyl, ethyl, n-propyl, isopropyl, n-butyl, isobutyl, sec-butyl, tert-butyl, n-pentyl, isopentyl, 2-methylbutyl, neopentyl, 1-ethylpropyl, n-hexyl, isohexyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1,2-dimethylpropyl, etc. The term "C1-4alkyl" used herein refers to examples of C1-6alkyl containing 1 to 4 carbon atoms.

The term "halo-C1-6alkyl" used herein refers to a group derived from substitution of one or more hydrogen atoms of "C1-6alkyl" with one or more "halogen atoms", wherein the terms "halogen atom" and "C1-6alkyl" have the same meanings as defined above. The term "halo-C1-4alkyl" used herein refers to examples of halo-C1-6alkyl containing 1 to 4 carbon atoms.

The term "C2-6alkenyl" used herein refers to a linear, branched or cyclic alkenyl containing 2 to 6 carbon atoms and at least one double bond, including, e.g., "C2-4 alkenyl", etc. Its examples include, but are not limited to: ethenyl, 1-propenyl, 2-propenyl, 1-butenyl, 2-butenyl, 1,3-butadienyl, 1-pentenyl, 2-pentenyl, 3-pentenyl, 1,3-pentadienyl, 1,4-pentadienyl, 1-hexenyl, 2-hexenyl, 3-hexenyl, 1,4-hexadienyl, cyclopentenyl, 1,3-cyclopentadienyl, cyclohexenyl, 1,4-cyclohexadienyl, etc. The term "C2-4alkenyl" used herein referes to examples of C2-6alkenyl containing 2 to 4 carbon atoms.

The term "C2-6alkynyl" used herein refers to a linear or branched alkynyl containing 2 to 6 carbon atoms and at least one triple bond, including, e.g., "C2-4alkynyl" etc. Its examples include, but are not limited to: ethynyl, propinyl, 2-butynyl, 2-pentynyl, 3-pentynyl, 4-methyl-2-pentynyl, 2-hexynyl, 3-hexynyl, 5-methyl-2-hexynyl, etc. The term "C2-4 alkynyl" used herein refers to examples of C2-6 alkynyl containing 2 to 4 carbon atoms.

The term "C1-6alkoxy, C1-6alkylcarbonyl, C1-6alkylcarbonyloxy, C1-6alkylamino, di-C1-6alkylamino, C1-6alkylsulfonylamino, C1-6alkylsulfonyloxy, C1-6alkylsulfonyl, C1-6alkylsulfonylC1-6alkoxy" used herein refer to C1-6alkyl-O—, C1-6alkyl-C(O)—, C1-6alkyl-C(O)—O—, C1-6alkyl-NH—, (C1-6alkyl)2-N—, C1-6alkyl-SO2-NH—, C1-6alkyl-SO2-O—, C1-6alkyl-SO2-, C1-6alkyl-SO2-C1-6alkyl-O—, wherein the term "C1-6alkyl" has the same meanings as defined above. The term "C1-4alkoxy, C1-4alkylcarbonyl, C1-4alkylcarbonyloxy, C1-4alkylamino, diC1-4alkylamino, C1-4alkyl sulfonylamino, C1-4alkylsulfonyloxy, C1-4alkylsulfonyl, C1-4alkylsulfonylC1-4alkoxy" used herein refers to the above-mentioned examples in which the alkyl contains 1 to 4 carbon atoms.

The term used herein "3-8 membered cycloalkyl" refers to a saturated cyclic alkyl containing 3 to 8 carbon atoms, including, e.g., "3-6 membered cycloalkyl", "4-6 membered cycloalkyl" etc. Its examples include, but are not limited to: cyclopropyl, cyclobutyl, cyclopentyl, cyclohexyl, cycloheptyl, cyclooctyl, etc. "3-6 membered cycloalkyl" refers to a saturated cyclic alkyl containing 3 to 6 carbon atoms.

The term "3-14 membered ring structure" used herein refers to a cyclic group containing 3 to 14 ring atoms, including, but not limited to 6-8 membered aryl, 6-14 membered fused aryl, 3-8 membered cycloalkyl, 3-14 membered fused cyclyl, 3-14 membered spirocyclyl, 3-14 membered bridged cyclyl, 3-10 membered heterocyclyl, 3-14 membered fused heterocyclyl, 3-14 membered spiroheterocyclyl, 3-14 membered bridged heterocyclyl, 5-8 membered heteroaryl, 5-14 membered fused heteroaryl. The term used herein "3-10 membered ring structure" refers to examples of 3-14 membered ring structure containing 3 to 10 ring atoms.

The term "6-8 membered aryl" used herein refers to a monocyclic aryl containing 6 to 8 ring carbon atoms. Its examples include, but are not limited to: phenyl, cyclooctatetraenyl, etc.

The term "6-14 membered fused aryl" used herein refers to an unsaturated, aromatic cyclic group containing 6 to 14 ring carbon atoms, formed by two or more ring structures that share two adjacent atoms. Its examples include, but are not limited to: naphthyl, anthryl, phenanthrenyl, etc. The term "6-10 membered fused aryl" used herein refers to examples of 6-14 membered fused aryl of which the number of ring atom is 6 to 10.

The term used herein "3-14 membered fused cyclyl" refers to a ring structure containing 3 to 14 carbon atoms and/or heteroatoms, formed by two or more ring structures that share two adjacent atoms, including, e.g., "4-11 membered fused cyclyl", "6-11 membered fused cyclyl", "5-10 membered fused cyclyl", "7-10 membered fused cyclyl", "3-12 membered fused cyclyl", "9-10 membered fused cyclyl", "3-10 membered fused cyclyl", etc. Its examples include, but are not limited to:

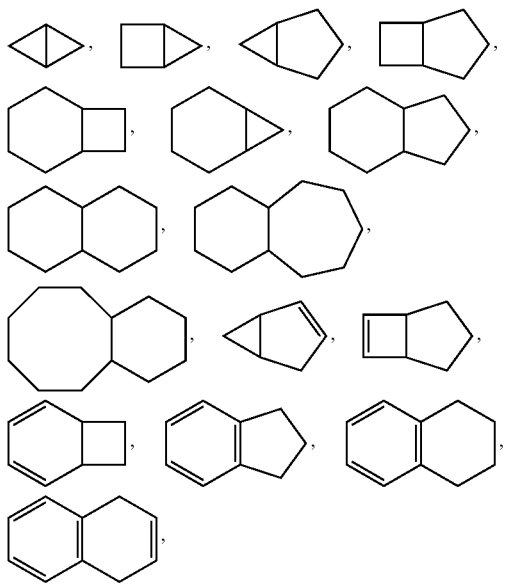

etc. The term "3-10 membered fused cyclyl" used herein refers to examples of 3-14 membered fused cyclyl containing 3 to 10 ring atoms.

The term used herein "3-14 membered spirocyclyl" refers to a ring structure containing 3 to 14 ring carbon atoms, formed by two or more ring structures that share one carbon atom. Optionally, the carbon atoms in the ring structure can be oxo. "3-14 membered spirocyclyl" includes, e.g., "4-11 membered spirocyclyl", "6-11 membered spirocyclyl", "5-10 membered spirocyclyl", "7-10 membered spirocyclyl", "7-9 membered spirocyclyl", "7-8 membered spirocyclyl", "9-10 membered spirocyclyl", "3-10 membered spirocyclyl", etc. Its examples include, but are not limited to:

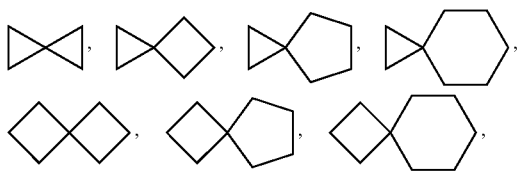

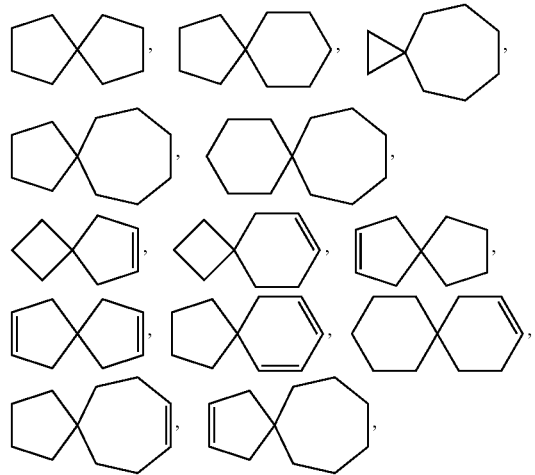

etc. The term "3-10 membered spirocyclyl" used herein refers to examples of 3-14 membered spirocyclyl containing 3 to 10 ring atoms.

The term "3-14 membered bridged cyclyl" used herein refers a ring structure containing 3-14 ring carbon atoms, formed by two or more ring structures that share two non-adjacent carbon atoms. Optionally the carbon atoms in the ring structure can be oxo. "3-14 membered bridged cyclyl" includes, e.g., "5-11 membered bridged cyclyl", "6-11 membered bridged cyclyl", "5-10 membered bridged cyclyl", "7-10 membered bridged cyclyl", "7-9 membered bridged cyclyl", "7-8 membered bridged cyclyl", "9-10 membered bridged cyclyl", "3-10 membered bridged cyclyl", etc. Its examples include, but are not limited to:

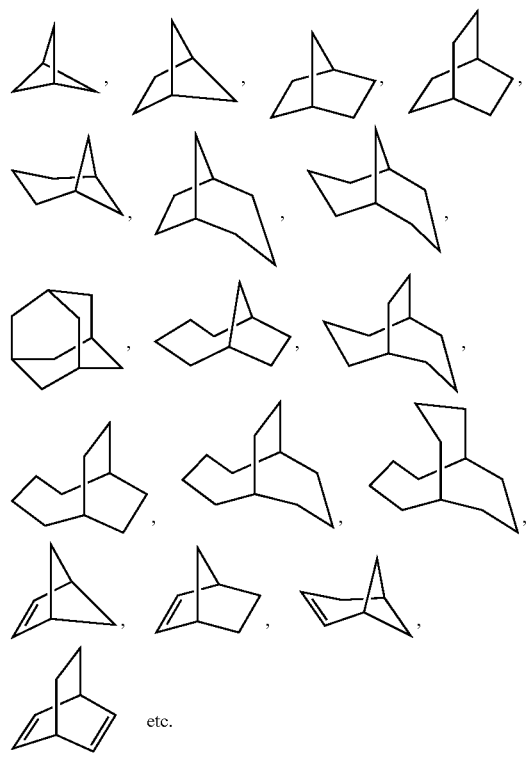

etc.

The term "3-10 membered heterocyclyl" used herein refers to a ring structure containing 3 to 10 ring atoms (wherein at least one ring atom is heteroatom, such as nitrogen atom, oxygen atom or sulfur atom). Optionally, the ring atom (such as carbon atom, nitrogen atom, or sulfur atom) in the ring structure can be oxo. "3-10 membered heterocyclyl" includes, e.g., "3-10 membered N-containing heterocyclyl", "3-10 membered O-containing heterocyclyl", "3-8 membered heterocyclyl", "3-7 membered heterocyclyl", "3-6 membered heterocyclyl", "3-6 membered O-containing heterocyclyl", "4-7 membered heterocyclyl", "4-6 membered heterocyclyl", "5-7 membered heterocyclyl", "5-6 membered heterocyclyl", "5-6 membered N-containing heterocyclyl", "6-8 membered heterocyclyl", etc., preferably, "5-6 membered heterocyclyl". Its examples include, but are not limited to: aziridinyl, 2H-aziridinyl, diazacyclopropyl, 3H-diazacyclopropenyl, azetidinyl, 1,4-dioxanyl, 1,3-dioxanyl, 1,3-dioxacyclopentyl, 1,4-dioxacyclohexadienyl, tetrahydrofuranyl, dihydropyrrolyl, pyrrolidinylyl, imidazolidinyl, 4,5-dihydroimidazolyl, pyrazolidinyl, 4,5-dihydropyrazolyl, 2,5-dihydrothienyl, tetrahydrothienyl, 4,5-dihydrothiazolyl, thiazolidinyl, piperidyl, tetrahydropyridinyl, piperidin-one-yl, tetrahydropyridin-one-yl, dihydropiperidin-one-yl, piperazinyl, morpholinyl, 4,5-dihydrooxazolyl, 4,5-dihydroisoxazolyl, 2,3-dihydroisoxazolyl, oxazolidinyl, 2H-1,2-oxazinyl, 6H-1,3-oxazinyl, 4H-1,3-thiazinyl, 6H-1,3-thiazinyl, 2H-pyranyl, 2H-pyran-2-one, 3,4-dihydro-2H-pyranyl, etc. The terms "3-8 membered heterocyclyl" and "3-6 membered heterocyclyl" refers to examples of 3-10 membered heterocyclyl containing 3 to 8 ring atoms and containing 3 to 6 ring atoms, respectively.

The term "3-10 membered N-containing heterocyclyl" used herein refers to a heterocyclyl containing 3 to 10 ring atoms, at least one of which is nitrogen atom, including, e.g., "5-6 membered N-containing heterocyclyl", "5-10 membered N-containing heterocyclyl", "9-10 membered N-containing heterocyclyl", etc.

The term "3-10 membered O-containing heterocyclyl" used herein refers to a heterocyclyl containing 3 to 10 ring atoms, at least one of which is oxygen atom, including, e.g., "3-6 membered O-containing heterocyclyl", "5-6 membered O-containing heterocyclyl", "9-10 membered O-containing heterocyclyl", etc.

The term "3-14 membered fused heterocyclyl" used herein refers to a ring structure containing 3 to 14 ring atoms (wherein at least one ring atom is a heteroatom, such as nitrogen atom, oxygen atom or sulfur atom), formed by two or more ring structures that share two adjacent atoms. Optionally, the ring atom (such as carbon atom, nitrogen atom or sulfur atom) in the ring structure can be oxo. "3-14 membered fused heterocyclyl" includes, e.g., "3-14 membered N-containing fused heterocyclyl", "4-12 membered fused heterocyclyl", "6-11 membered fused heterocyclyl", "5-10 membered fused heterocyclyl", "7-10 membered fused heterocyclyl", "3-10 membered fused heterocyclyl", "3-10 membered N-containing fused heterocyclyl", "9-10 membered fused heterocyclyl", "9-10 membered N-containing fused heterocyclyl", etc. Its examples include, but are not limited to: tetrahydroimidazo[4,5-c]pyridinyl, 3,4-dihydroquinazolinyl, 1,2-dihydroquinoxalinyl, benzo[d][1,3]dioxacyclopentenyl, 1,3-dihydroisobenzofuranyl, 2H-chromenyl, 2H-chromen-2-one, 4H-chromenyl, 4H-chromen-4-one, chromanyl, 4H-1,3-benzoxazinyl, 4,6-dihydro-1H-furo[3,4-d]imidazolyl, 3a,4,6,6a-tetrahydro-1H-furo[3,4-d]imidazolyl, 4,6-dihydro-1H-thieno[3,4-d]imidazolyl, 4,6-dihydro-1H-pyrrolo[3,4-d]imidazolyl, benzimidazolidinyl, octahydro-benzo[d]imidazolyl, decahydroquinolinyl, hexahydro-thienoimidazolyl, hexahydro-furoimidazolyl, 4,5,6,7-tetrahydro-1H-benzo[d]imidazolyl, octahydro-cyclopenta[c]pyrrolyl, dihydroindolyl, dihydroisoindolyl, benzoxazolidinyl, benzothiazolidinyl, 1,2,3,4-tetrahydroisoquinolyl, 1,2,3,4-tetrahydro-quinolyl, 4H-1,3-benzoxazinyl, etc.

The term "3-14 membered N-containing fused heterocyclyl" used herein refers to 3-14 membered fused heterocyclyl containing at least one ring nitrogen atom. Its examples include, but are not limited to: "3-10 membered N-containing fused heterocyclyl", "6-11 membered N-containing fused heterocyclyl", "7-10 membered N-containing fused heterocyclyl", "9-10 membered N-containing fused heterocyclyl", etc.

The term "3-14 membered spiroheterocyclyl" used herein refers to a ring structure containing 3 to 14 ring atoms (wherein at least one ring atom is a heteroatom, such as nitrogen atom, oxygen atom or sulfur atom), formed by two or more ring structures that share one ring atom. Optionally, the ring atom (such as carbon atom, nitrogen atom or sulfur atom) in the ring structure can be oxo. "3-14 membered spiroheterocyclyl" include, e.g., "5-11 membered spiroheterocyclyl", "6-11 membered spiroheterocyclyl", "5-10 membered spiroheterocyclyl", "7-11 membered spiroheterocyclyl", "7-10 membered spiroheterocyclyl", "7-9 membered spiroheterocyclyl", "7-8 membered spiroheterocyclyl", "9-10 membered spiroheterocyclyl", "3-10 membered spiroheterocyclyl" etc. Its examples include, but are not limited to:

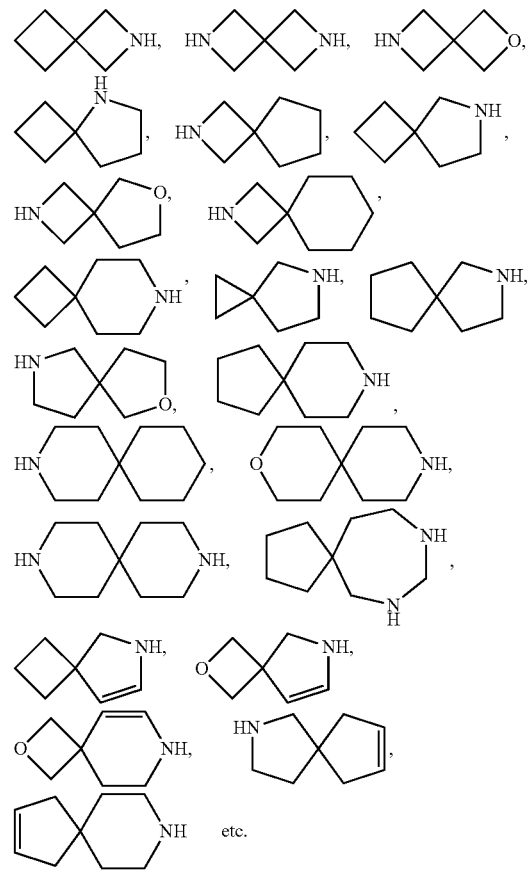

The term "3-10 membered spiroheterocyclyl" used herein refers to examples of 3-14 membered spiroheterocyclyl containing 3 to 10 ring atoms.

The term "3-14 membered bridged heterocyclyl" used herein refers to a ring structure containing 3 to 14 ring atoms (wherein at least one ring atom is a heteroatom, such as nitrogen atom, oxygen atom or sulfur atom), formed by two or more ring structures that share two non-adjacent ring atoms. Optionally, the ring atom (such as carbon atom, nitrogen atom or sulfur atom) in the ring structure can be oxo. "3-14 membered bridged heterocyclyl" includes, for example, "5-10 membered bridged heterocyclyl", "6-11 membered bridged heterocyclyl", "6-9 membered bridged heterocyclyl", "6-10 membered bridged heterocyclyl", "7-10 membered bridged heterocyclyl", "7-9 membered bridged heterocyclyl", "7-8 membered bridged heterocyclyl", "8 membered bridged heterocyclyl", "9-10 membered bridged heterocyclyl", "3-10 membered bridged heterocyclyl", etc. Its examples include, but are not limited to:

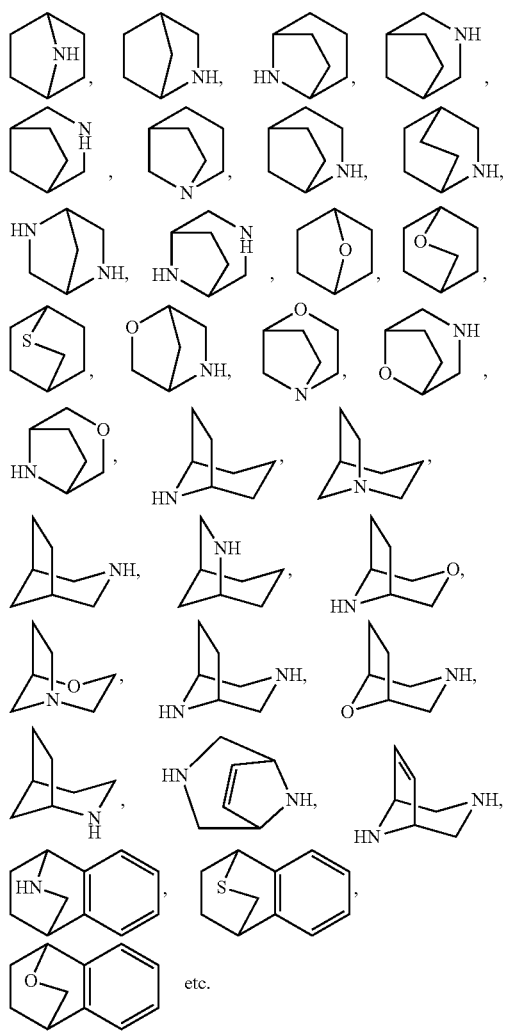

The "3-10 membered bridged heterocyclyl" refers to examples of 3-14 membered bridged heterocyclyl containing 3 to 10 ring atoms.

The term "5-8 membered heteroaryl" used herein refers to an aromatic ring structure containing 5 to 8 ring atoms (wherein at least one ring atom is a heteroatom, such as nitrogen atom, oxygen atom or sulfur atom). Optionally, the ring atom (such as carbon atom, nitrogen atom or sulfur atom) in the ring structure can be oxo. "5-8 membered heteroaryl" includes, e.g., "5-7 membered heteroaryl", "5-6 membered heteroaryl" etc. Its examples include, but are not limited to: furanyl, thienyl, pyrrolyl, thiazolyl, isothiazolyl, thiadiazolyl, oxazolyl, isoxazolyl, oxadiazolyl, imidazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, pyridyl, 2-pyridone-yl, 4-pyridone-yl, pyrimidinyl, 1,4-dioxacyclohexadienyl, pyridazinyl, pyrazinyl, 1,2,3-triazinyl, 1,3,5-triazinyl, 1,2,4,5-tetrazinyl, azepinyl, 1,3-diazepinyl, azocinyl, etc. The term 5-6 membered heteroaryl" refers to examples of 5-8 membered heteroaryl containing 5 to 6 ring atoms.

The term "5-14 membered fused heteroaryl" used herein refers to an unsaturated, aromatic ring structure containing 5 to 14 ring atoms (wherein at least one ring atom is a heteroatom, such as nitrogen atom, oxygen atom or sulfur atom), formed by two or more ring structures that share two adjacent atoms. Optionally, the ring atom (such as carbon atom, nitrogen atom or sulfur atom) in the ring structure can be oxo. "5-14 membered fused heteroaryl" includes, e.g., "5-10 membered fused heteroaryl", "7-10 membered fused heteroaryl", "9-10 membered fused heteroaryl", etc. Its examples include, but are not limited to: benzofuranyl, isobenzofuranyl, benzothienyl, indolyl, isoindolyl, benzoxazolyl, benzoimidazolyl, indazolyl, benzotriazolyl, quinolinyl, 2-quinolin-one-yl, 4-quinolin-one-yl, 1-isoquinolin-one-yl, isoquinolinyl, acridinyl, phenanthridinyl, benzopyridazinyl, phthalazinyl, quinazolinyl, quinoxalinyl, pteridinyl, purinyl, naphthyridinyl, phenazinyl, phenothiazinyl, etc. The term "5-10 membered fused heteroaryl" refers to examples of 5-14 membered fused heteroaryl containing 5 to 10 ring atoms.

The term "carbon atom, nitrogen atom or sulfur atom is oxo" used herein refers to the formation of C=O, N=O or S=O structure.

"A pharmaceutically acceptable salt" of the compound of Formula (I) according to the invention refers to a salt formed by the reaction of acidic group(s) (e.g., —COOH, —OH, —SO3H etc.) in the compound of Formula (I) with suitable inorganic or organic cation(s) (base), including a salt formed with alkaline metal or alkaline earth metal, ammonium salt, and a salt formed with a nitrogen-containing organic base; and a salt formed by the reaction of the basic group(s) (e.g., —NH2, etc.) in the compound of Formula (I) with suitable inorganic or organic anion(s) (acid), including a salt formed with inorganic acid and organic acid (e.g., carboxylic acid, etc.).

"An ester" of the compound of Formula (I) according to the invention refers to an ester formed by the esterification reaction of the compound of Formula (I) with an alcohol when the compound has a carboxyl group; or an ester formed by the esterification reaction of the compound of Formula (I) with an organic acid, inorganic acid, or organic acid salt, etc., when the compound has a hydroxyl group. In the presence of acid or base, the ester may be hydrolyzed to produce the corresponding acid or alcohol.

"A solvate" of the compound of Formula (I) according to the invention refers to a substance formed by its association with solvent molecule(s). The solvent may be an organic solvent (e.g., methanol, ethanol, propanol, acetonitrile, etc.), and water, etc. For example, the compound of Formula (I) according to the invention may form an alcholate with ethanol, or form a hydrate with water.

"Stereoisomerism" of the compound according to the invention is divided into conformational isomerism and configurational isomerism, wherein configurational isomerism is further divided into cis-trans isomerism and optical isomerism. Conformational isomerism refers to a stereoisomerism in which rotations or distortions of single C—C bonds result in different spatial arrangements of atoms or atomic groups in an organic molecule with a certain configuration, commonly found in alkane and cycloalkane compounds, such as chair and boat conformers of cyclohexane. "Stereoisomers" means that when the compound according to the invention has one or more asymmetry centers, it can be racemes and racemic mixtures, single enantiomers, diastereoisomer mixtures, and single diastereoisomers. The compound according to the invention has asymmetry centers, each of which independently lead to two optical isomers. The scope of the invention includes all the possible optical isomers and diastereoisomer mixtures, as well as pure or partially pure compounds. If the compounds according to the invention have alkene carbon-carbon double bond, unless otherwise specified, the compounds according to the invention include cis-isomers and trans-isomers. The compounds according to the invention may be present in form of tautomers, which have different hydrogen connection sites due to one or more double-bond shifts. For example, ketone and its enol form are keto-enol tautomers. Various tautomers and mixtures thereof are all included in the compounds according to the invention. All the enantiomers, diastereoisomers, racemes, cis-trans-isomers, tautomers, geometric isomers, and epimerides of the compound of Formula (I), and mixtures thereof fall into the scope of the invention.

As used herein, the term "EGFR" refers to epidermal growth factor receptor, which is a transmembrane protein belonging to the receptor tyrosine kinase ERBB family, and plays an important role in tumor transformation and proliferation. The amino acid sequence of EGFR is known by a person skilled in the art and can be found in public databases, such as NCBI database. The exemplary amino acid sequence of EGFR may, for example, be set forth in SEQ ID NO: 1. In the invention, when the amino acid sequence of EGFR is mentioned, it is described by the sequence set forth in SEQ ID NO: 1. For example, the expression "amino acid residue at position 790 of EGFR" refers to the amino acid residue at position 790 of the sequence set forth in SEQ ID NO: 1. However, a person skilled in the art understands that mutations or variations (incluing, but not limited to, substitution, deletion and/or addition) may occur naturally in or are introduced artificially into the amino acid sequence of EGFR without affecting its biological properties. Therefore, in the invention, the term "EGFR" intends to comprise all such sequences, for example, including the sequence set forth in SEQ ID NO: 1 and its natural or artificial mutants. In addition, when positions or fragments of EGFR are described, they include not only the positions or fragments of the sequence set forth in SEQ ID NO: 1, but also the corresponding positions or fragments of the natural or artificial mutants of the sequence set forth in SEQ ID NO: 1. For example, the expression "amino acid residue at position 790 of EGFR" comprises amino acid residue at position 790 of the sequence set forth in SEQ ID NO: 1 and at the corresponding position of the mutants (natural or artificial mutants) of the sequence set forth in SEQ ID NO: 1. For example, the expression "amino acid residues from positions 746 to 750 of EGFR" comprises amino acid residues from positions 746 to 750 of the sequence set forth in SEQ ID NO: 1 and the corresponding fragment of the mutants (natural or artificial mutants) of the sequence set forth in SEQ ID NO: 1.

According to the invention, the expression "corresponding sequence fragments" or "corresponding fragments" refers to fragments that are located in equal positions of sequences when the sequences are subjected to optimized alignment, namely, the sequences are aligned to obtain a highest percentage of identity. According to the invention, the expression "corresponding positions" refers to the positions that are located in equal sites of sequences when the sequences are subjected to optimized alignment, namely, the sequences are aligned to obtain a highest percentage of identity. As used herein, the term "identity" refers to the match degree of sequences between two polypeptides or between two nucleic acids. When two sequences for comparison have the same base or amino acid monomer sub-unit at a certain site (e.g., each of two DNA molecules has an adenine at a certain site, or each of two polypeptides has a lysine at a certain site), the two molecules are identical at the site. The percentage of identity between two sequences is a function of the number of identical sites shared by the two sequences divided by the total number of sites for comparison and multiplied by 100. For example, if 6 of 10 sites of two sequences are matched, these two sequences have an identity of 60%. For example, DNA sequences: CTGACT and CAGGTT share an identity of 50% (3 of 6 sites are matched). Generally, the comparison of two sequences is conducted in a manner to produce maximum identity. Such alignment can be conducted conveniently by a computer program such as Align program (DNAstar, Inc.) which is based on the method of Needleman, et al. (J. Mol. Biol. 48:443-453, 1970). The percentage of identity between two amino acid sequences can be determined by using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percentage of identity between two amino acid sequences can be determined by the algorithm of Needleman and Wunsch (J. Mol. Biol. 48:444-453 (1970)) which has been incorporated into the GAP program in the GCG software package (available at http://www.gcg.com), using either a Blossum 62 matrix or a PAM250 matrix, and a gap weight of 16, 14, 12, 10, 8, 6 or 4 and a length weight of 1, 2, 3, 4, 5 or 6.

In addition, in the invention, unless otherwise specified, or can be determined directly according to the context, when EGFR is mentioned, it includes not only wild-type EGFR, but also various mutants of wild-type EGFR (natural or artificial mutants). For example, the expression "overexpression of EGFR" involves the overexpression of wild-type EGFR and mutant EGFR. Also, for example, a person skilled in the art would readily understand that the expression "EGFR or mutant thereof" referes to wild-type EGFR or mutant thereof. In addition, as used herein, "EGFR mutant" and "mutant EGFR" have the same meanings, and can be used interchangeably.

As used herein, unless otherwise specified, "activity of EGFR" refers to tyrosine kinase activity of EGFR. As used herein, "overactivity of EGFR" refers to the tyrosine kinase activity of EGFR in a cell is higher than the tyrosine kinase activity of EGFR in a cell under the natural state (i.e., physiological state or normal state), which, for example, may result in proliferation of cells in an uncontrollable manner (i.e., hyperproliferation). Overactivity of EGFR may, for example, be resulted from overexpression of EGFR and/or EGFR mutation. As used herein, "a disease associated with overactivity of EGFR" means that the cell from a subject with the disease exhibits overactivity of EGFR. In the disease, overactivity of EGFR may trigger the development of the disease, accelerate the progress of the disease, and/or affect the response of a subject with the disease to therapy. A disease associated with overactivity of EGFR may include, but is not limited to hyperproliferative disease, such as cancer and non-cancerous disease.

As used herein, "drug resistance caused by EGFR mutant" refers to insensitivity of cells to EGFR TKI due to mutation of EGFR. Several EGFR mutations, which can result in drug resistance to EGFR TKI, have been reported, including, but not limited to: T790M mutation, L858R mutation, and d746-750 mutation.

As used herein, T790M mutation of EGFR referes to mutation of the amino acid residue from T to M at position 790 of EGFR. As used herein, L858R mutation of EGFR referes to mutation of the amino acid residue from L to R at position 858 of EGFR. As used herein, d746-750 mutation of EGFR refers to deletion of the amino acid residues at positions 746-750 of EGFR. A person skilled in the art would understand that other similar expressions have similar meanings.

As used herein, the term "an effective amount" refers to an amount that is sufficient to achieve or at least partially achieve a desired effect. For example, an effective amount for preventing a disease (such as a disease associated with overactivity of EGFR) refers to an amount that is sufficient to prevent, suppress or delay the development of the disease (such as a disease associated with overactivity of EGFR); a therapeutically effective amount refers to an amount that is sufficient to cure or at least partially suppress a disease and its complications in a patient with the disease. It is completely within the ability of a person skilled in the art to determine such an effective amount. For example, a therapeutically effective amount will depend on the severity of a disease to be treated, the overall state of the immune system in a patient, general conditions of a patient such as age, body weight and gender, administration route of a drug, other therapy used in combination, and the like.

The invention also provides methods for preparing the compound of Formula (I), but not limited to the following methods:

Scheme I:

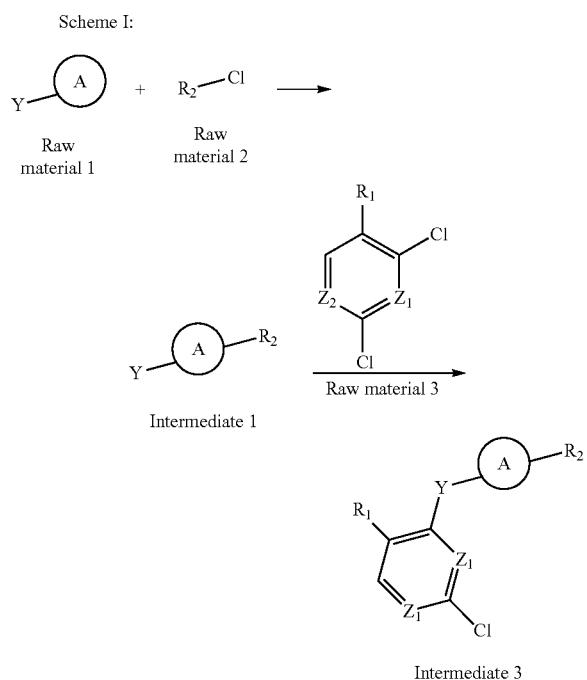

Scheme II:

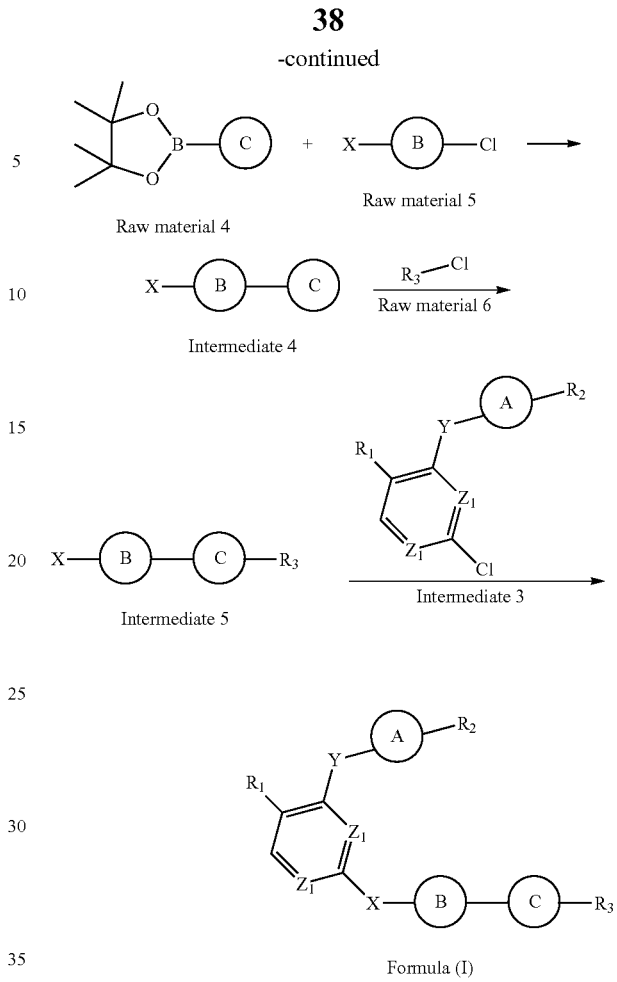

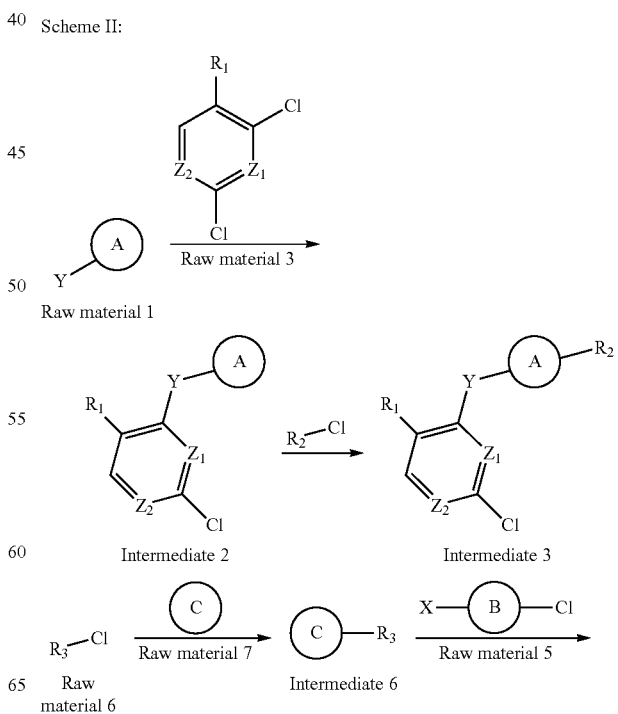

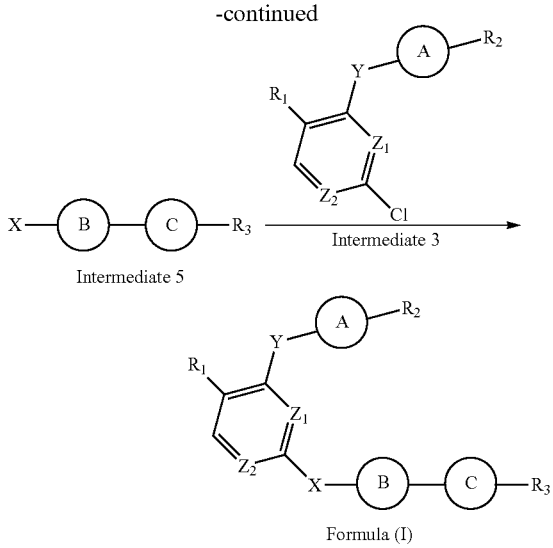

wherein $R_1$, $R_2$, $R_3$, $Z_1$, $Z_2$, A, B, C, X and Y in the schemes have the same meanings as defined above.

Steps of Scheme I:

1. Preparation of Intermediate 1

Raw material 1 is dissolved in a suitable organic solvent (e.g., tetrahydrofuran, ethanol, methanol), and Raw material 2 (R2Cl) is added at a low temperature (e.g., 0° C.). The mixture is stirred at room temperature until the reaction is finished, and water is added to quench the reaction. The resultant mixture is extracted with organic solvent (e.g., ethyl acetate, dichloromethane), and the organic phase is dried, concentrated and purified to obtain Intermediate 1.

2. Preparation of Intermediate 3

Intermediate 1 and base (e.g, triethylamine, diethylamine) are dissolved in a suitable solvent (e.g., tetrahydrofuran, ethanol, methanol), and Raw material 3 was added slowly. The mixture is stirred at room temperature until the reaction is finished, and water is added to quench the reaction. The resultant mixture is extracted with organic solvent (e.g., ethyl acetate, dichloromethane), and the organic phase is dried, concentrated and purified to obtain Intermediate 3.

3. Preparation of Intermediate 4

Raw material 4 and Raw material 5 are dissolved in a suitable solvent (e.g., N,N-dimethylformamide, thionyl chloride), and a suitable amount of base (e.g., sodium carbonate, potassium carbonate, cesium carbonate) and a suitable metal palladium catalyst (e.g., [1,1'-bis(diphenylphosphino)ferrocene]dichloropalladium (II)) are added. Under the protection of nitrogen gas, the reaction is carried out under heating (e.g., 90° C.). After the reaction, the temperature is reduced to room temperature, and water is added to quench the reaction. The resultant mixture is extracted with organic solvent (e.g, ethyl acetate), and the organic phase is dried, concentrated and purified to obtain Intermediate 4.

4. Preparation of Intermediate 5

Intermediate 4 is dissolved in a suitable solvent (e.g., dichloromethane, ethanol, acetonitrile), and triethylamine is added, followed by the addition of Raw material 6 ($R_3Cl$). The mixture is stirred at room temperature until the reaction is finished, and water is added to quench the reaction. The resultant mixture is extracted with dichloromethane, and the organic phase is dried, concentrated and purified to obtain Intermediate 5.

5. Preparation of the compound of Formula (I)

Intermediate 3 and Intermediate 5 are dissolved in a suitable solvent (e.g., 1,4-dioxane), and a suitable amount of trifluoroacetic acid is added. Under the protection of nitrogen gas, the reaction is carried out under heating (e.g., 70° C.). After the reaction, the temperature is reduced to room temperature, and the organic phase is dried, concentrated and purified to obtain the compound of Formula (I).

Steps of Scheme II:

1. Preparation of Intermediate 2

Raw material 1 and base (e.g., triethylamine, diethylamine) are dissolved in a suitable organic solvent (e.g., tetrahydrofuran, ethanol, methanol), and Raw material 3 is added slowly. The mixture is stirred at room temperature until the reaction is finished, and water is added to quench the reaction. The resultant mixture is extracted with organic solvent (e.g., ethyl acetate, dichloromethane), and the organic phase is dried, concentrated and purified to obtain Intermediate 2.

2. Preparation of Intermediate 3

Intermediate 2 is dissolved in a suitable solvent (e.g., dichloromethane, ethanol, acetonitrile), and $R_2Cl$ is added at a low temperature (e.g., 0° C.). The mixture is stirred at room temperature until the reaction is finished, and water is added to quench the reaction. The resultant mixture is extracted with organic solvent (e.g., dichloromethane, ethyl acetate), and the organic phase is dried, concentrated and purified to obtain Intermediate 3.

3. Preparation of Intermediate 6

Raw material 7 is dissolved in a suitable solvent (e.g., tetrahydrofuran, ethanol), and triethylamine is added, followed by the addition of Raw material 6 ($R_3Cl$). The mixture is stirred at room temperature until the reaction is finished, and water is added to quench the reaction. The resultant mixture is extracted with organic solvent (e.g., ethyl acetate, dichloromethane), and the organic phase is dried, concentrated and purified to obtain Intermediate 6.

4. Preparation of Intermediate 5

Raw material 5 and Intermediate 6 are dissolved in a suitable solvent (e.g., acetonitrile, methanol, dichloromethane), and a suitable amount of base (e.g., cesium carbonate, sodium carbonate, potassium carbonate) is added. The mixture is heated until the reaction is finished. The temperature is reduced to room temperature, and water is added to quench the reaction. The resultant mixture is extracted with organic solvent (e.g., ethyl acetate, ethanol, acetonitrile), and the organic phase is dried, concentrated and purified to obtain Intermediate 5.

5. Preparation of the compound of Formula (I)

Intermediate 3 and Intermediate 5 are dissolved in a suitable solvent (e.g., 1,4-dioxane, thionyl chloride, ethanol, acetonitrile), and potassium carbonate, a suitable metal palladium catalyst (e.g., tris(dibenzylideneacetone)dipalladium)) and a ligand (e.g., 2-dicyclohexylphosphino-2',4',6'-triisopropylbiphenyl) are added. Under the protection of nitrogen gas, the reaction is carried out under heating (e.g., by microwave heating to 110° C.). After the reaction, the temperature is reduced to room temperature, and water is added to quench the reaction. The resultant mixture is extracted with organic solvent (e.g., ethyl acetate, dichloromethane), and the organic phase is dried, concentrated and purified to obtain the compound of Formula (I).

The invention also relates to a pharmaceutical composition comprises a compound of Formula (I), or a pharmaceutically acceptable salt, ester, or solvate thereof, or their stereoisomers, and optionally one or more pharmaceutically acceptable carriers and/or diluents. The pharmaceutical composition may be prepared in any pharmaceutically acceptable dosage form. For example, the compound or pharmaceutical composition according to the invention may be prepared into tablets, capsules, pills, granules, solutions, suspensions, syrups, injections (including injectio, sterile powder for injection and concentrated solution for injection), suppositories, inhalants, or spraying agents.

In addition, the pharmaceutical composition according to the invention may be administered to a patient or subject in need thereof by any suitable route, such as orally, parenterally, rectally, intrapulmonarily, or topically, etc. When administered orally, the pharmaceutical composition may be prepared into an oral formulation, e.g., an oral solid formulation, such as tablet, capsule, pill, and granule; or may be prepared into an oral liquid formulation, such as oral solution, oral suspension, and syrup. When prepared as an oral formulation, the pharmaceutical composition may further comprise suitable fillers, binding agents, disintegrating agents, lubricants, and the like. When administered parenterally, the pharmaceutical composition may be prepared into an injection, including injectio, sterile powder for injection and concentrated solution for injection. When prepared into an injection, the pharmaceutical composition may be produced by conventional methods in pharmaceutical field. When preparing an injection, additives may not be added, or suitable additives may be added to the pharmaceutical composition depending on the properties of drug. When administered rectally, the pharmaceutical composition may be prepared into a suppository, etc. When administered intrapulmonarily, the pharmaceutical composition may be prepared into inhalant, or spraying agent, etc.

In some preferred embodiments, the compound, or a pharmaceutically acceptable salt, ester, or solvate thereof, or their stereoisomers according to the invention is present in a therapeutically and/or prophylactically effective amount in a pharmaceutical composition or a medicament. In some preferred embodiments, the compound, or a pharmaceutically acceptable salt, ester, or solvate thereof, or their stereoisomers according to the invention is present in a form of unit dose in a pharmaceutical composition or a medicament.

The compound of Formula (I), or a pharmaceutically acceptable salt, ester, or solvate thereof, or their stereoisomers according to the invention can be administered alone, or is used in combination with one or more second therapeutic agents. Therefore, in some preferred embodiments, the pharmaceutical composition further comprises one or more second therapeutic agents. In some preferred embodiments, the second therapeutic agent is selected from: DNA replication inhibitors (e.g., topoisomerase inhibitors and alkylating agents), mitotic inhibitors, angiogenesis inhibitors, growth factor inhibitors, antibodies, antimetabolites, antitumor hormone drugs, platinum drugs, immunosuppressors, and additional tyrosine kinase inhibitors. In some preferred embodiments, the second therapeutic agent is selected from: methotrexate, capecitabine, gemcitabine, doxifluridine, pemetrexed disodium, pazopanib, imatinib, erlotinib, lapatinib, gefitinib, vandetanib, herceptin, bevacizumab, rituximab, trastuzumab, paclitaxel, vinorelbine, docetaxel, doxorubicin, hydroxycamptothecine, mitomycin, epirubicin, pirarubicin, letrozole, tamoxifen, fulvestrant, triptorelin, flutamide, leuprorelin, anastrozole, ifosfamide, busulfan, cyclophosphamide, carmustine, nimustine, semustine, mechlorethamine, melphalan, chlorambucil, carboplatin, cisplatin, oxaliplatin, lobaplatin, camptothecin, topotecan, everolimus, sirolimus, temsirolimus, 6-mercaptopurine, 6-thioguanine, azathioprine, actinomycin D, daunorubicin, adriamycin, mitoxantrone, bleomycin, mithramycin or aminoglutethimide.

Components to be combined (e.g., the compound, or a pharmaceutically acceptable salt, ester, or solvate thereof, or their stereoisomers according to the invention, and a second therapeutic agent) can be administered simultaneously or sequentially. For example, the second therapeutic agent is administered before, at the same time or after administration of the compound, or a pharmaceutically acceptable salt, ester, or solvate thereof, or their stereoisomers according to the invention. In addition, the components to be combined may be administered in the same dosage form, or administered in combination in separate and different dosage forms.

The compound of Formula (I), or a pharmaceutically acceptable salt, ester, or solvate thereof, or their stereoisomers according to the invention can be used to treat a disease associated with overactivity of EGFR. Therefore, the present application also relates to use of the compound of Formula (I), or a pharmaceutically acceptable salt, ester, or solvate thereof, or their stereoisomers according to the invention for the manufacture of a medicament for the treatment and/or prevention of a disease associated with overactivity of EGFR in a subject. In addition, the present application further relates to a method for treating and/or preventing a disease associated with overactivity of EGFR in a subject, comprising administering to the subject in need thereof a therapeutically and/or prophylactically effective amount of the compound of Formula (I), or a pharmaceutically acceptable salt, ester, or solvate thereof, or their stereoisomers according to the invention, or the pharmaceutical composition according to the invention. In addition, the present application further relates to the compound of Formula (I), or a pharmaceutically acceptable salt, ester, or solvate thereof, or their stereoisomers according to the invention, for use in treating and/or preventing a disease associated with overactivity of EGFR in a subject.

In some preferred embodiments, the disease is hyperproliferative disease, e.g., cancer and noncancerous disease. In some preferred embodiments, the cancer is selected from: esophageal cancer (e.g., esophageal adenocarcinoma and esophageal squamous cancer), brain tumor, lung cancer (e.g., small cell lung cancer and non-small cell lung cancer), squamous cell cancer, bladder cancer, gastric cancer, ovarian cancer, peritoneal cancer, pancreatic cancer, breast cancer, head and neck cancer, cervical cancer, endometrial cancer, colorectal cancer, liver cancer, renal cancer, solid tumor, non-Hodgkin's lymphoma, central nervous system tumor (e.g., neuroglioma, glioblastoma multiforme, glioma or sarcoma), prostatic cancer and thyroid cancer. In some preferred embodiments, the noncancerous disease is benign hyperplasia of skin or prostate. In some preferred embodiments, the disease is chronic obstructive pulmonary disease.

In some preferred embodiments, overactivity of EGFR is resulted from overexpression of EGFR. In some preferred embodiments, overactivity of EGFR is resulted from mutation of EGFR.

In some preferred embodiments, the disease (e.g., cancerous disease) has drug resistance caused by EGFR mutant. Previous studies have shown that mutations of EGFR may result in resistance of cells to EGFR TKI. The mutations include, but are not limited to T790M mutation, L858R mutation, and d746-750 mutation. Therefore, in some preferred embodiments, the EGFR mutant comprises one or more of the following mutations: T790M mutation, L858R mutation, and d746-750 mutation. In some preferred embodiments, the EGFR mutant comprises T790M mutation. In some preferred embodiments, the EGFR mutant comprises T790M mutation and L858R mutation. In some preferred embodiments, the EGFR mutant comprises T790M mutation and d746-750 mutation. In some preferred embodiments, the EGFR mutant comprises T790M mutation, L858R mutation, and d746-750 mutation.

In some preferred embodiments, the subject is mammal, such as bovine, equine, caprid, suidae, canine, feline, rodent, and primate; wherein the particularly preferred subject is human.

In some preferred embodiments, the medicament further comprises one or more second therapeutic agents. In some preferred embodiments, the method further comprises administering to the subject one or more second therapeutic agents. In some preferred embodiments, the compound, or a pharmaceutically acceptable salt, ester, or solvate thereof, or their stereoisomers is used in combination with one or more second therapeutic agents.

In some preferred embodiments, the second therapeutic agent is selected from: DNA replication inhibitors (e.g., topoisomerase inhibitors and alkylating agents), mitotic inhibitors, angiogenesis inhibitors, growth factor inhibitors, antibodies, antimetabolites, antitumor hormone drugs, platinum drugs, immunosuppressors, and additional tyrosine kinase inhibitors. In some preferred embodiments, the second therapeutic agent is selected from: methotrexate, capecitabine, gemcitabine, doxifluridine, pemetrexed disodium, pazopanib, imatinib, erlotinib, lapatinib, gefitinib, vandetanib, herceptin, bevacizumab, rituximab, trastuzumab, paclitaxel, vinorelbine, docetaxel, doxorubicin, hydroxycamptothecine, mitomycin, epirubicin, pirarubicin, letrozole, tamoxifen, fulvestrant, triptorelin, flutamide, leuprorelin, anastrozole, ifosfamide, busulfan, cyclophosphamide, carmustine, nimustine, semustine, mechlorethamine, melphalan, chlorambucil, carboplatin, cisplatin, oxaliplatin, lobaplatin, camptothecin, topotecan, everolimus, sirolimus, temsirolimus, 6-mercaptopurine, 6-thioguanine, azathioprine, actinomycin D, daunorubicin, adriamycin, mitoxantrone, bleomycin, mithramycin or aminoglutethimide.

In some preferred embodiments, the second therapeutic agent is administered before, at the same time or after administration of the compound, or a pharmaceutically acceptable salt, ester, or solvate thereof, or their stereoisomers, or the pharmaceutical composition.

The compound of Formula (I), or a pharmaceutically acceptable salt, ester, or solvate thereof, or their stereoisomers according to the invention can be used as tyrosine kinase inhibitor, or can be used to reduce or inhibit activity of EGFR or mutant thereof in a cell. Therefore, the present application also relates to use of the compound of Formula (I), or a pharmaceutically acceptable salt, ester, or solvate thereof, or their stereoisomers according to the invention for the manufacture of a formulation, which can be used as tyrosine kinase inhibitor, or can be used to reduce or inhibit activity of EGFR or mutant thereof in a cell. In addition, the present application further relates to a method for reducing or inhibiting activity of EGFR or mutant thereof in a cell, comprising administering to the cell an effective amount of the compound of Formula (I), or a pharmaceutically acceptable salt, ester, or solvate thereof, or their stereoisomers according to the invention. In addition, the present application further relates to the compound of Formula (I), or a pharmaceutically acceptable salt, ester, or solvate thereof, or their stereoisomers according to the invention, for use in reducing or inhibiting activity of EGFR or mutant thereof in a cell.

In some preferred embodiments, the formulation, or the compound, or a pharmaceutically acceptable salt, ester, or solvate thereof, or their stereoisomers is administered in vivo or in vitro. In some preferred embodiments, the formulation, or the compound, or a pharmaceutically acceptable salt, ester, or solvate thereof, or their stereoisomers is administered to a subject (e.g., mammal, such as bovine, equine, caprid, suidae, canine, feline, rodent, and primate; e.g., human), to reduce or inhibit activity of EGFR or mutant thereof in the cell of the subject. In some preferred embodiments, the formulation, or the compound, or a pharmaceutically acceptable salt, ester, or solvate thereof, or their stereoisomers is administered to an in vitro cell (e.g., a cell line or a cell from a subject such as a cancer cell), to reduce or inhibit activity of EGFR or mutant thereof in the in vitro cell.

In some preferred embodiments, the method is carried out in vivo or in vitro. In some preferred embodiments, the method is carry out in vivo, for example, is applied to a subject (e.g., mammal, such as bovine, equine, caprid, suidae, canine, feline, rodent, and primate; e.g., human), to reduce or inhibit activity of EGFR or mutant thereof in the cell of the subject. In some preferred embodiments, the method is carried out in vitro, for example is applied to an in vitro cell (e.g., a cell line or a cell from a subject such as a cancer cell), to reduce or inhibit activity of EGFR or mutant thereof in the in vitro cell.

In some preferred embodiments, the EGFR mutant comprises one or more of the following mutations: T790M mutation, L858R mutation, and d746-750 mutation. In some preferred embodiments, the EGFR mutant comprises T790M mutation. In some preferred embodiments, the EGFR mutant comprises T790M mutation and L858R mutation. In some preferred embodiments, the EGFR mutant comprises T790M mutation and d746-750 mutation. In some preferred embodiments, the EGFR mutant comprises T790M mutation, L858R mutation, and d746-750 mutation.

In some preferred embodiments, the cell is selected from esophageal cancer cell (e.g., esophageal adenocarcinoma cell and esophageal squamous cancer cell), brain tumor cell, lung cancer cell (e.g., small cell lung cancer cell and non-small cell lung cancer cell), squamous cell cancer cell, bladder cancer cell, gastric cancer cell, ovarian cancer cell, peritoneal cancer cell, pancreatic cancer cell, breast cancer cell, head and neck cancer cell, cervical cancer cell, endometrial cancer cell, colorectal cancer cell, liver cancer cell, renal cancer cell, solid tumor cell, non-Hodgkin's lymphoma cell, central nervous system tumor cell (e.g., neuroglioma cell, glioblastoma multiforme cell, glioma cell or sarcoma cell), prostatic cancer cell and thyroid cancer cell.

In some preferred embodiments, the cell is the primary cell from the subject or culture thereof, or an established cell line. In some preferred embodiments, the subject is mammal, such as bovine, equine, caprid, suidae, canine, feline, rodent, and primate; wherein the particularly preferred subject is human.

The present application also relates to a kit comprising the compound of Formula (I), or a pharmaceutically acceptable salt, ester, or solvate thereof, or their stereoisomers according to the invention, and optionally, instructions.

In some preferred embodiments, the kit is used to reduce or inhibit activity of EGFR or mutant thereof in a cell. In some preferred embodiments, the EGFR mutant comprises one or more of the following mutations: T790M mutation, L858R mutation, and d746-750 mutation. In some preferred embodiments, the EGFR mutant comprises T790M mutation. In some preferred embodiments, the EGFR mutant comprises T790M mutation and L858R mutation. In some preferred embodiments, the EGFR mutant comprises T790M mutation and d746-750 mutation. In some preferred embodiments, the EGFR mutant comprises T790M mutation, L858R mutation, and d746-750 mutation.

In some preferred embodiments, the cell is selected from esophageal cancer cell (e.g., esophageal adenocarcinoma cell and esophageal squamous cancer cell), brain tumor cell, lung cancer cell (e.g., small cell lung cancer cell and non-small cell lung cancer cell), squamous cell cancer cell, bladder cancer cell, gastric cancer cell, ovarian cancer cell, peritoneal cancer cell, pancreatic cancer cell, breast cancer cell, head and neck cancer cell, cervical cancer cell, endometrial cancer cell, colorectal cancer cell, liver cancer cell, renal cancer cell, solid tumor cell, non-Hodgkin's lymphoma cell, central nervous system tumor cell (e.g., neuroglioma cell, glioblastoma multiforme cell, glioma cell or sarcoma cell), prostatic cancer cell and thyroid cancer cell. In some preferred embodiments, the cell is the primary cell from the subject or culture thereof, or an established cell line. In some preferred embodiments, the subject is mammal, such as bovine, equine, caprid, suidae, canine, feline, rodent, and primate; wherein the particularly preferred subject is human.

Beneficial Effects of the Invention

Relative to the prior art, the techincal solutions of the invention have the following advantages.

(1) The compound of Formula (I), or a pharmaceutically acceptable salt, ester, or solvate thereof, or their stereoisomers according to the invention has excellent activity of inhibiting EGFR kinase, exhibits excellent antitumor effect, and has good therapeutic effect on hyperproliferative disease and chronic obstructive pulmonary disease.

(2) The compound of Formula (I), or a pharmaceutically acceptable salt, ester, or solvate thereof, or their stereoisomers according to the invention has higher activity (i.e., lower IC50) in inhibition of EGFR mutant, in comparison with inhibition of the wild-type EGFR. That is, the compound according to the invention has higher activity and specificity to EGFR mutant (particularly EGFR comprising T790M mutation). Therefore, the compound according to the invention can be used in a lower dose and significantly reduce the side effects caused by inhibition of wild-type EGFR, such as erythra and diarrhoea.

(3) The compound of Formula (I), or a pharmaceutically acceptable salt, ester, or solvate thereof, or their stereoisomers according to the invention can inhibit the tyrosine kinase activity of EGFR mutant. Therefore, the compound according to the invention can be used to treat drug-resistant diseases (e.g., cancerous diseases, such as lung cancer), particularly diseases (e.g., cancerous disease, such as lung cancer) having drug resistance caused by EGFR mutation (e.g., T790M mutation of EGFR).

(4) The compound of Formula (I), or a pharmaceutically acceptable salt, ester, or solvate thereof, or their stereoisomers according to the invention can be prepared by simple process, is stable in quality, has good physical and chemical properites, and can be easily produced in large scale industrially.

Specific Modes for Carrying Out the Invention

The invention is further described, but is not restricted by the following embodiments. A person skilled in the art, based on the teachings of the invention, can make various modification or improvement without departing from the basic spirit and scope of the invention.

EXPERIMENTS

The exemplified experiments are provided for a part of the compounds according to the invention, to show the advantageous activity and beneficial technical effects of the compounds according to the invention. However, it should be understood that the following experiments are provided merely for the purpose of illustration, rather than restricting the scope of the invention. A person skilled in the art, based on the teachings of the description, can make appropriate modification or improvement to the technical solutions of the invention without departing from the spirit and scope of the invention.

Experiment Example 1: Assay on In Vitro Enzyme-Inhibiting Activity of the Compounds According to the Invention Test compounds: a part of compounds of the invention, the chemical names and preparation methods of which can be found in their preparation examples.

Control agent: CO-1686, the structure of which can be found in the Background Art, prepared by the inventors (please refer to Patent WO2012061299A1 for the preparation methods).

The meanings represented by the abbreviations in the experiments are described as follows.
EDTA: eathylene diamine tetraacetic acid
DMSO: dimethyl sulfoxide
SD: standard deviation
FAM: carboxyfluorescein
Brij-35: polyethylene glycol dodecyl ether
HEPES: N-2-hydroxyethylpiperazine-N'-2-ethanesulfonic acid
DTT: dithiothreitol Experimental method: the compounds were screened in the presence of Km ATP by Mobility Shift Assay using the kinases EGFR and EGFR_T790M.

1. Preparation of Reagents (1) 1-fold kinase buffer for detecting the kinases wild-type EGFR (WT EGFR or WT for short), EGFR (d746-750) (d746-750 for short), EGFR (d746-750)-T790M ((d746-750)-T790M for short): 50 mM HEPES (pH 7.5), 0.0015% Brij-35, 10 mM MgCl2, 10 mM MnCl2, and 2 mM DTT;

(2) 1-fold kinase buffer for detecting the kinases EGFR T790M (T790M for short), EGFR L858R (L858R for short), EGFR T790M-L858R (T790M-L858R for short): 50 mM HEPES (pH 7.5), 0.0015% Brij-35, 5 mM MgCl2, and 2 mM DTT.

(3) Stop Solution
100 mM HEPES (pH 7.5), 0.015% Brij-35, 0.2% Coating Reagent #3, and 50 mM EDTA 2. Preparation of a Compound Solution (1) To the second well of a 96-well plate, 5 μL 10 mM compound (dissolved in DMSO) was added, and 95 μL 100% DMSO was added to prepare 100 μL 0.5 mM compound.

(2) To other wells, 60 μL 100% DMSO was added. 20 μL compound from the second well was added to the third well, and 4-fold dilution was further performed to get 10 diluted concentrations.

(3) To the first well and the twelfth well of the 96-well plate, 100 μL 100% DMSO was separately added, and the two wells were used as control wells.

(4) 10 μL from each well of the 96-well plate was added to another 96-well plate, and 90 μL 1-fold kinase buffer was added.

(5) 5 μL from the 96-well plate was added to another 384-well plate, for example, transferred from A1 well of the 96-well plate to A1 and A2 wells of the 384-well plate, and transferred from A2 well of the 96-well plate to A3 and A4 wells of the 384-well plate, and so on.

3. Kinase reaction (1) Preparation of 2.5-fold enzyme solution

Kinase was added to 1-fold kinase buffer to form 2.5-fold enzyme solution.

(2) Preparation of 2.5-fold substrate solution

FAM-tagged polypeptide and ATP were added to 1-fold kinase buffer to form 2.5-fold substrate solution.

(3) Addition of 2.5-fold enzyme solution to 384-well plate

To 384-well plate, 10 μL 2.5-fold enzyme solution was added, and incubated at room temperature for 10 min.

(4) Addition of 2.5-fold substrate solution to 384-well plate

To 384-well plate, 10 μL 2.5-fold substrate solution was added.

(5) Kinase reaction and stop

After incubation at 28° C. for a period of time (depending on kinase), 25 μL stop solution was added.

4. Data on percent conversion was read by Caliper.

5. Data analysis (1) Data on enzyme activity was obtained by Caliper program;

(2) Inhibition rate of enzyme activity was calculated from the data on enzyme activity by the following formula:

Inhibition rate(%)=(maximal value−the measured value of a test compound)/(maximal value−minimal value)×100, wherein, the maximal value represents the measured value of DMSO control; and the minimal value represents the measured value of blank control.

(3) Calculation of IC50 value by XLFit excel.

Experimental Results and Conclusion:

1. Results on the measurement of IC50 value of the compounds according to the invention for wild-type EGFR and EGFR T790M

TABLE 1

IC50 value and selectivity of the compounds according to the invention for wild-type EGFR and EGFR T790M

| Compound | $IC_{50}$ WT EGFR (nM) | $IC_{50}$ EGFR T790M (nM) | Selectivity (WT/T790M) |
|---|---|---|---|
| CO-1686 | 145 | 2.1 | 69.0 |
| Compound 1 | 323 | 5.7 | 56.7 |
| Compound 2 | 552 | 6.2 | 89.0 |
| Compound 3 | 699 | 4.7 | 148.7 |

TABLE 2

IC$_{50}$ value and selectivity of the compounds according to the invention for wild-type EGFR and EGFR T790M

| Compound | $IC_{50}$ WT EGFR (nM) | $IC_{50}$ EGFR T790M (nM) | Selectivity (WT/T790M) |
|---|---|---|---|
| CO-1686 | 163 | 2.8 | 58.2 |
| Compound 11 | 640 | 13 | 49.2 |

TABLE 3

IC$_{50}$ value and selectivity of the compounds according to the invention for wild-type EGFR and EGFR T790M

| Compound | $IC_{50}$ WT EGFR (nM) | $IC_{50}$ EGFR T790M (nM) | Selectivity (WT/T790M) |
|---|---|---|---|
| CO-1686 | 180 | 1.3 | 138.5 |
| Compound 4 | 423 | 7.2 | 58.8 |
| Compound 5 | 995 | 8.9 | 111.8 |

TABLE 4

IC$_{50}$ value and selectivity of the compounds according to the invention for wild-type EGFR and EGFR T790M

| Compound | $IC_{50}$ WT EGFR | $IC_{50}$ EGFR T790M | Selectivity (WT/T790M) |
|---|---|---|---|
| CO-1686 | 153 | 2.5 | 61.2 |
| Compound 7 | 332 | 6.2 | 53.5 |
| Compound 17 | 1369 | 16 | 85.6 |
| Compound 23 | 294 | 3.9 | 75.4 |
| Compound 25 | 683 | 7.1 | 96.2 |
| Compound 26 | 25 | 0.51 | 49.0 |
| Compound 27 | 871 | 9.6 | 90.7 |
| Compound 28 | 73 | 1.2 | 60.8 |
| Compound 29 | 11 | 0.32 | 34.4 |
| Compound 37 | 1284 | 9.9 | 129.7 |
| Compound 41 | 82 | 1.4 | 58.6 |
| Compound 43 | 159 | 3.6 | 44.2 |

2. Results on the measurement of IC$_{50}$ value of the compounds according to the invention for EGFR double-mutation kinase

TABLE 5

IC$_{50}$ value (nM) and selectivity of the compounds according to the invention for EGFR double-mutation kinase

| | | | | | Selectivity | | |
|---|---|---|---|---|---|---|---|
| Compound | WT EGFR | EGFR L858R | EGFR T790M-L858R | EGFR (d746-750) | WT/L858R | WT/T790M-L858R | WT/d746-750 |
| CO-1686 | 137.0 | 39.1 | 2.3 | 11.2 | 3.5 | 60.1 | 12.3 |
| Compound 1 | 240.0 | 84.7 | 4.4 | 20.3 | 2.8 | 54.3 | 11.8 |
| Compound 2 | 344.0 | 91.8 | 2.5 | 24.2 | 3.7 | 140.2 | 14.2 |
| Compound 3 | 733.0 | 153.7 | 6.0 | 51.4 | 4.8 | 122.9 | 14.2 |

TABLE 6

IC$_{50}$ value (nM) and selectivity of the compounds according to the invention for EGFR double-mutation kinase

| Compound | WT EGFR | EGFR L858R | EGFR T790M | EGFR T790M-L858R | EGFR (d746-750)- | EGFR (d746-750)-T790M | Selectivity WT/ L858R | WT/ T790M | WT/ T790M-L858R | WT/ d746-750 | WT/ (d746-750)-T790M |
|---|---|---|---|---|---|---|---|---|---|---|---|
| CO-1686 | 200 | 29 | 3 | 2.6 | 27 | 2.7 | 6.9 | 66.7 | 76.9 | 7.4 | 74.1 |
| Compound 21 | 236 | 35 | 3.5 | 3.3 | 28 | 3.5 | 6.7 | 67.4 | 71.5 | 8.4 | 67.4 |

TABLE 7

IC$_{50}$ value (nM) and selectivity of the compounds according to the invention for EGFR double-mutation kinase

| Compound | WT EGFR | EGFR L858R | EGFR T790M | EGFR T790M-L858R | EGFR (d746-750)- | Selectivity WT/ L858R | WT/ T790M | WT/ T790M-L858R | WT/ d746-750 |
|---|---|---|---|---|---|---|---|---|---|
| CO-1686 | 171.98 | 28.40 | 2.93 | 4.28 | 22.94 | 6.1 | 58.8 | 40.2 | 7.5 |
| Compound 4 | 423 | 82 | 7.2 | 5.2 | 40 | 5.2 | 58.8 | 81.3 | 10.6 |
| Compound 5 | 995 | 125 | 8.9 | 8.3 | 71.6 | 8.0 | 111.8 | 119.9 | 13.9 |
| Compound 9-1 | 559.78 | 119.45 | 9.00 | 12.57 | 92.70 | 4.7 | 62.2 | 44.5 | 6.0 |
| Compound 22 | 181.25 | 28.18 | 2.70 | 4.06 | 28.31 | 6.4 | 67.2 | 44.6 | 6.4 |
| Compound 24 | 666.15 | 108.88 | 9.10 | 10.19 | 91.72 | 6.1 | 73.2 | 65.4 | 7.3 |
| Compound 31 | 210.26 | 39.27 | 3.55 | 4.73 | 28.57 | 5.4 | 59.2 | 44.4 | 7.4 |

TABLE 8

IC$_{50}$ value (nM) of the compounds according to the invention for EGFR double-mutation kinase

| Compound | EGFR L858R | EGFRT790M-L858R | EGFR (d746-750) | EGFR (d746-750)-790M |
|---|---|---|---|---|
| Compound 27 | 88 | 9.8 | 36 | 3.6 |
| Compound 28 | 11 | 1.5 | 5.5 | 0.8 |

Experimental Conclusion:

If the IC$_{50}$ value of a compound is higher for wild-type EGFR and lower for EGFR mutant (e.g., T790M), the better the selectivity of the compound is for EGFR mutant (e.g., T790M). According to the experimental data above, the compounds according to the invention have better or comparable activity and selectivity for wild-type EGFR, EGFR L858R, and EGFR T790M, compared with the control agent; the compounds according to the invention have better or comparable activity and selectivity for EGFR mutant (EGFR T790M-L858R, EGFR (d746-750), EGFR (d746-750)-T790M), compared with the control agent.

Experiment Example 2: Assay on In Vitro Cytologic Activity of the Compounds According to the Invention Test compounds: a part of compounds of the invention, the chemical names and preparation methods of which can be found in their preparation examples.

Control agent: CO-1686, the structure of which can be found in the Background Art, prepared by the inventors (please refer to Patent WO02012061299A1 for the preparation methods).

Cells used: H1975 cell (which is a cell comprising EGFR-T790M/L858R double mutation), and A431 cell (which is a cell comprising wild-type EGFR gene).

The meanings represented by the abbreviations in the following experiments are described as follows.

PBS: phosphate-buffered saline
DMSO: dimethyl sulfoxide
FBS: fetal bovine serum

1. Cell Culture 1.1 Preparation of Cell Suspension

Culture medium was removed from culture bottle;
PBS was added to wash the cells;
pancreatin was added for digestion, and the cells were collected by centrifugation;
the cells were resuspended in a culture medium containing 10% fetal bovine serum, counted and adjusted to a concentration of $2\times10^4$/mL or $3\times10^4$/mL (cell viability must be greater than 90%);
the cell suspension was added to a 96-well plate, at 100 µL for each well, i.e., 2000/well for H1975 cell; 3000/well for A431 cell; and
the cells were cultured at 37° C. in 5% CO$_2$ incubator overnight.

2. Preparation of a compound solution

Dilution of a compound in DMSO (or water for injection)
① The compound was 5-fold diluted with DMSO from 10 mM to 2 mM, and then 4-fold diluted from 2 mM, to get 10 concentrations;

High control (HC, control without compound inhibition): 0.5% DMSO;

Low control (LC, control with compound inhibition): 1000 nM.

3. Treatment of cells with a compound (adding the compound 24 h after plating cells)

i. To each well, 99 µL growth medium containing 10% FBS was added, and then 1 µL diluted compound was added, the total volume of the well was 200 µL, and the final concentration of the compound was measured.

Concentration of the test compound: 10000, 2500, 625, 156.25, 39.06, 9.76, 2.44, 0.61, 0.15, 0.04 [nM]

ii. The cell plate was placed in an incubator for 72 h, and the measurement was carried out by Celltiter-Glo method.

The test plate was left at room temperature, and equilibrated for 30 min. 80 µL culture medium was discarded. 60 µL CTG reagent (Celltiter-Glo kit) was added, and shaked for 2 min in a fast shaker, and was placed at room temperature for 10 min. The values were read by Envision instrument.

4. Data analysis $IC_{50}$ was calculated by GraphPad Prism 5 software.

% inhibition(inhibition rate)=100×(HC-value of test compound)/(HC-LC)

Experimental Results

TABLE 9

$IC_{50}$ value of the compounds according to the invention for H1975 and A431 cells

| Compound | H1975 (nM) | A431 (nM) | Selectivity (A431/H1975) |
| --- | --- | --- | --- |
| CO-1686 | 106.7 | 910.7 | 8.5 |
| Compound 1 | 54.16 | 448.3 | 8.3 |
| Compound 2 | 104.3 | 1849 | 17.7 |
| Compound 11 | 178.7 | 1774 | 9.9 |

TABLE 10

$IC_{50}$ value of the compounds according to the invention for H1975 and A431 cells

| Compound | H1975 | A431 | Selectivity (A431/H1975) |
| --- | --- | --- | --- |
| CO-1686 | 465.3 | 2249 | 4.8 |
| Compound 21 | 210.7 | 2502 | 11.9 |
| Compound 25 | 308.1 | 3890 | 12.6 |
| Compound 26 | 35.85 | 352.3 | 9.8 |
| Compound 27 | 277.9 | 2786 | 10.0 |
| Compound 28 | 75.18 | 703.1 | 9.4 |
| Compound 29 | 22.46 | 271.6 | 12.1 |
| Compound 31 | 277.5 | 2717 | 9.8 |
| Compound 35 | 266.2 | 3598 | 13.5 |
| Compound 36 | 326.4 | 7004 | 21.5 |
| Compound 41 | 28.54 | 246.6 | 8.6 |
| Compound 43 | 429.8 | 2643 | 6.1 |

Experimental Conclusion:

the compounds according to the invention are characterized by selectively inhibiting cells having EGFR mutant (H1975), and having a weak effect on cells having wild-type EGFR (A431). As seen from the results above, as for H1975 cells having EGFR mutant and A431 cells having wild-type EGFR, the compounds according to the invention have a better or at least comparable selectivity for H1975, compared with control agents.

Experiment Example 3: Assay on Pharmacokinetics of the Compounds According to the Invention in Rat Test compounds: a part of compounds of the invention, the chemical names and preparation methods of which can be found in their preparation examples.

Test animal: male SD rat, 3 rats, weight: 200-250 g/rat

Preparation of Test Compound Solutions

Blank solvent for intragastric administration (po) of Compound 2, 27: 0.1% Tween 80+2% HPC (hydroxypropyl cellulose), Preparation: HPC (hydroxypropyl cellulose) (20 g) was weighed, and slowly added to purified water (1000 mL) under stirring, and Tween 80 (1 mL) was added. The mixture was stirred until it became clear, to get a blank solvent of 0.1% Tween 80+2% HPC. Compound 2 (3.21 mg) and Compound 27 (3.03 mg) were weighed, respectively, solvent was added, and the resultant mixture was placed in a tissue grinder, and ground at a speed of 1000 r/min. After homogeneous dispersion, a solution for intragastric administration at a theoretical concentration of 0.5 mg/mL was obtained. The control agent CO-1686 (6.14 mg) was weighed, solvent was added, and the resultant mixture was placed in a tissue grinder, and ground at a speed of 1000 r/min. After homogeneous dispersion, a solution for intragastric administration at a theoretical concentration of 1.0 mg/mL was obtained. The measured concentrations are shown in the following table.

A blank solvent for intravenous injection (iv) for Compound 2, 27, 31: 5% DMSO+10% PEG400+85% (28% HP-β-CD)

Compound 2 (2.98 mg), Compound 27 (2.98 mg), and Compound 31 (3.27 mg) were weighed, respectively, and blank solvent for intravenous injection was added. The resultant mixture was mixed homogeneously under vortexing, placed in a 50° C. constant temperature water bath for 20 min, and filtrated through a 0.22 µm filter membrane to get a clear and transparent solution for intravenous injection at a theoretical concentration of 0.5 mg/mL. The measured concentrations are shown in the following table.

Preparation of 28% HP-β-CD solution: HP-β-CD (hydroxypropyl-β-cyclodextrin) (2.8 g) was weighed, dissolved with a small amount of purified water ultrasonically, and purified water was added to a final volume of 10 mL, to get a 28% HP-β-CD solution.

Formulation of Compound 31 for intravenous injection (iv): 20% DMF+20% PEG400+60% sterile water for injection Compound 31 (3.10 mg) was weighed, and dissolved in 1.262 mL DMF (N,N-dimethylformamide) ultrasonically. 1.262 mL PEG400 was added, and the resultant mixture was mixed homogeneously under vortexing. 3.786 mL sterile water for injection was added. The mixture was vertexed homogeneously to get a clear and transparent solution for intravenous injection at a theoretical concentration of 0.5 mg/ml. The measured concentration is shown in the following table.

Experimental Method

Administration:

The test liquids are administered by the methods listed in the following table:

| Test compound | Number of Animals | Administration route | Administration dose (mg/kg) | Administration concentration (mg/mL) | Administration volume (mL/kg) |
|---|---|---|---|---|---|
| Compound 2, 27 | 3 | iv | 1 | 0.5 | 2 |
| | 3 | po | 2 | 0.5 | 4 |
| Compound 31 | 3 | iv | 0.74 | 0.37 | 2 |

Blood collection:

Collecting time point:

iv: 0.083 h, 0.25 h, 0.5 h, 1 h, 2 h, 4 h, 6 h, 8 h, 24 h after administration.

po: 0.167 h, 0.5 h, 1 h, 2 h, 4 h, 6 h, 8 h, 24 h after administration.

About 100 μL whole blood was collected from caudal vein at each time point, added to an anticoagulation tube containing $K_2EDTA$, and centrifuged at 8000 r/min for 6 min in a low-temperature centrifuge to separate the plasma; the plasma was stored in a refrigerator at −80° C.

Plasma Sample Analysis:

The plasma samples of Compound 2, 27, and 31 were analyzed by means of protein precipitation: to 30 μL plasma, 200 μL internal standard (acetonitrile solution containing 50 ng/mL CNX-2006, the structure of which is

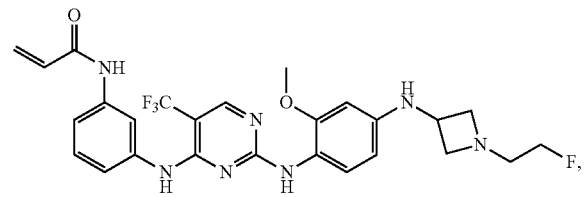 [SMILES: C=CC(=O)Nc1cccc(Nc2nc(Nc3ccc(NC4CN(CCF)C4)cc3OC)ncc2C(F)(F)F)c1]

prepared by reference to the method in Patent WO2012064706A1) was added; the resultant mixture was vortexted for 10 min at 1000 r/min, and centrifuged for 20 min at 4000 r/min; to 100 μL supernatant, 100 μL water was added; the resultant mixture was mixed homogeneously under vortexing and analyzed by LC-MS/MS.

Experimental Results

TABLE 11

PK evaluation result in SD rat (iv)

| Test compound | Dose (mg/kg) | $AUC_{last}$ (h*ng/mL) | CL (L/h/kg) | $V_{ss}$ |
|---|---|---|---|---|
| Compound 2 | 1 | 723 | 1.56 | 0.62 |
| Compound 27 | 1 | 774 | 1.36 | 1.57 |
| Compound 31 | 0.74 | 1019 | 0.73 | 0.29 |

TABLE 12

PK evaluation result in SD rat (po)

| Test compound | Dose (mg/kg) | $T_{max}$ | $C_{max}$ | $AUC_{last}$ (h*ng/mL) | F (%) |
|---|---|---|---|---|---|
| Compound 2 | 2 | 0.17 | 211 | 267 | 19 |
| Compound 27 | 2 | 0.5 | 313 | 754 | 49 |

$AUC_{last}$ represents area under concentration-time curve during administration 0→t.
CL represents clearance.
$V_{ss}$ represents apparent volume of distribution at steady state.
$T_{max}$ represents time of maximum blood concentration.
$C_{max}$ represents maximum blood concentration.
F % represents absolute bioavailability.

Experimental Conclusion:

As seen from the experimental results of Table 11 and Table 12, the compounds according to the invention have a low CL, and relatively high $AUC_{last}$ and F value, and the compounds according to the invention have good pharmacokinetic properties in SD rat.

Experiment Example 4: Assay on Pharmacokinetics of the Compounds According to the Invention in Dog Test compounds: a part of compounds of the invention, the chemical names and preparation methods of which can be found in their preparation examples.

Test animal: male Beagle dog, 3 dogs/administration route/compound, weight: 7-12 kg.

Preparation of Test Compound Solutions

Solvent for intraveneous injection (iv) of Compound 31: 20% DMF (N,N-dimethylformamide)+20% PEG400 (polyethylene glycol 400)+60% sterile water for injection Compound 31 (15.40 mg) was weighed, dissolved in solvent for intraveneous injection ultrasonically, and mixed homogeneously under vortexing, to get a clear and transparent compound solution at a theoretical concentration of 0.5 mg/mL.

Solvent for intraveneous injection (iv) of Compound 2, 28: 5% DMSO+10% PEG400+85% (28% HP-β-CD)

Compound 2 (20.72 mg) and Compound 28 (16.16 mg) were weighed, respectively, dissolved by adding solvent for intraveneous injection, mixed homogeneously under vortexing, placed in a 50° C. constant temperature water bath for 20 min, and mixed homogeneously under vortexing to get a clear and transparent compound solution at a theoretical concentration of 0.5 mg/mL. The actual concentrations are shown in the following table.

Preparation of 28% HP-β-CD: HP-β-CD (28 g) was weighed, and dissolved ultrasonically in a small amount of sterile water for injection, and sterile water for injection was added to a final volume of 100 mL, and the mixture was mixed homogeneously under vortexing to get the solution of 28% HP-β-CD.

Solvent for intragastric administration (po) of Compound 2, 28, 31: 0.1% Tween 80+2% HPC (hydroxypropyl cellulose)

Preparation: HPC (hydroxypropyl cellulose) (20 g) was weighed, and slowly added to purified water (1000 mL) under stirring. Tween 80 (1 mL) was added, and the mixture was stirred until it became clear, to get a solvent for intragastric administration. Compound 2 (41.77 mg), Compound 31 (31.35 mg) and Compound 28 (31.10 mg) were weighed, respectively, solvent for intragastric administration was added, and the resultant mixture was placed in a tissue grinder, and ground at a speed of 1000 r/min. After homogeneous dispersion, the solution for intragastric administration was obtained.

Experimental Method

Administration

The test liquids are administered by the methods listed in the following table:

| Test compound | Number of Animals | Administration route | Administration dose (mg/kg) | Administration concentration (mg/mL) | Administration volume (mL/kg) |
|---|---|---|---|---|---|
| Compound 2 | 3 | iv | 0.5 | 0.5 | 1 |
| | 3 | po | 0.54 | 0.27 | 2 |
| Compound 31 | 3 | iv | 0.5 | 0.5 | 1 |
| | 1 | po | 1 | 0.5 | 2 |
| Compound 28 | 3 | iv | 0.5 | 0.5 | 1 |
| | 3 | po | 1.28 | 0.64 | 2 |

Blood collection time point:

For IV group: 0.083, 0.25, 0.5, 1, 2, 4, 6, 8, 24 h after administration.

For PO group: 0.167, 0.5, 1, 2, 4, 6, 8, 24 h after administration.

Blood collection: 400 µL whole blood was collected from vein of dog fore limb at each time point, added to an anticoagulation tube containing K2EDTA, and centrifuged at 8000 r/min, 4° C. for 6 min in a centrifuge to separate the plasma; the separated plasma was stored in a refrigerator at −80° C.

Plasma Sample Analysis

By means of protein precipitation, to 30 µL plasma, 200 µL internal standard (acetonitrile solution containing 50 ng/mL CNX-2006) was added; the resultant mixture was vortexed for 10 min at 1500 r/min, and centrifuged at 12000 r/min for 5 min; to a suitable amount of supernatant, a suitable amount of water was added; the resultant mixture was mixed homogeneously under vortexing and analyzed by LC-MS/MS.

Experimental results

TABLE 13

PK evaluation result of the compounds according to the invention in dog (iv)

| Test compound | $AUC_{last}$ (h*ng/mL) | Cl (L/h/kg) | $V_{ss}$ (L/kg) |
|---|---|---|---|
| Compound 2 | 693 | 0.71 | 1.36 |
| Compound 31 | 1269 | 0.40 | 0.38 |
| Compound 28 | 1581 | 0.33 | 1.10 |

TABLE 14

PK evaluation result of the compounds according to the invention in dog (po)

| Test compound | $AUC_{last}$ (h*ng/mL) | $C_{max}$ (ng/mL) | $T_{max}$ (h) | F (%) |
|---|---|---|---|---|
| Compound 2 | 528 | 211 | 0.5 | 70 |
| Compound 31 | 545 | 261 | 1.0 | 23 |
| Compound 28 | 1825 | 523 | 1.0 | 46 |

$AUC_{last}$ represents area under concentration-time curve during administration 0→t.
CL represents clearance.
$V_{ss}$ represents apparent volume of distribution at steady state.
$T_{max}$ represents time of maximum blood concentration.
$C_{max}$ represents maximum blood concentration.
F % represents absolute bioavailability.

Experimental Conclusion:

As seen from the experimental results of Table 13 and Table 14, Compounds 2, 31 and 28 have a relatively high CL, AUClast, and F value, indicating that Compounds 2, 28, 31 have good pharmacokinetic properties.

Experiment Example 5: Assay on Pharmacokinetics of the Compounds According to the Invention in Nude Mouse Test compounds: a part of compounds of the invention, the chemical names and preparation methods of which can be found in their preparation examples.

Control agent: CO-1686, the structure of which can be found in the Background Art, prepared by the inventors (please refer to Patent WO2012061299A1 for the preparation methods).

Test animal: female nude mouse (BALB/c), weight: 20-25 g/mouse.

Preparation of Test Compound Solutions

Solvent for intraveneous injection (iv): 5% DMSO+10% PEG400+85% (28% HP-β-CD)

Solvent for intragastric administration (po): 2% HPC+0.1% Tween 80

Intraveneous Administration:

Control agent CO-1686: the control agent CO-1686 (4.042 mg) was weighed, and solvent for intraveneous injection was added to prepare a clear and transparent solution at a theoretical concentration of 1.0 mg/mL. 0.1283 mL and 0.1059 mL 1M hydrochloric acid solution were separately added to adjust pH to 4.

Compound 2, 27: Compound 27 (3.18 mg) and Compound 2 (3.17 mg) were weighed, respectively, and solvent for intraveneous injection was added to prepare a clear and transparent solution at a theoretical concentration of 1.0 mg/mL.

Intragastric Administration:

Control agent CO-1686, Compound 2: the control agent CO-1686 (3.59 mg), and Compound 2 (5.08 mg) were weighed, respectively, dissolved in blank solvent for intragastric administration (2% HPC+0.1% Tween 80), placed in a tissue grinder and ground at a speed of 1000 r/min. After homogeneous dispersion, a suspension at a theoretical concentration of 1.0 mg/mL was obtained.

Compound 27: solid dispersed sample of Compound 27 (22.9 mg) was weighed, followed by the addition of pH 4.0 buffer (5.84 mL), vortexed for 5 min, and ground in a tissue grinder at 400 rpm for 5 min, to get a suspension at a theoretical concentration of 1.0 mg/mL. The measured concentrations of the above solutions are shown in the following table.

Preparation of pH 4.0 buffer: Solution A: citric acid (21 g) or anhydrous citric acid (19.2 g) was dissolved in water to get a solution with a volume of 1000 mL, and the solution was stored in a refrigerator. Solution B: disodium hydrogen phosphate (71.63 g) was dissolved in water to get a solution with a volume of 1000 mL. 61.45 mL Solution A was mixed with 38.55 mL solution B homogeneously under shaking to get pH 4.0 buffer.

Experimental Method

Administration

The test liquids are administered by the methods listed in the following table:

| Test compound | Number of Animals | Administration route | Administration dose (mg/kg) | Administration concentration (mg/mL) | Administration volume (mL/kg) |
|---|---|---|---|---|---|
| CO-1686 | 6 | iv | 5 | 1 | 5 |
| Compound 27 | 6 | iv | 5 | 1 | 5 |
| Compound 2 | 6 | iv | 5 | 1 | 5 |
| CO-1686 | 6 | po | 13.2 | 1.32 | 10 |
| Compound 27 | 6 | po | 7.6 | 1 | 7.6 |
| Compound 2 | 6 | po | 10 | 1 | 10 |

Blood Collection

Collection time point: 0.083 h, 0.25 h, 0.5 h, 1 h, 2 h, 4 h, 6 h, 8 h after administration.

60 μL whole blood was collected from intraocular canthus at each time point, and was centrifuged at 8000 r/min for 6 min in a low-temperature centrifuge to separate plasma; the plasma was stored in a refrigerator at −80° C.

Plasma Sample Analysis

The plasma samples of Compound 27, and the control agent CO-1686 were analyzed by means of protein precipitation: to 10 μL plasma, 10 μL blank working fluid and 70 μL internal standard (acetonitrile solution containing 20 ng/mL CNX-2006) were added; the resultant mixture was vortexted for 3 min, and then centrifuged for 5 min at 12000 rpm; to 50 μL supernatant, 50 μL purified water was added; the resultant mixture was mixed homogeneously under vortexing and analyzed by LC-MS/MS.

The plasma sample of Compound 2 was analyzed by means of protein precipitation: 10 μL plasma was transferred to a 1.5 mL EP tube, 10 μL blank plasma was added, and the mixture was mixed homogeneously under vortexing. 200 μL internal standard (acetonitrile solution containing 25 ng/mL CNX-2006) was added; the resultant mixture was vortexed for 3 min, and then centrifuged at 12000 rpm for 5 min; 150 μL supernatant was accurately taken, to which 50 μL purified water was added. The resultant mixture was vortexed for 3 min and analyzed by LC-MS/MS.

Experimental results

TABLE 15

PK evaluation result in nude mouse (iv)

| Test compound | Dose (mg/kg) | $AUC_{last}$ (h*ng/mL) | CL (L/h/kg) | $V_{ss}$ |
|---|---|---|---|---|
| CO-1686 | 5 | 4069 | 1.23 | 0.78 |
| Compound 27 | 5 | 11593 | 0.43 | 0.53 |
| Compound 2 | 5 | 6295 | 0.79 | 0.71 |

TABLE 16

PK evaluation result in nude mouse (po)

| Test compound | Dose (mg/kg) | $T_{max}$ | $C_{max}$ | $AUC_{last}$ (h*ng/mL) | F (%) |
|---|---|---|---|---|---|
| CO-1686 | 13.2 | 0.5 | 1236 | 2375 | 22.1 |
| Compound 27 | 7.6 | 0.5 | 4720 | 9792 | 56 |
| Compound 2 | 10 | 0.25 | 3817 | 5662 | 48 |

$AUC_{last}$ represents area under concentration-time curve during administration 0→t.
CL represents clearance.
$V_{ss}$ represents apparent volume of distribution at steady state.
$T_{max}$ represents time of maximum blood concentration.
$C_{max}$ represents maximum blood concentration.
F % represents absolute bioavailability.

Experimental Conclusion:

As seen from the experimental results shown in Tables 15 and 16, compared with the control agent, the compounds according to the invention have good pharmacokinetic properties, and have significantly higher AUClast and F.

Experiment Example 6: Assay on Pharmacodynamics of the Compounds According to the Invention In Vivo Test compounds: a part of compounds of the invention, the chemical names and preparation methods of which can be found in their preparation examples.

Control agent: CO-1686, the structure of which can be found in the Background Art, prepared by the inventors (please refer to Patent WO2012061299A1 for the preparation methods).

| Abbreviation | Name | Abbreviation | Name |
|---|---|---|---|
| H1975 | human non-small cell lung cancer cell | PBS | phosphate-buffered saline |
| RPMI-1640 | 1640 culture medium | QD | once a day |
| RTV | relative tumor volume | TGI | tumor growth-inhibiting rate |
| BALB/c | inbred albino mouse | HPC | hydroxypropyl cellulose |

Experimental Method

1. Experimental Animal

Genus: Rodent, Line: BALB/c nude, age: 6-8 weeks, gender: female, body weight: 18-22 g. Provider of experimental animals: Beijing Ankaiyibo Biological Technology Co. Ltd., Production license No. SCXK(Jing) 2012-0009. Quality Certificate No. 11402400000256

2. Cell Culture:

H1975 cancer cells were cultured in RPMI-1640 culture medium containing inactivated 10% fetal bovine serum, 100 U/ml penicillin and 100 μg/ml streptomycin as well as 2 mM glutamine at 37° C. in a 5% $CO_2$ incubator. During cell culture, the initial concentration was $5\times10^5$ cells/mL, and the cells were passaged into separate bottles every 3 to 4 days when the cells reached confluence. The tumor cells in logarithmic growth phase were used in tumor inoculation in vivo.

3. Inoculation and Grouping of Tumor Cells

Experimental animals were inoculated subcutaneously at right lateral thorax with H1975 tumor cells at $5\times10^6$ cells/0.1 mL re-suspended in serum-free RPMI-1640 culture medium. When the tumor grew into a volume of about 100 $mm^3$, the animals were grouped and administered, 8 mice per group.

4. Preparation of Solvent and Test Compound Solutions 4.1 Selection and Preparation of Solvent CO-1686, Compound 2, Compound 28: 0.1% Tween 80+2% HPC Solvent control: pH 4.0 citric acid buffer, 0.1% Tween 80+2% HPC 0.1% Tween 80+2% HPC: 2 g hydroxypropyl cellulose was weighed, and dissolved in double distilled water, and 0.5 mL Tween-80 was added; the final volume of the mixture was 100 mL; the mixture was mixed homogeneously, filtrated through a 0.22 μm filtrator to remove bacteria, and stored at 4° C.

Preparation of pH 4.0 buffer: Solution A: 21 g citric acid was dissolved in water to get a solution with a volume of 1000 mL, and the solution was stored in a refrigerator. Solution B: 71.63 g disodium hydrogen phosphate was dissolved in double distilled water to get a solution with a volume of 1000 mL. 61.45 mL Solution A was mixed with 38.55 mL solution B homogeneously under shaking to get pH 4.0 buffer which was stored at 4° C.

4.2. Preparation of Test Compound Solutions:

Test compound solutions were prepared immediately before administration every day.

| Test compound | Preparation | Concentration |
|---|---|---|
| CO-1686 | Sample (33.33 mg) was added to solvent, and ground to a homogenous suspension. | 10 mg/mL |
| | 0.9 mL 10 mg/mL sample suspension was added to solvent, and ground to a homogeneous suspension. | 3 mg/mL |
| | 0.73 mL 3 mg/mL sample suspension was added to solvent, and ground to a homogeneous suspension. | 1 mg/mL |
| Compound 2 | Sample (30.24 mg) was added to solvent, and ground to a homogeneous suspension, to get 10 mg/mL test sample; 10 mg/mL test sample (0.66 mL 10 mg/mL) was added to solvent, and ground to a homogenous suspension. | 3 mg/mL |
| | Sample (2.33 mg) was added to solvent, and ground to a homogenous suspension. | 1 mg/mL |
| Compound 28 | Sample (65.27 mg) was dissolved in solvent, and mixed homogeneously under vortexing. | 10 mg/mL |

5. Result Observation and Measurement

Vernier caliper was used to measure the volume of tumor twice a week. The long diameter and short diameter of tumor were measured. The volume was calculated by the formula: volume=$0.5 \times$long diameter$\times$short diameter$^2$. According to the measurement results, relative tumor volume (RTV) and relative tumor volume increasing rate (T/C) were calculated. RTV=$V_t/V_0$, wherein $V_t$ is the average value of tumor volume on day t after grouping and administration, $V_0$ is the average value of tumor volume at the day when grouping. T/C=TRTV/CRTV$\times$100%, wherein TRTV is the RTV in the treatment group, and CRTV is the RTV in the solvent control group. Tumor growth-inhibiting rate (%, TGI) was calculated by the formula, TGI=(1−T/C)$\times$100%.

6. Statistical Analysis

One-Way ANOVA test was carried out by SPSS17.0 statistic software. Tumor volume was analysed in statistics among groups. $P<0.05$ is indicative of significant difference.

7. Experimental Results

TABLE 17

Anti-tumor effect of the compounds according to the invention on H1975 human non-small cell lung cancer xenograft tumor-bearing nude mice (PO administration)

| Group | Case number | Dose (mg/kg) | Body weight (g)[a] Before administration | Body weight (g)[a] After administration | 19 days after inoculation TV (mm$^3$)[a] | 19 days after inoculation RTV (%)[a] | T/C (%) | TGI (%) | P[b] |
|---|---|---|---|---|---|---|---|---|---|
| Solvent control | 8 | — | 20.1 ± 0.6 | 21.3 ± 0.5 | 1.111 ± 79 | 970 ± 49 | — | — | — |
| CO-1686 | 8 | 100 | 20.6 ± 0.4 | 21.5 ± 0.5 | 317 ± 44 | 280 ± 36 | 28.8 | 71.2 | <0.001 |
| CO-1686 | 8 | 30 | 20.6 ± 0.3 | 22.1 ± 0.3 | 666 ± 30 | 594 ± 36 | 61.2 | 38.8 | 0.011 |
| Compound 28 | 8 | 100 | 20.8 ± 0.4 | 21.5 ± 0.3 | 53 ± 7 | 46 ± 6 | 4.7 | 95.3 | <0.001 |

Note:
[a]mean ± standard error;
[b]compared with control group.

TABLE 18

Anti-tumor effect of the compounds according to the invention on H1975 human non-small cell lung cancer xenograft tumor-bearing nude mice (PO administration)

| Group | Case number | Dose (mg/kg) | Period of treatment | Body weight (g)[a] Before administration | Body weight (g)[a] After administration | 23 days after inoculation TV (mm$^3$)[a] | 23 days after inoculation RTV (%)[a] | T/C (%) | TGI (%) | P[b] |
|---|---|---|---|---|---|---|---|---|---|---|
| Solvent control | 8 | — | QD × 18 | 21.1 ± 0.5 | 22.8 ± 0.6 | 1.046 ± 132 | 1.123 ±150 | — | — | — |
| CO-1686 | 8 | 30 | QD × 18 | 21.8 ± 0.3 | 22.4 ± 0.3 | 485 ± 65 | 500 ± 63 | 44.6 | 55.4 | 0.050 |
| CO-1686 | 8 | 10 | QD × 18 | 20.7 ± 0.4 | 22.4 ± 0.5 | 729 ± 78 | 777 ± 88 | 69.2 | 30.8 | 0.590 |
| Compound 2 | 8 | 30 | QD × 18 | 21.6 ± 0.4 | 22.6 ± 0.5 | 489 ± 49 | 513 ± 54 | 45.7 | 54.3 | 0.049 |
| Compound 2 | 8 | 10 | QD × 18 | 21.1 ± 0.4 | 22.6 ± 0.3 | 588 ± 81 | 630 ± 105 | 56.1 | 43.9 | 0.174 |

Note:
[a]mean ± standard error;
[b]compared with control group.

Experimental Conclusion:

It can be concluded from data in Tables 17 and 18 that the compounds according to the invention have good therapeutic effect in vivo, and have a significant tumor-inhibiting effect.

Preparation Schemes

The contents of the invention are further described by the following embodiments in the Examples. However, it shall not be understood that the scope of the invention is restricted by the following examples. The technical solutions belong to the scope of the invention as long as they can be carried out based on the contents of the invention.

The meanings represented by the abbreviations in the below examples are described as follows.

Pd (dppf)Cl$_2$: [1,1'-bis(diphenylphosphino)ferrocene]dichloropalladium (II)

Pd/C: palladium-carbon

NBS: N-bromobutanimide

DMF: N,N-dimethylformamide

DCM: dichloromethane

THF: tetrahydrofuran

LC-MS: Liquid Chromatography-Mass Spectrometry

TLC: Thin layer chromatography

Pd$_2$(dba)$_3$: tris(dibenzylideneacetone)dipalladium

XPhos: 2-dicyclohexylphosphino-2',4',6'-triisopropylbiphenyl

PPA: Polyphosphoric Acid

Preparation Example 1 Preparation of N-(6-aminopyridin-2-yl)acrylamide

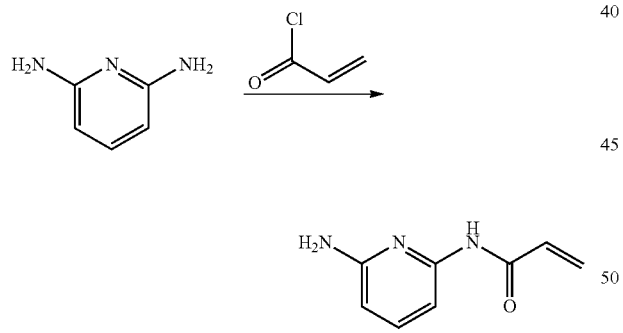

Pyridine-2,6-diamine (5.0 g, 45.8 mmol) and triethylamine (4.6 g, 45.8 mmol) were dissolved in dichloromethane (50 mL), and acryloyl chloride (2.1 g, 22.9 mmol) was added dropwisely at 0° C. The reaction was carried out at room temperature for 1 h. Water (50 mL) and dichloromethane (30 mL) were added, and the water phase and the organic phase were separated. The water phase was extracted with dichloromethane (50 mL×2), and the organic phases were combined, washed with saturated NaCl aqueous solution, dried with anhydrous sodium sulfate, filtrated, and concentrated in vacuum to get the crude product. The crude product was further separated by preparative chromatography to get the title compound as a white powder (1.6 g, yield: 43%).

Preparation Example 2 Preparation of tert-butyl 4-(3-methoxy-4-nitrophenyl)-3,6-dihydropyridin-1(2H)-carboxylate

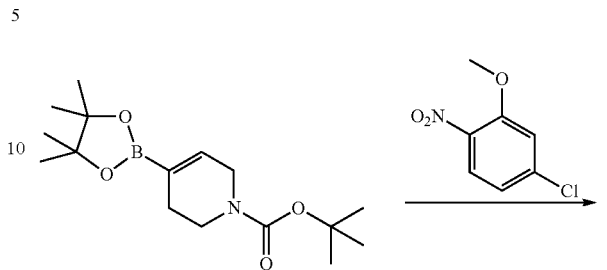

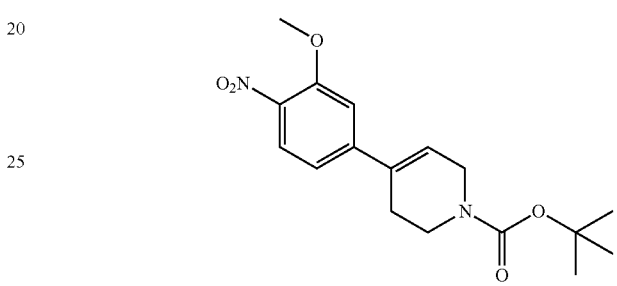

4-Chloro-2-methoxy-1-nitrobenzene (5.0 g, 26.7 mmol) and tert-butyl 4-(4,4,5,5-tetramethyl-1,3,2-dioxaborolan-2-yl)-3,6-dihydropyridin-1(2H)-carboxylate (9.9 g, 32 mmol) were dissolved in a mixed solvent of N,N-dimethylformamide (50 mL) and water (10 mL), and sodium carbonate (5.66 g, 53.4 mmol) and Pd(dppf)Cl$_2$ (978 mg, 1.3 mmol) were added. Under the protection of nitrogen gas, the reaction was carried out at 90° C. for 16 h. The resultant mixture was cooled to room temperature, and water (100 mL) and ethyl acetate (200 mL) were added, and the water phase and the organic phase were separated. The water phase was extracted with ethyl acetate (100 mL×2), and the organic phases were combined, washed with saturated saline solution, dried with anhydrous sodium sulfate, filtrated, and concentrated to get the crude product. The crude product was purified by silica gel column chromatography (petroleum ether: ethyl acetate=10:1) to get the title compound as a yellow powder (6.2 g, yield: 70%).

Preparation Example 3 Preparation of 4-(3-methoxy-4-nitrophenyl)-1,2,3,6-tetrahydropyridine

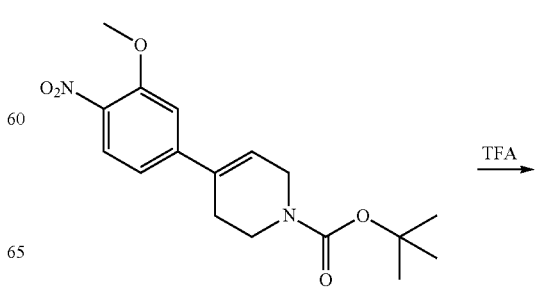

-continued

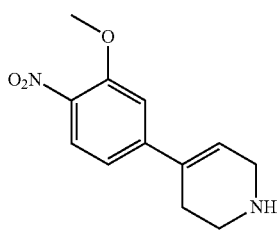

Tert-butyl 4-(3-methoxy-4-nitrophenyl)-3,6-dihydropyridin-1(2H)-formate (1 g, 2.99 mmol) was dissolved in dichloromethane (50 mL), and trifluoroacetic acid (5 mL) was added. The mixture was stirred at room temperature for 12 h. TLC detection showed that the raw materials disappeared. Water was added, and the resultant mixture was extracted with dichloromethane. The organic phases were combined, dried with anhydrous sodium sulfate, and concentrated to get the title compound (0.665 g, yield: 95%).

Preparation Example 4 Preparation of 1-(4-(3-methoxy-4-nitrophenyl)-3,6-dihydropyridin-1(2H)-yl) ethanone

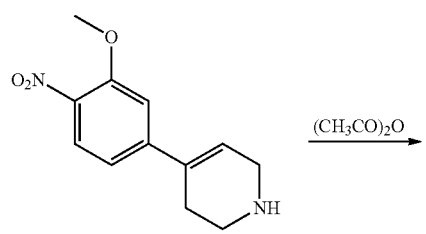

4-(3-Methoxy-4-nitrophenyl)-1,2,3,6-tetrahydropyridine (4.04 g, 17.3 mmol) was dissolved in dichloromethane (50 mL). The mixture was cooled in an ice-water bath. Triethylamine (3.5 g, 34.6 mmol) was added slowly, and acetic anhydride (1.94 g, 19.0 mmol) was then added. The mixture was stirred at 0° C. for 1 h, and stirred at room temperature for 2 h. After the reaction, the mixture was washed with water (50 mL×2). The organic phase was dried, filtrated, and concentrated to get the title compound (4.44 g, yield: 93%).

Preparation Example 5 Preparation of 1-(4-(4-amino-3-methoxyphenyl)piperidin-1-yl) ethanone

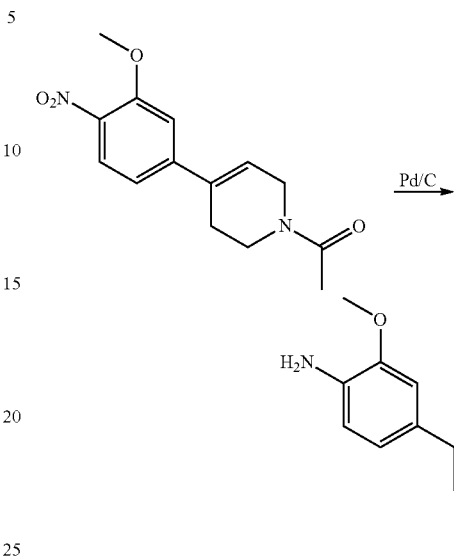

1-(4-(3-Methoxy-4-nitrophenyl)-3,6-dihydropyridin-1 (2H)-yl) ethanone (2.22 g, 8.0 mmol) was dissolved in methanol (50 mL). Under the protection of nitrogen gas, Pd/C (200 mg) was added to the system. In the atmosphere of hydrogen gas, the mixture was reacted at room temperature under stirring for 16 h. After the reaction, the mixture was filtrated. The filtrate was concentrated to get the title compound (1.7 g, yield: 87%).

Preparation Example 6 Preparation of 1-(4-(4-amino-3-methoxyphenyl)-3,6-dihydropyridin-1(2H)-yl) ethanone

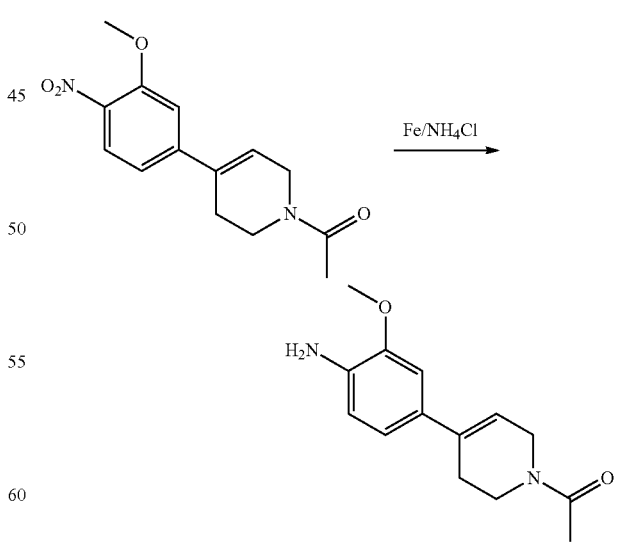

1-(4-(3-Methoxy-4-nitrophenyl)-3,6-dihydropyridin-1 (2H)-yl) ethanone (2.22 g, 8.0 mmol) was dissolved in a mixed solvent of ethanol (50 mL) and water (10 mL), and ferrous powder (2.2 g, 40 mmol) and ammonium chloride (53 mg, 1 mmol) were added. The mixture was reacted at 80° C. for 2 h. The resultant mixture was cooled to room temperature, filtrated, and concentrated. The residue was dissolved in ethyl acetate (100 mL), washed with sodium bicarbonate solution and saturated NaCl aqueous solution, dried with anhydrous sodium sulfate, filtrated, and concentrated to get the title compound as a tawny solid (1.55 g, yield: 79%).

Preparation Example 7 Preparation of tert-butyl (3-((2-chloro-5-(trifluoromethyl)pyrimidin-4-yl)amino)phenyl)amino carboxylate

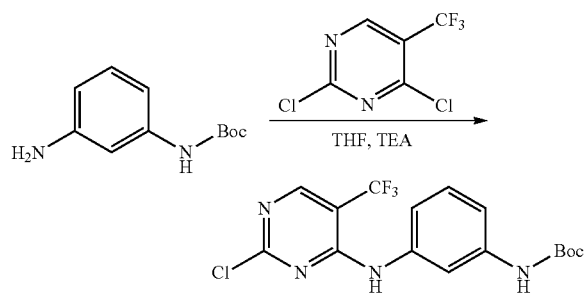

Tert-butyl (3-aminophenyl)amino carboxylate (8.32 g, 40 mmol) was dissolved in tetrahydrofuran (150 mL), and triethylamine (6.06 g, 60 mmol) was added. The mixture was cooled in an ice-water bath, and 2,4-dichloro-5-(trifluoromethyl)pyrimidine (8.68 g, 40 mmol) was added dropwisely. After the addition, the mixture was warmed to room temperature and reacted for 16 h. Water (200 mL) was added, and the mixture was extracted with ethyl acetate (250 mL×3). The organic phases were combined, washed with saturated NaCl aqueous solution, dried with anhydrous sodium sulfate, and concentrated. The crude product was subjected to silica gel column chromatography (ethyl acetate: petroleum ether=0-1:5), and then recrystallized by isopropanol and methanol (3:1) to get the title compound as a white solid (2.1 g, yield: 13.5%).

Preparation Example 8 Preparation of $N^1$-(2-chloro-5-(trifluoromethyl)pyrimidin-4-yl)phenyl-1,3-diamine

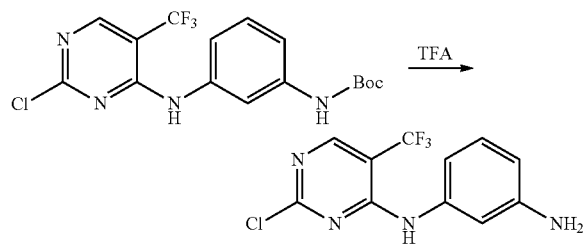

Tert-butyl (3-((2-chloro-5-(trifluoromethyl)pyrimidin-4-yl)amino)phenyl)amino carboxylate (2.1 g, 5.4 mmol) was dissolved in dichloromethane (30 mL), and trifluoroacetic acid (15 mL) was added. The mixture was stirred at room temperature for 3 h. The mixture was concentrated under reduced pressure to remove solvent, and saturated sodium bicarbonate solution was added. The mixture was extracted with ethyl acetate (150 mL×3). The organic phases were combined, washed with saturated NaCl aqueous solution, dried with anhydrous sodium sulfate, and concentrated under reduced pressure to remove solvent, so as to get the title compound as a white solid (1.45 g, yield: 93%).

Preparation Example 9 Preparation of N-(3-((2-chloro-5-(trifluoromethyl)pyrimidin-4-yl)amino)phenyl)acrylamide

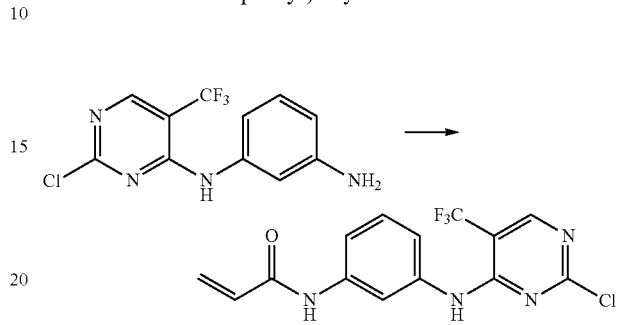

$N^1$-(2-chloro-5-(trifluoromethyl)pyrimidin-4-yl)phenyl-1,3-diamine (1.45 g, 5.0 mmol) was dissolved in tetrahydrofuran (150 mL). The mixture was cooled to −35° C., and acryloyl chloride (680 mg, 7.5 mmol) was added dropwisely. After the addition, the reaction was carried out at −35° C. for 2 h. The mixture was warmed to 0° C. and reacted for 2 h. Saturated sodium bicarbonate solution (100 mL) was added, and the water phase and the organic phase were separated. The water phase was extracted with ethyl acetate (150 mL×3). The organic phases were combined, washed with saturated NaCl aqueous solution, dried with anhydrous sodium sulfate, and concentrated. The crude product was purified by silica gel column chromatography (ethyl acetate: petroleum ether=0-1:2) to get the title compound as a white solid (1.2 g, yield: 69.5%).

Preparation Example 10 Preparation of $N^2$-(2-chloro-5-(trifluoromethyl)pyrimidin-4-yl)pyridine-2,6-diamine

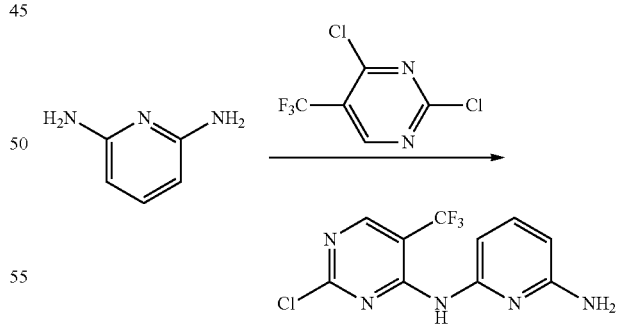

Pyridine-2,6-diamine (1.12 g, 10.3 mmol) was dissolved in tetrahydrofuran (50 mL), and triethylamine (2.08 g, 20.6 mmol) was added. The mixture was cooled in an ice-water bath, and 2,4-dichloro-5-(trifluoromethyl)pyrimidine (2.235 g, 10.3 mmol) was added dropwisely. After the addition, the mixture was warmed to room temperature and reacted for 16 h. Water (100 mL) was added, and the mixture was extracted with ethyl acetate (100 mL×3). The organic phases were combined, washed with saturated saline solution, dried with anhydrous sodium sulfate, and concentrated. The crude product was purified by silica gel column chromatography (ethyl acetate: petroleum ether=1:10) to get the title compound as a white solid (426 mg, yield: 14.3%).

Preparation Example 11 Preparation of N-(6-((2-chloro-5-(trifluoromethyl)pyrimidin-4-yl)amino)pyridin-2-yl)acrylamide

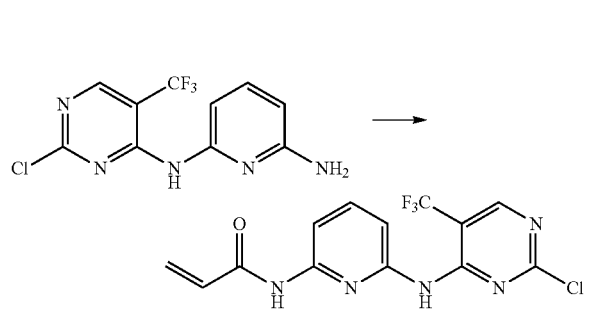

$N^2$-(2-chloro-5-(trifluoromethyl)pyrimidin-4-yl)pyridine-2,6-diamine (426 mg, 1.47 mmol) was dissolved in tetrahydrofuran (50 mL). The mixture was cooled to −35° C., and acryloyl chloride (399.4 mg, 4.41 mmol) was added dropwisely. After the addition, the mixture was reacted at −35° C. for 2 h. The mixture was warmed to 0° C. and reactioned for 2 h. Saturated sodium hydrogen carbonate solution (100 mL) was added, and the water phase and the organic phase were separated. The water phase was extracted with ethyl acetate (150 mL×3). The organic phases were combined, washed with saturated saline solution, dried with anhydrous sodium sulfate, and concentrated. The crude product was purified by silica gel column chromatography (ethyl acetate: petroleum ether=1:20) to get the title compound as a white solid (200 mg, yield: 39.6%).

Preparation Example 12 Preparation of tert-butyl (3-((2-chloro-5-(trifluoromethyl)pyridin-4-yl)amino)phenyl)amino carboxylate

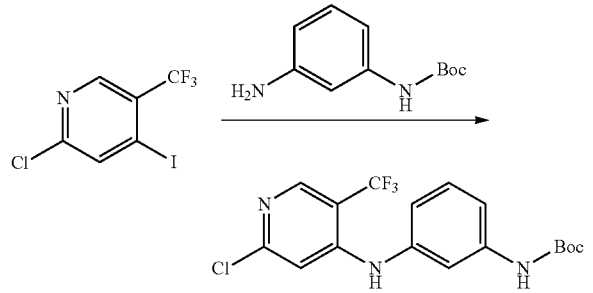

2-Chloro-4-iodo-5-(trifluoromethyl)pyridine (5 g, 16.3 mmol), tert-butyl (3-aminophenyl)amino carboxylate (3.7 g, 17.9 mmol), tris(dibenzylideneacetone)dipalladium (1.49 g, 1.63 mmol), 2-dicyclohexylphosphino-2',4',6'-triisopropyl-biphenyl (1.55 g, 3.26 mmol) and cesium carbonate (10.7 g, 32.6 mmol) were added to 1,4-dioxane (200 mL). Under the protection of nitrogen gas, the mixture was reacted at 80° C. for 12 h. The system was cooled to room temperature, and filtrated under reduced pressure. The resultant filtrate was concentrated. The crude product was purified by silica gel column chromatography (petroleum ether: ethyl acetate=30:1), and then recrystallized by dichloromethane to get the title compound as a light yellow solid (1.5 g, yield: 23.8%).

Preparation Example 13 Preparation of $N^1$-(2-chloro-5-(trifluoromethyl)pyridin-4-yl)phenylene-1,3-diamine

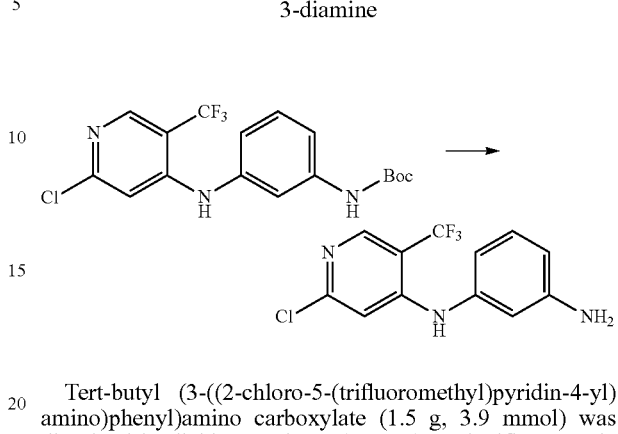

Tert-butyl (3-((2-chloro-5-(trifluoromethyl)pyridin-4-yl)amino)phenyl)amino carboxylate (1.5 g, 3.9 mmol) was dissolved in dichloromethane (20 mL), and trifluoroacetic acid (10 mL) was added. The mixture was reacted at room temperature for 2 h. The reaction solution was concentrated, and sodium hydrogen carbonate aqueous solution was added to neutralize the residual trifluoroacetic acid. The mixture was then extracted with dichloromethane. The organic phase was dried with anhydrous sodium sulfate, and concentrated in vacuum to get the title compound a brown oil (1 g, yield: 90.1%).

Preparation Example 14 Preparation of N-(3-((2-chloro-5-(trifluoromethyl)pyridin-4-yl)amino)phenyl)acrylamide

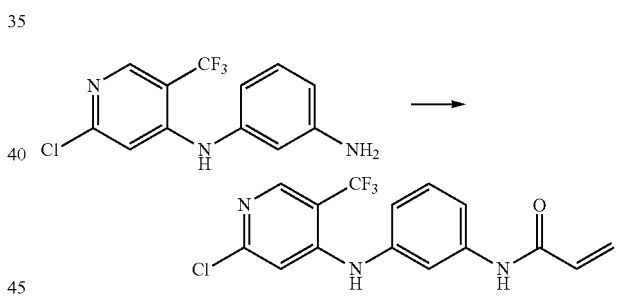

$N^1$-(2-chloro-5-(trifluoromethyl)pyridin-4-yl)phenylene-1,3-diamine (1 g, 3.5 mmol) was added to dichloromethane (30 mL), and cooled to −30° C. Acryloyl chloride (950 mg, 10.5 mmol) was added. After the addition, the mixture was warmed to room temperature and reacted for 24 h. Water was added to quench the reaction, and the water phase and the organic phase were separated. The organic phase was dried with anhydrous sodium sulfate, and concentrated. The crude product was purified by silica gel column chromatography (dichloromethane:methanol=40:1) to get the title compound as a white solid (377 mg, yield: 31.6%).

Preparation Example 15 Preparation of methyl (4-methoxyphenylethyl)amino carboxylate

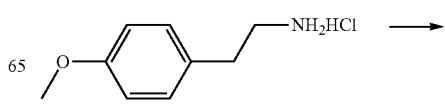

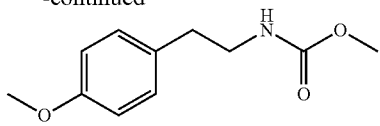

4-Methoxyphenyl ethylamine hydrochloride (22.5 g, 120 mmol) was added to tetrahydrofuran (300 mL), and triethylamine (30.3 g, 300 mmol) was added. The mixture was cooled in an ice-water bath, and methyl chloroformate (56.7 g, 600 mmol) was added carefully. After the addition, the reaction was carried out in an ice-water bath for 4 h. The mixture was warmed to room temperature and reacted for 16 h, and poured into water. The mixture was extracted with ethyl acetate (250 mL×3). The organic phases were combined, washed with saturated saline solution, dried with anhydrous sodium sulfate, and concentrated. The crude product was added to ethyl acetate, and the solid was filtrated out. The filtrate was concentrated to get the title compound as a light yellow solid (19 g, yield: 75.8%).

Preparation Example 16 Preparation of 7-methoxy-3,4-dihydroisoquinolin-1(2H)-one

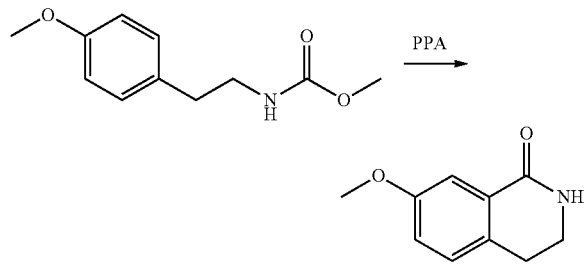

Polyphosphoric acid (150 g) was heated to 120° C., and methyl (4-methoxyphenylethyl)amino carboxylate (19 g, 90.9 mmol) was added in batches under stirring. After the addition, the mixture was warmed to 140° C. and reacted for 20 min, and cooled to 70° C. The mixture was poured into ice-water (300 mL), and extracted with dichloromethane (200 mL×5). The organic phases were combined, washed with saturated saline solution, dried with anhydrous sodium sulfate, and concentrated to get the title compound as a greyish-white solid (5.4 g, yield: 33.6%).

Preparation Example 17 Preparation of 7-methoxy-1,2,3,4-tetrahydroisoquinoline

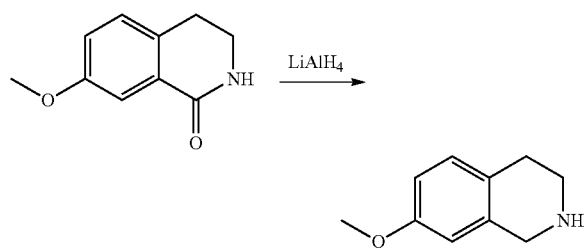

7-Methoxy-3,4-dihydroisoquinolin-1(2H)-one (5.4 g, 30.51 mmol) was dissolved in anhydrous tetrahydrofuran (150 mL). The mixture was cooled in an ice-water bath, and lithium aluminum hydride (1.28 g, 33.7 mmol) was added. After the addition, the mixture was warmed to 70° C. and reacted for 5 h. The resultant mixture was cooled to room temperature. Water was added carefully to quench the reaction. 3 mol/L NaOH solution was added and filtrated with diatomaceous earth. The water phase and the organic phase were separated, and the water phase was extracted with ethyl acetate (150 mL×3). The organic phases were combined, washed with saturated saline solution, dried with anhydrous sodium sulfate, and concentrated to get the title compound as a light yellow oil (3.9 g, yield: 78.4%), which was directly used in the next step without purification.

Preparation Example 18 Preparation of tert-butyl 7-methoxy-3,4-dihydroisoquinolin-2(1H)-carboxylate

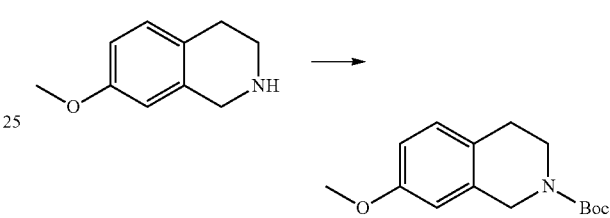

7-Methoxy-1,2,3,4-tetrahydroisoquinoline (3.9 g, 23.9 mmol) and triethylamine (4.83 g, 47.8 mmol) were dissolved in dichloromethane (50 mL), and di-tert-butyl dicarbonate (7.8 g, 35.8 mmol) was added. The mixture was stirred at room temperature for 4 h, and concentrated. The crude product was purified by silica gel column chromatography (ethyl acetate: petroleum ether=0-1:10) to get the title compound as a light yellow oil (3.65 g, yield: 58.1%).

Preparation Example 19 Preparation of tert-butyl 7-methoxy-6-nitro-3,4-dihydroisoquinolin-2(1H)-carboxylate

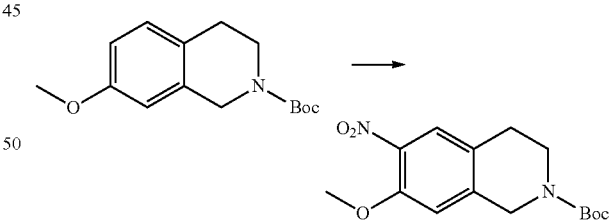

Tert-butyl 7-methoxy-3,4-dihydroisoquinolin-2(1H)-carboxylate (3.65 g, 13.88 mmol) was dissolved in nitromethane (50 mL), and acetic anhydride (7.08 g, 69.4 mmol) was added. The mixture was cooled in an ice-water bath, and concentrated nitric acid (mass percentage 65%, 2.02 g, 20.8 mmol) was added dropwisely. After the addition, the mixture was stirred for 5 h in an ice-water bath. Saturated sodium bicarbonate solution (100 mL) was added, and the water phase and the organic phase were separated. The water phase was extracted with ethyl acetate (150 mL×3). The organic phases were combined, washed with saturated saline solution, dried with anhydrous sodium sulfate, and concentrated. The crude product was purified by silica gel column chromatography (ethyl acetate: dichloromethane=0-1:6) to get the title compound as a light yellow solid (1.41 g, yield: 33.0%).

Preparation Example 20 Preparation of 7-methoxy-6-nitro-1,2,3,4-tetrahydroisoquinoline

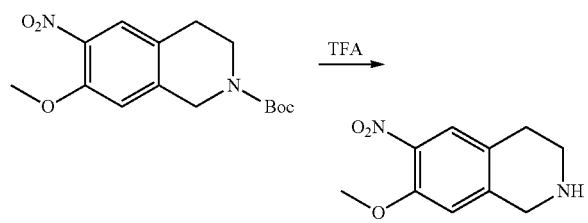

Tert-butyl 7-methoxy-6-nitro-3,4-dihydroisoquinolin-2 (1H)-carboxylate (400 mg, 1.3 mmol) was dissolved in dichloromethane (10 mL), and trifluoroacetic acid (10 mL) was added. The mixture was stirred at room temperature for 3 h. The solvent was removed under reduced pressure, and saturated sodium bicarbonate solution was added. The mixture was extracted with ethyl acetate (50 mL×3). The organic phases were combined, washed with saturated saline solution, dried with anhydrous sodium sulfate, and concentrated to get the title compound as a light yellow oil (260 mg, yield: 96%).

Preparation Example 21 Preparation of 1-(7-methoxy-6-nitro-3,4-dihydroisoquinolin-2(1H)-yl) ethan-1-one

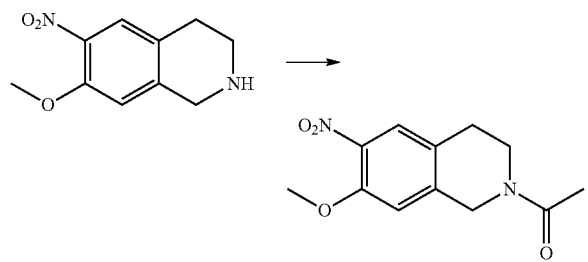

7-Methoxy-6-nitro-1,2,3,4-tetrahydroisoquinoline (260 mg, 1.25 mmol) and triethylamine (379 mg, 3.75 mmol) were dissolved in dichloromethane (50 mL), and acetic anhydride (255 mg, 2.5 mmol) was added. The mixture was stirred at room temperature for 4 h, and concentrated. The crude product was purified by silica gel column chromatography (petroleum ether: ethyl acetate=8:1) to get the title compound as a light yellow solid (300 mg, yield: 96%).

Preparation Example 22 Preparation of 1-(6-amino-7-methoxy-3,4-dihydroisoquinolin-2(1H)-yl)ethan-1-one

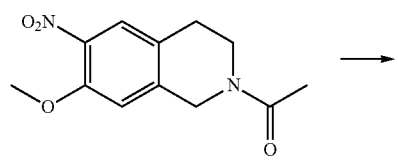

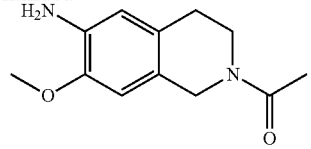

1-(7-Methoxy-6-nitro-3,4-dihydroisoquinolin-2(1H)-yl) ethan-1-one (300 mg, 1.2 mmol) and palladium-carbon (30 mg) were suspended in methanol (50 mL). The system was vacuumized, and hydrogen gas was introduced. The reaction was carried out at room temperature for 16 h, and the reaction solution was filtrated with diatomaceous earth. The solvent was removed under reduced pressure, and the crude product was purified by silica gel column chromatography (methanol: dichloromethane=0-1:10) to get the title compound as a white solid (250 mg, yield: 95%).

Preparation Example 23 Preparation of 5-nitro-1,2,3,4-tetrahydroisoquinoline

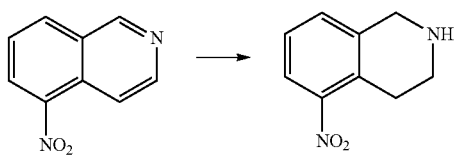 [SMILES: O=[N+]([O-])c1cccc2cnccc12 ; O=[N+]([O-])c1cccc2c1CCNC2]

In an ice-water bath, 5-nitroisoquinoline (3.48 g, 20 mmol) was dissolved in acetic acid (15 mL), and sodium borohydride (3.78 g, 100 mmol) was added slowly. After the addition, the mixture was warmed to room temperature and reacted for 1 h. After the reaction, the reaction solution was poured into ice (50 g). The mixture was extracted with ethyl acetate (100 mL×2). The organic phase was dried with anhydrous sodium sulfate, concentrated, and purified by silica gel column chromatography (petroleum ether: ethyl acetate=5:1) to get the title compound (2.32 g, yield: 65%).

Preparation Example 24 Preparation of 1-(4-(3-methoxy-4-nitrophenyl)piperazin-1-yl)ethan-1-one

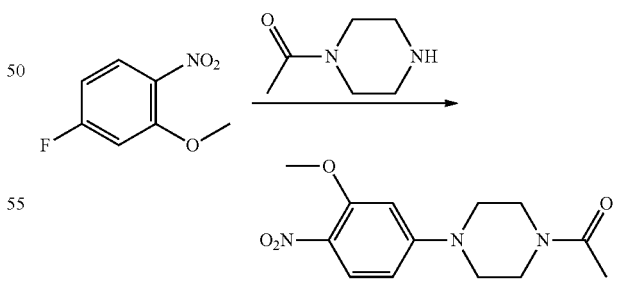

1-(Piperazin-1-yl)ethan-1-one (2.56 g, 20 mmol) and 4-fluoro-2-methoxy-1-nitrobenzene (3.42 g, 20 mmol) were dissolved in N,N-dimethylformamide (30 mL), and potassium carbonate (5.52 g, 40 mmol) was added. The reaction was carried out at 70° C. for 16 h. The reaction solution was cooled to room temperature, and poured into water (150 mL). The mixture was extracted with ethyl acetate (150 mL×4), and the water phase and the organic phase was separated. The organic phases were combined, washed with saturated saline solution, dried with anhydrous sodium sulfate, and concentrated. The crude product was purified by silica gel column chromatography (ethyl acetate: petroleum ether=1:10-2:1) to get the title compound as a light yellow solid (4.8 g, yield: 86.0%).

Preparation Example 25 Preparation of 1-(4-(4-amino-3-methoxyphenyl)piperazin-1-yl)ethan-1-one

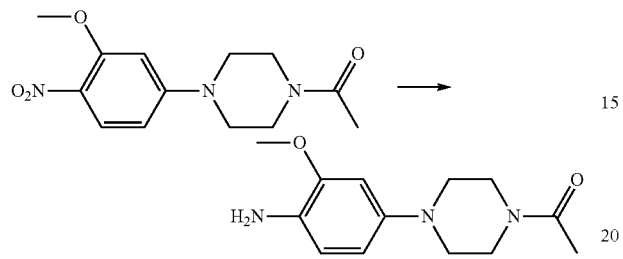

1-(4-(3-Methoxy-4-nitrophenyl)piperazin-1-yl)ethan-1-one (2.4 g, 8.6 mmol) was added to methanol (100 mL), and palladium-carbon (0.24 g) was added to the system. Hydrogen gas was introduced, and the reaction was carried out at room temperature for 12 h. The reaction solution was filtrated through diatomaceous earth under reduced pressure, and the filtrate was concentrated in vacuum to get the title compound as a bronzing solid (2 g, yield: 93.4%).

Preparation Example 26 Preparation of 1,2,3,4-tetrahydroisoquinoline-8-ol

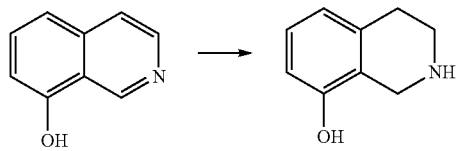 [SMILES: Oc1cccc2ccncc12 ; Oc1cccc2c1CNCC2]

In an ice-water bath, isoquinolin-8-ol (2.9 g, 20 mmol) was dissolved in acetic acid (15 mL), and sodium borohydride (3.78 g, 100 mmol) was added slowly. After the addition, the mixture was warmed to room temperature and reacted for 1 h. After the reaction, the reaction solution was poured into ice (50 g), and extracted with ethyl acetate (100 mL×2). The organic phase was dried with anhydrous sodium sulfate, concentrated, and purified by silica gel column chromatography (petroleum ether: ethyl acetate=5:1) to get the title compound (2.12 g, yield: 71%).

Preparation Example 27 Preparation of 2-acetyl-1,2,3,4-tetrahydroisoquinoline-8-yl acetate

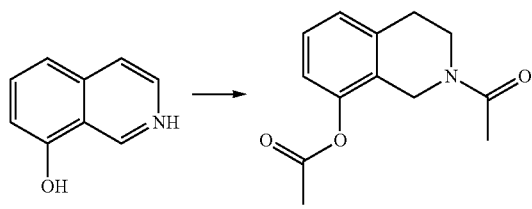 [SMILES: Oc1cccc2ccncc12 ; CC(=O)Oc1cccc2c1CN(C(C)=O)CC2]

In an ice-water bath, 1,2,3,4-tetrahydroisoquinoline-8-ol (2.0 g, 13.4 mmol) and triethylamine (5.41 g, 53.6 mmol) were dissolved in dichloromethane (40 mL), and acetyl chloride (3.16 g, 40.2 mmol) was added slowly. After the addition, the mixture was warmed to room temperature and reacted for 2 h. After the reaction, the mixture was filtrated. The filtrate was concentrated, and purified by silica gel column chromatography (the eluent was petroleum ether: ethyl acetate=5:1) to get the title compound (2.22 g, yield: 71%).

Preparation Example 28 Preparation of 1-(8-hydroxy-3,4-dihydroisoquinolin-2(1H)-yl)ethan-1-one

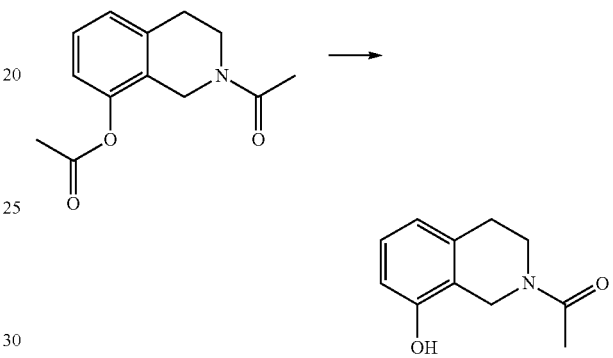

2-Acetyl-1,2,3,4-tetrahydroisoquinoline-8-yl acetate (2.0 g, 8.57 mmol) was dissolved in methanol (10 mL), and NaOH (1M, 15 mL) was added dropwise. The reaction was carried out at room temperature for 8 h. After the reaction, the solvent was dried by distillation to get the crude title compound as a solid (2.3 g), which was used directly in the next step without purification.

Preparation Example 29 Preparation of 1-(8-methoxy-3,4-dihydroisoquinolin-2(1H)-yl)ethan-1-one

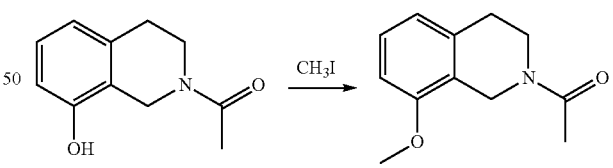

1-(8-Hydroxy-3,4-dihydroisoquinolin-2(1H)-yl)ethan-1-one (2.3 g crude product) was dissolved in N,N-dimethylformamide (30 mL), and potassium carbonate (2.37 g, 17.14 mol) was added. Iodomethane (1.46 g, 10.28 mmol) was added dropwise under stirring. The mixture was stirred at room temperature for 12 h. After the reaction, water (100 mL) was added to the reaction solution. The mixture was extracted with ethyl acetate (150 mL×2). The organic phase was separated, dried with anhydrous sodium sulfate, concentrated, and purified by silica gel column chromatography (petroleum ether: ethyl acetate=5:1) to get the title compound (1.05 g, two-step yield: 60%).

Preparation Example 30 Preparation of
1,2-di(bromomethyl)-3-methoxyphenyl

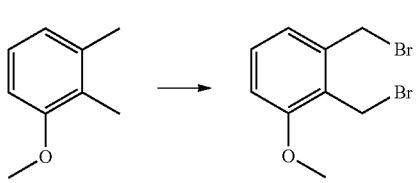

1-Methoxy-2,3-dimethylbenzene (13.6 g, 100 mmol), NBS (39.2 g, 220 mmol) and benzoperoxide (242 mg, 1 mmol) were dissolved in carbon tetrachloride (200 mL). The mixture was heated to 90° C. and reacted for 12 h. After the reaction, the mixture was cooled to room temperature, and filtrated. The filtrate was concentrated to get the title compound as a crude product (30 g).

Preparation Example 31 Preparation of
2-benzyl-4-methoxyisoindoline

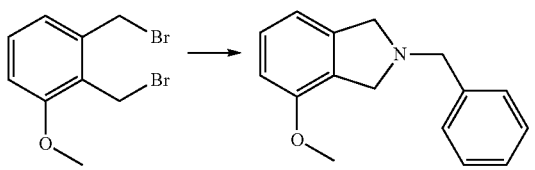 [SMILES: COc1cccc(CBr)c1CBr ; COc1cccc2c1CN(Cc1ccccc1)C2]

In an ice-water bath, crude 1,2-di(bromomethyl)-3-methoxyphenyl (30 g) and phenyl triethyl ammonium chloride (1.1 g, 5 mmol) were dissolved in a mixed solution of NaOH solution (50%, 50 mL) and toluene (200 mL). Under stirring, benzylamine (11.79 g, 110 mmol) was added. After the addition, the mixture was warmed to room temperature, and reacted under stirring for 12 h. After the reaction, the mixture was on standing and stratified. The organic phase was washed with saturated saline solution (100 mL×3), dried with anhydrous sodium sulfate, concentrated, and purified by silica gel column chromatography (petroleum ether: ethyl acetate=10:1) to get the title compound (5.02 g, two-step yield: 21%).

Preparation Example 32 Preparation of
4-methoxyisoindoline

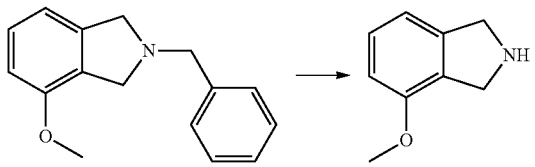 [SMILES: COc1cccc2c1CN(Cc1ccccc1)C2 ; COc1cccc2c1CNC2]

At room temperature, 2-benzyl-4-methoxyisoindoline (5 g, 20.9 mmol) was dissolved in methanol (100 mL), and palladium-carbon (10%, 0.5 g) was added. After the introduction of hydrogen gas, the mixture was reacted at room temperature for 12 h. After the reaction, the mixture was filtrated. The filtrate was concentrated to get the title compound (2.84 g, yield: 91%).

Preparation Example 33 Preparation of
1-(4-methoxyisoindolin-2-yl)ethan-1-one

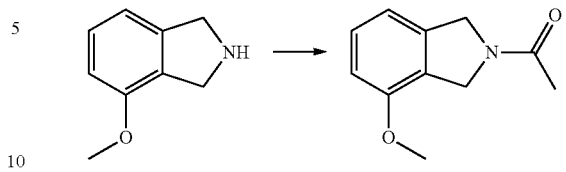

In an ice-water bath, 4-methoxyisoindoline (2.5 g, 16.8 mmol) and triethylamine (3.39 g, 33.6 mmol) were dissolved in dichloromethane (40 mL), and acetyl chloride (1.59 g, 20.2 mmol) was added slowly. After the addition, the mixture was warmed to room temperature and reacted for 2 h. After the reaction, the mixture was filtrated. The filtrate was concentrated, and purified by silica gel column chromatography (petroleum ether: ethyl acetate=5:1) to get the title compound (2.44 g, yield: 76%).

Example 1 Preparation of N-(6-((2-((4-(4-acetylpiperazin-1-yl)-2-methoxyphenyl)amino)-5-(trifluoromethyl) pyrimidin-4-yl)amino)pyridin-2-yl)acrylamide
(Compound 1)

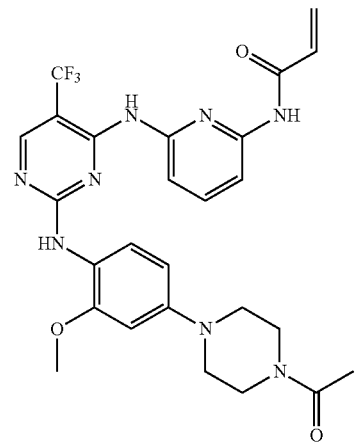 [SMILES: C=CC(=O)Nc1cccc(Nc2nc(Nc3ccc(N4CCN(C(C)=O)CC4)cc3OC)ncc2C(F)(F)F)n1]

(1) Preparation of 1-(4-(4-((4-chloro-5-(trifluoromethyl)pyrimidin-2-yl)amino)-3-methoxyphenyl)piperazin-1-yl)ethanone

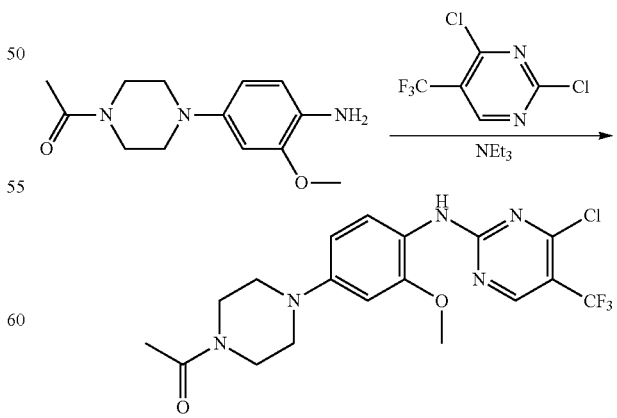

1-(4-(4-Amino-3-methoxyphenyl))piperazin-1-yl))ethan-1-one (1.0 g, 4.0 mmol) and triethylamine (0.41 g, 4.0 mmol) were dissolved in dichloromethane (30 mL). The mixture was placed in an ice-water bath. 2,4-Dichloro-5-(trifluoromethyl)pyrimidine (0.87 g, 4.0 mmol) was dissolved in anhydrous dichloromethane (10 mL), and was added slowly to the above system. The reaction mixture was slowly warmed to room temperature and stirred for 4 h. The resultant mixture was concentrated, and separated by reversed phase chromatography (water:methanol=1.5:1-1:1.1) to get the title compound (620 mg, yield: 36%).

(2) Preparation of N-(6-((2-((4-(4-acetylpiperazin-1-yl)-2-methoxyphenyl)amino)-5-(trifluoromethyl)pyrimidin-4-yl)amino)pyridin-2-yl)acrylamide

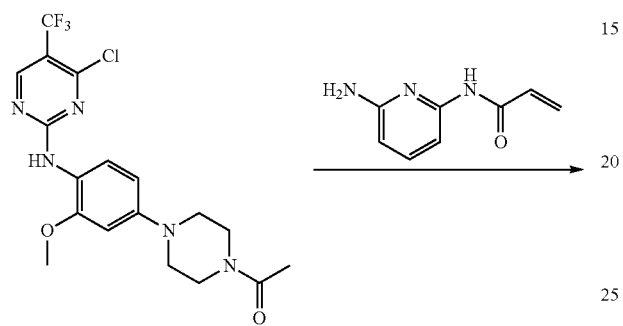

1-(4-(4-((4-Chloro-5-(trifluoromethyl)pyrimidin-2-yl)amino)-3-methoxyphenyl)piperazin-1-yl)ethanone (430 mg, 1.0 mmol), N-(6-aminopyridin-2-yl)acrylamide (164 mg, 1.0 mmol), tris(dibenzylideneacetone)dipalladium (43 mg, 0.05 mmol), 2-dicyclohexylphosphino-2',4',6'-triisopropylbiphenyl (86 mg, 0.18 mmol), and potassium carbonate (210 mg, 1.5 mmol) were dissolved in 1,4-dioxane (5 mL). The mixture was reacted at 110° C. under microwave for 1 h, and separated by reversed phase chromatography (water:methanol=3:1-1:1.5) to get the product (56 mg, yield: 10%).

Molecular formula: $C_{26}H_{27}F_3N_8O_3$ Molecular weight: 556 LC-MS (m/z): 557 (M+H$^+$) $^1$H-NMR (400 MHz, MeOD) δ: 8.28 (s, 1H), 7.80-7.85 (m, 1H), 7.50-7.79 (m, 3H), 6.69 (s, 1H), 6.51-6.68 (m, 1H), 6.37-6.50 (m, 2H), 5.79-5.82 (m, 1H), 3.82 (s, 3H), 3.69-3.76 (m, 4H), 3.15-3.22 (m, 4H), 2.16 (s, 3H).

Example 2 Preparation of N-(3-((2-((4-(1-acetylpiperidin-4-yl)-2-methoxyphenyl)amino)-5-(trifluoromethyl)pyrimidin-4-yl)amino)phenyl) acrylamide (Compound 2)

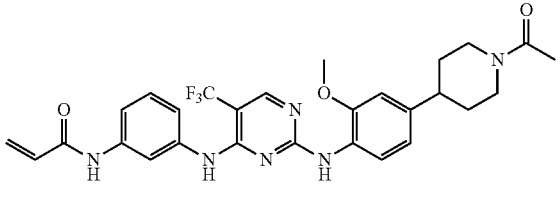 [SMILES: C=CC(=O)Nc1cccc(Nc2nc(Nc3ccc(C4CCN(C(C)=O)CC4)cc3OC)ncc2C(F)(F)F)c1]

(1) Preparation of N-(3-((2-((4-(1-acetylpiperidin-4-yl)-2-methoxyphenyl)amino)-5-(trifluoromethyl)pyrimidin-4-yl)amino)phenyl)acrylamide

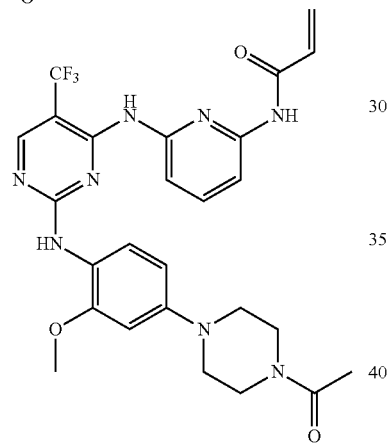

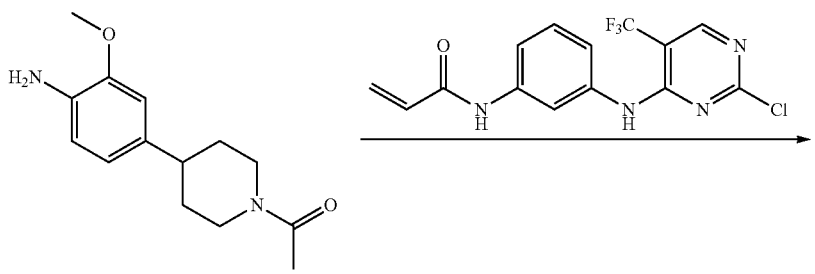

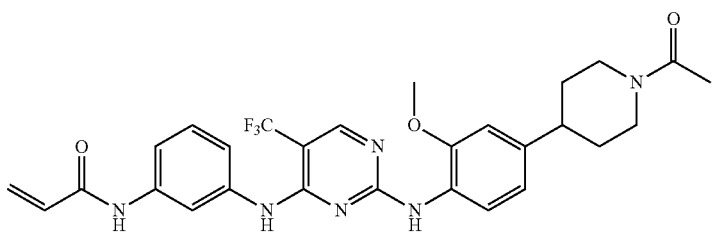

1-(4-(4-Amino-3-methoxyphenyl)piperidin-1-yl)etha-none (52 mg, 0.21 mmol) and N-(3-((2-chloro-5-(trifluoromethyl)pyrimidin-4-yl)amino)phenyl)acrylamide (60 mg, 0.18 mmol) were dissolved in 1,4-dioxane (10 mL), and a catalytic amount of trifluoroacetic acid was added to the system. The mixture was heated to 70° C. and reacted under stirring for 16 h. After the reaction, ethyl acetate (50 mL) was added to the reaction solution, and then the reaction solution was washed with water (50 mL×2). The organic phase was dried, concentrated, and separated by preparative chromatography to get the title compound (18 mg, yield: 18%).

Molecular formula: $C_{28}H_{29}F_3N_6O_3$ Molecular weight: 554.56 LC-MS (m/z): 555.3 (M+H$^+$)

$^1$H-NMR (400 MHz, MeOD) δ: 8.26 (s, 1H), 7.86-7.88 (m, 1H), 7.72-7.75 (m, 2H), 7.37-7.39 (m, 1H), 7.14-7.16 (m, 1H), 6.81 (s, 1H), 6.34-6.48 (m, 3H), 5.76-5.78 (m, 1H), 4.64-4.66 (m, 1H), 3.99-4.03 (m, 1H), 3.87 (s, 3H), 3.16-3.22 (m, 1H), 2.67-2.70 (m, 2H), 2.15 (s, 3H), 1.78-1.82 (m, 2H), 1.40-1.63 (m, 2H).

Example 3 Preparation of N-(3-((2-((4-(1-acetyl-1,2,3,6-tetrahydropyridin-4-yl)-2-methoxyphenyl)amino)-5-(trifluoromethyl)pyrimidin-4-yl)amino)phenyl)acrylamide (Compound 3)

1-(4-(4-Amino-3-methoxyphenyl)-3,6-dihydropyridin-1(2H)-yl)ethanone (69 mg, 0.28 mmol) and N-(3-((2-chloro-5-(trifluoromethyl)pyrimidin-4-yl)amino)phenyl)acrylamide (80 mg, 0.23 mmol) were dissolved in 1,4-dioxane (10 mL), and a catalytic amount of trifluoroacetic acid was added to the system. The mixture was heated to 70° C., and reacted under stirring for 16 h. After the reaction, ethyl acetate (50 mL) was added to the reaction solution, and then the reaction solution was washed with water (50 mL×2), dried, concentrated, and separated by preparative chromatography to get the title compound (35 mg, yield: 27.6%).

Molecular formula: $C_{28}H_{27}F_3N_6O_3$ Molecular weight: 552.55 LC-MS (m/z): 553.3 (M+H$^+$)

$^1$H-NMR (400 MHz, MeOD) δ: 8.27 (s, 1H), 7.92 (d, J=8.0 Hz, 1H), 7.71-7.77 (m, 2H), 7.39 (t, J=8.0 Hz, 1H), 7.13 (d, J=8.0 Hz, 1H), 6.97 (s, 1H), 6.66 (s, 1H), 6.31-6.39 (m, 2H), 6.03 (s, 1H), 5.73-5.76 (m, 1H), 4.18 (s, 2H), 3.90 (s, 3H), 3.69-3.78 (m, 2H), 2.47-2.55 (m, 2H), 2.14-2.19 (m, 3H).

Example 4 Preparation of N-(6-((2-((4-(1-acetylpiperidin-4-yl)-2-methoxyphenyl)amino)-5-(trifluoromethyl)pyrimidin-4-yl)amino)pyridin-2-yl)acrylamide (Compound 4)

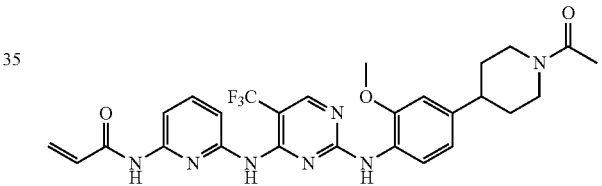

(1) Preparation of N-(3-((2-((4-(1-acetyl-1,2,3,6-tetrahydropyridin-4-yl)-2-methoxyphenyl)amino)-5-(trifluoromethyl)pyrimidin-4-yl)amino)phenyl)acrylamide

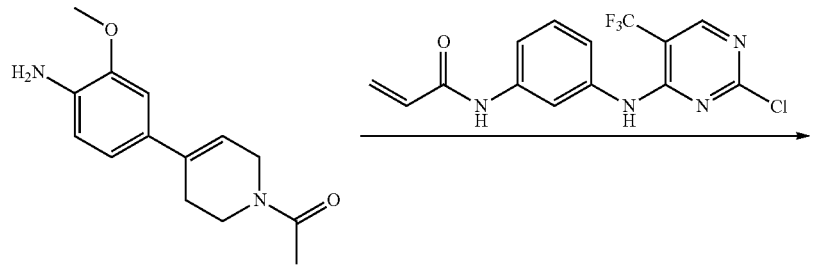

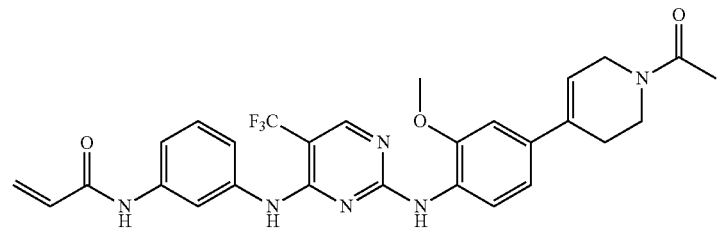

(1) Preparation of 1-(4-(4-((4-chloro-5-(trifluoromethyl)pyrimidin-2-yl)amino)-3-methoxyphenyl)piperidin-1-yl)ethanone

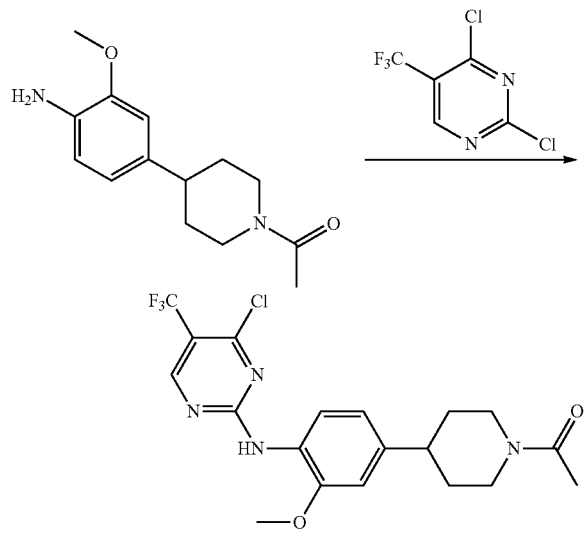

1-(4-(4-Amino-3-methoxyphenyl)piperidin-1-yl)ethanone (1.7 g, 6.9 mmol) and 2,4-dichloro-5-(trifluoromethyl)pyrimidine (1.8 g, 8.3 mmol) were dissolved in dichloromethane (50 mL), and triethylamine (1.0 g, 10.3 mmol) was added. The mixture was stirred at room temperature for 16 h, washed with water (50 mL×2), dried with anhydrous sodium sulfate, filtrated, concentrated, and separated by preparative chromatography to get the title compound as a tawny solid (400 mg, yield: 13%).

(2) Preparation of N-(6-((2-((4-(1-acetylpiperidin-4-yl)-2-methoxyphenyl)amino)-5-(trifluoromethyl)pyrimidin-4-yl)amino)pyridin-2-yl)acrylamide

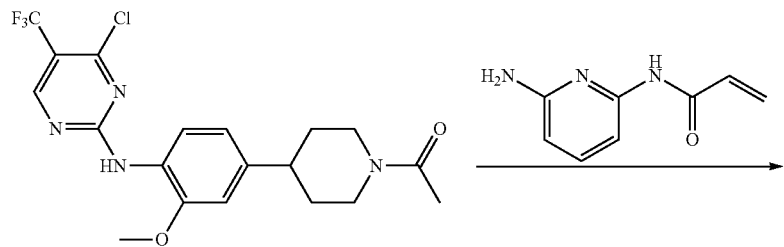

1-(4-(4-((4-Chloro-5-(trifluoromethyl)pyrimidin-2-yl)amino)-3-methoxyphenyl)piperidin-1-yl)ethanone (100 mg, 0.23 mmol) and N-(6-aminopyridin-2-yl)acrylamide (190 mg, 1.17 mmol) were dissolved in 1,4-dioxane (20 mL), and 2-dicyclohexylphosphino-2',4',6'-triisopropylbiphenyl (19 mg, 0.04 mmol), cesium carbonate (149 mg, 0.46 mmol) and tris(dibenzylideneacetone)dipalladium (18 mg, 0.02 mmol) were added. Under the protection of nitrogen gas, the mixture was heated to 110° C. and reacted for 16 h. The resultant mixture was cooled to room temperature, and concentrated. Water was added, and the mixture was extracted with ethyl acetate (50 mL×2). The organic phases were combined, washed with saturated NaCl aqueous solution, dried with anhydrous sodium sulfate, and concentrated. The crude product was purified by silica gel column chromatography (DCM:MeOH=15:1) to get the title compound as a light yellow solid (28 mg, yield: 22%).

Molecular formula: $C_{27}H_{28}F_3N_7O_3$ Molecular weight: 555.55 LC-MS (m/z): 556.3 (M+H$^+$) $^1$H-NMR (400 MHz, MeOD-d$_4$) δ: 8.30 (s, 1H), 7.86-7.88 (m, 1H), 7.73-7.75 (m, 2H), 7.61 (s, 1H), 6.90 (s, 1H), 6.75-6.77 (m, 1H), 6.37-6.49 (m, 2H), 5.78-5.81 (m, 1H), 4.66-4.69 (m, 1H), 4.02-4.05 (m, 1H), 3.85 (s, 3H), 3.19-3.25 (m, 1H), 2.67-2.83 (m, 2H), 2.15 (s, 3H), 1.85-1.93 (m, 2H), 1.55-1.75 (m, 2H).

Example 5 Preparation of N-(6-((2-((4-(1-acetyl-1,2,3,6-tetrahydropyridin-4-yl)-2-methoxyphenyl)amino)-5-(trifluoromethyl)pyrimidin-4-yl)amino)pyridin-2-yl)acrylamide (Compound 5)

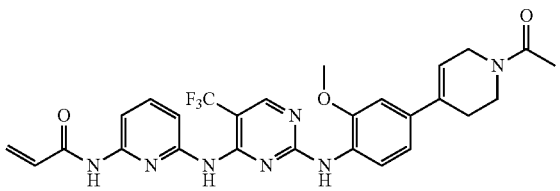 [SMILES: C=CC(=O)Nc1cccc(Nc2nc(Nc3ccc(C4=CCN(C(C)=O)CC4)cc3OC)ncc2C(F)(F)F)n1]

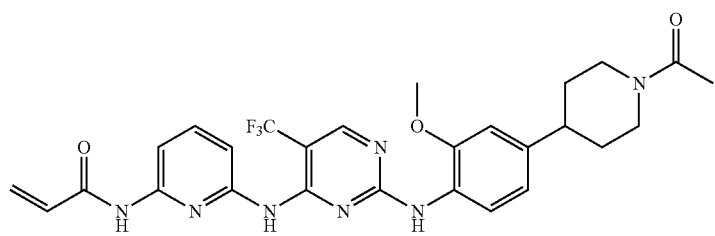

(1) Preparation of 1-(4-(4-((4-chloro-5-(trifluoromethyl)pyrimidin-2-yl)amino)-3-methoxyphenyl)-3,6-dihydropyridin-1-(2H)-yl)ethanone

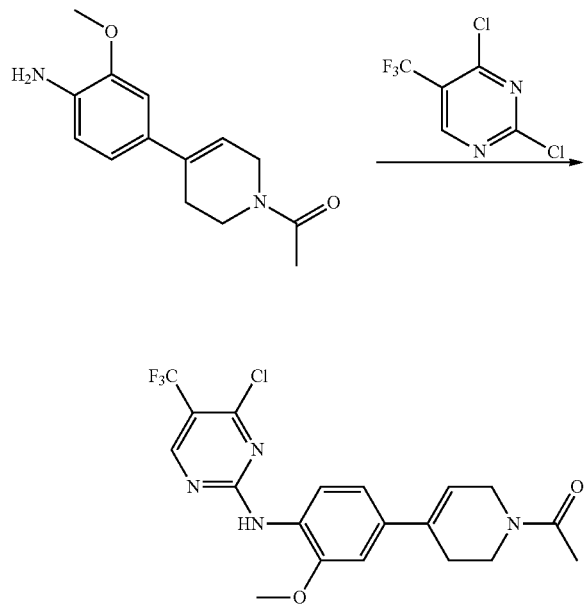

1-(4-(4-Amino-3-methoxyphenyl)-3,6-dihydropyridin-1 (2H)-yl)ethanone (1.5 g, 6.1 mmol) and 2,4-dichloro-5-(trifluoromethyl)pyrimidine (1.6 g, 7.3 mmol) were dissolved in dichloromethane (50 mL), and triethylamine (924 mg, 9.1 mmol) was added. The mixture was stirred at room temperature for 16 h and washed with water (50 mL×2). The organic phase was separated, dried with anhydrous sodium sulfate, filtrated, concentrated, and purified by reversed phase chromatography to get the title compound as a tawny solid (227 mg, yield: 9%).

(2) Preparation of N-(6-((2-((4-(1-acetyl-1,2,3,6-tetrahydropyridin-4-yl)-2-methoxyphenyl)amino)-5-(trifluoromethyl)pyrimidin-4-yl)amino)pyridin-2-yl)acrylamide

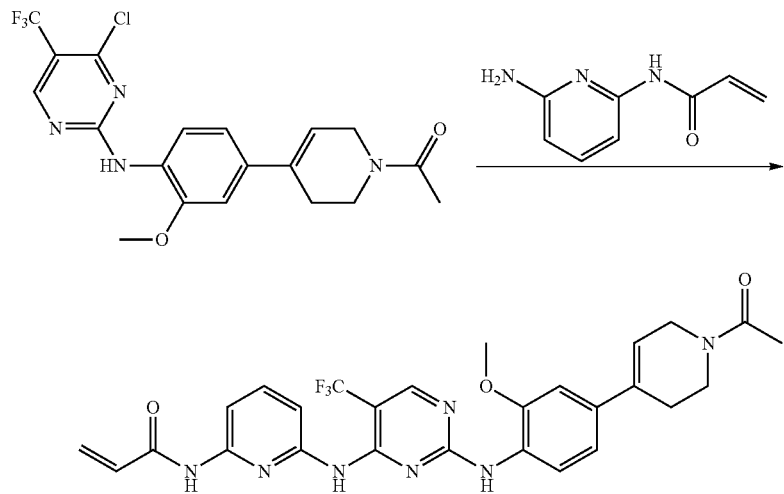

1-(4-(4-((4-Chloro-5-(trifluoromethyl)pyrimidin-2-yl)amino)-3-methoxyphenyl)-3,6-dihydropyridin-1-(2H)-yl)ethanone (100 mg, 0.23 mmol) and N-(6-aminopyridin-2-yl)acrylamide (190 mg, 1.17 mmol) were dissolved in 1,4-dioxane (20 mL), and 2-dicyclohexylphosphino-2',4',6'-triisopropylbiphenyl (19 mg, 0.04 mmol), cesium carbonate (149 mg, 0.46 mmol) and tris(dibenzylideneacetone)dipalladium (18 mg, 0.02 mmol) were added. Under the protection of nitrogen gas, the mixture was heated to 110° C. and reacted for 16 h. The resultant mixture was cooled to room temperature, and concentrated. Water was added, and the mixture was extracted with ethyl acetate (50 mL×2). The organic phases were combined, washed with saturated NaCl aqueous solution, dried with anhydrous sodium sulfate, and concentrated. The crude product was purified by silica gel column chromatography (dichloromethane:methanol=15:1) to get the title compound as a light yellow solid (10 mg, yield: 8%).

Molecular formula: $C_{27}H_{26}F_3N_7O_3$ Molecular weight: 553.54 LC-MS (m/z): 554.3 (M+H$^+$)

$^1$H-NMR (400 MHz, MeOD) δ: 8.35 (s, 1H), 7.87-7.91 (m, 2H), 7.75-7.73 (m, 1H), 7.65-7.69 (m, 1H), 7.07 (s, 1H), 6.94-6.97 (m, 1H), 6.38-6.50 (m, 2H), 6.14 (s, 1H), 5.78-5.82 (m, 1H), 4.20-4.22 (m, 2H), 3.90 (s, 3H), 3.79-3.82 (m, 1H), 3.73-3.76 (m, 1H), 2.64 (s, 1H), 2.56 (s, 1H), 2.16-2.21 (m, 3H).

Example 6 Preparation of N-(3-((2-((4-(8-acetyl-3,8-diazabicyclo[3.2.1]octan-3-yl)-2-methoxyphenyl)amino)-5-(trifluoromethyl)pyrimidin-4-yl)amino)phenyl)acrylamide (Compound 7)

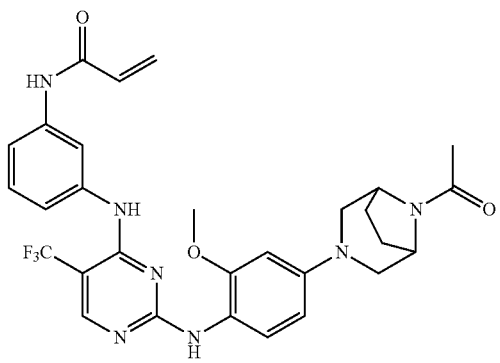 [SMILES: C=CC(=O)Nc1cccc(Nc2nc(Nc3ccc(N4CC5CCC(C4)N5C(C)=O)cc3OC)ncc2C(F)(F)F)c1]

(1) Preparation of tert-butyl 8-acetyl-3,8-diazabicyclo[3.2.1]octan-3-carboxylate

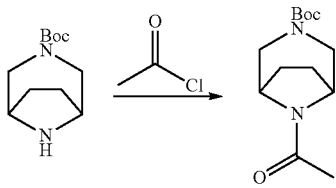

Tert-butyl 3,8-diazabicyclo[3.2.1]octan-3-carboxylate (212 mg, 1.0 mmol) was dissolved in tetrahydrofuran (20 mL), and triethylamine (202 mg, 2.0 mmol) and acetyl chloride (117 mg, 1.5 mmol) were added. The reaction was carried out at room temperature overnight. After the reaction, the solvent was dried by evaporation under rotation. Ethyl acetate (30 mL) and water (20 mL) were added, and the water phase and the organic phase were separated. The water phase was extracted with ethyl acetate (20 mL). The organic phases were combined, and concentrated. The residue was purified by column chromatography (petroleum ether: ethyl acetate=2:1) to get the title compound (220 mg, yield: 86.6%).

(2) Preparation of 1-(3,8-diazabicyclo[3.2.1]octan-8-yl)ethan-1-one

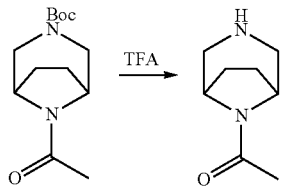 [SMILES: CC(=O)N1C2CCC1CN(C(=O)OC(C)(C)C)C2 ; CC(=O)N1C2CCC1CNC2]

Tert-butyl 8-acetyl-3,8-diazabicyclo[3.2.1]octan-3-carboxylate (220 mg, 0.866 mmol) was dissolved in dichloromethane (10 mL), and trifluoroacetic acid (2 mL) was added. The reaction was carried out at room temperature for 4 h. After the reaction, the solvent was dried by evaporation under rotation. Ethyl acetate (50 mL) and sodium bicarbonate solution (10 mL) were added, and the water phase and the organic phase were separated. The water phase was extracted with ethyl acetate (40 mL). The organic phases were combined, dried with anhydrous sodium sulfate, and concentrated to get the title compound (100 mg, yield: 74.9%).

(3) Preparation of 1-(3-(3-methoxy-4-nitrophenyl)-3,8-diazabicyclo[3.2.1]octan-8-yl)ethan-1-one

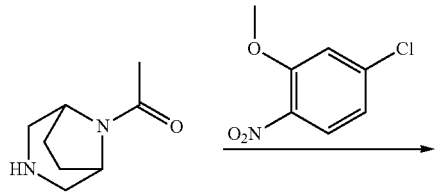

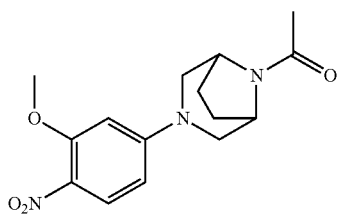

1-(3,8-Diazabicyclo[3.2.1]octan-8-yl)ethan-1-one (100 mg, 0.649 mmol) and 4-chloro-2-methoxy-1-nitrobenzene (121.7 mg, 0.649 mmol) were dissolved in 1,4-dioxane (15 mL), and tris(dibenzylideneacetone)dipalladium (59.5 mg, 0.065 mmol), 2-dicyclohexylphosphino-2',4',6'-triisopropylbiphenyl (62 mg, 0.13 mmol) and cesium carbonate (632.8 mg, 1.95 mmol) were added. The mixture was heated to 110° C., and the reaction was carried out overnight. After the reaction, the reaction solution was filtrated. The filtrate was concentrated, and the residue was purified by silica gel column chromatography (dichloromethane:methanol=30:1) to get the title compound (140 mg, yield: 70.7%).

(4) Preparation of 1-(3-(4-amino-3-methoxyphenyl)-3,8-diazabicyclo[3.2.1]octan-8-yl)ethan-1-one

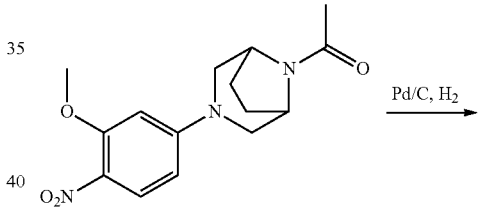

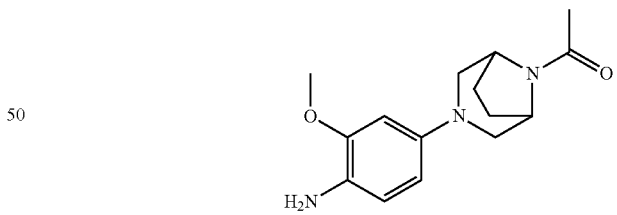

1-(3-(3-Methoxy-4-nitrophenyl)-3,8-diazabicyclo[3.2.1]octan-8-yl)ethan-1-one (140 mg, 0.458 mmol) was dissolved in methanol (20 mL). Under the protection of nitrogen gas, palladium-carbon (10%, 20 mg) was added. In the atmosphere of hydrogen gas, the reaction was carried out at room temperature overnight. After the reaction, the reaction solution was filtrated, and the filtrate was concentrated. The residue (crude product 100 mg) was directly used in the next step.

(5) Preparation of N-(3-((2-((4-(8-acetyl-3,8-diazabicyclo[3.2.1]octan-3-yl)-2-methoxyphenyl)amino)-5-(trifluoromethyl)pyrimidin-4-yl)amino)phenyl)acrylamide

Example 7 Preparation of N-(3-((2-((4-(8-acetyl-8-azabicyclo[3.2.1]octan-3-yl)-2-methoxyphenyl)amino)-5-(trifluoromethyl)pyrimidin-4-yl)amino)phenyl)acrylamide (Compound 8)

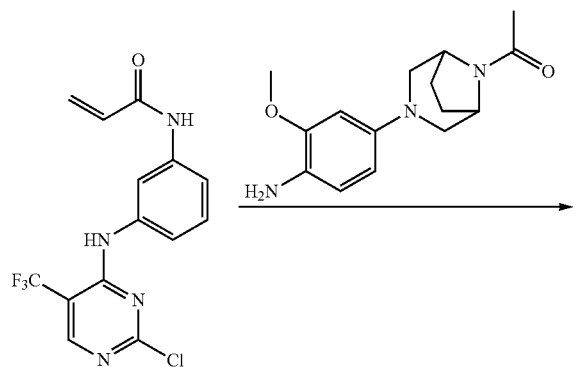

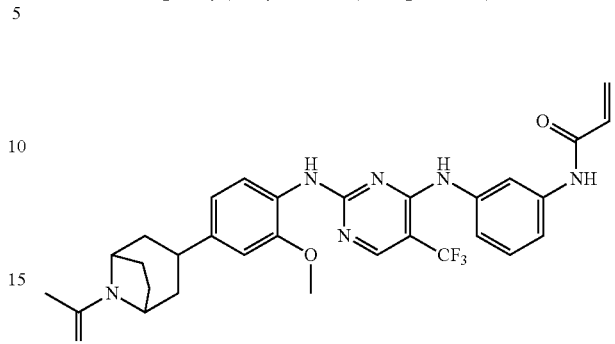

(1) Preparation of tert-butyl 3-oxo-8-azabicyclo[3.2.1]octan-8-carboxylate

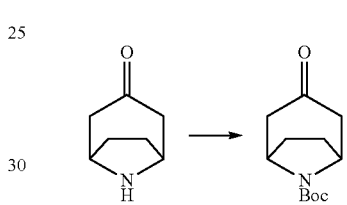

8-Azabicyclo[3.2.1]octan-3-one (5.0 g, 40 mmol) was dissolved in dichloromethane (100 mL), and di-tert-butyl dicarbonate (10.5 g, 48 mmol), triethylamine (8.1 g, 80 mmol) and 4-dimethylaminopyridine (488 mg, 4 mmol) were added. The mixture was reacted at room temperature under stirring for 16 h. After the reaction, water (100 mL) was added, and the water phase and the organic phase were separated. The organic phase was dried with anhydrous sodium sulfate, filtrated, and concentrated to get the crude product. The crude product was purified by silica gel column chromatography (petroleum ether: ethyl acetate=10:1) to get the title compound (8.5 g, yield: 94%).

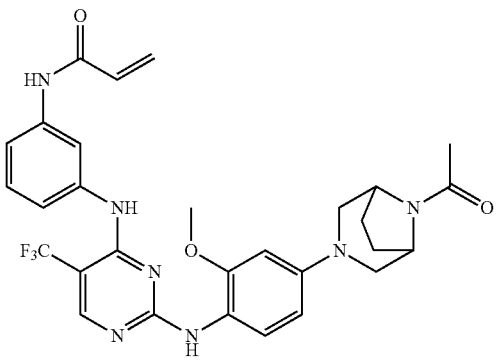

1-(3-(4-Amino-3-methoxyphenyl)-3,8-diazabicyclo[3.2.1]octan-8-yl)ethan-1-one (100 mg, 0.364 mmol) and N-(3-((2-chloro-5-(trifluoromethyl)pyrimidin-4-yl)amino)phenyl)acrylamide (186.4 mg, 0.545 mmol) were dissolved in 1,4-dioxane (15 mL), and tris(dibenzylideneacetone)dipalladium (33 mg, 0.036 mmol), 2-dicyclohexylphosphino-2',4',6'-triisopropylbiphenyl (34 mg, 0.071 mmol) and cesium carbonate (355 mg, 1.09 mmol) were added. The mixture was heated to 110° C., and the reaction was carried out overnight. LC-MS detection showed that the reaction was finished. The reaction solution was filtrated. The filtrate was concentrated, and the residue was purified by silica gel column chromatography (dichloromethane:methanol=15:1) to get the title compound (15 mg, yield: 7.1%).

Molecular formula: $C_{29}H_{30}F_3N_7O_3$ Molecular weight: 581.59 LC-MS (m/z): 582.3 (M+H$^+$)

$^1$H-NMR (400 MHz, DMSO-$d_6$) δ: 10.15 (s, 1H), 8.6 (brs, 1H), 8.25 (s, 1H), 8.06 (s, 1H), 7.7 (brs, 1H), 7.42-7.52 (m, 2H), 7.12-7.25 (m, 2H), 6.42-6.49 (m, 2H), 6.22-6.39 (m, 2H), 5.73-5.76 (m, 1H), 4.57 (s, 1H), 4.30-4.33 (m, 1H), 3.74 (s, 3H), 3.36-3.41 (m, 2H), 2.67-2.76 (m, 2H), 2.01 (s, 3H), 1.75-1.89 (m, 4H).

(2) Preparation of tert-butyl 3-(((trifluoromethylsulfonyl)oxy)-8-azabicyclo[3.2.1]octan-2-en-8-carboxylate

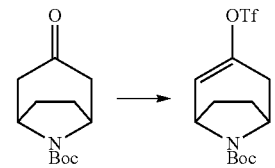 [SMILES: CC(C)(C)OC(=O)N1C2CCC1CC(=O)C2 ; CC(C)(C)OC(=O)N1C2C=C(OS(=O)(=O)C(F)(F)F)CC1CC2]

Tert-butyl 3-oxo-8-azabicyclo[3.2.1]octan-8-carboxylate (8.5 g, 37.8 mmol) was dissolved in tetrahydrofuran (80 mL), and a solution of lithium diisopropylamide in tetrahydrofuran/n-heptane/ethylbenzene (28 mL, 56 mmol, 2 M) was added slowly to the system at −78° C. After stirring for 10 min, a solution of 1,1,1-trifluoro-N-phenyl-N-((trifluoromethyl)sulfonyl)methanesulfonamide (14.8 g, 41.6 mmol) in tetrahydrofuran (50 mL) was added. After stirring for 30 min, the reaction was carried out at room temperature for 2 h. After the reaction, the mixture was concentrated to get the crude product. The crude product was purified by silica gel column chromatography (petroleum ether: ethyl acetate=20:1) to get the title compound (9.8 g, yield: 72.6%).

(3) Preparation of tert-butyl 3-(4,4,5,5-tetramethyl-1,3,2-dioxaborolan-2-yl)-8-azabicyclo[3.2.1]octan-2-en-8-carboxylate

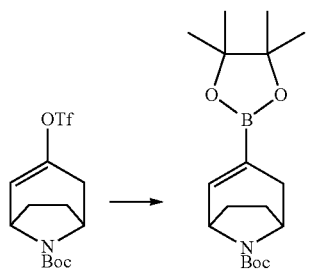

Tert-butyl 3-(((trifluoromethyl)sulfonyl)oxy)-8-azabicyclo[3.2.1]octan-2-en-8-carboxylate (9.8 g, 27.4 mmol), bis(pinacolato)diboron (10.4 g, 40.9 mmol), potassium acetate (5.4 g, 55 mmol), [1,1'-bis(diphenylphosphino)ferrocene] dichloropalladium (II) dichloromethane complex (1.15 g, 1.4 mmol) and 1,1'-bis(diphenyphosphino)ferrocene (776 mg, 1.4 mmol) were dissolved in 1,4-dioxane (100 mL). Under the protection of nitrogen gas, the reaction was carried out at 80° C. under stirring for 16 h. After the reaction, the mixture was cooled to room temperature, and water (100 mL) was added. The mixture was extracted with ethyl acetate (100 mL×2). The organic phases were combined, dried with anhydrous sodium sulfate, filtrated, and concentrated to get the crude product. The crude product was purified by silica gel column chromatography (petroleum ether: ethyl acetate=20:1) to get the title compound (7.3 g, yield: 79%).

(4) Preparation of tert-butyl 3-(3-methoxy-4-nitrophenyl)-8-azabicyclo[3.2.1]octan-2-en-8-carboxylate

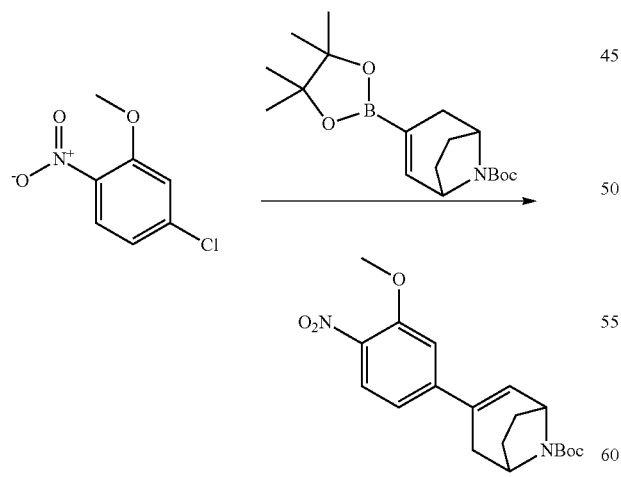

4-Chloro-2-methoxy-1-nitrobenzene (2.0 g, 10.7 mmol) and tert-butyl 3-(4,4,5,5-tetramethyl-1,3,2-dioxaborolan-2-yl)-8-azabicyclo[3.2.1]octan-2-en-8-carb oxylate (4.3 g, 12.8 mmol) were dissolved in a mixed solvent of 1,4-dioxane (50 mL) and water (10 mL). Sodium carbonate (2.27 g, 21.4 mmol) and [1,1'-bis(diphenylphosphino)ferrocene]dichloropalladium (II) dichloromethane complex (436 mg, 0.54 mmol) were added to the system. Under the protection of nitrogen gas, the reaction was carried out at 90° C. under stirring for 16 h. After the reaction, the mixture was cooled to room temperature, and water (100 mL) was added. The mixture was extracted with ethyl acetate (100 mL×2). The organic phases were combined, dried with anhydrous sodium sulfate, filtrated, and concentrated to get the crude product. The crude product was purified by silica gel column chromatography (petroleum ether: ethyl acetate=10:1) to get the title compound (2.4 g, yield: 62%).

(5) Preparation of 3-(3-methoxy-4-nitrophenyl)-8-azabicyclo[3.2.1]octan-2-ene

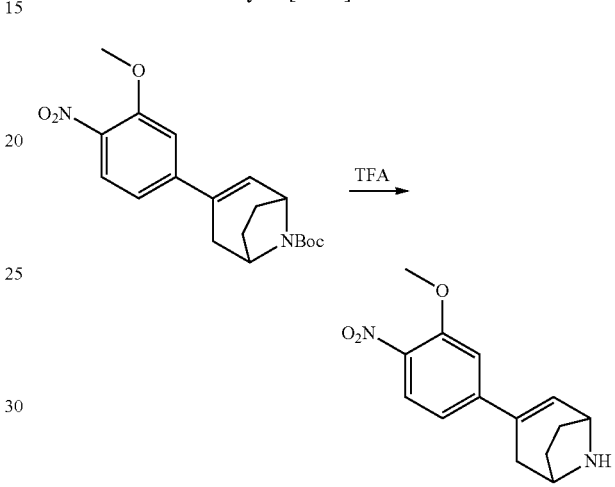

Tert-butyl 3-(3-methoxy-4-nitrophenyl)-8-azabicyclo[3.2.1]octan-2-en-8-carboxylate (2.4 g, 6.7 mmol) was dissolved in dichloromethane (20 mL), and trifluoroacetic acid (10 mL) was added. The mixture was stirred for 2 h. After the reaction, the reaction solution was concentrated, and washed with sodium bicarbonate solution and then with saline solution, dried with anhydrous sodium sulfate, filtrated, and concentrated to get the title compound (1.65 g, yield: 95%).

(6) Preparation of 1-(3-(3-methoxy-4-nitrophenyl)-8-azabicyclo[3.2.1]octan-2-en-8-yl)ethan-1-one

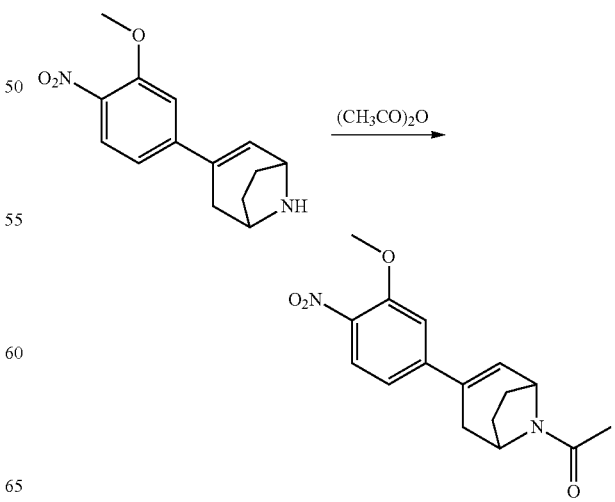

3-(3-Methoxy-4-nitrophenyl)-8-azabicyclo[3.2.1]octan-2-ene (1.65 g, 6.3 mmol) was dissolved in dichloromethane (50 mL). The mixture was cooled in an ice-water bath, triethylamine (1.27 g, 12.6 mmol) was added slowly, and acetic anhydride (771 mg, 7.6 mmol) was then added. The mixture was stirred at 0° C. for 1 h. The mixture was warmed to room temperature and stirred for 2 h. After the reaction, the mixture was washed with water (50 mL×2), and the water phase and the organic phase were separated. The organic phase was dried, and concentrated to get the title compound (1.8 g, yield: 94.7%).

(7) Preparation of 1-(3-(4-amino-3-methoxyphenyl)-8-azabicyclo[3.2.1]octan-8-yl)ethan-1-one

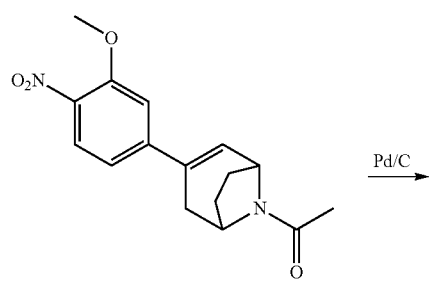

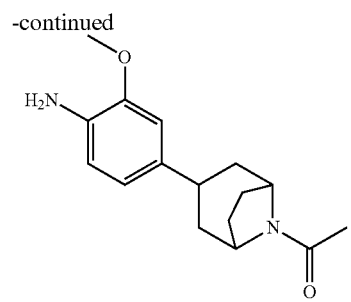

1-(3-(3-Methoxy-4-nitrophenyl)-8-azabicyclo[3.2.1]octan-2-en-8-yl)ethan-1-one (1.8 g, 5.96 mmol) was dissolved in methanol (30 mL). Under the protection of nitrogen gas, palladium-carbon (200 mg) was added, and in the atmosphere of hydrogen gas, the mixture was then stirred at room temperature for 16 h. After the reaction, the mixture was filtrated, and the filtrate was concentrated to get the title compound (1.5 g, yield: 92%).

(8) Preparation of N-(3-((2-((4-(8-acetyl-8-azabicyclo[3.2.1]octan-3-yl)-2-methoxyphenyl)amino)-5-(trifluoromethyl)pyrimidin-4-yl)amino)phenyl)acrylamide

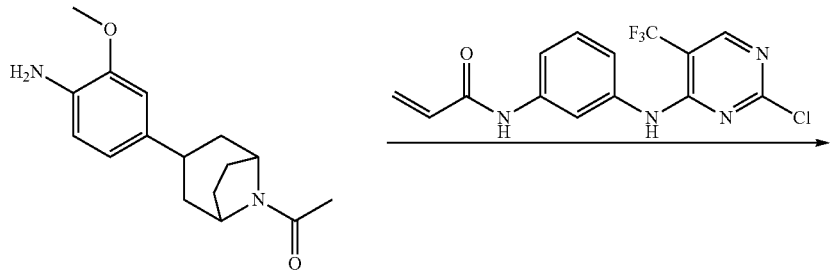

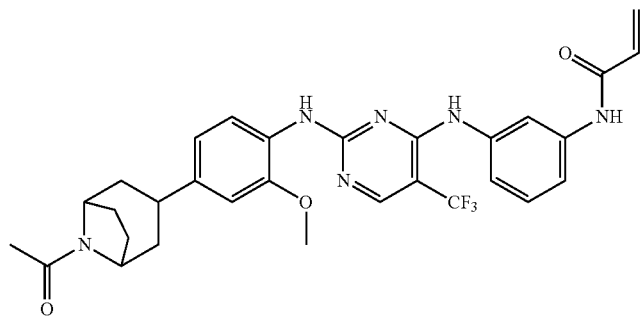

1-(3-(4-Amino-3-methoxyphenyl)-8-azabicyclo[3.2.1]
octan-8-yl)ethan-1-one (100 mg, 0.36 mmol) and N-(3-((2-
chloro-5-(trifluoromethyl)pyrimidin-4-yl)amino)phenyl)
acrylamide (137 mg, 0.4 mmol) were added to isopropanol
(10 mL), and a catalytic amount of trifluoroacetic acid was
added. The system was heated to 70° C. The reaction was
carried out under stirring for 16 h. After the reaction, ethyl
acetate (50 mL) was added to the reaction solution. The
mixture was washed with water (50 mL×2), and the water
phase and the organic phase were separated. The organic
phase was dried, and concentrated. The crude product was
purified by silica gel column chromatography (dichlo-
romethane:methanol=10:1) to get the title compound (51
mg, yield: 24.5%).

Molecular formula: $C_{30}H_{31}F_3N_6O_3$ Molecular weight:
580.60 LC-MS (m/z): 581.3 (M+H$^+$)

$^1$H-NMR (400 MHz, MeOD) δ: 8.25 (s, 1H), 7.66-7.86
(m, 3H), 7.35-7.40 (m, 1H), 7.13 (d, J=7.2 Hz, 1H), 6.79-
6.83 (m, 1H), 6.34-6.52 (m, 3H), 5.78 (d, J=8.8 Hz, 1H),
4.60-4.66 (m, 1H), 4.28-4.33 (m, 1H), 3.87 (s, 3H), 2.34-
2.51 (m, 2H), 2.07-2.14 (m, 4H), 1.93-1.97 (m, 2H), 1.61-
1.80 (m, 4H).

Example 8 Preparation of N-(3-((2-((4-((cis)-5-
acetylhexahydropyrrolo[3,4-c]pyrrol-2(1H)-yl)-2-
methoxyphenyl) amino)-5-(trifluoromethyl)pyrimi-
din-4-yl)amino)phenyl)acrylamide (Compound 9-1)

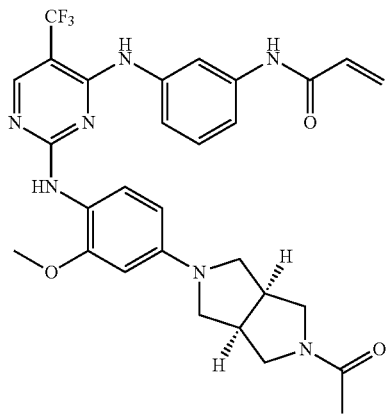 [SMILES: C=CC(=O)Nc1cccc(Nc2nc(Nc3ccc(N4C[C@H]5CN(C(C)=O)C[C@H]5C4)cc3OC)ncc2C(F)(F)F)c1]

(1) Preparation of cis-tert-butyl 5-acetylhexahydro-
pyrrolo[3,4-c]pyrrol-2(1H)-carboxylate

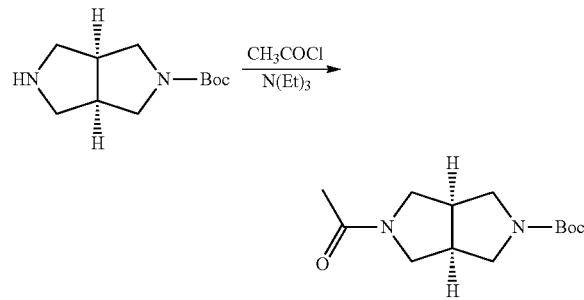

Cis-tert-butyl hexahydropyrrolo[3,4-c]pyrrol-2(1H)-car-
boxylate (318 mg, 1.5 mmol) and triethylamine (227 mg,
2.25 mmol) were dissolved in dichloromethane (5 mL). The
mixture was cooled in an ice-water bath, and acetyl chloride
(142 mg, 1.8 mmol) was added slowly. After the addition,
the mixture was stirred at room temperature for 30 min.
Water (20 mL) was added to the reaction system, and the
resultant mixture was extracted with dichloromethane. The
organic phase was dried, and concentrated to get the crude
product (370 mg), which was used directly in the next step
without purification.

(2) Preparation of 1-((cis)-hexahydropyrrolo[3,4-c]
pyrrol-2-(1H)-yl)ethan-1-one

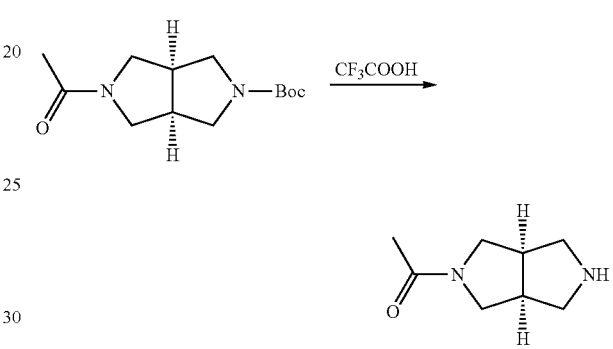

Cis-tert-butyl 5-acetylhexahydropyrrolo[3,4-c]pyrrol-2
(1H)-carboxylate (370 mg) was dissolved in a mixed solvent
of dichloromethane and trifluoroacetic acid (5 mL, 1:1). The
mixture was stirred at room temperature for 30 min, and the
solvent was removed under reduced pressure. Saturated
sodium bicarbonate solution (10 mL) was added, and the
mixture was extracted with dichloromethane. The organic
phase was dried with anhydrous sodium sulfate and con-
centrated. The crude product was purified by silica gel
column chromatography (dichloromethane:methanol=10:1)
to get the product (180 mg, two-step yield: 78%).

(3) Preparation of
4-fluoro-2-methoxy-1-nitrobenzene

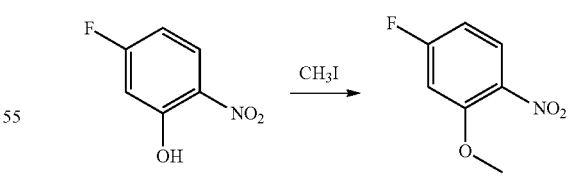

5-Fluoro-2-nitrophenol (7.85 g, 0.05 mol), iodomethane
(8.52 g, 0.06 mol) and potassium carbonate (10.35 g, 0.075
mol) were added to acetonitrile (150 mL). The mixture was
heated at 50° C. for 3 h, and the solvent was removed under
reduced pressure. Water (200 mL) was added, and the
mixture was extracted with ethyl acetate (200 mL). The
organic phase was dried and concentrated to get the product
(8.4 g, yield: 98%).

(4) Preparation of 1-((cis)-5-(3-methoxy-4-nitrophenyl)hexahydropyrrolo[3,4-c]pyrrol-2(1H)-yl)ethan-1-one

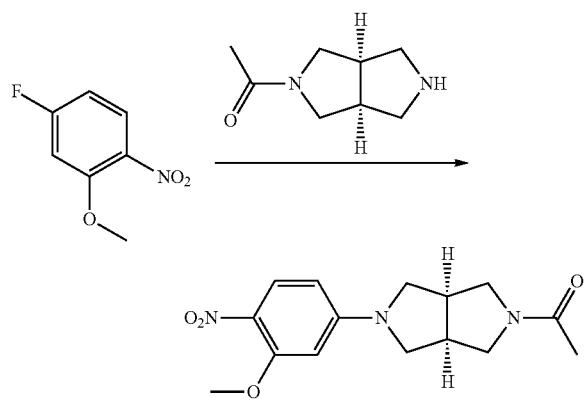

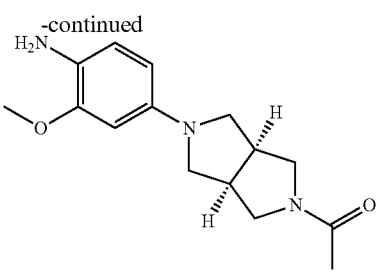

4-Fluoro-2-methoxy-1-nitrobenzene (220 mg, 1.29 mmol), 1-((cis)-hexahydropyrrolo[3,4-c]pyrrol-2-(1H)-yl)ethan-1-one (180 mg, 1.17 mmol) and potassium carbonate (242 mg, 1.76 mmol) were added to N,N-dimethylacetamide (5 mL). The mixture was heated at 120° C. for 5 h. Ethyl acetate (50 mL) was added, and the mixture was washed with saturated saline water (50 mL). The organic phase was dried, concentrated, and purified by silica gel column chromatography (petroleum ether: ethyl acetate=5:1) to get the product (198 mg, yield: 56%).

(5) Preparation of 1-((cis)-5-(4-amino-3-methoxyphenyl)hexahydropyrrolo[3,4-c]pyrrol-2(1H)-yl)ethan-1-one

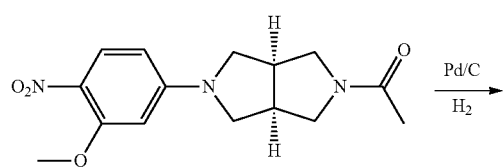

1-((Cis)-5-(3-methoxy-4-nitrophenyl)hexahydropyrrolo[3,4-c]pyrrol-2(1H)-yl)ethan-1-one (198 mg, 0.65 mmol) was dissolved in methanol (5 mL), and palladium-carbon catalyst (10%, 30 mg) was added. Hydrogen gas was introduced to replace air. The mixture was stirred at room temperature for 2 h, then filtrated under suction, and washed with a small amount of methanol. The filtrate was concentrated, and the crude product was purified by silica gel column chromatography (dichloromethane:methanol=10:1) to get the product (149 mg, yield: 84%).

(6) Preparation of N-(3-((2-((4-((cis)-5-acetylhexahydropyrrolo[3,4-c]pyrrol-2(1H)-yl)-2-methoxyphenyl)amino)-5-(trifluoromethyl)pyrimidin-4-yl)amino)phenyl)acrylamide

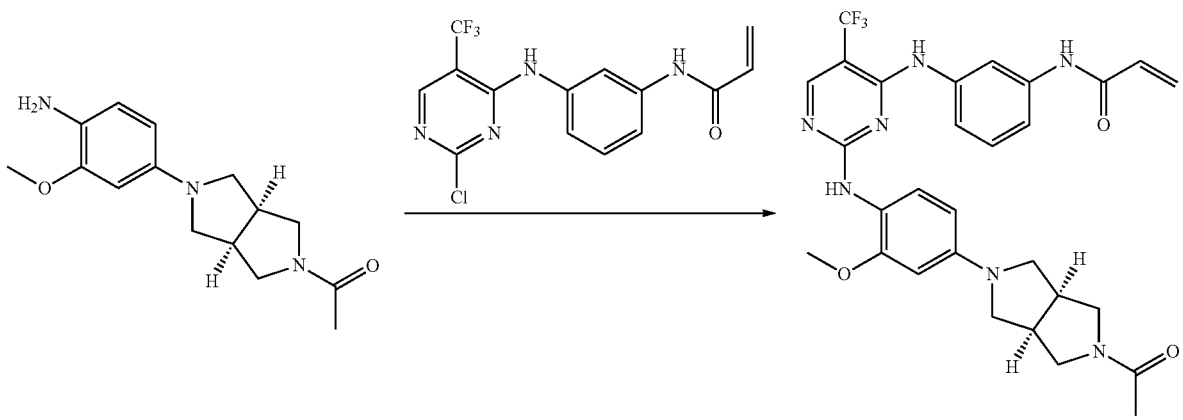

1-((Cis)-5-(4-amino-3-methoxyphenyl)hexahydropyrrolo[3,4-c]pyrrol-2(1H)-yl)ethan-1-one (40 mg, 0.146 mmol), N-(3-((2-chloro-5-(trifluoromethyl)pyrimidin-4-yl)amino)phenyl)acrylamide (50 mg, 0.146 mmol) and a catalytic amount of trifluoroacetic acid (10 mg) were added to isopropanol (3 mL). The mixture was heated at 70° C. for 1.5 h. Ethyl acetate (20 mL) was added, and the mixture was washed with saturated sodium bicarbonate solution (20 mL). The organic phase was dried, concentrated, and separated by preparative chromatography to get the product (24 mg, yield: 28%).

Molecular formula: $C_{29}H_{30}F_3N_7O_3$ Molecular weight: 581 LC-MS (m/z): 582 (M+H$^+$)

$^1$H-NMR (400 MHz, CDCl$_3$) δ: 8.26 (s, 1H), 7.87 (d, J=8.8 Hz, 2H), 7.50-7.78 (m, 2H), 7.41-7.50 (m, 1H), 7.28-7.38 (m, 1H), 7.12-7.19 (m, 1H), 6.84 (s, 1H), 6.42 (dd, $J_1$=1.2 Hz, $J_2$=16.8 Hz, 1H), 6.12-6.20 (m, 1H), 6.11 (d, J=2.0 Hz, 1H), 6.00 (brs., 1H), 5.73 (dd, J=1.2 Hz, $J_2$=10.0 Hz, 1H), 3.85 (s, 3H), 3.74-3.78 (m, 2H), 3.47-3.54 (m, 3H), 3.38 (dd, J=5.2 Hz, $J_2$=10.0 Hz, 1H), 3.17-3.22 (m, 2H), 2.99-3.10 (m, 2H), 2.05 (d, J=3.6 Hz, 3H).

Example 9 Preparation of N-(3-((2-((4-(((cis))-2-acetyloctahydrocyclopenta[c]pyrrol-5-yl)-2-methoxyphenyl) amino)-5-(trifluoromethyl)pyrimidin-4-yl)amino)phenyl)acrylamide (Compound 10)

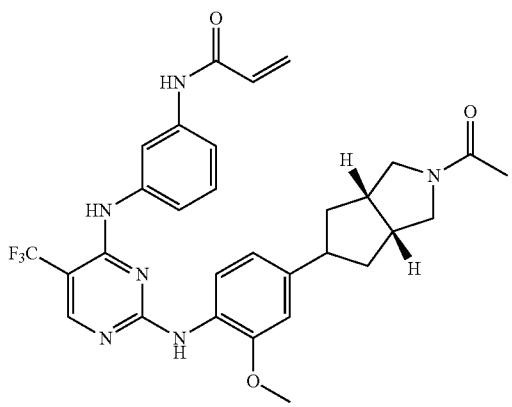 [SMILES: C=CC(=O)Nc1cccc(Nc2nc(Nc3ccc(C4C[C@@H]5CN(C(C)=O)C[C@@H]5C4)cc3OC)ncc2C(F)(F)F)c1]

(1) Preparation of tert-butyl (cis)-5-oxohexahydrocyclopenta[c]pyrrol-2(1H)-carboxylate

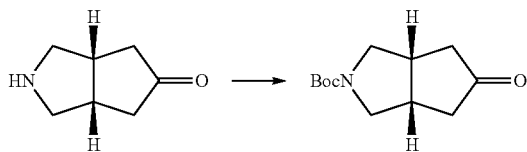 [SMILES: O=C1C[C@H]2CNC[C@H]2C1 ; CC(C)(C)OC(=O)N1C[C@H]2CC(=O)C[C@H]2C1]

(Cis)-hexahydrocyclopenta[c]pyrrol-5(1H)-one (2.0 g, 16 mmol) was dissolved in dichloromethane (50 mL), and di-tert-butyl dicarbonate (5.2 g, 24 mmol), triethylamine (3.2 g, 32 mmol) and 4-dimethylaminopyridine (195 mg, 1.6 mmol) were added. The mixture was reacted at room temperature under stirring for 16 h. After the reaction, water (100 mL) was added, and the water phase and the organic phase were separated. The organic phase was dried with anhydrous sodium sulfate, filtrated, and concentrated to get the crude product. The crude product was purified by silica gel column chromatography (petroleum ether: ethyl acetate=10:1) to get the title compound (3.4 g, yield: 94.4%).

(2) Preparation of tert-butyl (cis)-5-(((trifluoromethyl)sulfonyl)oxy)-3,3a,4,6a-tetrahydrocyclopenta[c]pyrrol-2(1H)-carboxylate

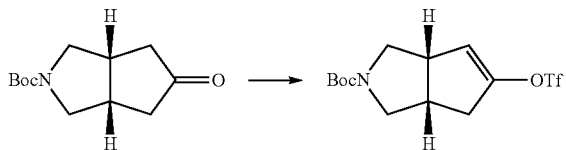 [SMILES: CC(C)(C)OC(=O)N1C[C@H]2CC(=O)C[C@H]2C1 ; CC(C)(C)OC(=O)N1C[C@H]2CC(OS(=O)(=O)C(F)(F)F)=C[C@H]2C1]

Tert-butyl (cis)-5-oxohexahydrocyclopenta[c]pyrrol-2(1H)-carboxylate (3.4 g, 15.1 mmol) was dissolved in tetrahydrofuran (50 mL). At −78° C., a solution of lithium diisopropylamide in tetrahydrofuran/n-heptane/ethylbenzene (11 mL, 22 mmol, 2 M) was slowly added to the system. After stirring for 10 min, a solution of 1,1,1-trifluoro-N-phenyl-N-((trifluoromethyl)sulfonyl)methanesulfonamide (6.47 g, 18.1 mmol) in tetrahydrofuran (20 mL) was added. After stirring for 30 min, the mixture was warmed to room temperature and reacted for 2 h. After the reaction, the mixture was concentrated to get the crude product. The crude product was purified by silica gel column chromatography (petroleum ether: ethyl acetate=20:1) to get the title compound (4.15 g, yield: 77%).

(3) Preparation of tert-butyl (cis)-5-(4,4,5,5-tetramethyl-1,3,2-dioxaborolan-2-yl)-3,3a,4,6a-tetrahydrocyclopenta[c]pyrrol-2(1H)-carboxylate

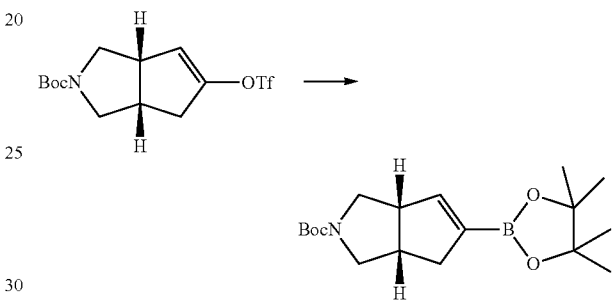

Tert-butyl (cis)-5-(((trifluoromethyl)sulfonyl)oxy)-3,3a,4,6a-tetrahydrocyclopenta[c]pyrrol-2(1H)-carboxylate (4.15 g, 11.6 mmol), bis(pinacolato)diboron (4.4 g, 17.4 mmol), potassium acetate (2.3 g, 23.5 mmol), [1,1'-bis(diphenylphosphino)ferrocene]dichloropalladium (II) dichloromethane complex (473 mg, 0.6 mmol) and 1,1'-bis(diphenyphosphino)ferrocene (332 mg, 0.6 mmol) were dissolved in 1,4-dioxane (50 mL). Under the protection of nitrogen gas, the reaction was carried out under stirring at 80° C. for 16 h. After the reaction, the mixture was cooled to room temperature. Water (100 mL) was added, and the resultant mixture was extracted with ethyl acetate (100 mL×2). The organic phases were combined, dried with anhydrous sodium sulfate, filtrated, and concentrated to get the crude product. The crude produce was purified by silica gel column chromatography (petroleum ether: ethyl acetate=20:1) to get the title compound (2.95 g, yield: 76%).

(4) Preparation of tert-butyl (cis)-5-(3-methoxy-4-nitrophenyl)-3,3a,4,6a-tetrahydrocyclopenta[c]pyrrol-2(1H)carboxylate

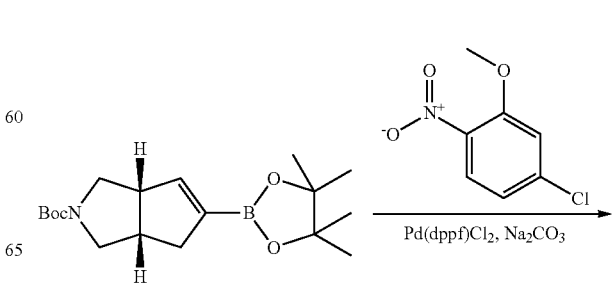

-continued

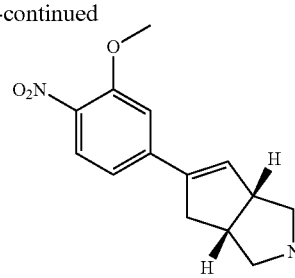

4-Chloro-2-methoxy-1-nitrobenzene (1.36 g, 7.3 mmol) and tert-butyl (cis)-5-(4,4,5,5-tetramethyl-1,3,2-dioxaborolan-2-yl)-3,3a,4,6a-tetrahydrocyclopenta[c]pyrrol-2(1H)-carboxylate (2.95 g, 8.8 mmol) were dissolved in a mixed solvent of 1,4-dioxane (30 mL) and water (10 mL). To the reaction system, sodium carbonate (1.55 g, 14.6 mmol) and [1,1′-bis(diphenylphosphino)ferrocene]dichloropalladium (II) dichloromethane complex (326 mg, 0.4 mmol) were added. Under the protection of nitrogen gas, the reaction was carried out under stirring at 90° C. for 16 h. After the reaction, the mixture was cooled to room temperature. Water (100 mL) was added, and the resultant mixture was extracted with ethyl acetate (100 mL×2). The organic phases were combined, dried with anhydrous sodium sulfate, filtrated, and concentrated to get the crude product. The crude product was purified by silica gel column chromatography (petroleum ether: ethyl acetate=10:1) to get the title compound (1.7 g, yield: 65%).

(5) Preparation of (cis)-5-(3-methoxy-4-nitrophenyl)-1,2,3,3a,4,6a-hexahydrocyclopenta[c] pyrrole

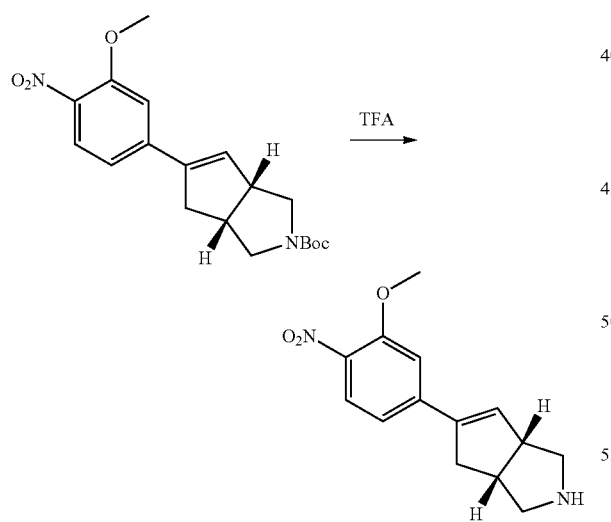

Tert-butyl (cis)-5-(3-methoxy-4-nitrophenyl)-3,3a,4,6a-tetrahydrocyclopenta[c]pyrrol-2(1H)carboxylate (1.7 g, 4.7 mmol) was dissolved in dichloromethane (20 mL), and trifluoroacetic acid (10 mL) was added. The mixture was stirred for 2 h. After the reaction, the reaction solution was concentrated, washed with NaHCO₃ solution and then with saline solution, dried with anhydrous Na₂SO₄, filtrated, and concentrated to get the title compound (1.11 g, yield: 91%).

(6) Preparation of 1-((cis)-5-(3-methoxy-4-nitrophenyl)-3,3a,4,6a-tetrahydrocyclopenta[c]pyrrol-2(1H)-yl 1)ethanone

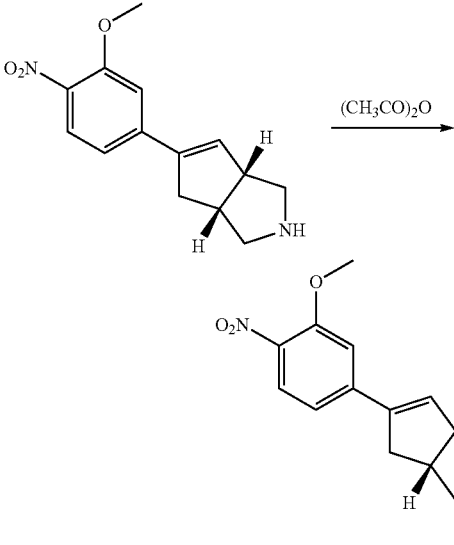

(Cis)-5-(3-methoxy-4-nitrophenyl)-1,2,3,3a,4,6a-hexahydrocyclopenta[c]pyrrole (1.11 g, 4.27 mmol) was dissolved in dichloromethane (50 mL), and cooled in an ice-water bath. Triethylamine (863 mg, 8.54 mmol) was added slowly, followed by the addition of acetic anhydride (653 mg, 6.4 mmol). The mixture was stirred at 0° C. for 1 h, and at room temperature for 2 h. After the reaction, the reaction mixture was washed with water (50 mL×2), dried, filtered, and concentrated to get the title compound (1.1 g, yield: 85%).

(7) Preparation of 1-((cis)-5-(4-amino-3-methoxyphenyl)hexahydrocyclopenta[c]pyrrol-2(1H)-yl)ethanone

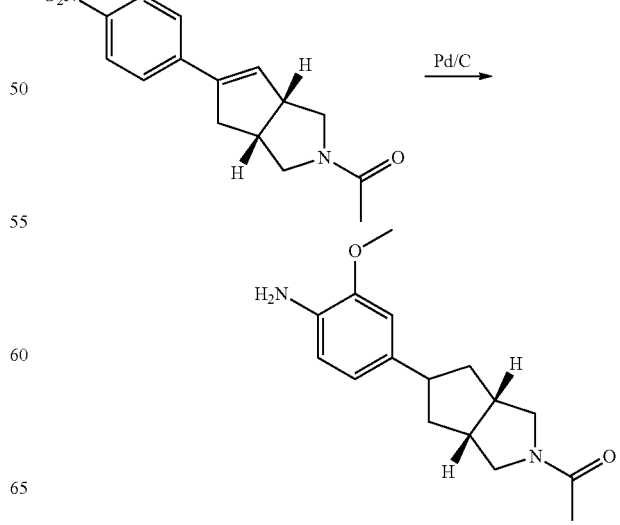

1-((Cis)-5-(3-methoxy-4-nitrophenyl)-3,3a,4,6a-tetrahydrocyclopenta[c]pyrrol-2(1H)-yl)ethanone (1.1 g, 3.64 mmol) was dissolved in methanol (30 mL). Under the protection of nitrogen gas, Pd/C (100 mg) was added to the system, and the system was then reacted in the atmosphere of hydrogen gas under stirring at room temperature for 16 h. After the reaction, the mixture was filtrated, and the filtrate was concentrated to get the title compound (967 mg, yield: 97%).

(8) Preparation of N-(3-((2-((4-((((cis))-2-acetyloctahydrocyclopenta[c]pyrrol-5-yl)-2-methoxyphenyl)amino)-5-(trifluoromethyl)pyrimidin-4-yl)amino)phenyl)acrylamide trated, and purified by silica gel column chromatography (dichloromethane:methanol=10:1) to get the title compound (62 mg, yield: 29.8%).

Molecular formula: $C_{30}H_{31}F_3N_6O_3$ Molecular weight: 580.60 LC-MS (m/z): 581.3 (M+H$^+$) $^1$H-NMR (400 MHz, DMSO-d$_6$) δ: 10.13 (s, 1H), 8.79 (s, 1H), 8.28 (s, 1H), 8.03 (s, 1H), 7.64-7.73 (m, 2H), 7.53 (d, J=8.0 Hz, 1H), 7.26 (t, J=8.0 Hz, 1H), 7.07-7.11 (m, 1H), 6.82 (s, 1H), 6.38-6.45 (m, 2H), 6.20-6.25 (m, 1H), 5.72 (dd, $J_1$=2.0 Hz, $J_2$=10.0 Hz, 1H), 3.78 (s, 3H), 3.58-3.63 (m, 1H), 3.41-3.50 (m, 1H), 3.00-3.16 (m, 1H), 2.64-2.75 (m, 2H), 2.15-2.20 (m, 2H), 1.95 (s, 3H), 1.33-1.39 (m, 2H).

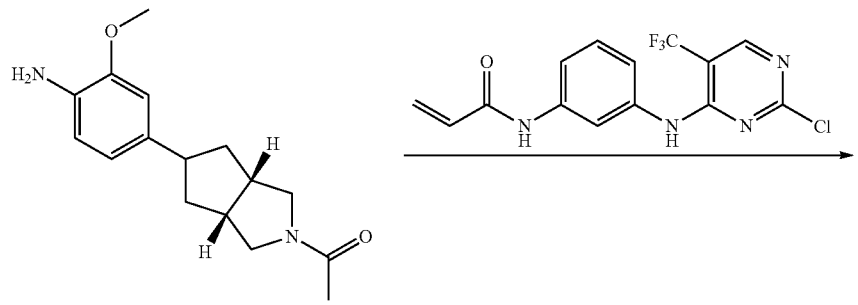

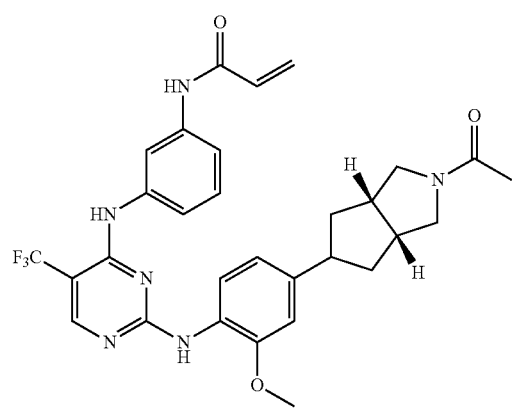

1-((Cis)-5-(4-amino-3-methoxyphenyl)hexahydrocyclopenta[c]pyrrol-2(1H)-yl)ethanone (100 mg, 0.36 mmol) and N-(3-((2-chloro-5-(trifluoromethyl)pyrimidin-4-yl)amino)phenyl)acrylamide (137 mg, 0.4 mmol) were added to isopropanol (10 mL). A catalytic amount of trifluoroacetic acid was added to the system. The system was heated to 70° C. and reacted under stirring for 16 h. After the reaction, ethyl acetate (50 mL) was added to the reaction solution. The mixture was washed with water (50 mL×2), dried, concen- Example 10 Preparation of N-(3-((2-((2-acetyl-7-methoxy-1,2,3,4-tetrahydroisoquinolin-6-yl)amino)-5-(trifluoromethyl)pyrimidin-4-yl)amino)phenyl)acrylamide (Compound 11)

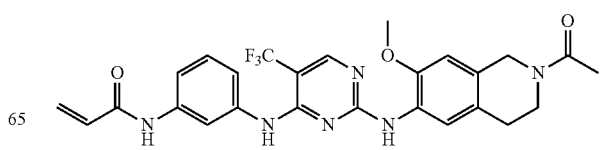

(1) Preparation of N-(3-((2-((2-acetyl-7-methoxy-1,2,3,4-tetrahydroisoquinolin-6-yl)amino)-5-(trifluoromethyl)pyrimidin-4-yl)amino)phenyl)acryl amide

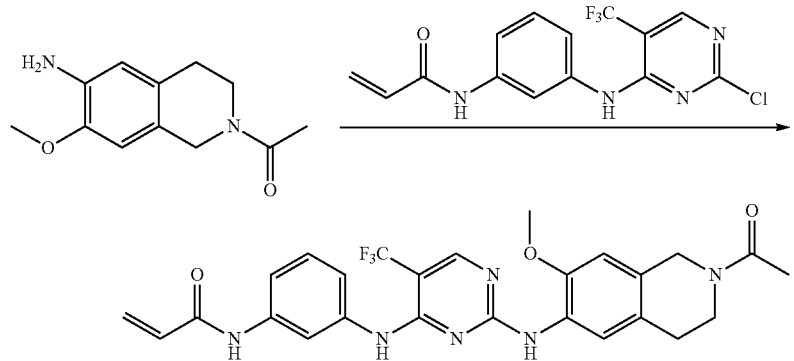

N-(3-((2-chloro-5-(trifluoromethyl)pyrimidin-4-yl)amino)phenyl)acrylamide (343 mg, 1.0 mmol) and 1-(6-amino-7-methoxy-3,4-dihydroisoquinolin-2(1H)-yl)ethanone (220 mg, 1.0 mmol) were dissolved in isopropanol (40 mL), and trifluoroacetic acid (34 mg, 0.3 mmol) was added. Under the protection of nitrogen gas, the reaction was carried out at 70° C. for 16 h. The resultant mixture was cooled to room temperature, and concentrated. Saturated sodium bicarbonate solution was added, and the mixture was extracted with ethyl acetate (100 mL×3). The organic phases were combined, washed with saturated NaCl aqueous solution, dried with anhydrous sodium sulfate, and concentrated. The crude product was purified by silica gel column chromatography (methanol: dichloromethane=0-1:10) to get the title compound as a greyish-white solid (360 mg, yield: 68%).

Molecular formula: $C_{26}H_{25}F_3N_6O_3$ Molecular weight: 526.5 LC-MS (m/z): 527.3 (M+H$^+$)

$^1$H-NMR (400 MHz, DMSO-d$_6$) δ: 10.17-10.19 (m, 1H), 8.81 (brs, 1H), 8.33 (s, 1H), 8.05 (s, 1H), 7.70-7.80 (m, 1H), 7.49-7.61 (m, 2H), 7.28-7.32 (m, 1H), 7.10-7.16 (m, 1H), 6.80-6.82 (m, 1H), 6.37-6.44 (m, 1H), 6.21-6.27 (m, 1H), 5.72-5.76 (m, 1H), 4.47-4.52 (m, 2H), 3.76-3.77 (m, 3H), 3.49-3.54 (m, 2H), 2.31-2.45 (m, 2H), 2.04 (s, 3H).

Example 11 Preparation of N-(6-((2-((2-acetyl-7-methoxy-1,2,3,4-tetrahydroisoquinolin-6-yl)amino)-5-(trifluoromethyl)pyrimidin-4-yl)amino)pyridin-2-yl)acrylamide (Compound 12)

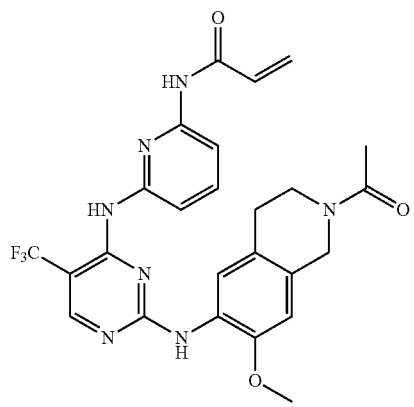 [SMILES: C=CC(=O)Nc1cccc(Nc2nc(Nc3cc4c(cc3OC)CN(C(C)=O)CC4)ncc2C(F)(F)F)n1]

(1) N-(6-((2-((2-acetyl-7-methoxy-1,2,3,4-tetrahydroisoquinolin-6-yl)amino)-5-(trifluoromethyl)pyrimidin-4-yl)amino)pyridin-2-yl)acrylamide

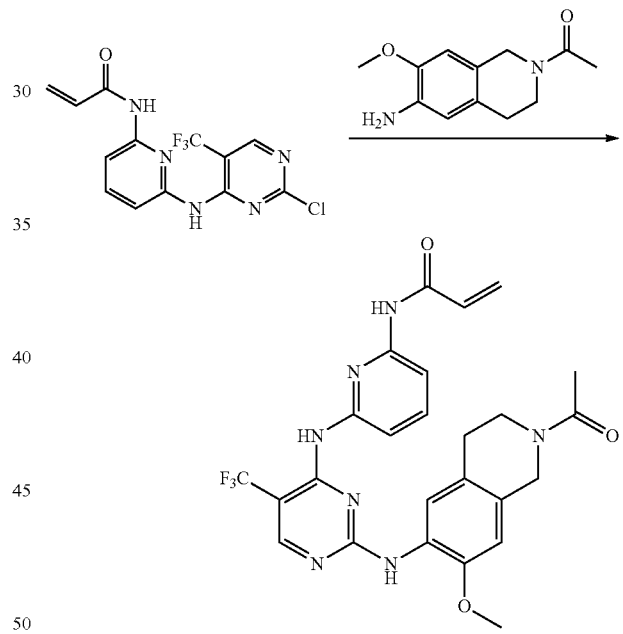

N-(6-((2-chloro-5-(trifluoromethyl)pyrimidin-4-yl)amino)pyridin-2-yl)acrylamide (200 mg, 0.58 mmol) and 1-(6-amino-7-methoxy-3,4-dihydroisoquinolin-2(1H)-yl)ethan-1-one (128 mg, 0.58 mmol) were dissolved in isopropanol (40 mL), and trifluoroacetic acid (20 mg, 0.17 mmol) was added. Under the protection of nitrogen gas, the reaction was carried out at 70° C. for 16 h. The resultant mixture was cooled to room temperature and concentrated. Saturated sodium bicarbonate solution was added, and the mixture was extracted with ethyl acetate (100 mL×3). The organic phases were combined, washed with saturated saline solution, dried with anhydrous sodium sulfate, and concentrated. The crude product was purified by silica gel column chromatography (methanol: dichloromethane=0-1:10) to get the title compound as a greyish-white solid (125 mg, yield: 40.9%).

Molecular formula: $C_{25}H_{24}F_3N_7O_3$ Molecular weight: 527.5 LC-MS (m/z): 528.2 (M+H$^+$)

$^1$H-NMR (400 MHz, DMSO-d$_6$) δ: 8.38 (s, 1H), 7.97-8.14 (m, 4H), 7.65-7.74 (m, 2H), 7.36 (s, 1H), 6.62-6.65 (m, 1H), 6.47-6.51 (m, 1H), 6.28-6.35 (m, 1H), 5.84 (d, J=10.4 Hz, 1H), 4.60-4.70 (m, 2H), 3.83-3.89 (m, 3H), 3.80-3.82 (m, 2H), 2.71-2.76 (m, 2H), 2.20-2.21 (m, 3H).

Example 12 Preparation of N-(3-((2-((2-acetyl-6-methoxyisoindolin-5-yl)amino)-5-(trifluoromethyl)pyrimidin-4-yl)amino)phenyl)acrylamide (Compound 13)

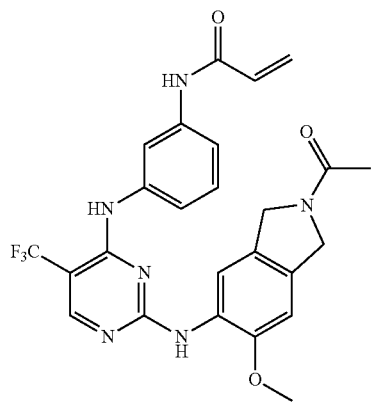 [SMILES: C=CC(=O)Nc1cccc(Nc2nc(Nc3cc4c(cc3OC)CN(C(C)=O)C4)ncc2C(F)(F)F)c1]

(1) Preparation of methyl 2-cyano-4-methoxybenzoate

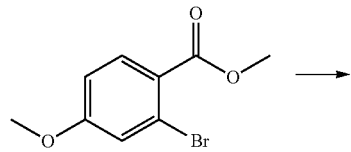

Methyl 2-bromo-4-methoxybenzoate (20 g, 0.082 mol) was dissolved in N,N-dimethylformamide (100 mL), and cuprous cyanide (10.95 g, 0.123 mol) was added. The reaction was carried out at 150° C. for 4 h. The mixture was cooled, and was poured into saturated ammonium chloride aqueous solution. The mixture was extracted with ethyl acetate (150 mL×3). The organic phases were combined, dried with anhydrous sodium sulfate, filtrated, and concentrated. The crude product was purified by silica gel column chromatography (petroleum ether: ethyl acetate=5:1) to get the title compound (9.8 g, yield: 62%).

(2) Preparation of 5-methoxyisoindolin-1-one

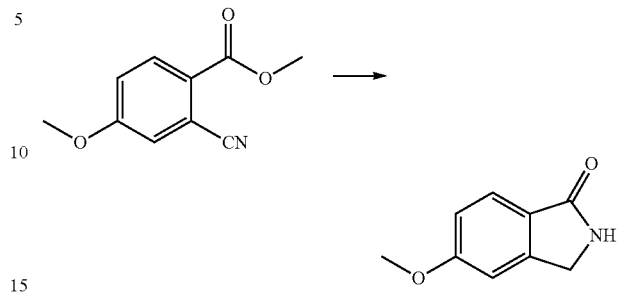

Methyl 2-cyano-4-methoxybenzoate (5 g, 0.026 mmol) was dissolved in methanol (150 mL), and ammonia water (10 mL) and Raney Nickel (1 g) were added. At the atmosphere of hydrogen gas, the reaction was carried out at room temperature overnight. The mixture was filtrated, and the filtrate was concentrated. The crude product was purified by silica gel column chromatography (petroleum ether: ethyl acetate=1:1) to get the title compound (3.2 g, yield: 76%).

(3) Preparation of 5-methoxy-6-nitroisoindolin-1-one

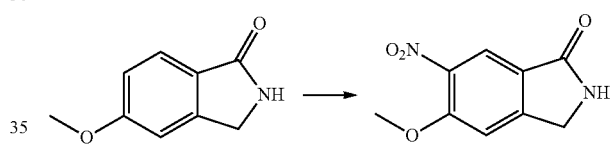

5-Methoxyisoindolin-1-one (3 g, 0.018 mol) was dissolved in acetonitrile (10 mL) and trifluoroacetic anhydride (10 mL), and at 0° C., potassium nitrate (2 g, 0.0198 mmol) was added in batches. The mixture was stirred at room temperature for 1 h, and the reaction mixture was poured into ice-water. The mixture was extracted with ethyl acetate (30 mL×3), washed with saturated sodium bicarbonate solution, dried with anhydrous sodium sulfate, filtrated, and concentrated. The crude product was purified by silica gel column chromatography (eluted with ethyl acetate) to get the title compound (1.1 g, yield: 29%).

(4) Preparation of tert-butyl 5-methoxy-6-nitroisoindolin-2-carboxylate

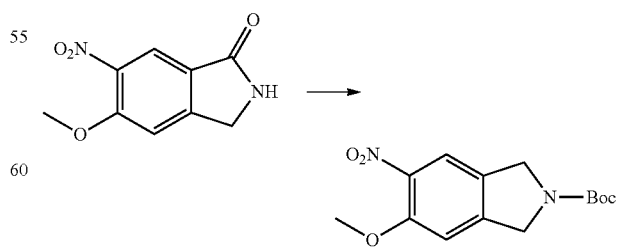

5-Methoxy-6-nitroisoindolin-1-one (1 g, 4.8 mmol) was dissolved in tetrahydrofuran (50 mL). At 0° C., borane-dimethyl sulfide solution (2 mol/L, 9.6 mL, 19.2 mmol) was added dropwisely. After the addition, the reaction was carried out under reflux overnight. The mixture was cooled to 0° C., methanol (10 mL) was added dropwisely to quench the reaction. Hydrochloric acid (4 mol/L, 10 mL) was added, and the mixture was refluxed for 4 h. After cooling, the mixture was dried by evaporation under rotation, and diluted with water. NaOH solution was added to adjust pH of the mixture to 10. Di-tert-butyl dicarbonate (1.05 g, 4.8 mmol) was added, and the resultant mixture was stirred at room temperature for 1 h and extracted with ethyl acetate (30 mL×3). The organic phases were combined, dried with anhydrous sodium sulfate, filtrated, and concentrated. The crude product was purified by silica gel column chromatography (petroleum ether: ethyl acetate=2:1) to get the title compound (0.45 g, yield: 32%).

(5) Preparation of 5-methoxy-6-nitroisoindoline

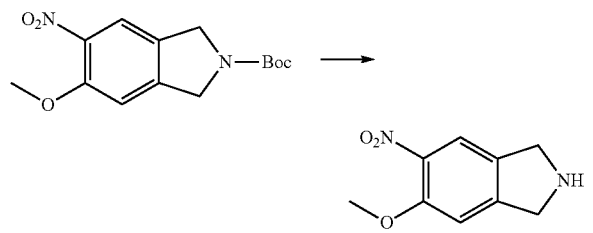

Tert-butyl 5-methoxy-6-nitroisoindolin-2-carboxylate (0.4 g, 1.36 mmol) was dissolved in dichloromethane (3 mL), and trifluoroacetic acid (3 mL) was added. The reaction was carried out at room temperature for 1 h. The mixture was concentrated, and the crude product was purified by silica gel column chromatography (petroleum ether: ethyl acetate=2:1) to get the title compound (0.25 g, yield: 96%).

(6) Preparation of 1-(5-methoxy-6-nitroisoindolin-2-yl)ethan-1-one

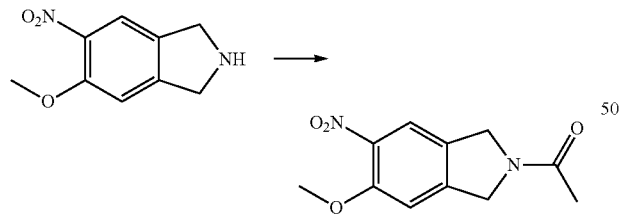

5-Methoxy-6-nitroisoindoline (0.25 g, 1.29 mmol) was dissolved in dichloromethane (5 mL), and triethylamine (196 mg, 1.94 mmol) was added slowly. The mixture was cooled to 0° C., and acetyl chloride (121 mg, 1.55 mmol) was added. After the addition, the mixture was warmed to room temperature and stirred for 2 h. The reaction solution was washed with saturated sodium bicarbonate solution, and the organic phase was concentrated. The crude product was purified by silica gel column chromatography (petroleum ether: ethyl acetate=5:1) to get the title compound (0.22 g, yield: 72%).

(7) Preparation of 1-(5-amino-6-methoxyisoindolin-2-yl)ethan-1-one

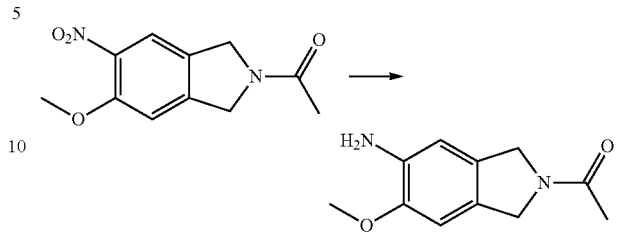

1-(5-Methoxy-6-nitroisoindolin-2-yl)ethan-1-one (0.22 g, 0.93 mmol) was dissolved in tetrahydrofuran (10 mL), and zinc powder (1.21 g, 18.6 mmol) was added. The mixture was cooled to 0° C., and hydrochloric acid (4 mol/L, 2.33 mL, 9.3 mmol) was added. After the addition, the mixture was warmed to room temperature and stirred for 1 h. The mixture was filtrated, and the filtrate was concentrated. The crude product was purified by silica gel column chromatography (petroleum ether: ethyl acetate=1:1) to get the title compound (0.15 g, yield: 79%).

(8) Preparation of N-(3-((2-((2-acetyl-6-methoxyisoindolin-5-yl)amino)-5-(trifluoromethyl)pyrimidin-4-yl)amino)phenyl)acrylamide

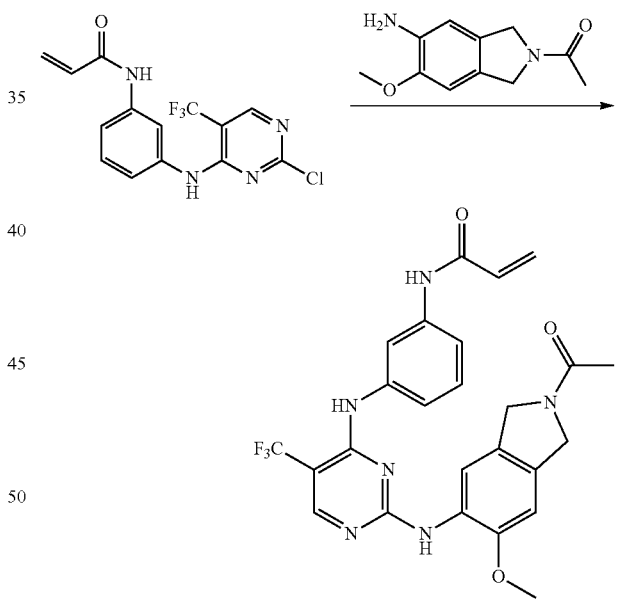

N-(3-((2-chloro-5-(trifluoromethyl)pyrimidin-4-yl)amino)phenyl)acrylamide (100 mg, 0.29 mmol) and 1-(5-amino-6-methoxyisoindolin-2-yl)ethan-1-one (60 mg, 0.29 mmol) were dissolved in isopropanol (8 mL), and trifluoroacetic acid (6.6 mg, 0.058 mmol) was added. The mixture was heated to 75° C. and the reaction was carried out overnight. The resultant mixture was cooled to room temperature, and concentrated in vacuum. The crude product was purified by silica gel column chromatography (methanol: dichloromethane=0-1:20, containing 0.5% triethylamine) to get the title compound as a white solid (35 mg, yield: 23.5%).

Molecular formula: $C_{25}H_{23}F_3N_6O_3$ Molecular weight: 512.5 LC-MS (m/z): 513 (M+H+)

1H-NMR (400 MHz, MeOD-d4) δ: 8.27 (s, 1H), 8.06-7.91 (m, 1H), 7.81 (s, 1H), 7.62-7.39 (m, 2H), 7.16-7.12 (m, 1H), 6.91-6.89 (m, 1H), 6.46-6.29 (m, 2H), 5.77-5.73 (m, 1H), 4.60 (s, 4H), 3.89-3.88 (m, 3H), 2.17-2.15 (m, 3H).

Example 13 Preparation of N-(3-((2-((2-acetyl-7-methoxy-1,2,3,4-tetrahydroisoquinolin-6-yl)amino)-5-(trifluoromethyl)pyrimidin-4-yl)amino)phenyl) acrylamide (Compound 14)

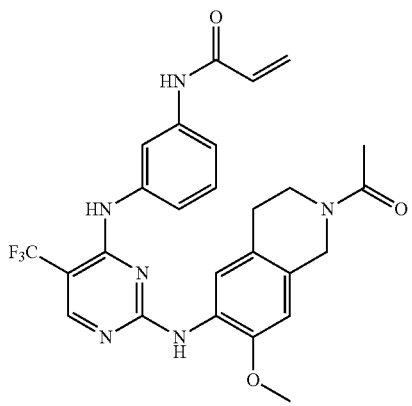 [SMILES: C=CC(=O)Nc1cccc(Nc2nc(Nc3cc4c(cc3OC)CN(C(C)=O)CC4)ncc2C(F)(F)F)c1]

(1) Preparation of 1-(6-methoxy-3,4-dihydroisoquinolin-2(1H)-yl)ethan-1-one

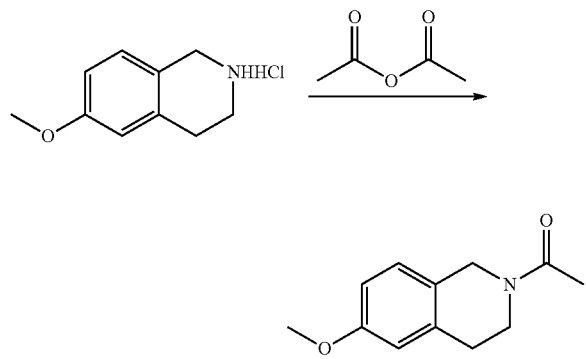

6-Methoxy-1,2,3,4-tetrahydroisoquinoline hydrochloride (2.0 g, 10 mmol) and triethylamine (3.03 g, 30 mmol) were dissolved in dichloromethane (100 mL), and acetic anhydride (1.53 g, 15 mmol) was added. The mixture was reacted at room temperature for 2 h. Water (50 mL) was added, and the water phase and the organic phase were separated. The water phase was extracted with dichloromethane (50 mL×2). The organic phases were combined, washed with saturated saline solution, dried with anhydrous sodium sulfate, and concentrated in vacuum to get the title compound as a light yellow oil (2.2 g crude product).

(2) Preparation of 1-(6-methoxy-7-nitro-3,4-dihydroisoquinolin-2(1H)-yl)ethan-1-one

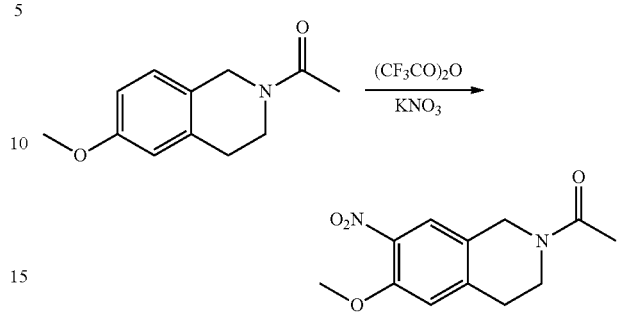

1-(6-Methoxy-3,4-dihydroisoquinolin-2(1H)-yl)ethan-1-one (2.2 g crude product, 10 mmol) was dissolved in acetonitrile (50 mL). The mixture was cooled in an ice-water bath, and trifluoroacetic anhydride (10 mL) and potassium nitrate (1.21 g, 12 mmol) were added. The reaction was carried out in an ice-water bath for 4 h. Methanol (20 mL) was added, and the solvent was removed by distillation under reduced pressure. Water (50 mL) and ethyl acetate (100 mL) were added, and the water phase and the organic phase were separated. The water phase was extracted with ethyl acetate (100 mL×2). The organic phases were combined, washed with saturated saline solution, dried with anhydrous sodium sulfate, and concentrated in vacuum. The crude product was purified by silica gel column chromatography (ethyl acetate: petroleum ether=0-1:7) to get the title compound as a light yellow solid (1.2 g, yield: 48%).

(3) Preparation of 1-(7-amino-6-methoxy-3,4-dihydroisoquinolin-2(1H)-yl)ethan-1-one

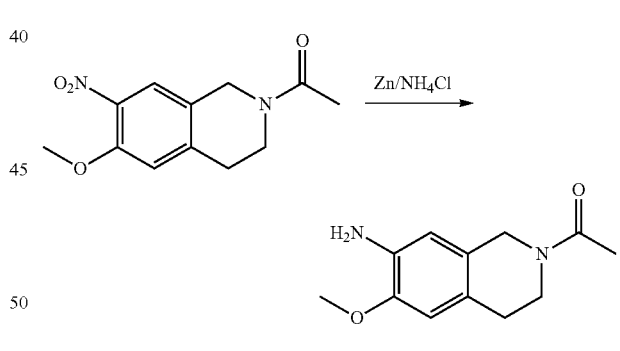

1-(6-Methoxy-7-nitro-3,4-dihydroisoquinolin-2(1H)-yl)ethan-1-one (400 mg, 1.6 mmol) was dissolved in ethanol and water (2:1, 60 mL), and saturated ammonium chloride aqueous solution (10 mL) and zinc powder (523 mg, 8.0 mmol) were added. The mixed was heated to 70° C. and reacted for 3 h. The resultant mixture was cooled to room temperature, and filtrated through diatomaceous earth. The filtrate was concentrated, and water (50 mL) was added. The mixture was extracted with ethyl acetate (100 mL×3). The organic phases were combined, washed with saturated saline solution, dried with anhydrous sodium sulfate, and concentrated. The crude product was purified by silica gel column chromatography (ethyl acetate: petroleum ether=0-1:4) to get the title compound as a light yellow oil (260 mg, yield: 74%).

(4) Preparation of N-(3-((2-((2-acetyl-7-methoxy-1,2,3,4-tetrahydroisoquinolin-6-yl)amino)-5-(trifluoromethyl)pyrimidin-4-yl)amino)phenyl)acrylamide

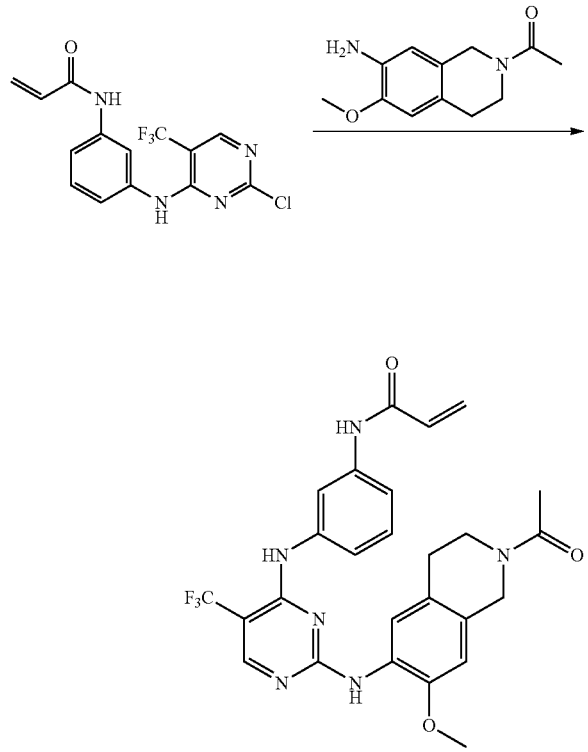

N-(3-((2-chloro-5-(trifluoromethyl)pyrimidin-4-yl)amino)phenyl)acrylamide (335 mg, 0.98 mmol) and 1-(7-amino-6-methoxy-3,4-dihydroisoquinolin-2(1H)-yl)ethan-1-one (260 mg, 1.18 mmol) were dissolved in isopropanol (30 mL), and trifluoroacetic acid (223 mg, 1.96 mmol) was added. Under the protection of nitrogen gas, the reaction was carried out at 70° C. for 16 h. The resultant mixture was cooled to room temperature and concentrated. Saturated sodium bicarbonate solution (50 mL) was added, and the mixture was extracted with ethyl acetate (100 mL×3). The organic phases were combined, washed with saturated saline solution, dried with anhydrous sodium sulfate, and concentrated. The crude product was purified by silica gel column chromatography (methanol: dichloromethane=0-1:15) to get the title compound as a greyish-white solid (300 mg, yield: 58%).

Molecular formula: $C_{26}H_{25}F_3N_6O_3$ Molecular weight: 526.51 LC-MS (m/z): 527.3 (M+H+)

1H-NMR (400 MHz, DMSO-d6) δ: 10.18-10.11 (m, 1H), 8.85-8.70 (m, 1H), 8.34-8.33 (m, 1H), 8.05-8.04 (m, 1H), 7.82-7.77 (m, 1H), 7.56-7.30 (m, 3H), 7.20-7.12 (m, 1H), 6.78-6.77 (m, 1H), 6.41-6.37 (m, 1H), 6.25-6.20 (m, 1H), 5.75-5.71 (m, 1H), 4.23-4.10 (m, 2H), 3.79-3.77 (m, 3H), 3.58-3.55 (m, 2H), 2.77-2.74 (m, 1H), 2.65-2.63 (m, 1H), 2.06-2.01 (m, 3H).

Example 14 Preparation of N-(3-((2-((2-acetyl-4-methoxyisoindolin-5-yl)amino)-5-(trifluoromethyl)pyrimidin-4-yl)amino)phenyl)acrylamide (Compound 15)

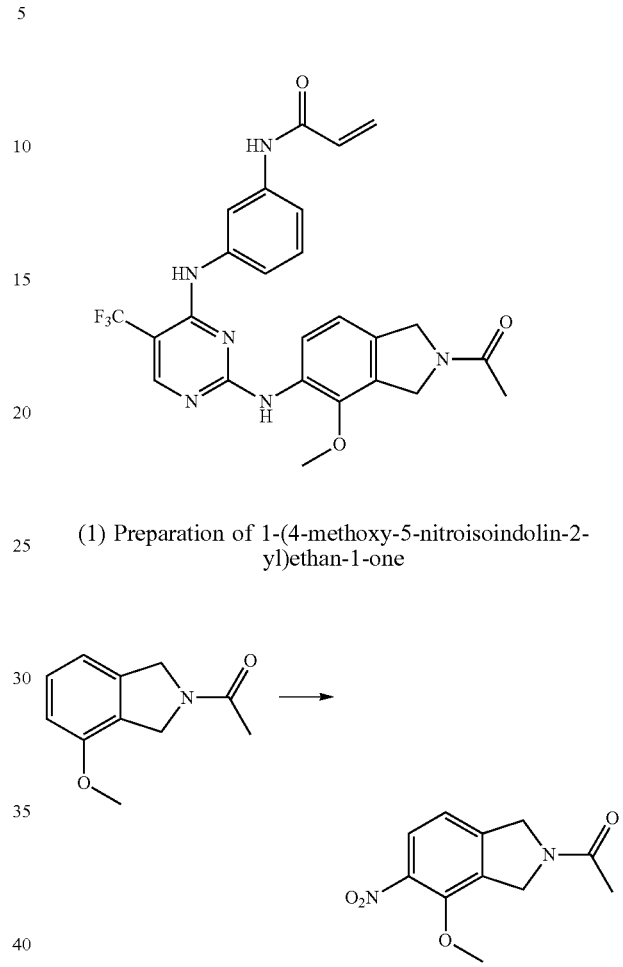

(1) Preparation of 1-(4-methoxy-5-nitroisoindolin-2-yl)ethan-1-one

At −20° C., 1-(4-methoxyisoindolin-2-yl)ethan-1-one (2.0 g, 10.46 mmol) was dissolved in a mixed solution of acetic acid and acetic anhydride (10 mL, at a volume ratio of 1:1), and fuming nitric acid (725 mg, 11.5 mmol) was added dropwisely. After the addition, the mixture was warmed to room temperature and reacted for 30 min, and then cooled to 0° C. Water (30 mL) was added to the reaction solution, and the reaction solution was extracted with ethyl acetate (50 mL×2). The organic phases were combined, dried with anhydrous sodium sulfate, concentrated, and purified by silica gel column chromatography (petroleum ether: ethyl acetate=1:1) to get the title compound (0.77 g, yield: 31%).

(2) Preparation of 1-(5-amino-4-methoxyisoindolin-2-yl)ethan-1-one

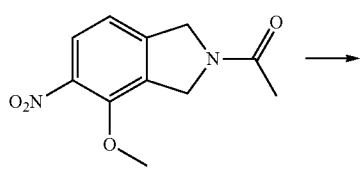

-continued

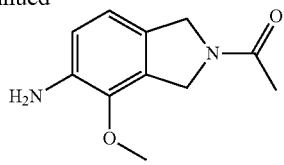

1-(4-Methoxy-5-nitroisoindolin-2-yl)ethan-1-one (0.6 g, 2.54 mmol) and palladium-carbon (10%, 60 mg) were suspended in methanol (50 mL). The system was vacuumized, and hydrogen gas was introduced. The mixture was reacted at room temperature for 3 h, and filtrated. The filtrate was concentrated, and purified by silica gel column chromatography (dichloromethane:methanol=20:1) to get the title compound (0.47 g, yield: 90%).

(3) Preparation of N-(3-((2-((2-acetyl-4-methoxy-isoindolin-5-yl)amino)-5-(trifluoromethyl)pyrimidin-4-yl)amino)phenyl)acrylamide

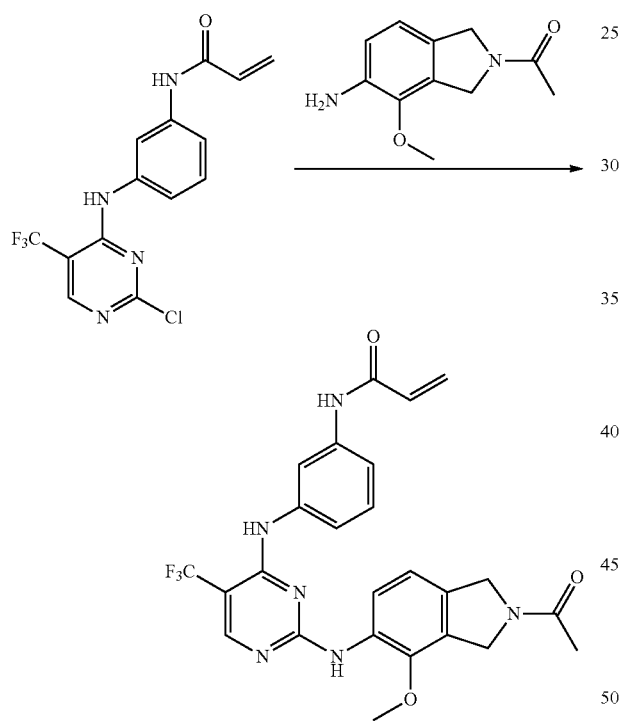

1-(5-Amino-4-methoxyisoindolin-2-yl)ethan-1-one (100 mg, 0.48 mmol) and N-(3-((2-chloro-5-(trifluoromethyl)pyrimidin-4-yl)amino)phenyl)acrylamide (164.5 mg, 0.48 mmol) were dissolved in isopropanol (10 mL), and a drop of trifluoroacetic acid was added. The mixture was heated to 70° C. and reacted for 12 h. After the reaction, the solution was dried by distillation, and purified by silica gel column chromatography (dichloromethane:methanol=10:1) to get the title compound (115.6 mg, yield: 47%).

Molecular formula: C25H23F3N6O3 Molecular weight: 512.48 LC-MS (m/z): 513.2 (M+H+)

1H-NMR (400 MHz, DMSO-d6) δ: 10.15 (s, 1H), 8.74 (s, 1H), 8.48 (d, J=4.8 Hz, 1H), 8.33 (s, 1H), 7.80 (d, J=10.4 Hz, 1H), 7.61-7.64 (m, 1H), 7.42-7.47 (m, 1H), 7.23-7.27 (m, 1H), 7.14 (d, J=8.0 Hz, 1H), 6.70-6.75 (m, 1H), 6.39-6.45 (m, 1H), 6.24 (dd, J1=4.8 Hz, J2=2.4 Hz, 1H), 5.72-5.75 (m, 1H), 4.88 (s, 1H), 4.68 (d, J=18.0 Hz, 2H), 4.50 (s, 1H), 3.75 (d, J=3.6 Hz, 3H), 2.05 (d, J=10.4 Hz, 3H).

Example 15 Preparation of N-(3-((2-((2-acetyl-5-methoxy-1,2,3,4-tetrahydroisoquinolin-6-yl)amino)-5-(trifluoromethyl)pyrimidin-4-yl)amino)phenyl)acrylamide (Compound 16)

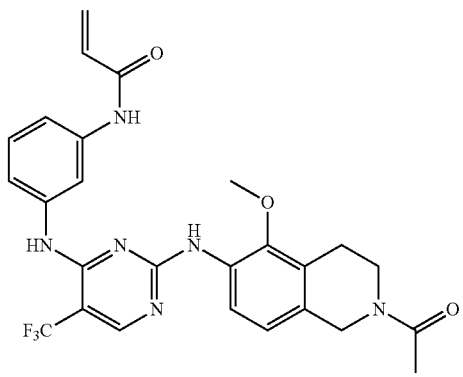 [SMILES: C=CC(=O)Nc1cccc(Nc2nc(Nc3ccc4c(c3OC)CCN(C(C)=O)C4)ncc2C(F)(F)F)c1]

(1) Preparation of 2-acetyl-1,2,3,4-tetrahydroisoquinoline-5-yl acetate

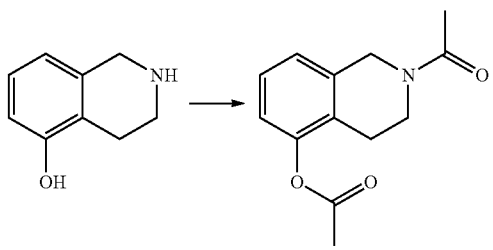 [SMILES: Oc1cccc2c1CCNC2 ; CC(=O)Oc1cccc2c1CCN(C(C)=O)C2]

In an ice-water bath, 1,2,3,4-tetrahydroisoquinoline-5-ol (1.49 g, 10 mmol) and triethylamine (4.04 g, 40 mmol) were dissolved in dichloromethane (40 mL), and acetyl chloride (2.4 g, 30 mmol) was slowly added dropwisely. After the addition, the mixture was warmed to room temperature and reacted for 2 h. After the reaction, the filtrate was concentrated, and purified by silica gel column chromatography (petroleum ether: ethyl acetate=5:1) to get the title compound (1.8 g, yield: 77%).

(2) Preparation of 1-(5-hydroxy-3,4-dihydroisoquinolin-2(1H)-yl)ethan-1-one

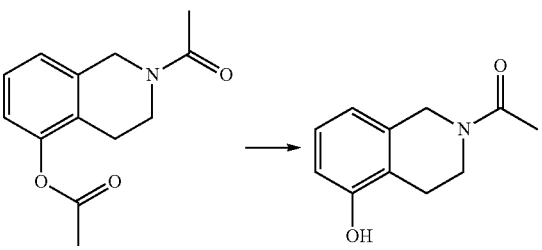 [SMILES: CC(=O)Oc1cccc2c1CCN(C(C)=O)C2 ; CC(=O)N1CCc2c(O)cccc2C1]

2-Acetyl-1,2,3,4-tetrahydroisoquinoline-5-yl acetate (1.17 g, 5 mmol) was dissolved in methanol (10 mL), and NaOH (1M, 15 mL) was added dropwise. The reaction was carried out at room temperature for 8 h. After the reaction, the solvent was dried by distillation to get the title compound as a solid (1.5 g, crude product), which was directly used in the next step without purification.

(3) Preparation of 1-(5-methoxy-3,4-dihydroisoquinolin-2(1H)-yl)ethan-1-one

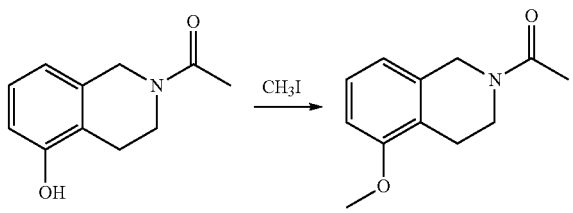

1-(5-Hydroxy-3,4-dihydroisoquinolin-2(1H)-yl)ethan-1-one (1.5 g crude product) was dissolved in DMF (20 mL), potassium carbonate (1.38 g, 10 mol) was added, and iodomethane (1.07 g, 7.5 mmol) was added dropwise under stirring. The mixture was reacted at room temperature under stirring for 8 h. After the reaction, water (50 mL) was added to the reaction solution. The reaction solution was extracted with ethyl acetate (50 mL×2), and the organic phases were combined, and dried with anhydrous sodium sulfate. The filtrate was concentrated, and purified by silica gel column chromatography (petroleum ether: ethyl acetate=5:1) to get the title compound (0.78 g, two-step yield: 76%).

(4) Preparation of 1-(5-methoxy-6-nitro-3,4-dihydroisoquinolin-2(1H)-yl)ethan-1-one

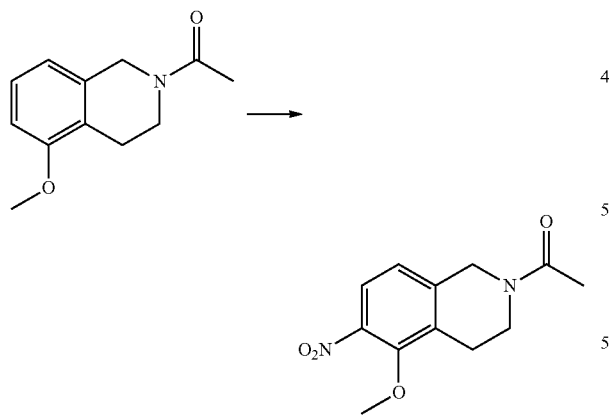

At −20° C., 1-(5-methoxy-3,4-dihydroisoquinolin-2(1H)-yl)ethan-1-one (0.7 g, 3.4 mmol) was dissolved in a mixed solution of acetic acid and acetic anhydride (5 mL,V:V=1:1), and fuming nitric acid (14 mg) was added dropwise. After the addition, the mixture was warmed to room temperature and reacted for 30 min, and then cooled to 0° C. Water (10 mL) was added to the reaction solution, and the reaction solution was extracted with ethyl acetate (30 mL×2). The organic phases were combined, dried with anhydrous sodium sulfate, concentrated, and purified by silica gel column chromatography (petroleum ether: ethyl acetate=1:1) to get the title compound (0.3 g, yield: 35%).

(5) Preparation of 1-(6-amino-5-methoxy-3,4-dihydroisoquinolin-2(1H)-yl)ethan-1-one

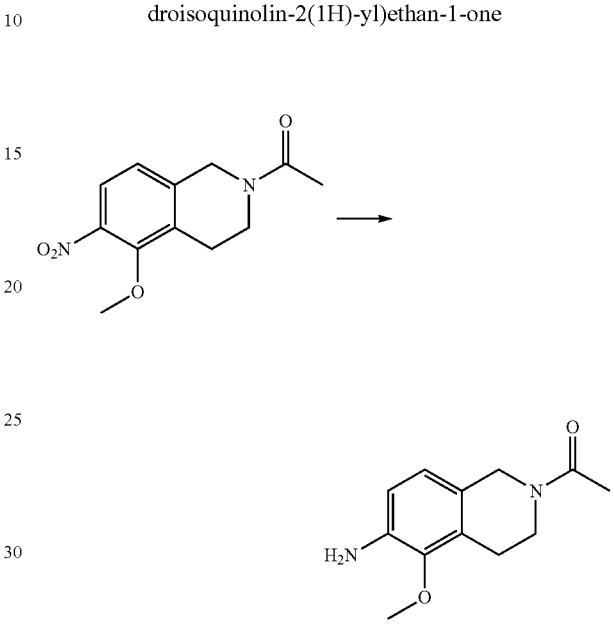

1-(5-Methoxy-6-nitro-3,4-dihydroisoquinolin-2(1H)-yl)ethan-1-one (0.3 g, 1.2 mmol) and palladium-carbon (30 mg) were suspended in methanol (20 mL). The system was vacuumized, and hydrogen gas was introduced. The mixture was reacted at room temperature for 6 h, filtrated, concentrated, and purified by column chromatography (dichloromethane:methanol=10:1) to get the title compound (0.23 g, yield: 87%).

(6) Preparation of N-(3-((2-((2-acetyl-5-methoxy-1,2,3,4-tetrahydroisoquinolin-6-yl)amino)-5-(trifluoromethyl)pyrimidin-4-yl)amino)phenyl)acrylamide

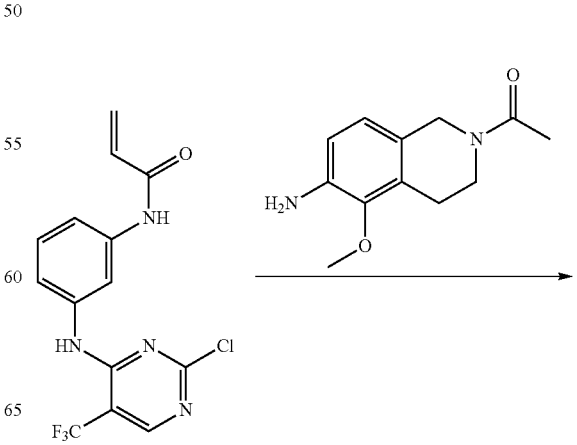

117

-continued

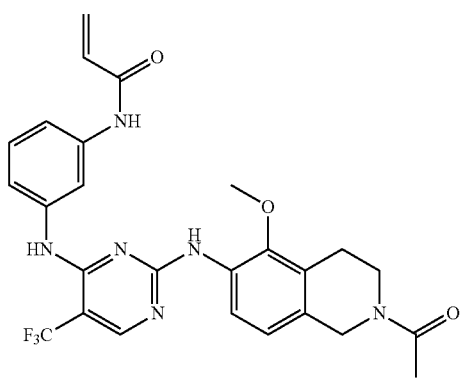

1-(6-Amino-5-methoxy-3,4-dihydroisoquinolin-2(1H)-yl)ethan-1-one (100 mg, 0.45 mmol) and N-(3-((2-chloro-5-(trifluoromethyl)pyrimidin-4-yl)amino)phenyl)acrylamide (154 mg, 0.45 mmol) were dissolved in isopropanol (10 mL), and a drop of trifluoroacetic acid was added. The mixture was heated to 70° C. and reacted for 12 h. After the reaction, the solution was dried by distillation, and purified by silica gel column chromatography (the eluent was dichloromethane:methanol=10:1) to get the title compound (152 mg, yield: 64%).

Molecular formula: C26H25F3N6O3 Molecular weight: 526.52 LC-MS (m/z): 527.3 (M+H+)

1H NMR (400 MHz, DMSO-d6) δ: 10.15 (s, 1H), 8.74 (s, 1H), 8.401 (s, 1H), 8.396 (s, 1H), 7.80 (d, J=8.0 Hz, 1H), 7.56 (dd, J1=8.0 Hz, J2=5.2 Hz, 1H), 7.41-7.42 (m, 1H), 7.22-7.26 (m, 1H), 7.21-7.15 (m, 1H), 6.66 (brs., 1H), 6.39-6.46 (m, 1H), 6.24 (dd, J1=2.0 Hz, J2=15.2 Hz, 1H), 5.73-5.76 (m, 1H), 4.50 (d, J=18.8 Hz, 2H), 3.63 (s, 3H), 3.60 (dd, J1=5.2 Hz, J2=5.2 Hz, 2H), 2.78 (t, J=6.0 Hz, 1H), 2.68 (t, J=5.6 Hz, 1H), 2.06 (d, J=3.6 Hz, 3H).

Example 16 Preparation of N-(3-((2-((2-acetyl-8-methoxy-1,2,3,4-tetrahydroisoquinoline-7-yl)amino)-5-(trifluoromethyl)pyrimidin-4-yl)amino)phenyl)acrylamide (Compound 17)

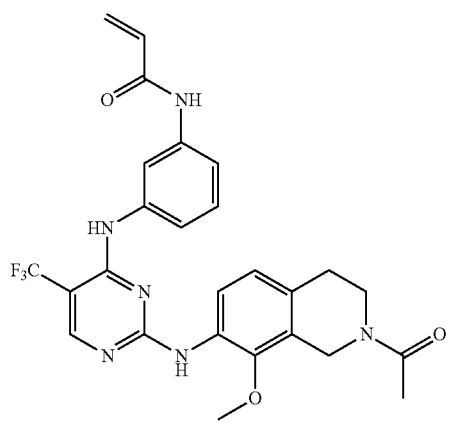 [SMILES: C=CC(=O)Nc1cccc(Nc2nc(Nc3ccc4c(c3OC)CN(C(C)=O)CC4)ncc2C(F)(F)F)c1]

118

1-(8-methoxy-7-nitro-3,4-dihydroisoquinolin-2(1H)-yl)ethan-1-one

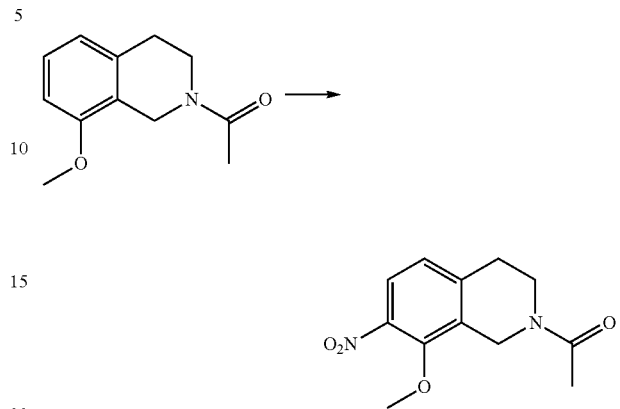

At 0° C., 1-(8-methoxy-3,4-dihydroisoquinolin-2(1H)-yl)ethan-1-one (1.0 g, 4.87 mmol) was dissolved in a mixed solution of acetic acid and acetic anhydride (10 mL, at a volume ratio of 1:1), and fuming nitric acid (337 mg, 5.36 mL) was added dropwisely. After the addition, the mixture was warmed to room temperature and reacted for 30 min, and then cooled to 0° C. Water (40 mL) was added to the reaction solution, and the reaction solution was extracted with ethyl acetate (100 mL×2). The organic phases were combined, dried with anhydrous sodium sulfate, concentrated, and purified by silica gel column chromatography (petroleum ether: ethyl acetate=1:1) to get the title compound (0.41 g, yield: 34%).

(2) Preparation of 1-(7-amino-8-methoxy-3,4-dihydroisoquinolin-2(1H)-yl)ethan-1-one

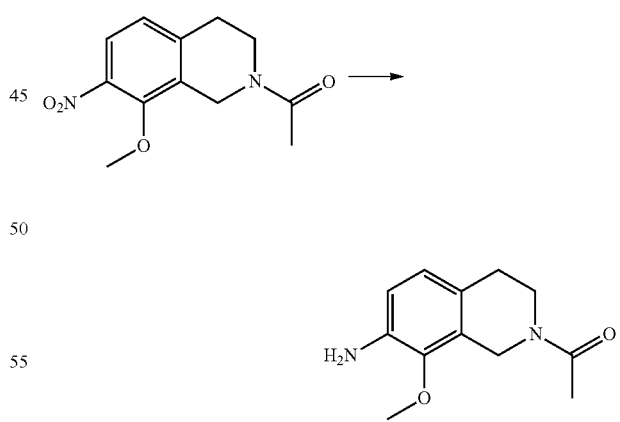

1-(8-Methoxy-7-nitro-3,4-dihydroisoquinolin-2(1H)-yl)ethan-1-one (0.4 g, 1.6 mmol) and palladium-carbon (10%, 40 mg) were suspended in methanol (20 mL). The system was vacuumized, and hydrogen gas was introduced. The mixture was reacted at room temperature for 6 h, filtrated, concentrated, and purified by silica gel column chromatography (dichloromethane:methanol=10:1) to get the title compound (0.3 g, yield: 86%).

(3) Preparation of N-(3-((2-((2-acetyl-8-methoxy-1,2,3,4-tetrahydroisoquinoline-7-yl)amino)-5-(trifluoromethyl)pyrimidin-4-yl)amino)phenyl)acrylamide

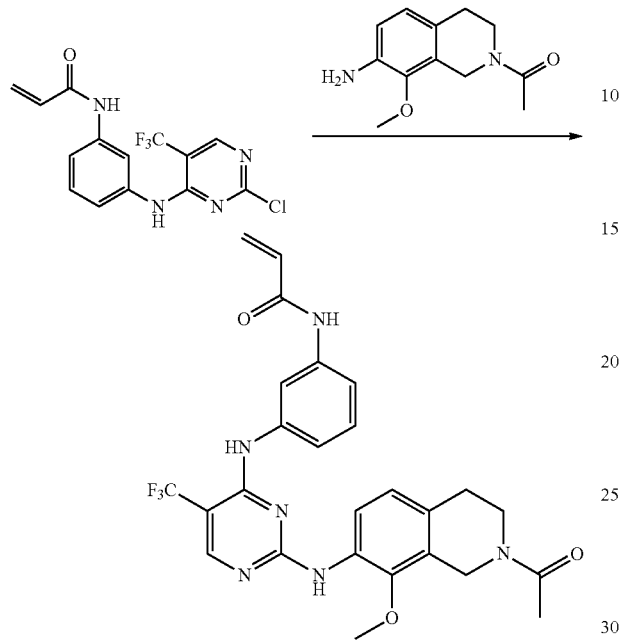

1-(7-Amino-8-methoxy-3,4-dihydroisoquinolin-2(1H)-yl)ethan-1-one (150 mg, 0.68 mmol) and N-(3-((2-chloro-5-(trifluoromethyl)pyrimidin-4-yl)amino)phenyl)acrylamide (233 mg, 0.68 mmol) were dissolved in isopropanol (10 mL), and a drop of trifluoroacetic acid was added. The mixture was heated to 70° C. and reacted for 12 h. After the reaction, the solution was dried by distillation, and purified by silica gel column chromatography (dichloromethane:methanol=10:1) to get the title compound (168 mg, yield: 47%).

Molecular formula: C26H25F3N6O3 Molecular weight: 526.52 LC-MS (m/z): 527.2 (M+H+)

1HNMR (400 MHz, DMSO-d6) δ: 10.15 (s, 1H), 8.69 (s, 1H), 8.50 (d, J=18.40 Hz, 1H), 8.32 (s, 1H), 7.78 (d, J=6.0 Hz, 1H), 7.40-7.49 (m, 2H), 7.16-7.25 (m, 2H), 6.66-6.68 (d, J=8.0 Hz, 1H), 6.41-6.45 (m, 1H), 6.24 (dd, J1=1.6 Hz, J2=16.8 Hz, 1H), 5.75 (dd, J1=2.0 Hz, J2=10.0 Hz, 1H), 4.54 (d, J=3.2 Hz, 1H), 3.36-3.66 (m, 5H), 2.75 (t, J=5.8 Hz, 1H), 2.62-2.66 (m, 1H), 2.06 (d, J=3.2 Hz, 3H).

Example 17 Preparation of N-(3-((2-((4-(4-acetylpiperazin-1-yl)-2-methoxyphenyl)amino)-5-(trifluoromethyl)pyridin-4-yl)amino)phenyl)acrylamide (Compound 18)

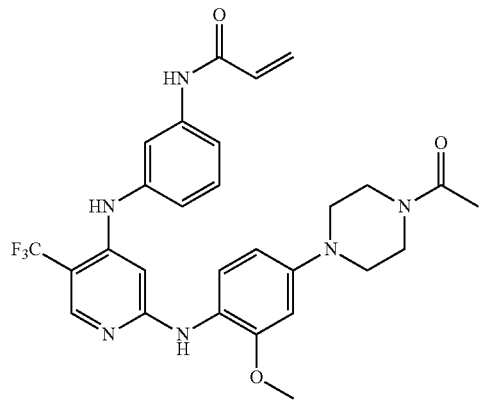 [SMILES: C=CC(=O)Nc1cccc(Nc2cc(Nc3ccc(N4CCN(C(C)=O)CC4)cc3OC)ncc2C(F)(F)F)c1]

N-(3-((2-((4-(4-acetylpiperazin-1-yl)-2-methoxyphenyl)amino)-5-(trifluoromethyl)pyridin-4-yl)amino)phenyl)acrylamide

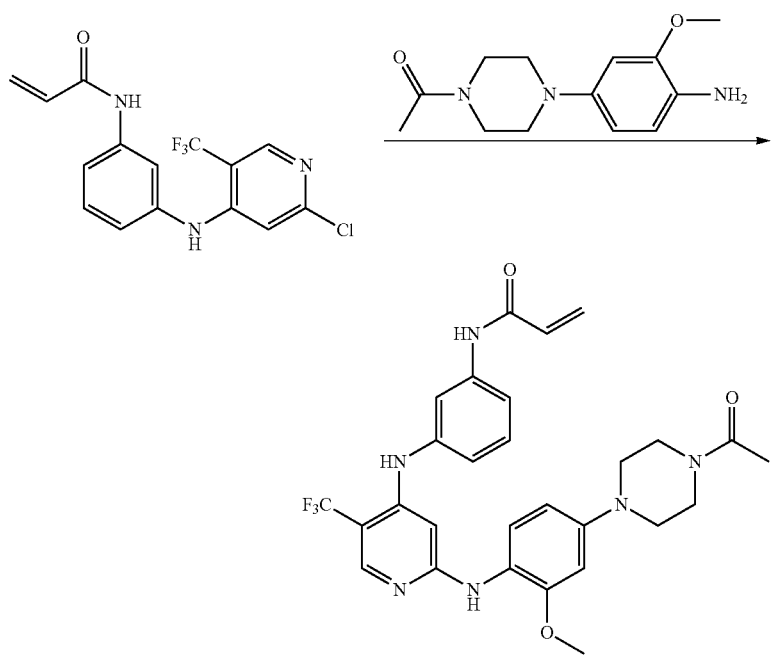

1-(4-(4-Amino-3-methoxyphenyl)piperazin-1-yl)ethan-1-one (275 mg, 1.1 mmol), N-(3-((2-chloro-5-(trifluoromethyl)pyridin-4-yl)amino)phenyl)acrylamide (377 mg, 1.1 mmol), 4,5-bis(diphenylphosphino)-9,9-dimethyl xanthene (128.7 mg, 0.22 mmol), bis(dibenzylideneacetone)palladium (101.2 mg, 0.176 mmol) and potassium tert-butoxide (246 mg, 2.2 mmol) were dissolved in 1,4-dioxane (15 mL), and reacted under microwave at 140° C. for 2 h. After the reaction, the mixture was filtrated under suction at reduced pressure. The solid was washed with methanol for several times, and the filtrate was concentrated in vacuum. The crude product was separated by reversed phase column chromatography (methanol/water, 0-50%, containing 0.2% trifluoroacetic acid) to get the title compound as a white solid (20 mg, yield: 3.3%).

Molecular formula: C28H29F3N6O3 Molecular weight: 554.56 LC-MS (m/z): 555.3 (M+H+)

1H-NMR (400 MHz, MeOD-d4) δ: 8.03 (s, 1H), 7.69 (s, 1H), 7.40 (d, J=8.0 Hz, 1H), 7.35-7.23 (m, 2H), 6.96-6.93 (m, 1H), 6.59-6.58 (m, 1H), 6.50-6.37 (m, 2H), 6.19-6.17 (m, 1H), 5.80 (dd, J1=1.8 Hz, J2=9.8 Hz, 1H), 3.77 (s, 3H), 3.74-3.59 (m, 4H), 3.16-3.01 (m, 4H), 2.14 (s, 3H).

Example 18 Preparation of N-(3-((6-((4-(4-acetylpiperazin-1-yl)-2-methoxyphenyl)amino)-3-(trifluoromethyl)pyridin-2-yl)amino)phenyl)acrylamide (Compound 19)

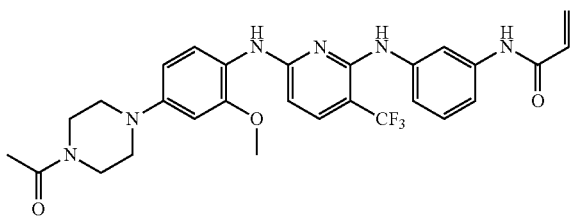 [SMILES: C=CC(=O)Nc1cccc(Nc2nc(Nc3ccc(N4CCN(C(C)=O)CC4)cc3OC)ccc2C(F)(F)F)c1]

(1) Preparation of 1-(4-(4-((6-chloro-5-(trifluoromethyl)pyridin-2-yl)amino)-3-methoxyphenyl)piperazin-1-yl)ethan-1-one

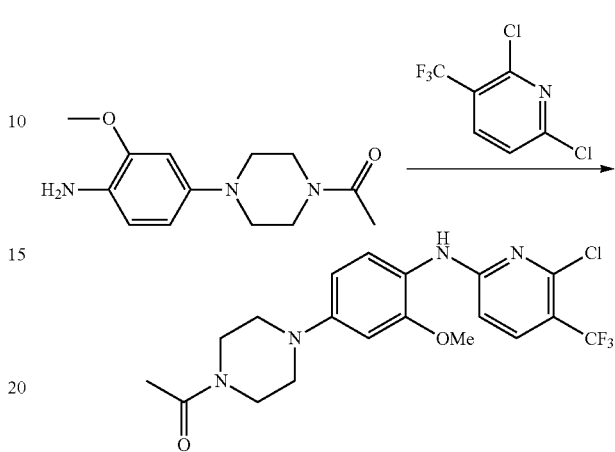

1-(4-(4-Amino-3-methoxyphenyl)piperazin-1-yl)ethan-1-one (3.9 g, 15.6 mmol) and 2,6-dichloro-3-(trifluoromethyl)pyridine (3.37 g, 15.6 mmol) were dissolved in dimethyl sulfoxide (30 mL), and N,N-diisopropylethylamine (4.03 g, 31.2 mmol) was added. The reaction was carried out at 85° C. for 17 h. The reaction solution was cooled to room temperature, poured into water (150 mL), and extracted with ethyl acetate (150 mL×3). The organic phases were combined, washed with water (150 mL×2), washed with saturated saline solution, dried with anhydrous sodium sulfate, and concentrated. The crude product was purified by silica gel column chromatography (ethyl acetate: petroleum ether=0-1:5) to get the title compound as a light yellow solid (3.2 g, yield: 47.8%).

(2) Preparation of tert-butyl (3-((6-((4-(4-acetylpiperazin-1-yl)-2-methoxyphenyl)amino)-3-(trifluoromethyl)pyridin-2-yl)amino)phenyl)amino carboxylate

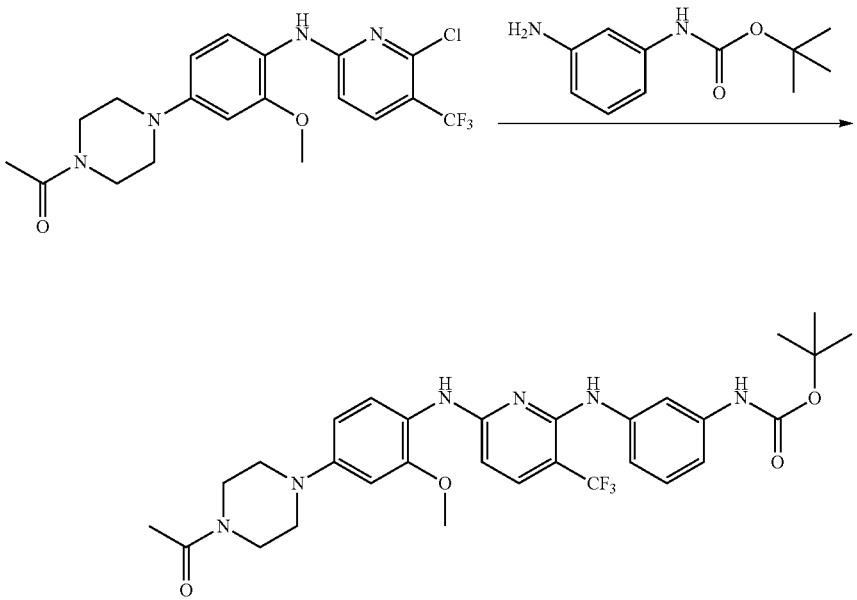

1-(4-(4-((6-Chloro-5-(trifluoromethyl)pyridin-2-yl) amino)-3-methoxyphenyl)piperazin-1-yl)ethan-1-one (0.2 g, 0.46 mmol), tert-butyl (3-aminophenyl)amino carboxylate (0.2 g, 0.96 mmol) and cesium carbonate (0.3 g, 0.92 mmol) were dissolved in DMSO (3 mL). Under the protection of N2, tris(dibenzylideneacetone)dipalladium (45 mg, 0.05 mmol) and 2-dicyclohexylphosphino-2',4',6'-triisopropylbiphenyl (47 mg, 0.1 mmol) were added to the system, and the reaction was carried out under microwave at 150° C. for 3 h. After the reaction, the mixture was diluted with ethyl acetate (20 mL) and washed with water twice. The organic phase was dried with anhydrous sodium sulfate, and filtrated. The filtrate was concentrated, and the residue was separated by preparative TLC (petroleum ether: ethyl acetate=1:5) to get the title compound (0.12 g, yield: 42.8%).

(3) Preparation of 1-(4-(4-((6-((3-aminophenyl) amino)-5-(trifluoromethyl)pyridin-2-yl)amino)-3-methoxyphenyl)piperazin-1-yl)ethan-1-one

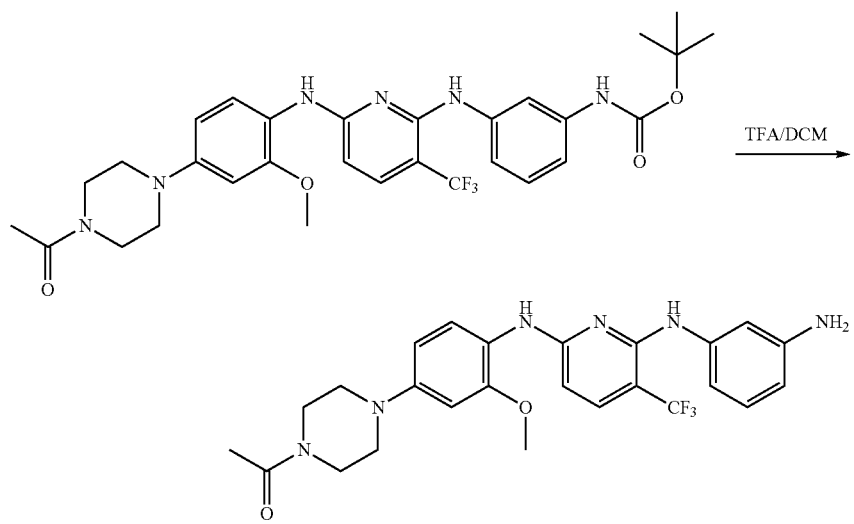

Tert-butyl (3-((6-((4-(4-acetylpiperazin-1-yl)-2-methoxyphenyl)amino)-3-(trifluoromethyl)pyridin-2-yl)amino)phenyl)amino carboxylate (0.12 g, 0.2 mmol) was dissolved in dichloromethane (5 mL), and trifluoroacetic acid (5 mL) was added. The mixture was stirred at 25° C. for 1 h. After the reaction, the reaction solution was concentrated, and dichloromethane (20 mL) was added. The mixture was washed with sodium bicarbonate solution and then with saline solution. The organic phase was dried with anhydrous sodium sulfate, and filtrated. The filtrate was dried by distillation to get the title compound (80 mg, yield: 80%).

(4) Preparation of N-(3-((6-((4-(4-acetylpiperazin-1-yl)-2-methoxyphenyl)amino)-3-(trifluoromethyl) pyridin-2-yl)amino)phenyl)acrylamide

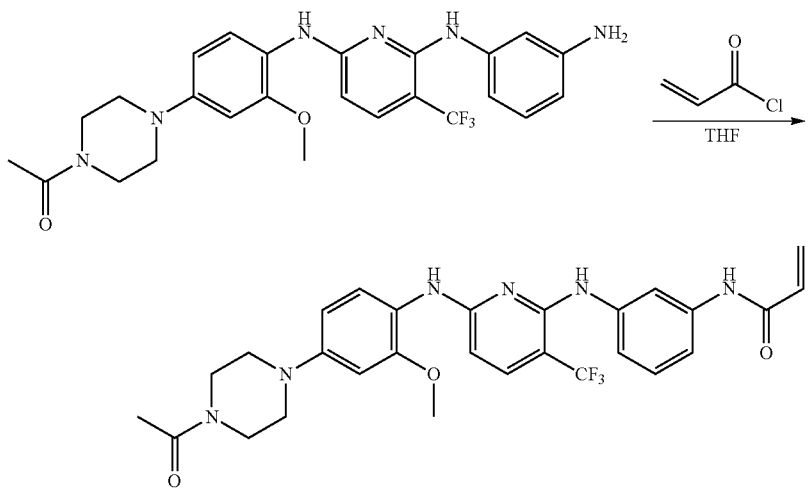

At room temperature, acryloyl chloride (29 mg, 0.32 mmol) was added dropwisely to a solution of 1-(4-(4-((6-((3-aminophenyl)amino)-5-(trifluoromethyl)pyridin-2-yl)amino)-3-methoxyphenyl)piperazin-1-yl)ethan-1-one (80 mg, 0.16 mmol) in tetrahydrofuran (5 mL). The mixture was reacted at 25° C. under stirring for 1 h. After the reaction, the reaction solution was concentrated, and dichloromethane (20 mL) was added. The mixture was washed with NaHCO3 solution and then with saline solution. The organic phase was dried with anhydrous Na2SO4, and filtrated. The filtrate was dried by distillation, and the residue was separated by preparative TLC (petroleum ether: ethyl acetate=1:5) to get the title compound (15 mg, yield: 16.9%).

Molecular formula: C28H29F3N6O3 Molecular weight: 554.6 LC-MS (m/z): 555.3 (M+H+)

1H-NMR (400 MHz, CDCl3) δ: 7.84 (s, 2H), 7.55 (d, J=8.4 Hz, 2H), 7.27-7.35 (m, 2H), 7.15 (d, J=7.6 Hz, 1H), 6.86 (s, 1H), 6.72 (s, 1H), 6.53 (s, 1H), 6.32-6.48 (m, 2H), 6.07-6.28 (m, 2H), 5.74 (d, J=10.0 Hz, 1H), 3.88 (s, 3H), 3.78 (s, 2H), 3.61 (s, 2H), 3.10 (s, 4H), 2.15 (s, 3H).

Example 19 Preparation of N-(3-((2-((4-(4-acetylpiperazin-1-yl)-2-methoxy-5-methylphenyl)amino)-5-(trifluoromethyl)pyrimidin-4-yl)amino)phenyl)acrylamide (Compound 20)

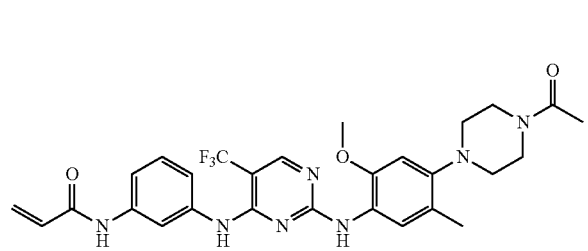 [SMILES: C=CC(=O)Nc1cccc(Nc2nc(Nc3cc(C)c(N4CCN(C(C)=O)CC4)cc3OC)ncc2C(F)(F)F)c1]

(1) Preparation of 5-fluoro-4-methyl-2-nitrophenol

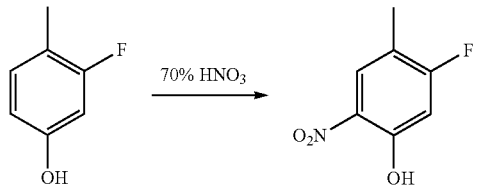

3-Fluoro-4-methylphenol (5.0 g, 39.7 mmol) was dissolved in dichloromethane (100 mL), and nitric acid (70%, 5 mL) was added to the system. The reaction was carried out at room temperature for 1 h. After the reaction, the mixture was washed with water (50 mL×2). The organic phase was dried with anhydrous sodium sulfate, filtrated, and concentrated to get the title compound (4.48 g, yield: 66%).

(2) Preparation of 1-fluoro-5-methoxy-2-methyl-4-nitrobenzene

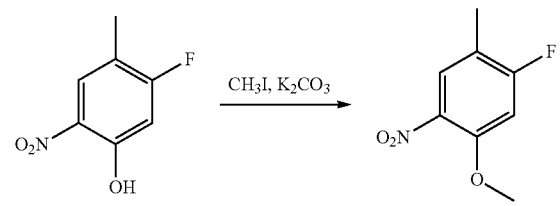

5-Fluoro-4-methyl-2-nitrophenol (4.48 g, 26.2 mmol) was dissolved in N,N-dimethylformamide (50 mL), and potassium carbonate (5.4 g, 39.3 mmol) and iodomethane (4.46 g, 31.4 mmol) were added to the system. The mixture was stirred at room temperature for 16 h. After the reaction, the reaction solution was poured into water (100 mL), and stirred until solids were precipitated. Filtration was performed and the filter cake was washed with water and dried to get the title compound (4.2 g, yield: 87%).

(3) Preparation of 1-(4-(5-methoxy-2-methyl-4-nitrophenyl)piperazin-1-yl)ethan-1-one

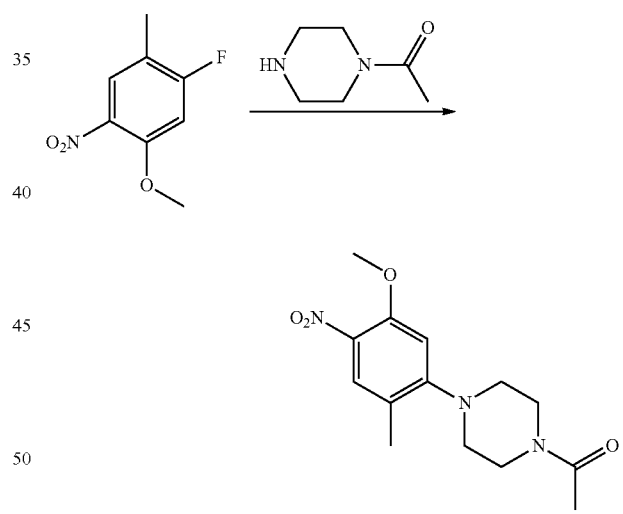

1-Fluoro-5-methoxy-2-methyl-4-nitrobenzene (4.2 g, 22.7 mmol) and 1-(piperazin-1-yl)ethan-1-one (2.9 g, 22.7 mmol) were dissolved in N,N-dimethylformamide (20 mL), and potassium carbonate (6.3 g, 45.4 mmol) was added. The resultant mixture was stirred at 120° C. for 16 h. After the reaction, the mixture was cooled to room temperature. Water (50 mL) was added, and the mixture was extracted with ethyl acetate (50 mL×2). The organic phases were combined, dried, filtrated, concentrated, and purified by silica gel column chromatography (petroleum ether: ethyl acetate=1:2) to get the title compound (2.26 g, yield: 34%).

(4) Preparation of 1-(4-(4-amino-5-methoxy-2-methylphenyl)piperazin-1-yl)ethan-1-one

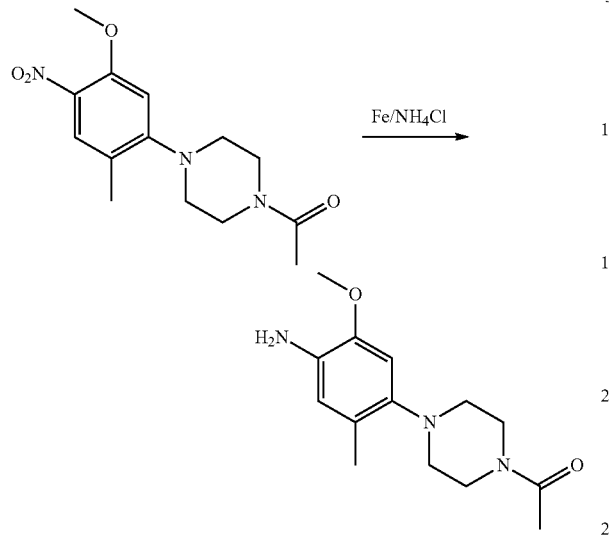

1-(4-(5-Methoxy-2-methyl-4-nitrophenyl)piperazin-1-yl)ethan-1-one (2.26 g, 7.7 mmol) was dissolved in a mixed solvent of ethanol (50 mL) and water (10 mL), and ferrous powder (2.1 g, 38.5 mmol) and ammonium chloride (53 mg, 1 mmol) were added to the system. The mixture was heated to 80° C. and reacted under stirring for 2 h. After the reaction, the mixture was cooled to room temperature, and filtrated. The filtrate was washed with sodium bicarbonate solution and satured saline solution, dried, filtrated, and concentrated to get the title compound (1.64 g, yield: 81%).

(5) Preparation of N-(3-((2-((4-(4-acetylpiperazin-1-yl)-2-methoxy-5-methylphenyl)amino)-5-(trifluoromethyl)pyrimidin-4-yl)amino)phenyl)acrylamide

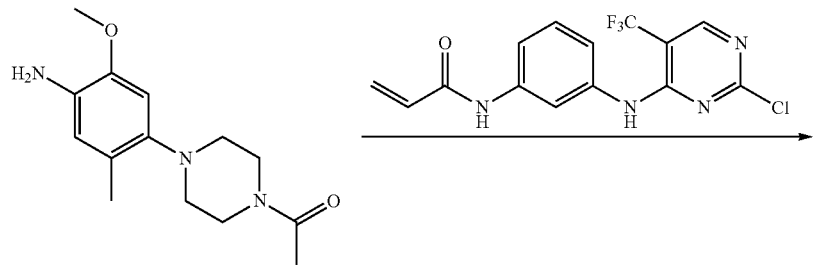

1-(4-(4-Amino-5-methoxy-2-methylphenyl)piperazin-1-yl)ethan-1-one (92 mg, 0.35 mmol) and N-(3-((2-chloro-5-(trifluoromethyl)pyrimidin-4-yl)amino)phenyl)acrylamide (100 mg, 0.29 mmol) were added to 1,4-dioxane (10 mL), and a catalytic amount of trifluoroacetic acid (20 mg) was added to the system. The mixture was heated to 70° C. and reacted under stirring for 16 h. After the reaction, the reaction solution was treated with ethyl acetate (50 mL), and then washed with water (50 mL×2), dried, concentrated, and separated and purified by preparative chromatography to get the title compound (24 mg, yield: 14.5%).

Molecular formula: C28H30F3N7O3 Molecular weight: 569.58 LC-MS (m/z): 570.3 (M+H+)

1H-NMR (400 MHz, MeOD) δ: 8.24 (s, 1H), 7.74-7.66 (m, 3H), 7.35 (t, J=8.0 Hz, 1H), 7.20 (d, J=8.0 Hz, 1H), 6.66 (s, 1H), 6.39-6.31 (m, 2H), 5.76 (d, J=8.8 Hz, 1H), 3.84 (s, 3H), 3.69-3.64 (m, 4H), 2.85-2.79 (m, 4H), 2.14 (s, 3H), 1.96 (s, 3H).

Example 20 Preparation of N-(3-((2-((2-methoxy-4-(1-methyl-2-oxopiperidin-4-yl)phenyl)amino)-5-(trifluoromethyl)pyrimidin-4-yl)amino)phenyl)acrylamide (Compound 21)

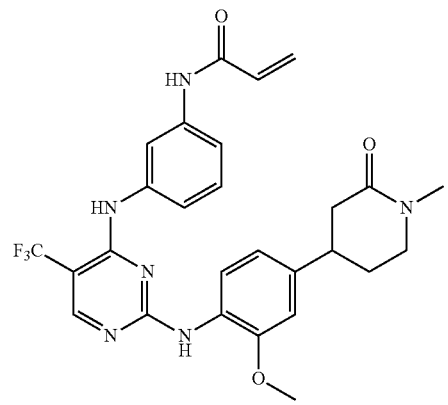 [SMILES: C=CC(=O)Nc1cccc(Nc2nc(Nc3ccc(C4CCN(C)C(=O)C4)cc3OC)ncc2C(F)(F)F)c1]

(1) Preparation of 4-bromo-1-methylpyridin-2(1H)-one

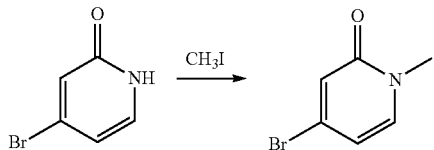

4-Bromopyridin-2(1H)-one (1.0 g, 5.75 mmol) was dissolved in tetrahydrofuran (20 mL). Under the protection of nitrogen gas, the mixture was cooled to 0° C., and sodium hydride (mass percentage 60%, 0.23 g, 5.75 mmol) was added. The mixture was warmed up to room temperature and stirred for 15 min. Iodomethane (1.10 mL, 17.24 mmol) was slowly added dropwisely. After the addition, the mixture was stirred at room temperature for 16 h. TLC detection showed that the reaction was finished. Water and ethyl acetate were added, and the water phase and the organic phase are separated. The organic phase was washed with saturated saline solution, dried with anhydrous sodium sulfate, and concentrated to get the title compound (1.02 g, yield: 94.4%).

(2) Preparation of tert-butyl (4-bromo-2-methoxyphenyl)amino carboxylate

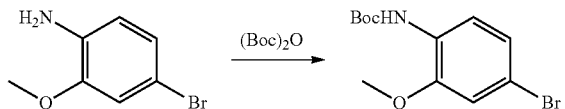

4-Bromo-2-methoxyaniline (6.8 g, 33.7 mmol) and di-tert-butyl dicarbonate (8.9 g, 40.8 mmol) were dissolved in tetrahydrofuran (100 mL). Under the protection of nitrogen gas, the reaction was carried out under reflux for 22 h, and the mixture was cooled. The solvent was removed by distillation under reduced pressure, and ethyl acetate (150 mL) was added. The mixture was washed with 1 mol/L hydrochloric acid, and the water phase and the organic phase were separated. The organic phase was dried with anhydrous sodium sulfate, and filtrated under suction. The filtrate was concentrated to get the title compound (8.3 g, yield: 81.6%).

(3) Preparation of tert-butyl (2-methoxy-4-(4,4,5,5-tetramethyl-1,3,2-dioxaborolan-2-yl)phenyl)amino carboxylate

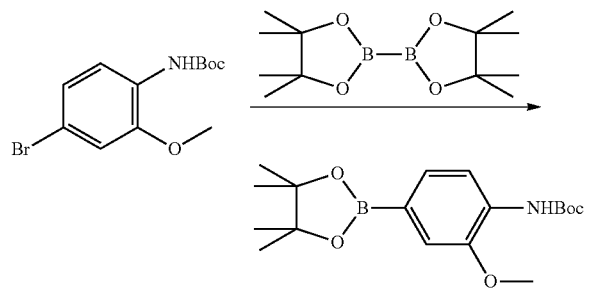

Tert-butyl (4-bromo-2-methoxyphenyl)amino carboxylate (5.0 g, 16.56 mmol), bis(pinacolato)diboron (5.05 g, 19.88 mmol) and potassium acetate (4.88 g, 49.80 mmol) were added to N,N-dimethylformamide (100 mL). Under the protection of nitrogen gas, [1,1'-bis(diphenyphosphino)ferrocene]dichloropalladium (II) dichloromethane complex (410 mg, 0.50 mmol) was added. The mixture was heated to 80° C. and reacted overnight. After cooling to room temperature, water and dichloromethane were added, and the water phase and the organic phase were separated. The organic phase was washed with saturated saline solution for 3 times, dried with anhydrous sodium sulfate, and concentrated. The crude product was purified by silica gel column chromatography (petroleum ether: ethyl acetate=100:1) to get the title compound (4.8 g, yield: 83.0%).

(4) Preparation of tert-butyl (2-methoxy-4-(1-methyl-2-oxo-1,2-dihydropyridin-4-yl)phenyl)amino carboxylate

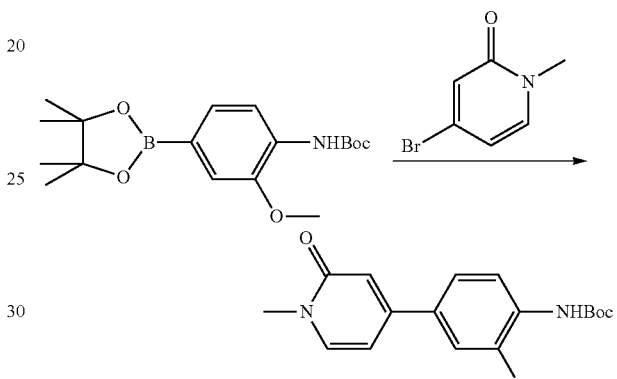

Tert-butyl (2-methoxy-4-(4,4,5,5-tetramethyl-1,3,2-dioxaborolan-2-yl)phenyl)amino carboxylate (1.49 g, 4.26 mmol), 4-bromo-1-methylpyridin-2(1H)-one (800 mg, 4.26 mmol) and potassium carbonate (1.18 g, 8.55 mmol) were added to 1,4-dioxane (50 mL) and water (10 mL). Under the protection of nitrogen gas, after the addition of [1,1'-bis(diphenyphosphino)ferrocene]dichloropalladium (II) (190 mg, 0.26 mmol), the temperature was increased to 90° C. The reaction mixture was stirred overnight, and filtrated under suction. The filtrate was concentrated, and the crude product was purified by silica gel column chromatography (petroleum ether: ethyl acetate=5:1) to get the title compound (816 mg, yield: 58.0%).

(5) Preparation of tert-butyl (2-methoxy-4-(1-methyl-2-oxopiperidin-4-yl)phenyl)amino carboxylate

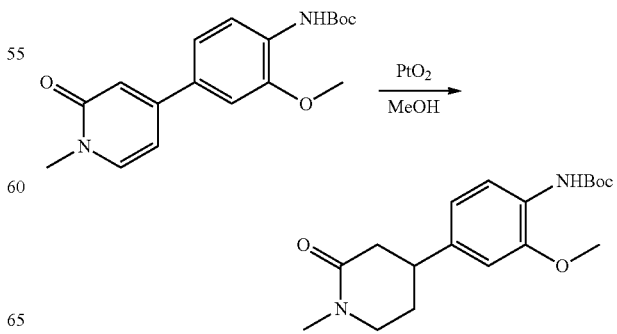

Tert-butyl (2-methoxy-4-(1-methyl-2-oxo-1,2-dihydropyridin-4-yl)phenyl)amino carboxylate (816 mg, 2.47 mmol) was dissolved in methanol (50 mL), and platinum dioxide (408 mg, the ratio of which to the carboxylate was 1:2) was added. At the atmosphere of hydrogen gas, the mixture was stirred at room temperature overnight, and filtrated under suction. The filtrate was concentrated to get the product, which was directly used in the next step.

(6) Preparation of 4-(4-amino-3-methoxyphenyl)-1-methylpiperidin-2-one

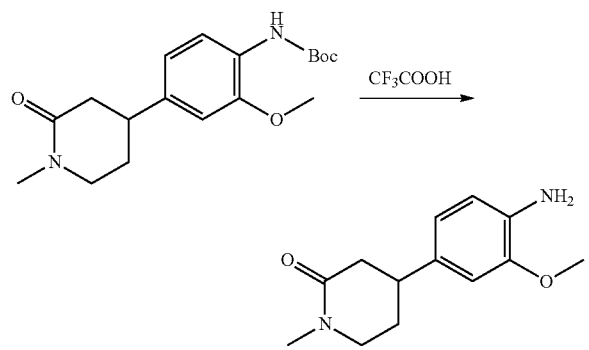

Tert-butyl (2-methoxy-4-(1-methyl-2-oxopiperidin-4-yl)phenyl)amino carboxylate (825 mg, 2.47 mmol) was dissolved in dichloromethane (6 mL) and trifluoroacetic acid (6 mL). The mixture was stirred at room temperature for 0.5 h, and concentrated under reduced pressure to get the product, which was directly used in the next step.

(7) Preparation of N-(3-((2-((2-methoxy-4-(1-methyl-2-oxopiperidin-4-yl)phenyl)amino)-5-(trifluoromethyl)pyrimidin-4-yl)amino)phenyl)acrylamide

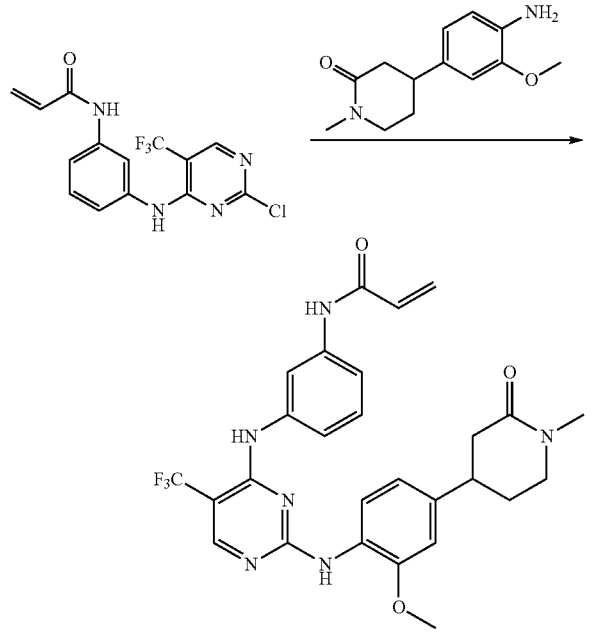

N-(3-((2-chloro-5-(trifluoromethyl)pyrimidin-4-yl)amino)phenyl)acrylamide (200 mg, 0.58 mmol) and 4-(4-amino-3-methoxyphenyl)-1-methylpiperidin-2-one (112.3 mg, 0.48 mmol) were added to isopropanol (20 mL), and a catalytic amount of trifluoroacetic acid was added. Under the protection of nitrogen gas, the mixture was stirred at 70° C. overnight. Aqueous ammonia was added to adjust pH of the solution to pH>7. The mixture was concentrated, and the crude product was purified by silica gel column chromatography (dichloromethane:methanol=15:1) to get the title compound (110 mg, yield: 42.4%).

Molecular formula: C27H27F3N6O3 Molecular weight: 540.5 LC-MS (m/z): 541.3 (M+H+)

1H-NMR (400 MHz, CDCl3) δ: 8.32 (s, 1H), 8.12 (d, J=7.6 Hz, 1H), 7.97 (s, 1H), 7.73 (s, 1H), 7.59 (s, 1H), 7.40-7.33 (m, 2H), 6.88 (s, 1H), 6.67 (d, J=1.6 Hz, 1H), 6.55 (s, 1H), 6.46 (dd, J1=1.2 Hz, J2=16.8 Hz, 1H), 6.32-6.26 (m, 1H), 5.79 (dd, J1=1.2 Hz, J2=10.0 Hz, 1H), 3.87 (s, 3H), 3.38-3.26 (m, 2H), 3.10-3.02 (m, 1H), 2.99 (s, 3H), 2.73-2.67 (m, 1H), 2.52-2.45 (m, 1H), 2.09-1.95 (m, 2H).

Example 21 Preparation of N-(3-((2-((2-methoxy-4-(2-oxopiperidin-4-yl)phenyl)amino)-5-(trifluoromethyl)pyrimidin-4-yl)amino)phenyl)acrylamide (Compound 22)

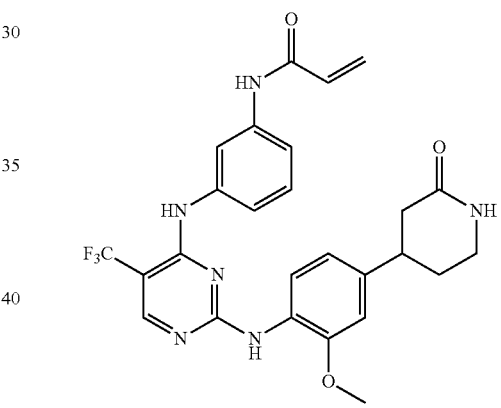

(1) Preparation of 4-(4,4,5,5-tetramethyl-1,3,2-dioxaborolan-2-yl)pyridin-2(1H)-one

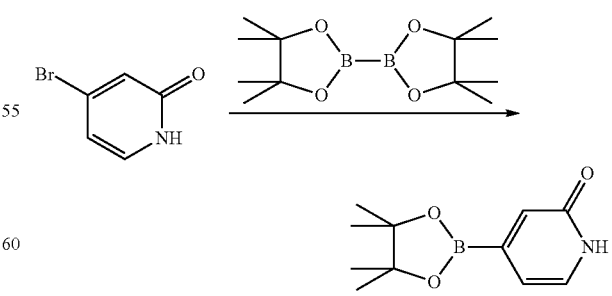

4-Bromopyridin-2-(1H)-one (1.0 g, 5.7 mmol), bis(pinacolato)diboron (1.6 g, 6.3 mmol) and potassium acetate (0.84 g, 8.55 mmol) were added to 1,4-dioxane (20 mL). Under the protection of nitrogen gas, tricyclohexyl phosphine (193 mg) and tris(dibenzylideneacetone)dipalladium (300 mg) were added. The mixture was heated to 85° C. and reacted for 3 h, then cooled to room temperature, and filtrated under suction. The filtrate was concentrated, and then directly used in the next step.

(2) Preparation of 4-(4-amino-3-methoxyphenyl) pyridin-2(1H)-one

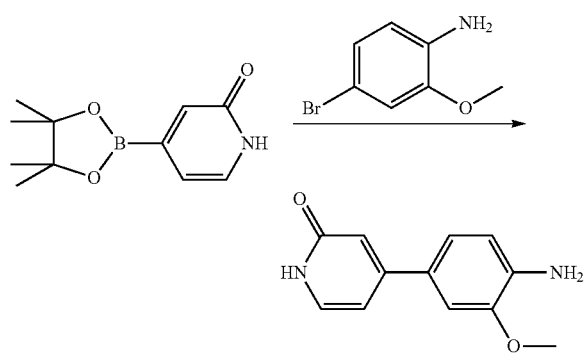

4-(4,4,5,5-Tetramethyl-1,3,2-dioxaborolan-2-yl)pyridin-2(1H)-one (1.27 g, 5.7 mmol), 4-bromo-2-methoxyaniline (1.16 g, 5.7 mmol) and potassium carbonate (1.97 g, 14.3 mmol) were added to 1,4-dioxane (50 mL) and water (10 mL). Under the protection of nitrogen gas, [1,1'-bis(diphenylphosphino)ferrocene]dichloropalladium (II) (417 mg) was added. The mixture was heated to 90° C. and reacted for 12 h, and then filtrated under suction. The filtrate was concentrated, and the crude product was purified by silica gel column chromatography (dichloromethane:methanol=50:1) to get the title compound (600 mg, yield: 48.8%).

(3) Preparation of 4-(4-amino-3-methoxyphenyl)piperidin-2-one

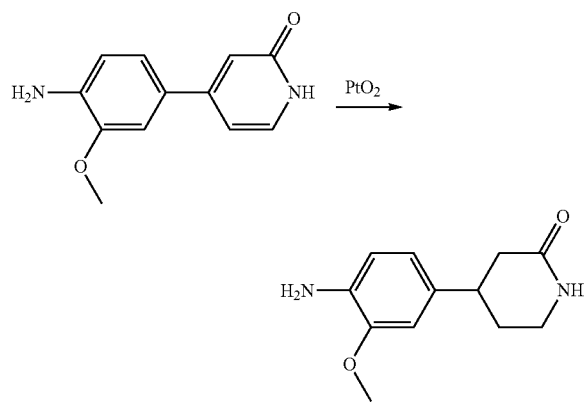

4-(4-Amino-3-methoxyphenyl)pyridin-2(1H)-one (600 mg, 2.78 mmol) was dissolved in methanol (50 mL), and platinum dioxide (300 mg, mass ratio of 50%) was added. At the atmosphere of hydrogen gas, the mixture was stirred at room temperature overnight, and filtrated under suction. The filtrate was concentrated to get the title compound (610 mg, yield: 99.8%).

(4) Preparation of N-(3-((2-((2-methoxy-4-(2-oxopiperidin-4-yl)phenyl)amino)-5-(trifluoromethyl)pyrimidin-4-yl)amino)phenyl)acrylamide

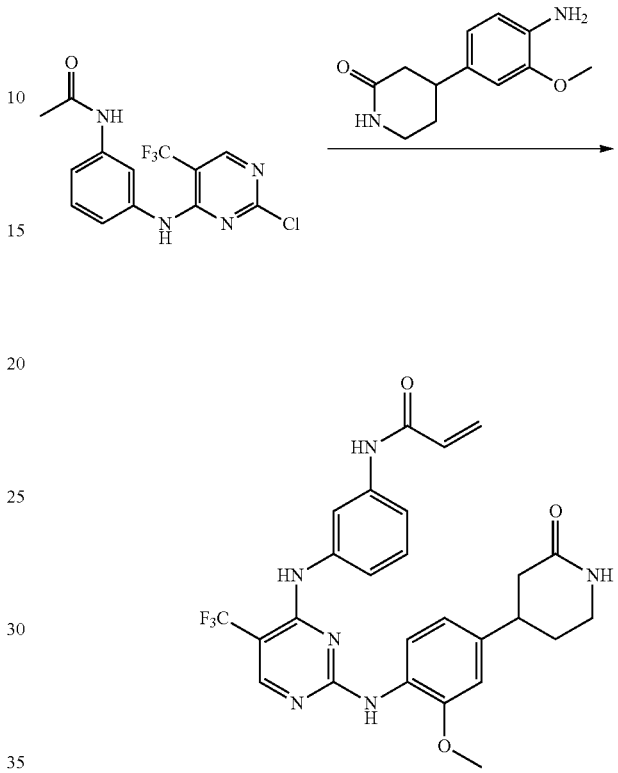

N-(3-((2-Chloro-5-(trifluoromethyl)pyrimidin-4-yl) amino)phenyl)acrylamide (100 mg, 0.29 mmol) and 4-(4-amino-3-methoxyphenyl)piperidin-2-one (59.4 mg, 0.27 mmol) were added to 1,4-dioxane (20 mL), and a catalytic amount of trifluoroacetic acid was added. Under the protection of nitrogen gas, the mixture was stirred at 50° C. overnight, and aqueous ammonia was added to adjust pH of the solution to pH>7. The mixture was concentrated, and the crude product was purified by silica gel column chromatography (dichloromethane:methanol=15:1), and then washed with methanol to get the title compound (100 mg, yield: 70%).

Molecular formula: $C_{26}H_{25}F_3N_6O_3$ Molecular weight: 526.5 LC-MS (m/z): 527.2 (M+H+)

1H-NMR (400 MHz, CDCl3) δ: 8.32 (s, 1H), 8.13 (d, J=6.8 Hz, 1H), 7.97 (s, 1H), 7.73 (s, 1H), 7.61 (s, 1H), 7.41-7.34 (m, 2H), 6.89 (s, 1H), 6.69 (s, 1H), 6.66 (s, 1H), 6.59 (d, J=12.0 Hz, 1H), 6.31-6.24 (m, 1H), 5.86 (s, 1H), 5.79 (d, J=10.0 Hz, 1H), 3.88 (s, 3H), 3.40-3.30 (m, 2H), 3.11-3.02 (m, 1H), 2.71-2.65 (m, 1H), 2.52-2.45 (m, 1H), 2.05-2.00 (m, 1H), 1.95-1.91 (m, 1H).

Example 22 Preparation of N-(3-((2-((4-(1-(2-fluoroethyl)-2-oxopiperidin-4-yl)-2-methoxyphenyl)amino)-5-(trifluoro methyl)pyrimidin-4-yl)amino)phenyl)acrylamide (Compound 23)

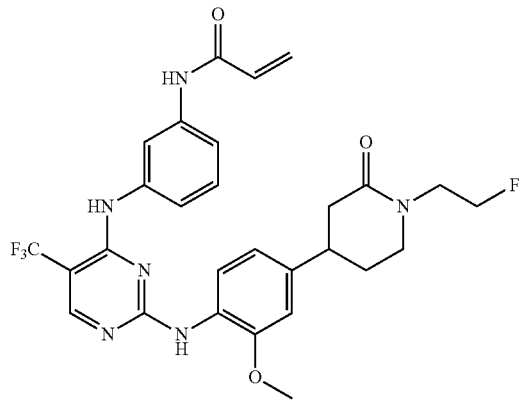

(1) Preparation of 4-bromo-1-(2-fluoroethyl)pyridin-2(1H)-one

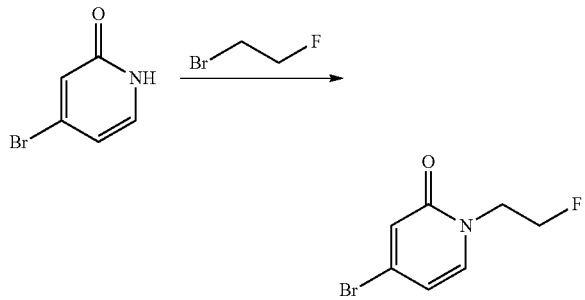

4-Bromopyridin-2(1H)-one (1.0 g, 5.75 mmol) was dissolved in acetonitrile (50 mL), and 1-bromo-2-fluoroethane (1.1 g, 8.66 mmol) and cesium carbonate (5.62 g, 17.25 mmol) were added. Under the protection of nitrogen gas, the mixture was reacted at 50° C. for 36 h, and then cooled to room temperature. The mixture was filtrated under suction. The filtrate was concentrated, and the crude product was purified by silica gel column chromatography (petroleum ether: ethyl acetate=3:1) to get the title compound (1.15 g, yield: 91%).

(2) Preparation of 1-(2-fluoroethyl)-4-(4,4,5,5-tetramethyl-1,3,2-dioxaborolan-2-yl)pyridin-2(1H)-one

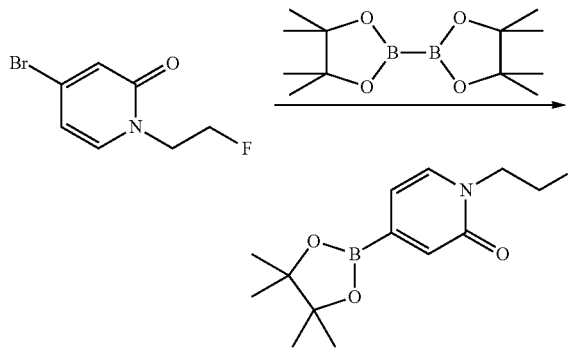

4-Bromo-1-(2-fluoroethyl)pyridin-2(1H)-one (1.0 g, 4.55 mmol), bis(pinacolato)diboron (1.27 g, 5 mmol) and potassium acetate (0.67 g, 6.84 mmol) were added to 1,4-dioxane (20 mL). Under the protection of nitrogen gas, tricyclohexyl phosphine (154 mg, 0.55 mmol) and tris(dibenzylideneacetone)dipalladium (210.6 mg, 0.23 mmol) were added. The mixture was heated to 85° C. and reacted for 3 h, and then cooled to room temperature and filtrated under suction. The filtrate was concentrated, and then directly used in the next step.

(3) Preparation of tert-butyl (4-(1-(2-fluoroethyl)-2-oxo-1,2-dihydropyridin-4-yl)-2-methoxyphenyl)amino carboxylate

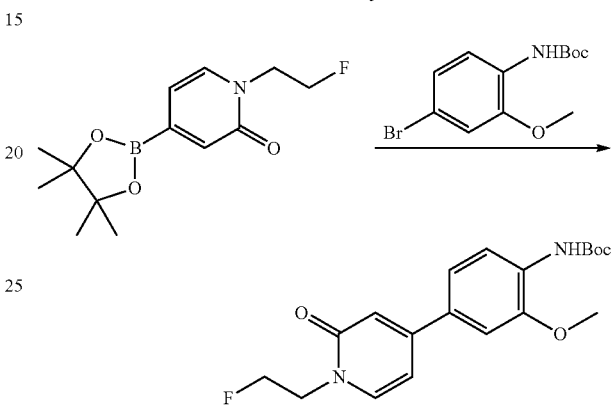

1-(2-Fluoroethyl)-4-(4,4,5,5-tetramethyl-1,3,2-dioxaborolan-2-yl)pyridin-2(1H)-one (1.21 g, 4.53 mmol), tert-butyl (4-bromo-2-methoxyphenyl)amino carboxylate (1.37 g, 4.53 mmol) and potassium carbonate (1.26 g, 9.13 mmol) were added to 1,4-dioxane (50 mL) and water (10 mL). Under the protection of nitrogen gas, [1,1'-bis(diphenyphosphino)ferrocene]dichloropalladium (II) (200 mg, 0.27 mmol) was added. The mixture was heated to 90° C. and reacted overnight, and then filtrated under suction. The filtrate was concentrated, and the crude product was purified by silica gel column chromatography (petroleum ether: ethyl acetate=5:1) to get the title compound (930 mg, yield: 56.7%).

(4) Preparation of tert-butyl (4-(1-(2-fluoroethyl)-2-oxopiperidin-4-yl)-2-methoxyphenyl)amino carboxylate

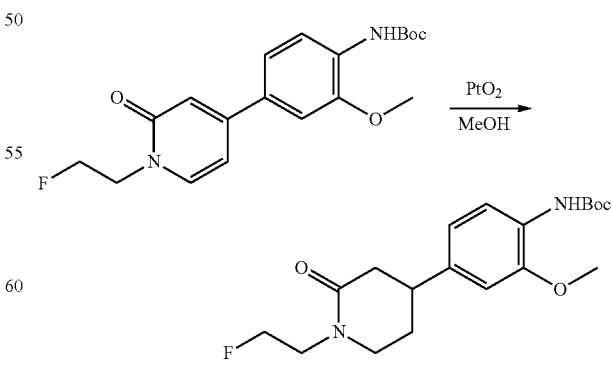

Tert-butyl (4-(1-(2-fluoroethyl)-2-oxo-1,2-dihydropyridin-4-yl)-2-methoxyphenyl)amino carboxylate (900 mg, 2.48 mmol) was dissolved in methanol (50 mL), and platinum dioxide (50%, 450 mg) was added. At the atmosphere of hydrogen gas, the mixture was stirred at room temperature overnight, and filtrated under suction. The filtrate was concentrated to get the product, which was directly used in the next step.

(5) Preparation of 4-(4-amino-3-methoxyphenyl)-1-(2-fluoroethyl)piperidin-2-one

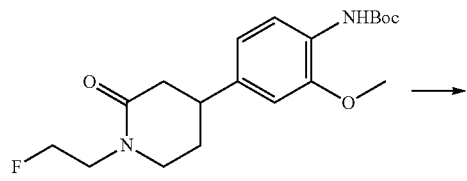

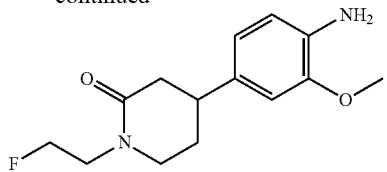

Tert-butyl (4-(1-(2-fluoroethyl)-2-oxopiperidin-4-yl)-2-methoxyphenyl)amino carboxylate (908 mg, 2.48 mmol) was dissolved in dichloromethane (6 mL) and trifluoroacetic acid (6 mL). The mixture was stirred at room temperature for 0.5 h, and concentrated to get the product, which was directly used in the next step.

(6) Preparation of N-(3-((2-((4-(1-(2-fluoroethyl)-2-oxopiperidin-4-yl)-2-methoxyphenyl)amino)-5-(trifluoro methyl)pyrimidin-4-yl)amino)phenyl)acrylamide

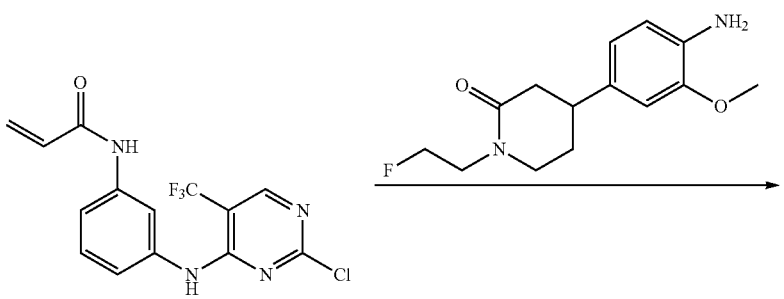

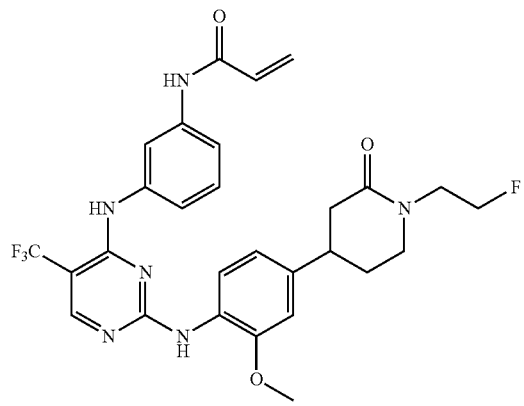 [SMILES: C=CC(=O)Nc1cccc(Nc2nc(Nc3ccc(C4CCN(CCF)C(=O)C4)cc3OC)ncc2C(F)(F)F)c1]

N-(3-((2-chloro-5-(trifluoromethyl)pyrimidin-4-yl) amino)phenyl)acrylamide (200 mg, 0.58 mmol) and 4-(4-amino-3-methoxyphenyl)-1-(2-fluoroethyl)piperidin-2-one (128 mg, 0.48 mmol) were added to isopropanol (20 mL), and a catalytic amount of trifluoroacetic acid was added. Under the protection of nitrogen gas, the reaction was carried out at 70° C. for 6 h, and aqueous ammonia was added to adjust pH of the solution to pH>7. The mixture was concentrated, and the crude product was purified by silica gel column chromatography (dichloromethane:methanol=20:1) to get the title compound (20 mg, yield: 7.3%).

Molecular formula: C28H28F4N6O3 Molecular weight: 572.2 LC-MS (m/z): 573.3 (M+H+)

1H-NMR (400 MHz, CDCl3) δ: 8.30 (s, 1H), 8.15-8.10 (m, 1H), 7.94 (s, 1H), 7.74 (s, 1H), 7.49-7.28 (m, 3H), 6.89 (s, 1H), 6.69 (s, 1H), 6.60 (s, 1H), 6.46 (dd, J1=1.2 Hz, J2=16.8 Hz, 1H), 6.29-6.21 (m, 1H), 5.79 (dd, J1=1.2 Hz, J2=10.4 Hz, 1H), 4.72-4.69 (m, 1H), 4.59-4.57 (m, 1H), 3.88 (s, 3H), 3.75-3.66 (m, 2H), 3.58-3.43 (m, 2H), 3.10-3.03 (m, 1H), 2.75-2.71 (m, 1H), 2.54-2.47 (m, 1H), 2.15-1.92 (m, 2H).

Example 23 Preparation of N-(3-((2-((2-methoxy-4-(1-propionylpiperidin-4-yl)phenyl)amino)-5-(trifluoromethyl)pyrimidin-4-yl)amino)phenyl)acrylamide (Compound 24)

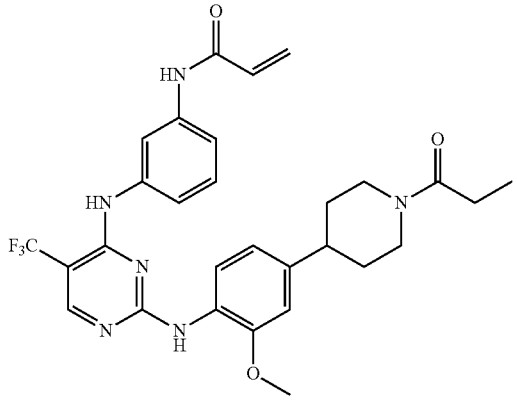 [SMILES: C=CC(=O)Nc1cccc(Nc2nc(Nc3ccc(C4CCN(C(=O)CC)CC4)cc3OC)ncc2C(F)(F)F)c1]

(1) Preparation of 1-(4-(3-methoxy-4-nitrophenyl)-3,6-dihydropyridin-1(2H)-yl)propan-1-one

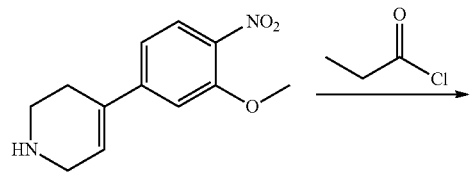

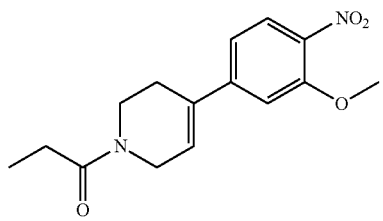

4-(3-Methoxy-4-nitrophenyl)-1,2,3,6-tetrahydropyridine (600 mg, 2.56 mmol) was dissolved in dichloromethane (20 mL), and triethylamine (775.7 mg, 7.68 mmol) was added. At 0° C., propionyl chloride (284.2 mg, 3.07 mmol) was added dropwisely. The mixture was stirred at room temperature for 12 h. TLC detection showed that raw materials disappeared. Water was added, and the mixture was extracted with ethyl acetate. The organic phases were combined, dried with anhydrous sodium sulfate, and concentrated to get the title compound (580 mg, yield: 78%).

(2) Preparation of 1-(4-(4-amino-3-methoxyphenyl) piperidin-1-yl)propan-1-one

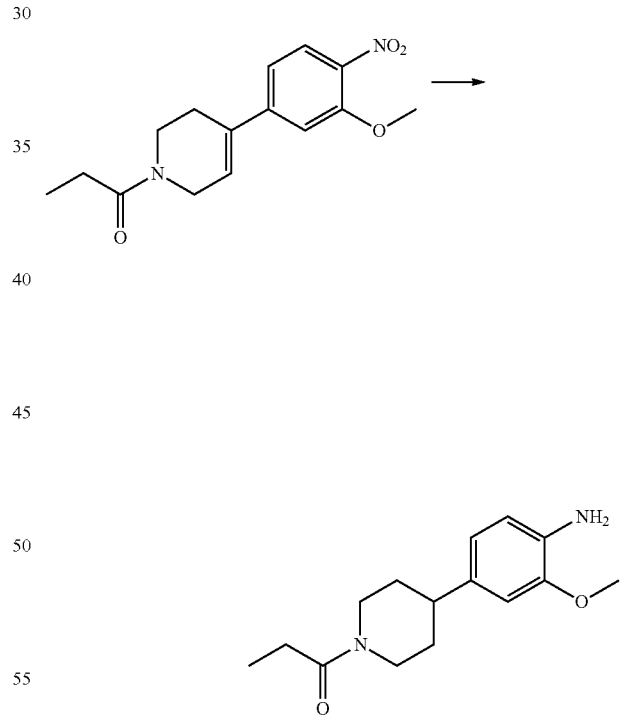

1-(4-(3-Methoxy-4-nitrophenyl)-3,6-dihydropyridin-1 (2H)-yl)propan-1-one (580 mg, 2.0 mmol) was dissolved in methanol (20 mL), and palladium-carbon (58 mg, mass ratio of 10%) was added. The mixture was stirred at room temperature for 12 h. After the reaction, the mixture was filtrated, and the solvent was removed to get the title product (500 mg, yield: 95.4%).

(3) Preparation of N-(3-((2-((2-methoxy-4-(1-propionylpiperidin-4-yl)phenyl)amino)-5-(trifluoromethyl)pyrimidin-4-yl)amino)phenyl)acrylamide

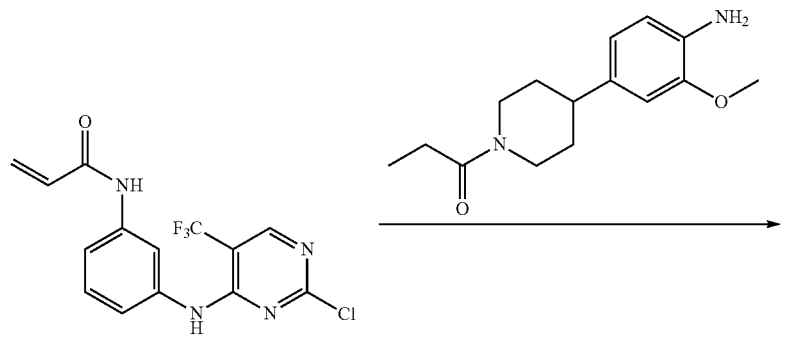

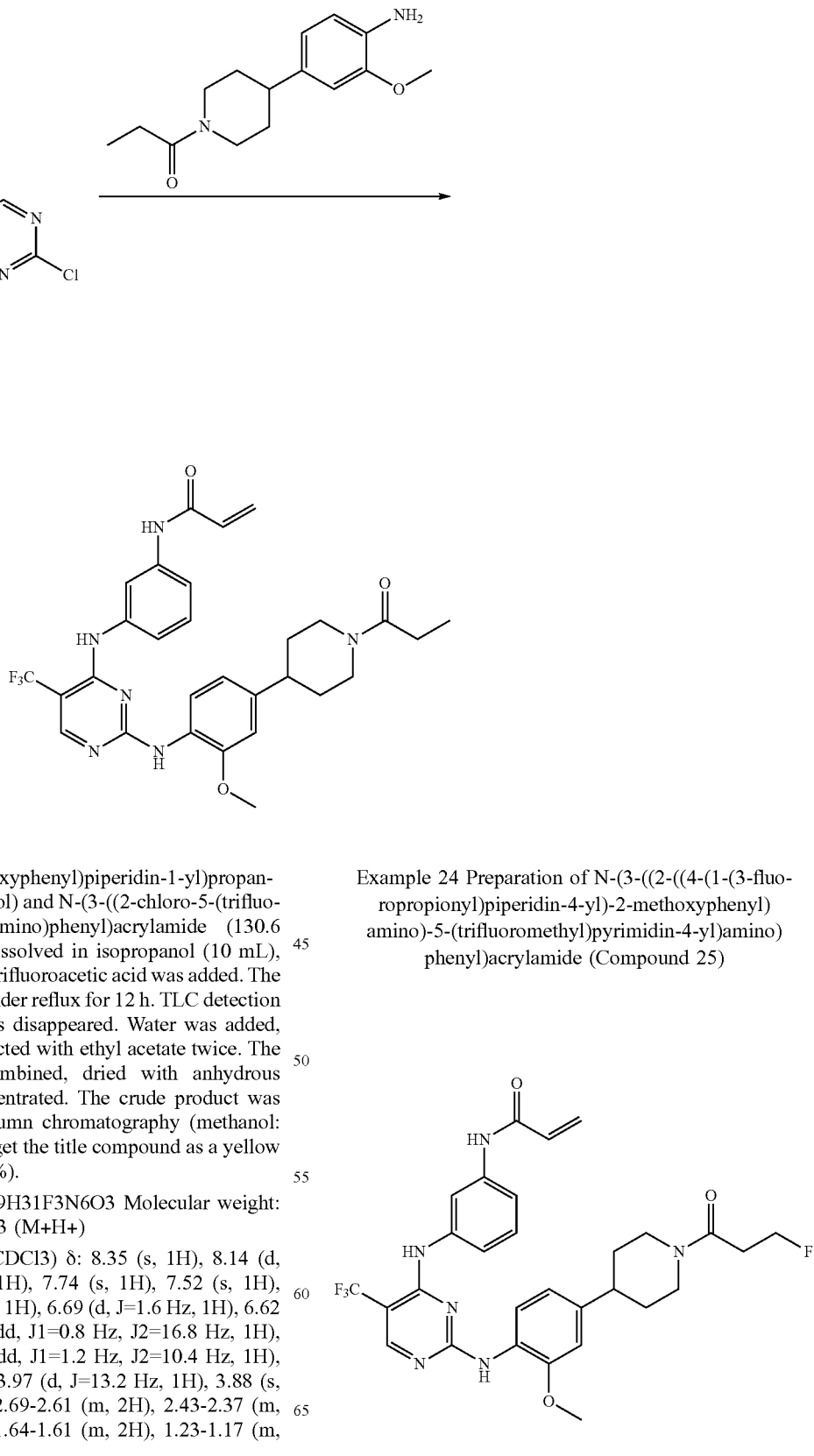

1-(4-(4-Amino-3-methoxyphenyl)piperidin-1-yl)propan-1-one (100 mg, 0.381 mmol) and N-(3-((2-chloro-5-(trifluoromethyl)pyrimidin-4-yl)amino)phenyl)acrylamide (130.6 mg, 0.381 mmol) were dissolved in isopropanol (10 mL), and a catalytic amount of trifluoroacetic acid was added. The reaction was carried out under reflux for 12 h. TLC detection showed that raw materials disappeared. Water was added, and the mixture was extracted with ethyl acetate twice. The organic phases were combined, dried with anhydrous sodium sulfate, and concentrated. The crude product was purified by silica gel column chromatography (methanol:dichloromethane=$_{1:50}$) to get the title compound as a yellow solid (50 mg, yield: 23.1%).

Molecular formula: C29H31F3N6O3 Molecular weight: 568.6 LC-MS (m/z): 569.3 (M+H+)

1H-NMR (400 MHz, CDCl3) δ: 8.35 (s, 1H), 8.14 (d, J=8.8 Hz, 1H), 7.87 (s, 1H), 7.74 (s, 1H), 7.52 (s, 1H), 7.38-7.26 (m, 3H), 6.88 (s, 1H), 6.69 (d, J=1.6 Hz, 1H), 6.62 (d, J=7.6 Hz, 1H), 6.46 (dd, J1=0.8 Hz, J2=16.8 Hz, 1H), 6.25-6.18 (m, 1H), 5.79 (dd, J1=1.2 Hz, J2=10.4 Hz, 1H), 4.81 (d, J=13.2 Hz, 1H), 3.97 (d, J=13.2 Hz, 1H), 3.88 (s, 3H), 3.15-3.05 (m, 1H), 2.69-2.61 (m, 2H), 2.43-2.37 (m, 2H), 1.86-1.84 (m, 2H), 1.64-1.61 (m, 2H), 1.23-1.17 (m, 3H).

Example 24 Preparation of N-(3-((2-((4-(1-(3-fluoropropionyl)piperidin-4-yl)-2-methoxyphenyl)amino)-5-(trifluoromethyl)pyrimidin-4-yl)amino)phenyl)acrylamide (Compound 25)

(1) Preparation of 3-hydroxy-1-(4-(3-methoxy-4-nitrophenyl)-3,6-dihydropyridin-(2H)-yl)propan-1-one

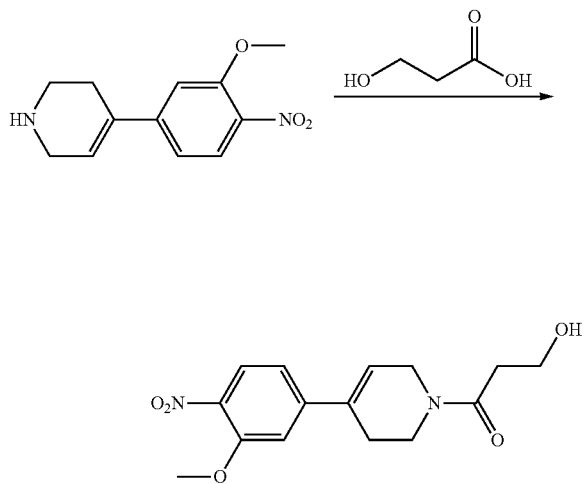

4-(3-Methoxy-4-nitrophenyl)-1,2,3,6-tetrahydropyridine (665 mg, 2.84 mmol) was dissolved in tetrahydrofuran (20 mL), and triethylamine (860.5 mg, 8.52 mmol), 2-(7-azabenzotriazol-1-yl)-N,N,N',N'-tetramethyluronium hexafluorophosphate (1.62 g, 4.26 mmol) and 3-hydroxypropionic acid (30% aqueous solution, 852.8 mg, 2.84 mmol) were added. The mixture was stirred at room temperature for 12 h. TLC detection showed that raw materials disappeared. Water was added, and the mixture was extracted with ethyl acetate twice. The organic phases were combined, dried with anhydrous sodium sulfate, and concentrated to get the title compound (500 mg, yield: 57.5%).

(2) Preparation of 3-fluoro-1-(4-(3-methoxy-4-nitrophenyl)-3,6-dihydropyridin-1(2H)-yl)propan-1-one

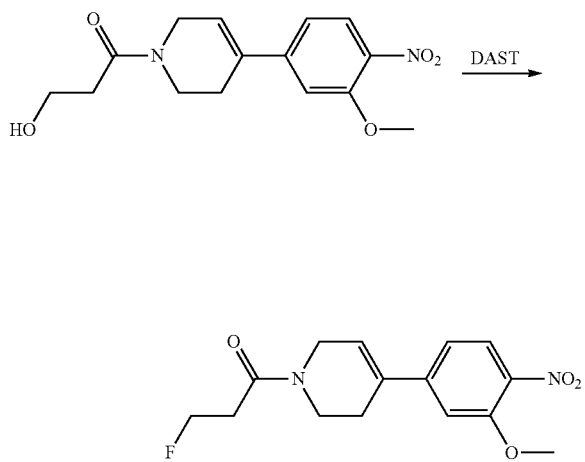

3-Hydroxy-1-(4-(3-methoxy-4-nitrophenyl)-3,6-dihydropyridin-1(2H)-yl)propan-1-one (500 mg, 1.63 mmol) was dissolved in dichloromethane (20 mL), and cooled to −78° C., and diethylaminosulphur trifluoride (525.5 mg, 3.26 mmol) was added. After the addition, the temperature was increased to room temperature. After TLC detection showed that the reaction was finished, water was added, and the mixture was extracted with ethyl acetate twice. The organic phases were combined, dried with anhydrous sodium sulfate, and concentrated. The crude product was purified by silica gel column chromatography (methanol:dichloromethane=1:100) to get the title compound as a yellow solid (75 mg, yield: 15%).

(3) Preparation of 1-(4-(4-amino-3-methoxyphenyl)piperidin-1-yl)-3-fluoropropan-1-one

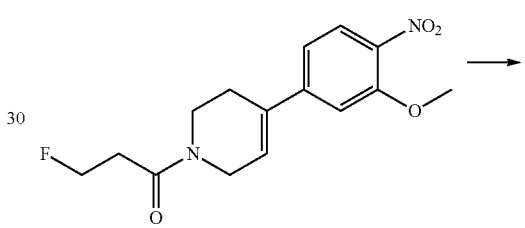

3-Fluoro-1-(4-(3-methoxy-4-nitrophenyl)-3,6-dihydropyridin-1(2H)-yl)propan-1-one (75 mg, 0.245 mmol) was dissolved in methanol (20 mL), and palladium-carbon (10%, 7.5 mg) was added. The mixture was stirred at room temperature for 12 h. After the reaction, palladium-carbon was removed by filtration. The solvent was removed under reduced pressure to get the title compound (60 mg, yield: 88%).

(4) Preparation of N-(3-((2-((4-(1-(3-fluoropropionyl)piperidin-4-yl)-2-methoxyphenyl)amino)-5-(trifluoromethyl)pyrimidin-4-yl)amino)phenyl)acrylamide

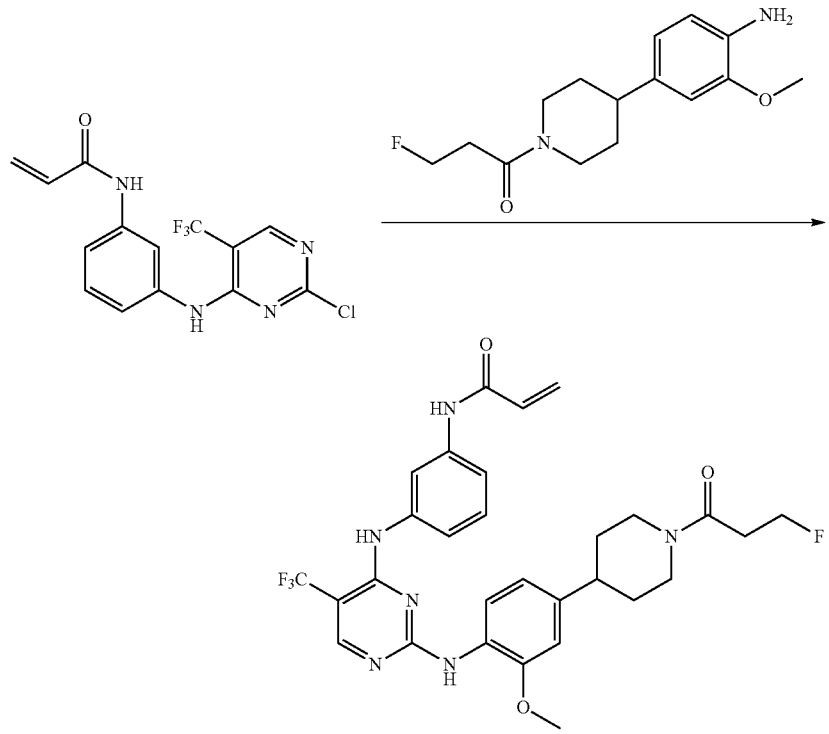

1-(4-(4-Amino-3-methoxyphenyl)piperidin-1-yl)-3-fluoropropan-1-one (60 mg, 0.214 mmol) and N-(3-((2-chloro-5-(trifluoromethyl)pyrimidin-4-yl)amino)phenyl)acrylamide (73.3 mg, 0.214 mmol) were dissolved in isopropanol (10 mL), and a catalytic amount of trifluoroacetic acid was added. The reaction was carried out under reflux for 12 h. TLC detection showed that raw materials disappeared. Water was added, and the mixture was extracted with ethyl acetate twice. The organic phases were combined, dried with anhydrous sodium sulfate, and concentrated. The crude product was purified by silica gel column chromatography (methanol:dichloromethane=1:50) to get the title compound as a white solid (20 mg, yield: 15.9%).

Molecular formula: C29H30F4N6O3 Molecular weight: 586.58 LC-MS (m/z): 587.3 (M+H+)

1H-NMR (400 MHz, CDCl3) δ: 8.31 (s, 1H), 8.13 (d, J=8.0 Hz, 1H), 7.86 (s, 1H), 7.74 (s, 1H), 7.61 (s, 1H), 7.52 (s, 1H), 7.37-7.26 (m, 2H), 6.89 (s, 1H), 6.68 (d, J=1.2 Hz, 1H), 6.60 (s, 1H), 6.45 (dd, J1=1.2 Hz, J2=16.8 Hz, 1H), 6.27-6.20 (m, 1H), 5.76 (dd, J1=0.8 Hz, J2=10.4 Hz, 1H), 4.89-4.86 (m, 1H), 4.81-4.74 (m, 2H), 3.98 (d, J=13.2 Hz, 1H), 3.87 (s, 3H), 3.18-3.08 (m, 1H), 2.84-2.76 (m, 2H), 2.68-2.63 (m, 2H), 1.90-1.84 (m, 2H), 1.64-1.57 (m, 2H).

Example 25 Preparation of N-(3-((2-((4-(1-(2-fluoroethyl)piperidin-4-yl)-2-methoxyphenyl)amino)-5-(trifluoromethyl) pyrimidin-4-yl)amino)phenyl)acrylamide (Compound 26)

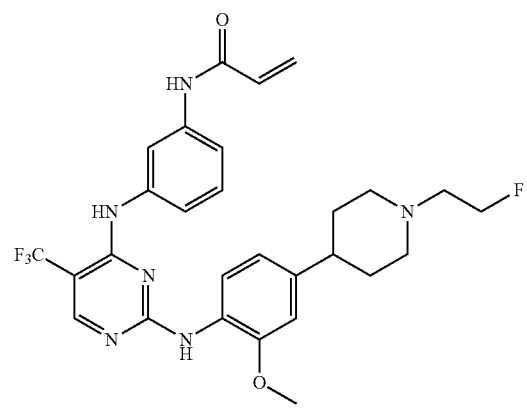 [SMILES: C=CC(=O)Nc1cccc(Nc2nc(Nc3ccc(C4CCN(CCF)CC4)cc3OC)ncc2C(F)(F)F)c1]

(1) Preparation of tert-butyl (4-bromo-2-methoxyphenyl)amino carboxylate

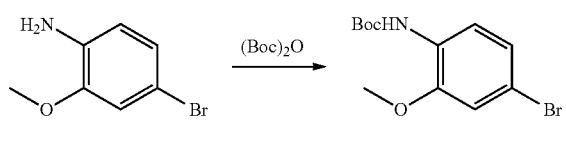

4-Bromo-2-methoxyaniline (6.8 g, 33.7 mmol) and di-tert-butyl dicarbonate (8.9 g, 40.8 mmol) were dissolved in tetrahydrofuran (100 mL). Under the protection of nitrogen gas, the mixture was reacted under reflux for 22 h, and cooled. The solvent was removed under reduced pressure, and ethyl acetate (150 mL) was added. The mixture was washed with hydrochloric acid (1 mol/L), and the water phase and the organic phase were separated. The organic phase was dried with anhydrous sodium sulfate, and filtrated under suction. The filtrate was concentrated under reduced pressure to get the title compound (8.3 g, yield: 81.6%).

(2) Preparation of tert-butyl (2-methoxy-4-(pyridin-4-yl)phenyl)amino carboxylate

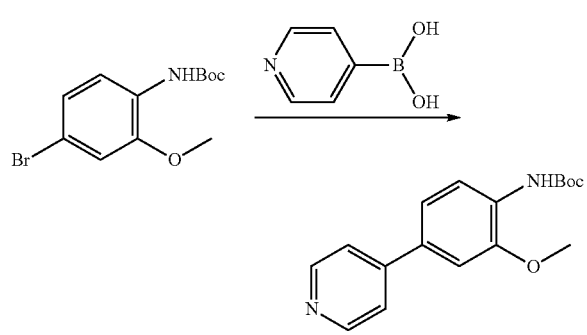

Pyridin-4-boric acid (1.19 g, 9.7 mmol), tert-butyl (4-bromo-2-methoxyphenyl)amino carboxylate (2.93 g, 9.7 mmol) and potassium carbonate (2.68 g, 19.4 mmol) were added to a mixed solvent of 1,4-dioxane (50 mL) and water (10 mL). Under the protection of nitrogen gas, [1,1'-bis(diphenyphosphino)ferrocene]dichloropalladium (II) (709 mg, 0.97 mmol) was added. The mixture was heated to 90° C. and reacted overnight, and then filtrated under suction. The filtrate was concentrated, and the crude product was purified by silica gel column chromatography (petroleum ether: ethyl acetate=1:1) to get the title compound (2.5 g, yield: 85.9%).

(3) Preparation of tert-butyl (2-methoxy-4-(piperidin-4-yl)phenyl)amino carboxylate

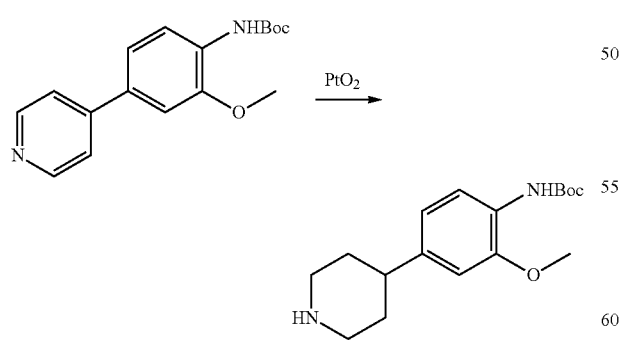

Tert-butyl (2-methoxy-4-(pyridin-4-yl)phenyl)amino carboxylate (1.2 g, 4 mmol) was dissolved in acetic acid (30 mL), and platinum dioxide (30%, 360 mg) and trifluoroacetic acid (912 mg, 8 mmol) were added. At the atmosphere of hydrogen gas, the mixture was stirred at room temperature overnight, and filtrated under suction. The filtrate was concentrated. Saturated sodium bicarbonate aqueous solution and ethyl acetate were added, and the water phase and the organic phase were separated. The organic phase was dried with anhydrous sodium sulfate, and concentrated to get the product, which was directly used in the next step.

(4) Preparation of tert-butyl (4-(1-(2-fluoroethyl)piperidin-4-yl)-2-methoxyphenyl)amino carboxylate

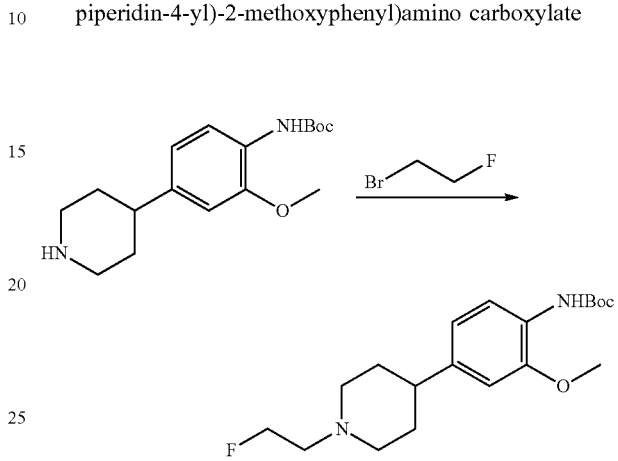

Tert-butyl (2-methoxy-4-(piperidin-4-yl)phenyl)amino carboxylate (306 mg, 1 mmol) was dissolved in acetonitrile (30 mL), and 1-bromo-2-fluoroethane (190 mg, 1.5 mmol) and cesium carbonate (814.5 mg, 2.5 mmol) were added. Under the protection of nitrogen gas, the mixture was reacted at 50° C. for 22 h, and then cooled to room temperature and filtrated under suction. The filtrate was concentrated, and the crude product was purified by silica gel column chromatography (dichloromethane:methanol=20:1) to get the title compound (200 mg, yield: 56.7%).

(5) Preparation of 4-(1-(2-fluoroethyl)piperidin-4-yl)-2-methoxyaniline

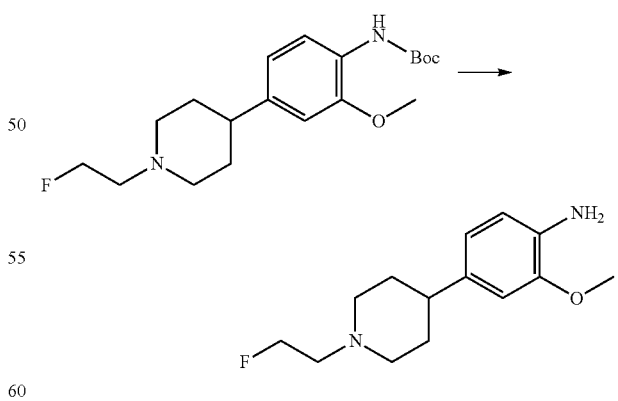

Tert-butyl (4-(1-(2-fluoroethyl)piperidin-4-yl)-2-methoxyphenyl)amino carboxylate (200 mg, 0.57 mmol) was dissolved in dichloromethane (4 mL) and trifluoroacetic acid (4 mL), and stirred at room temperature for 0.5 h. The mixture was concentrated to get the product, which was directly used in the next step.

(6) Preparation of N-(3-((2-((4-(1-(2-fluoroethyl) piperidin-4-yl)-2-methoxyphenyl)amino)-5-(trifluoromethyl) pyrimidin-4-yl)amino)phenyl)acrylamide

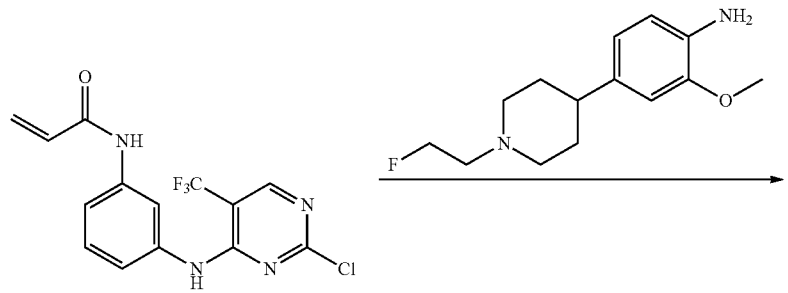

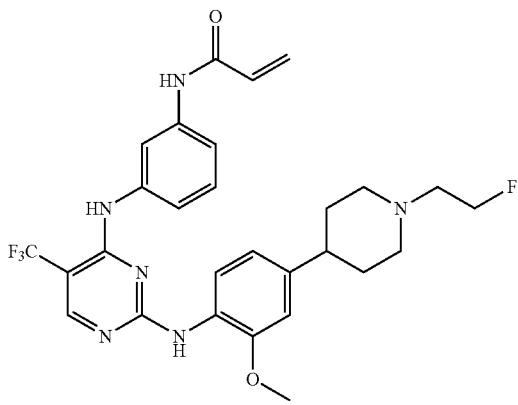

N-(3-((2-chloro-5-(trifluoromethyl)pyrimidin-4-yl) amino)phenyl)acrylamide (200 mg, 0.58 mmol) and 4-(1-(2-fluoroethyl)piperidin-4-yl)-2-methoxyaniline (121 mg, 0.48 mmol) were added to isopropanol (20 mL), and a catalytic amount of trifluoroacetic acid was added. Under the protection of nitrogen gas, the mixture was stirred at 70° C. for 6 h, and aqueous ammonia was added to adjust pH of the solution to pH>7. The mixture was concentrated, and the crude product was purified by silica gel column chromatography (dichloromethane:methanol=20:1) to get the title compound (210 mg, yield: 78.4%).

Molecular formula: C28H30F4N6O2 Molecular weight: 558.6 LC-MS (m/z): 559.3 (M+H+)

1H-NMR (400 MHz, CDCl3) δ: 10.17 (s, 1H), 8.76 (s, 1H), 8.31 (s, 1H), 8.06 (s, 1H), 7.78 (s, 1H), 7.64 (d, J=8.4 Hz, 1H), 7.54 (d, J=8.4 Hz, 1H), 7.28 (t, J=8.0 Hz, 1H), 7.12 (d, J=8.0 Hz, 1H), 6.83 (d, J=1.2 Hz, 1H), 6.45-6.38 (m, 2H), 6.24 (dd, J1=2.0 Hz, J2=17.2 Hz, 1H), 5.74 (dd, J1=2.0 Hz, J2=10.0 Hz, 1H), 4.59 (t, J=5.0 Hz, 1H), 4.47 (t, J=5.0 Hz, 1H), 3.78 (s, 3H), 2.95 (d, J=11.2 Hz, 2H), 2.65 (t, J=5.0 Hz, 1H), 2.58 (t, J=5.0 Hz, 1H), 2.42-2.33 (m, 1H), 2.08-2.02 (m, 2H), 1.68-1.59 (m, 4H).

Example 26 Preparation of N-(3-((2-((2-methoxy-4-(1-(methylsulfonyl)piperidin-4-yl)phenyl)amino)-5-(trifluoromethyl)pyrimidin-4-yl)amino)phenyl)acrylamide (Compound 27)

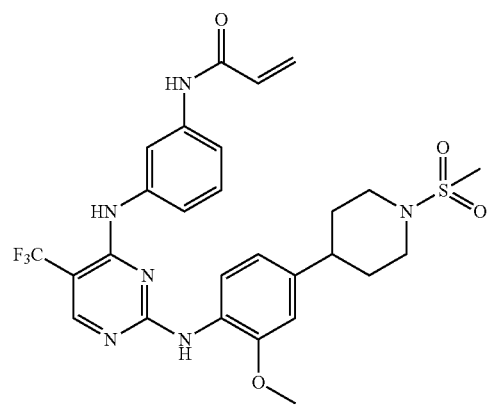 [SMILES: C=CC(=O)Nc1cccc(Nc2nc(Nc3ccc(C4CCN(S(C)(=O)=O)CC4)cc3OC)ncc2C(F)(F)F)c1]

(1) Preparation of tert-butyl (2-methoxy-4-(1-(methyl sulfonyl)piperidin-4-yl)phenyl)amino carboxylate

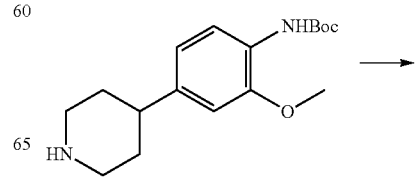

151

-continued

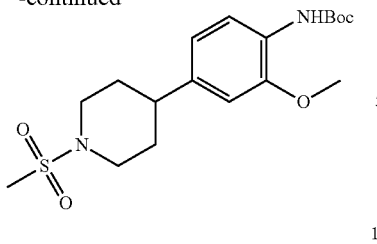

Tert-butyl (2-methoxy-4-(piperidin-4-yl)phenyl)amino carboxylate (214 mg, 0.7 mmol) was dissolved in dichloromethane (20 mL), and methylsufonyl chloride (160.4 mg, 1.4 mmol) and N,N-diisopropylethylamine (361.2 mg, 2.8 mmol) were added under stirring. The mixture was stirred at room temperature for 6 h, and concentrated. Water (50 mL) and ethyl acetate (50 mL) were added, and the water phase and the organic phase were separated. The organic phase was dried with anhydrous sodium sulfate, and concentrated. The crude product was purified by silica gel column chromatography (petroleum ether: ethyl acetate=1:1) to get the title compound (200 mg, 74.3%).

(2) Preparation of 2-methoxy-4-(1-(methylsulfonyl)piperidin-4-yl)aniline

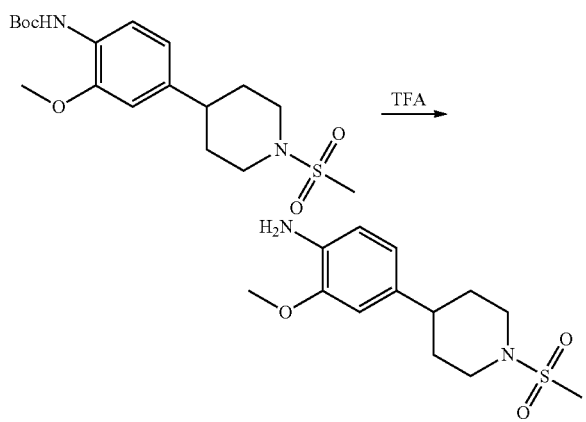

Tert-butyl (2-methoxy-4-(1-(methylsulfonyl)piperidin-4-yl)phenyl)amino carboxylate (200 mg, 0.52 mmol) was dissolved in dichloromethane (5 mL) and trifluoroacetic acid (5 mL), and stirred at room temperature for 0.5 h. The mixture was concentrated to get the product, which was directly used in the next step.

(3) Preparation of N-(3-((2-((2-methoxy-4-(1-(methylsulfonyl)piperidin-4-yl)phenyl)amino)-5-(trifluoromethyl)pyrimidin-4-yl)amino)phenyl)acrylamide

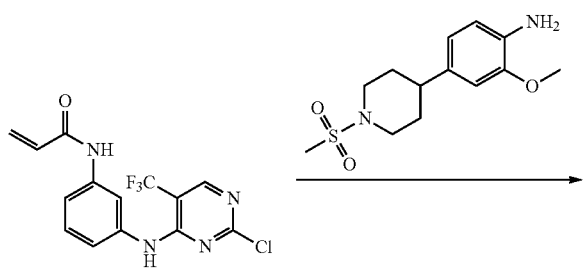

152

-continued

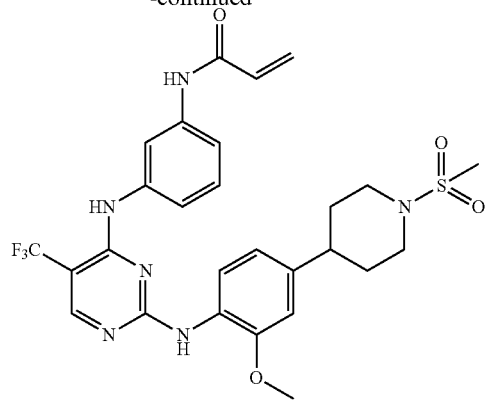

N-(3-((2-chloro-5-(trifluoromethyl)pyrimidin-4-yl)amino)phenyl)acrylamide (200 mg, 0.58 mmol) and 2-methoxy-4-(1-(methylsulfonyl)piperidin-4-yl)aniline (136 mg, 0.48 mmol) were added to isopropanol (20 mL), and a catalytic amount of trifluoroacetic acid was added. Under the protection of nitrogen gas, the mixture was stirred at 70° C. for 6 h, and aqueous ammonia was added to adjust pH of the solution to pH>7. The mixture was concentrated. The crude product was purified by silica gel column chromatography (dichloromethane:methanol=20:1) to get the title compound (220 mg, yield: 77.7%).

Molecular formula: $C_{27}H_{29}F_3N_6O_4S$ Molecular weight: 590.6 LC-MS (m/z): 591.2 (M+H+)

1H-NMR (400 MHz, DMSO-d6) δ: 10.30 (s, 1H), 9.52 (s, 1H), 8.88 (s, 1H), 8.47 (s, 1H), 7.80 (s, 1H), 7.57-7.55 (m, 2H), 7.36-7.32 (m, 1H), 7.09 (d, J=7.6 Hz, 1H), 6.90 (s, 1H), 6.48-6.41 (m, 2H), 6.25 (dd, J1=1.8 Hz, J2=17.0 Hz, 1H), 5.76-5.73 (m, 1H), 3.81 (s, 3H), 3.65 (d, J=11.6 Hz, 2H), 2.89 (s, 3H), 2.78-2.73 (m, 2H), 2.55-2.52 (m, 1H), 1.78 (d, J=12.0 Hz, 2H), 1.68-1.58 (m, 2H).

Example 27 Preparation of N-(3-((2-((2-methoxy-4-(4-morpholinopiperidin-1-yl)phenyl)amino)-5-(trifluoromethyl)pyrimidin-4-yl)amino)phenyl)acrylamide (Compound 28)

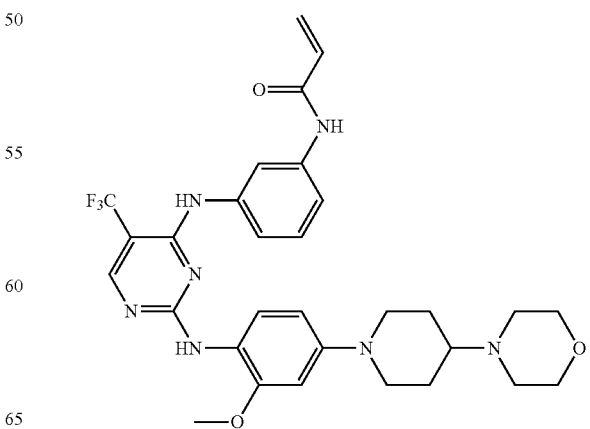

(1) Preparation of 4-fluoro-2-methoxy-1-nitrobenzene

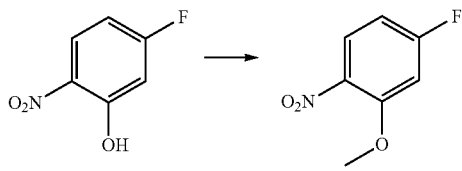

In an ice-water bath, 5-fluoro-2-nitrophenol (4.7 g, 30 mmol) was dissolved in N,N-dimethylformamide (50 mL), anhydrous potassium carbonate (12.4 g, 90 mmol) was added, and iodomethane (6.4 g, 45 mmol) was then slowly added dropwisely. After the addition, the mixture was heated to 60° C. and reacted for 5 h. After the reaction, the mixture was cooled to room temperature, and filtrated. The filter cake was washed with ethyl acetate (10 mL×3). Water (150 mL) was added to the filtrate, and the resultant mixture was extracted with ethyl acetate (50 mL×3). The organic phases were combined, and dried with anhydrous sodium sulfate. The solvent was dried by distillation to get the title compound (4.5 g, yield: 88%).

(2) Preparation of tert-butyl 4-morpholinopiperidin-1-carboxylate

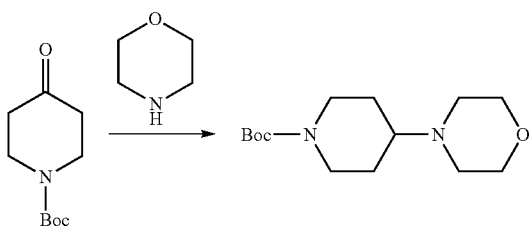

In an ice-water bath, tert-butyl 4-oxopiperidin-1-carboxylate (2.99 g, 15 mmol), morpholine (1.44 g, 16.5 mmol), and acetic acid (1.08 g, 18 mmol) were dissolved in dichloromethane (30 mL), and sodium triacetoxyborohydride (6.36 g, 30 mmol) was added under stirring. After the addition, the mixture was warmed to room temperature and reacted for 2 h. After the reaction, NaOH solution (2 N, 10 mL) was added, and the mixture was washed and separated to get the organic phase. The organic phase was dried with anhydrous sodium sulfate, and purified by silica gel column chromatography (petroleum ether: ethyl acetate=5:1) to get the title compound (3.49 g, yield: 86%).

(3) Preparation of 4-(piperidin-4-yl)morpholine

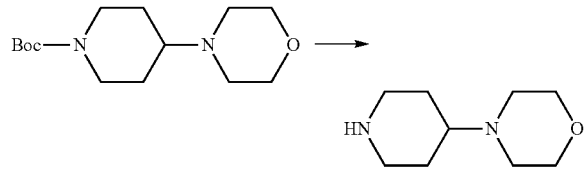

Tert-butyl 4-morpholinopiperidin-1-carboxylate (3.0 g, 11.1 mmol) was dissolved in dichloromethane (30 mL), and trifluoroacetic acid (5 mL) was added. The mixture was stirred at room temperature for 6 h, and the solvent was removed under reduced pressure. Saturated sodium bicarbonate solution was added dropwisely to adjust pH of the mixture to pH=8. The mixture was extracted with ethyl acetate (50 mL×3). The organic phases were combined, dried with anhydrous sodium sulfate, and concentrated to get the title compound (1.5 g, yield: 79%).

(4) Preparation of 4-(1-(3-methoxy-4-nitrophenyl)piperidin-4-yl)morpholine

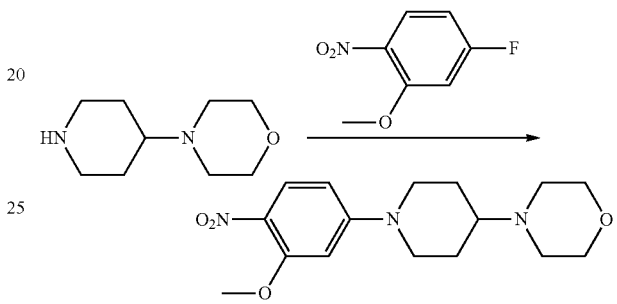

At room temperature, 4-(piperidin-4-yl)morpholine (1.5 g, 8.8 mmol), potassium carbonate (3.0 g, 22 mmol) was dissolved in N,N-dimethylformamide (30 mL), and 4-fluoro-2-methoxy-1-nitrobenzene (1.7 g, 9.7 mmol) was added. After the addition, the mixture was heated to 60° C. and reacted for 12 h. After the reaction, the reaction solution was poured into water (150 mL), and extracted with ethyl acetate (200 mL×3). The organic phases were combined, dried with anhydrous sodium sulfate, and purified by silica gel column chromatography (the eluent was petroleum ether: ethyl acetate=1:1) to get the title compound (2.0 g, yield: 71%).

(5) Preparation of 2-methoxy-4-(4-morpholinopiperidin-1-yl)aniline

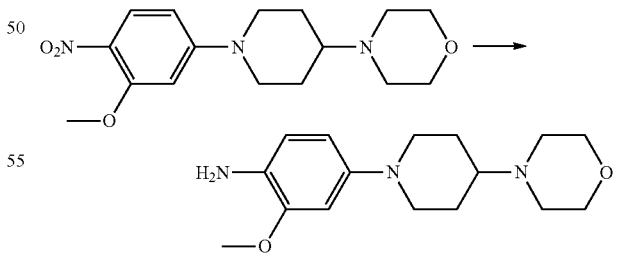

4-(1-(3-Methoxy-4-nitrophenyl)piperidin-4-yl)morpholine (2.0 g, 6.2 mmol) and palladium-carbon (10%, 200 mg) were suspended in methanol (100 mL). The system was vacuumized, and hydrogen gas was introduced. The mixture was reacted at room temperature for 3 h, and filtrated. The filtrate was dried by distillation to get the title compound (1.6 g, yield: 88%).

(6) Preparation of N-(3-((2-((2-methoxy-4-(4-morpholinopiperidin-1-yl)phenyl)amino)-5-(trifluoromethyl)pyrimidin-4-yl)amino)phenyl)acrylamide

Example 28 Preparation of N-(3-((2-((2-methoxy-4-(1-methylpiperidin-4-yl)phenyl)amino)-5-(trifluoromethyl)pyrimidin-4-yl)amino)phenyl)acrylamide (Compound 29)

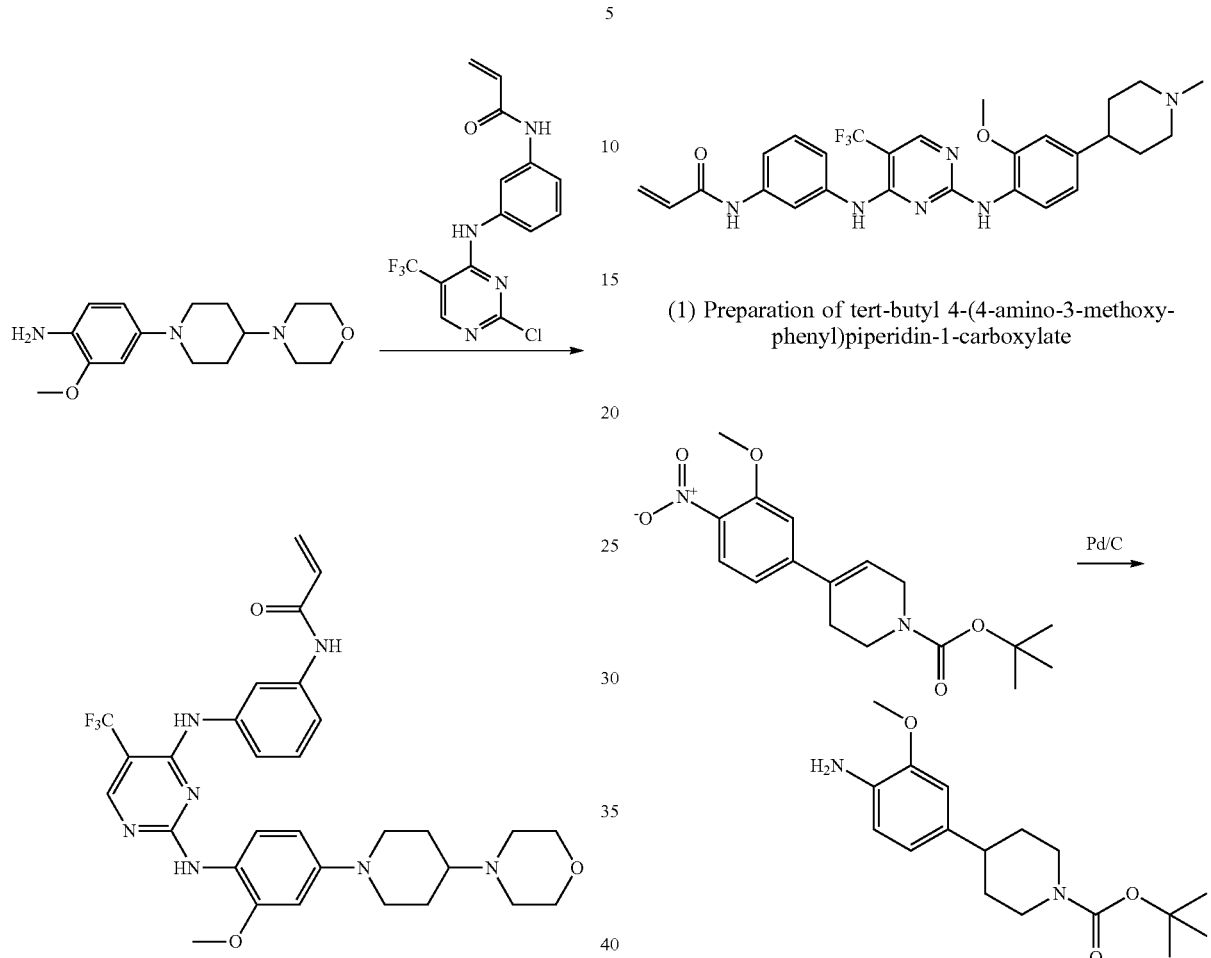

(1) Preparation of tert-butyl 4-(4-amino-3-methoxyphenyl)piperidin-1-carboxylate

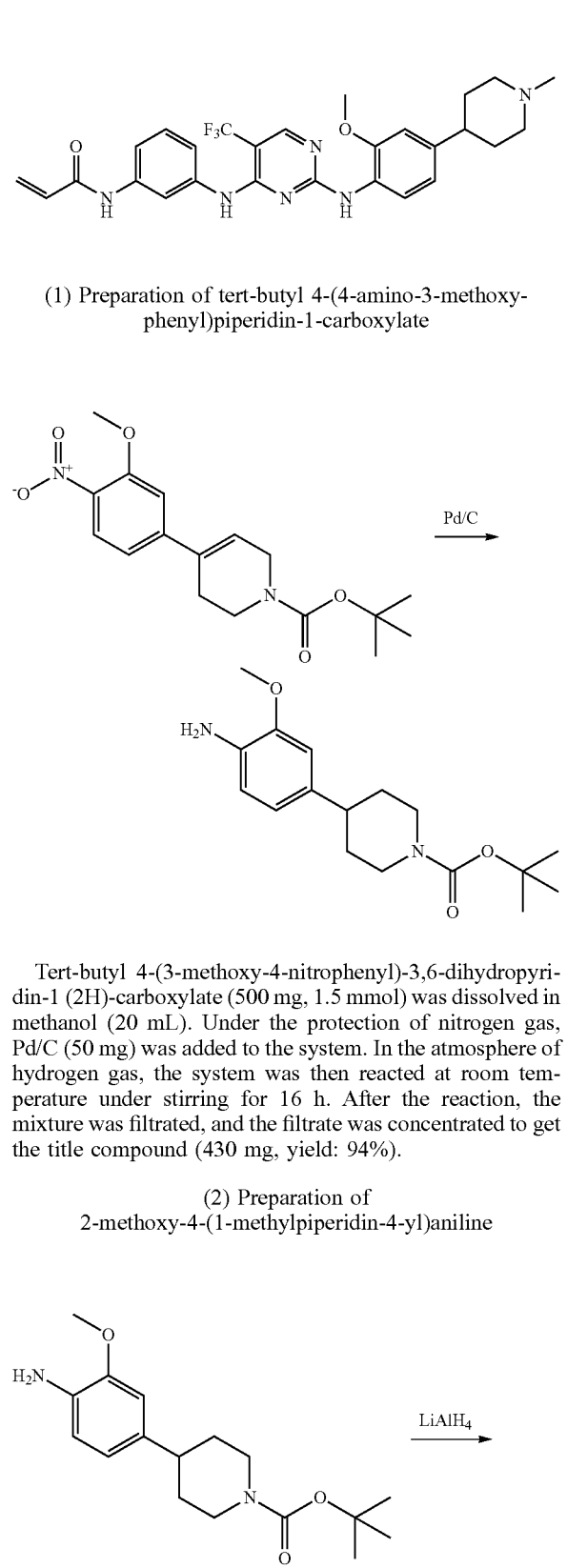

2-Methoxy-4-(4-morpholinopiperidin-1-yl)aniline (500 mg, 1.7 mmol) and N-(3-((2-chloro-5-(trifluoromethyl)pyrimidin-4-yl)amino)phenyl)acrylamide (583 mg, 1.7 mmol) were dissolved in isopropanol (10 mL), and a catalytic amount of trifluoroacetic acid was added dropwisely. The mixture was heated to 70° C. and reacted for 12 h. After the reaction, the solution was concentrated and purified by silica gel column chromatography (the eluent was dichloromethane:methanol=10:1) to get the title compound (760 mg, yield: 76%).

Molecular formula: C30H34F3N7O3 Molecular weight: 597.63 LC-MS (m/z): 598.0 (M+H+)

1H-NMR (400 MHz, DMSO-d6) δ: 10.83 (s, 1H), 10.26 (s, 1H), 8.64 ((s, 1H), 8.26 (s, 1H), 8.10 (s, 1H), 7.74 (brs, 1H), 7.56 (d, 1H, J=7.6 Hz), 7.47 (d, 1H, J=8.8 Hz), 7.23-7.27 (m, 1H), 7.15 (s, 1H), 6.44-6.50 (m, 1H), 6.25 (dd, 1H, J1=2.0 Hz, J2=17.2 Hz), 5.74-5.77 (m, 1H), 3.96 (s, 2H), 3.73-3.84 (m, 8H), 3.42-3.49 (m, 2H), 3.00-3.12 (m, 2H), 2.60 (t, 2H, J=12.2 Hz), 2.13 (d, 2H, J=10.8 Hz), 1.72-1.78 (m, 2H).

Tert-butyl 4-(3-methoxy-4-nitrophenyl)-3,6-dihydropyridin-1 (2H)-carboxylate (500 mg, 1.5 mmol) was dissolved in methanol (20 mL). Under the protection of nitrogen gas, Pd/C (50 mg) was added to the system. In the atmosphere of hydrogen gas, the system was then reacted at room temperature under stirring for 16 h. After the reaction, the mixture was filtrated, and the filtrate was concentrated to get the title compound (430 mg, yield: 94%).

(2) Preparation of 2-methoxy-4-(1-methylpiperidin-4-yl)aniline

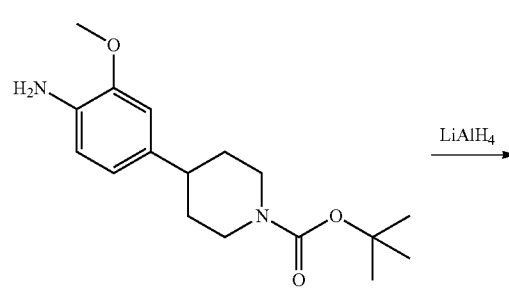

-continued

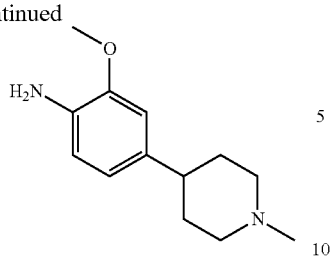

Tert-butyl 4-(4-amino-3-methoxyphenyl)piperidin-1-carboxylate (430 mg, 1.4 mmol) was dissolved in tetrahydrofuran (20 mL). The mixture was cooled in an ice-water bath, and lithium aluminum hydride (106 mg, 2.8 mmol) was added slowly. The mixture was stirred at room temperature for 2 h. After the reaction, the mixture was washed with water (50 mL×2), dried, filtrated, and concentrated to get the title compound (268 mg, yield: 87%).

(3) Preparation of N-(3-((2-((2-methoxy-4-(1-methylpiperidin-4-yl)phenyl)amino)-5-(trifluoromethyl) pyrimidin-4-yl)amino)phenyl)acrylamide

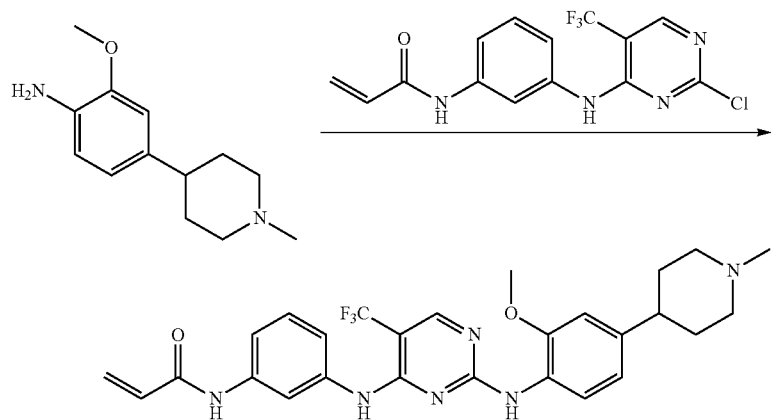

2-Methoxy-4-(1-methylpiperidin-4-yl)aniline (220 mg, 1.0 mmol) and N-(3-((2-chloro-5-(trifluoromethyl)pyrimidin-4-yl)amino)phenyl)acrylamide (342 mg, 1.0 mmol) were added to isopropanol (10 mL), and a catalytic amount of trifluoroacetic acid was added to the system. The mixture was heated to 70° C. and reacted under stirring for 16 h. After the reaction, ethyl acetate (50 mL) was added to the reaction solution. The reaction solution was washed with water (50 mL×2), dried, concentrated, and purified by silica gel column chromatography (dichloromethane:methanol=10:1) to get the title compound (35 mg, yield: 6.7%).

Molecular formula: C27H29F3N6O2 Molecular weight: 526.55 LC-MS (m/z): 527.3 (M+H+)

1H-NMR (400 MHz, CDCl3) δ: 8.31 (s, 1H), 8.12 (d, J=8.4 Hz, 1H), 7.91 (s, 1H), 7.71 (s, 1H), 7.49-7.54 (m, 1H), 7.29-7.41 (m, 1H), 6.87 (s, 1H), 6.76 (s, 1H), 6.67 (d, J=7.2 Hz, 1H), 6.43-6.47 (m, 1H), 6.18-6.24 (m, 1H), 5.78 (d, J=10.8 Hz, 1H), 3.86 (s, 3H), 2.98 (d, J=10.8 Hz, 2H), 2.38-2.46 (m, 1H), 2.33 (s, 3H), 2.00-2.07 (m, 2H), 1.72-1.82 (m, 4H).

Example 29 Preparation of N-(3-((2-((4-(1-(2-fluoroethyl)piperidin-4-yl)-2-methoxyphenyl)amino)-5-(trifluoromethyl) pyridin-4-yl)amino)phenyl)acrylamide (Compound 30)

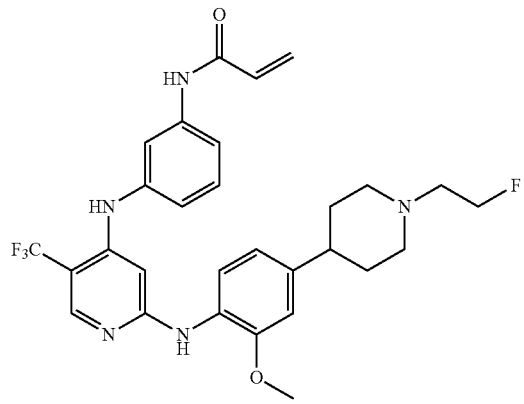 [SMILES: C=CC(=O)Nc1cccc(Nc2cc(Nc3ccc(C4CCN(CCF)CC4)cc3OC)ncc2C(F)(F)F)c1]

1-(2-fluoroethyl)-4-(3-methoxy-4-nitrophenyl)-1,2,3,6-tetrahydropyridine

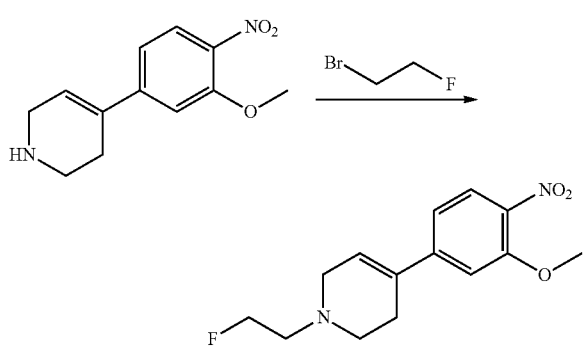

4-(3-Methoxy-4-nitrophenyl)-1,2,3,6-tetrahydropyridine (2.1 g, 9.0 mmol), 1-bromo-2-fluoro-ethane (1.36 g, 10.8 mmol) and potassium carbonate (2.5 g, 18.0 mmol) were added to acetonitrile (50 mL). The mixture was heated to 50° C. and reacted for 6 h. The mixture was filtrated under suction, and the filtrate was concentrated. The crude product was purified by silica gel column chromatography (dichloromethane:methanol=50:1) to get the title compound (1.1 g, yield: 43.6%).

(2) Preparation of 4-(1-(2-fluoroethyl)piperidin-4-yl)-2-methoxyaniline

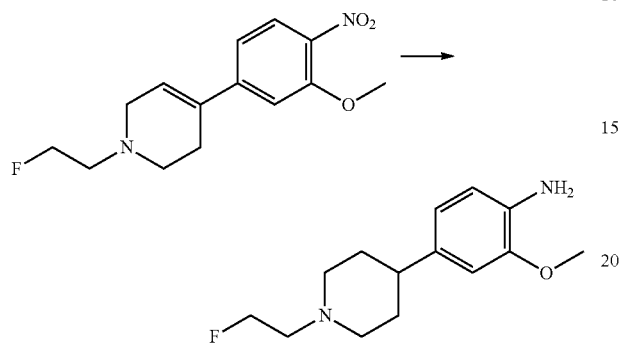

1-(2-Fluoroethyl)-4-(3-methoxy-4-nitrophenyl)-1,2,3,6-tetrahydropyridine (1.1 g, 3.9 mmol) was dissolved in methanol (100 mL), and palladium-carbon (390 mg) was added. At the atmosphere of hydrogen gas, the mixture was stirred at room temperature for 16 h, and filtrated under suction. The filtrate was concentrated to get the title compound (700 mg, yield: 71.2%).

(3) Preparation of tert-butyl (3-((2-((4-(1-(2-fluoroethyl)piperidin-4-yl)-2-methoxyphenyl)amino)-5-(trifluoromethyl)pyridin-4-yl)amino)phenyl)carbamate

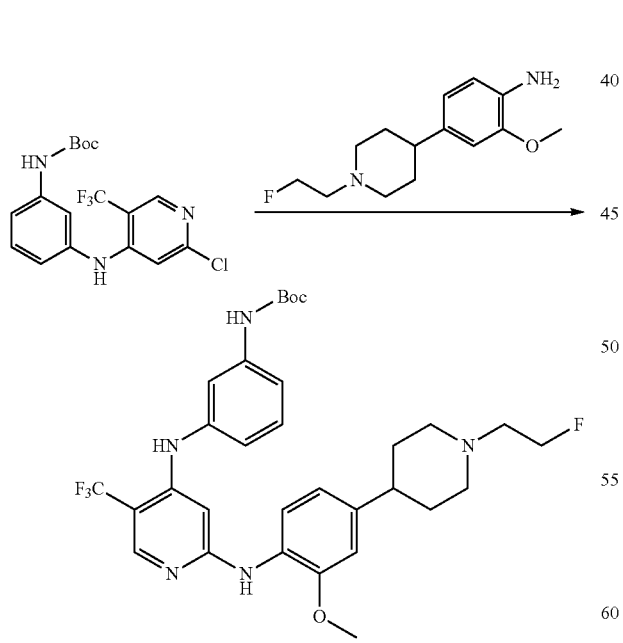

4-(1-(2-Fluoroethyl)piperidin-4-yl)-2-methoxyaniline (700 mg, 2.78 mmol), tert-butyl (3-((2-chloro-5-(trifluoromethyl)pyridin-4-yl)amino)phenyl)amino carboxylate (1.08 g, 2.78 mmol), tris(dibenzylideneacetone)dipalladium (256 mg, 0.28 mmol), 4,5-bis(diphenylphosphino)-9,9-dimethyl xanthene (318 mg, 0.55 mmol) and cesium carbonate (1.8 g, 5.5 mmol) were added to 1,4-dioxane (40 mL). Under the protection of nitrogen gas, the mixture was heated to 120° C. and reacted for 16 h, and then concentrated. The crude product was purified by silica gel column chromatography (dichloromethane:methanol=20:1) to get the title compound (360 mg, yield: 21.4%).

(4) Preparation of N4-(3-aminophenyl)-N2-(4-(1-(2-fluoroethyl)piperidin-4-yl)-2-methoxyphenyl)-5-(trifluoromethyl)pyridin-2,4-diamine

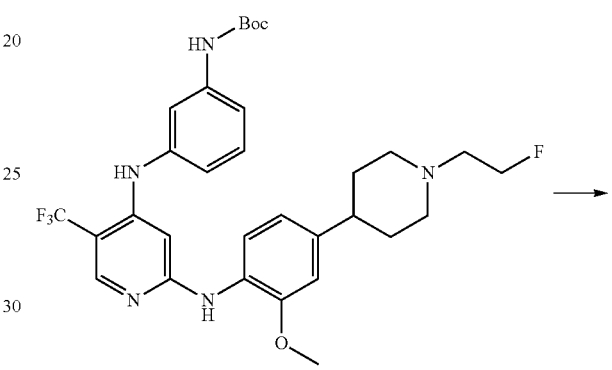

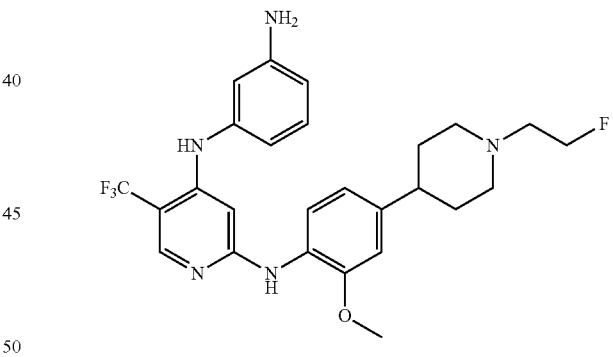

Tert-butyl (3-((2-((4-(1-(2-fluoroethyl)piperidin-4-yl)-2-methoxyphenyl)amino)-5-(trifluoromethyl)pyridin-4-yl)amino)phenyl)carbamate (360 mg, 0.60 mmol) was dissolved in dichloromethane (10 mL), and trifluoroacetic acid (1 mL) was added. The mixture was reacted at room temperature under stirring for 2 h. Dichloromethane (90 mL) and water (50 mL) were added, and the water phase and the organic phase were separated. The organic phase was washed with saturated sodium bicarbonate solution (50 mL) and saturated saline water (80 mL), dried with anhydrous sodium sulfate, and concentrated in vacuum to get the title compound (250 mg, yield: 82.8%).

(5) Preparation of N-(3-((2-((4-(1-(2-fluoroethyl) piperidin-4-yl)-2-methoxyphenyl)amino)-5-(trifluoromethyl) pyridin-4-yl)amino)phenyl)acrylamide Example 30 Preparation of N-(3-((2-((4-(6-acetyl-2, 6-diazaspiro[3.3]heptan-2-yl)-2-methoxyphenyl) amino)-5-(trifluoromethyl)pyrimidin-4-yl)amino) phenyl)acrylamide (Compound 31)

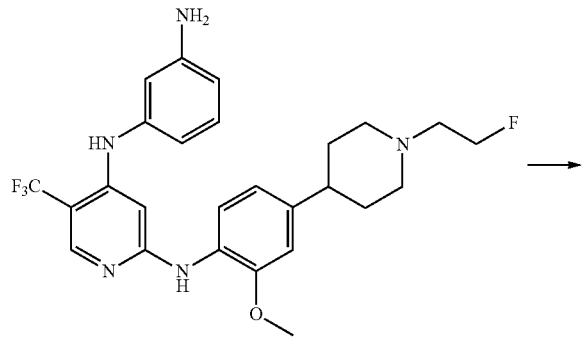

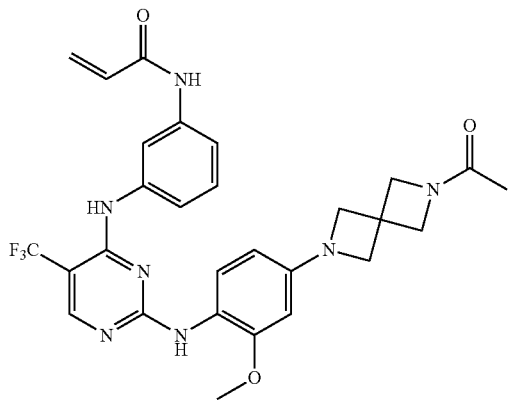 [SMILES: C=CC(=O)Nc1cccc(Nc2nc(Nc3ccc(N4CC5(CN(C(C)=O)C5)C4)cc3OC)ncc2C(F)(F)F)c1]

(1) Preparation of tert-butyl 6-acetyl-2,6-diazaspiro [3.3]heptan-2-carboxylate

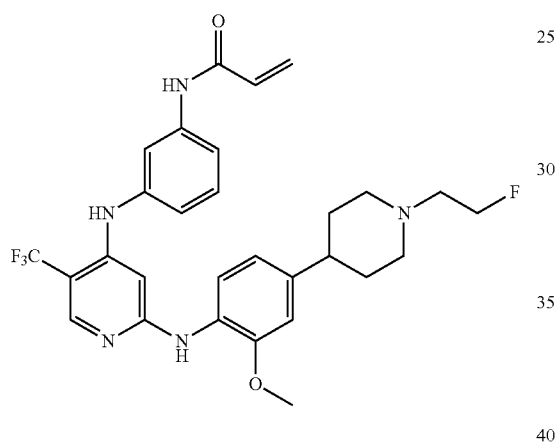

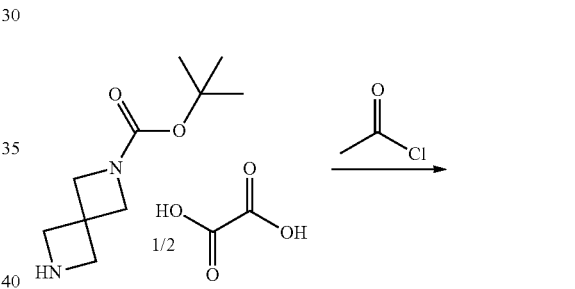

N4-(3-aminophenyl)-N2-(4-(1-(2-fluoroethyl)piperidin-4-yl)-2-methoxyphenyl)-5-(trifluoromethyl)pyridin-2,4-diamine (250 mg, 0.50 mmol) was dissolved in dichloromethane (10 mL), and cooled to −20° C., and acryloyl chloride (90 mg, 1.0 mmol) was added dropwisely. After the addition, the mixture was stirred for 0.5 h, and water (0.5 mL) and methanol (1 mL) were added to quench the reaction. The solution was concentrated, and the crude product was purified by silica gel column chromatography (dichloromethane:methanol=20:1) to get the title compound (40 mg, yield: 14.3%).

Molecular formula: $C_{29}H_{31}F_4N_5O_2$ Molecular weight: 557.6 LC-MS (m/z): 558.0 (M+H+)

1H-NMR (400 MHz, CDCl3) δ: 8.58 (s, 1H), 8.23 (s, 1H), 7.91 (s, 1H), 7.70 (d, J=8.4 Hz, 1H), 7.59 (s, 1H), 7.31-7.29 (m, 1H), 6.95-6.88 (m, 2H), 6.73-6.72 (m, 2H), 6.47-6.43 (m, 2H), 6.32-6.25 (m, 2H), 5.78 (dd, J1=1.2 Hz, J2=10.4 Hz, 1H), 4.66 (t, J=5.0 Hz, 1H), 4.54 (t, J=5.0 Hz, 1H), 3.77 (s, 3H), 3.07 (d, J=11.2 Hz, 2H), 2.77 (t, J=5.0 Hz, 1H), 2.70 (t, J=5.0 Hz, 1H), 2.46-2.41 (m, 1H), 2.17-2.15 (m, 2H), 1.81-1.78 (m, 4H).

Tert-butyl 2,6-diazaspiro[3.3]heptan-2-carboxylate hemioxalate (400 mg, 1.65 mmol) was dissolved in tetrahydrofuran (20 mL), and triethylamine (333 mg, 3.3 mmol) and acetyl chloride (193 mg, 2.5 mmol) were added. The reaction was carried out at room temperature overnight, and LC-MS detection showed that the reaction was finished. The solvent was concentrated. Ethyl acetate (30 mL) and water (20 mL) were added, and the water phase and the organic phase were separated. The water phase was extracted with ethyl acetate (20 mL), and the organic phases were combined and concentrated. The residue was purified by silica gel column chromatography (petroleum ether: ethyl acetate=2:1) to get the title compound (360 mg, yield: 90.9%).

(2) Preparation of 1-(2,6-diazaspiro[3.3]heptan-2-yl)ethan-1-one

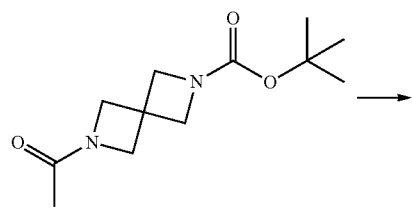

Tert-butyl 6-acetyl-2,6-diazaspiro[3.3]heptan-2-carboxylate (360 mg, 1.5 mmol) was dissolved in dichloromethane (10 mL), and trifluoroacetic acid (2 mL) was added. The reaction was carried out at room temperature for 4 h. LC-MS detection showed that the reaction was finished. The solvent was dried by evaporation under rotation. Ethyl acetate (50 mL) and saturated sodium bicarbonate solution (10 mL) were added, and the water phase and the organic phase were separated. The water phase was extracted with ethyl acetate (40 mL), and the organic phases were combined, dried with anhydrous sodium sulfate, and concentrated to get the title compound (140 mg, yield: 66.7%).

(3) Preparation of 1-(6-(3-methoxy-4-nitrophenyl)-2,6-diazaspiro[3.3]heptan-2-yl)ethan-1-one

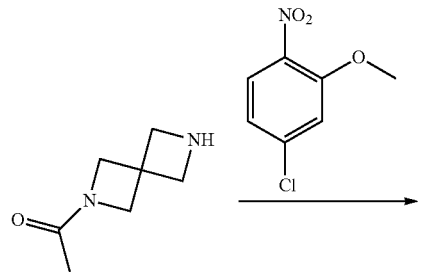

1-(2,6-Diazaspiro[3.3]heptan-2-yl)ethan-1-one (140 mg, 1.0 mmol) and 4-chloro-2-methoxy-1-nitrobenzene (187 mg, 1.0 mmol) were dissolved in 1,4-dioxane (15 mL), and tris(dibenzylideneacetone)dipalladium (92 mg, 0.1 mmol), 2-dicyclohexylphosphino-2',4',6'-triisopropylbiphenyl (95 mg, 0.2 mmol) and cesium carbonate (975 mg, 3.0 mmol) were added. The mixture was heated to 110° C., and the reaction was carried out overnight. LC-MS detection showed that the reaction was finished. The reaction solution was filtrated, and the filtrate was concentrated. The residue was purified by silica gel column chromatography (dichloromethane:methanol=30:1) to get the title compound (195 mg, yield: 67%).

(4) Preparation of 1-(6-(4-amino-3-methoxyphenyl)-2,6-diazaspiro[3.3]heptan-2-yl)ethan-1-one

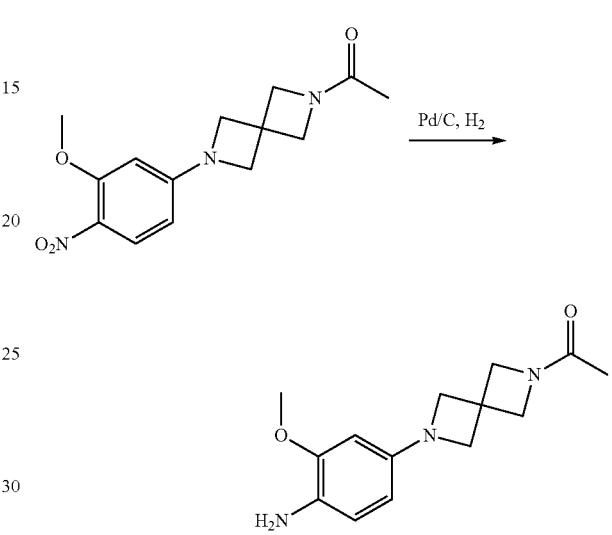

1-(6-(3-Methoxy-4-nitrophenyl)-2,6-diazaspiro[3.3]heptan-2-yl)ethan-1-one (195 mg, 0.67 mmol) was dissolved in methanol (20 mL). Under the protection of nitrogen gas, palladium-carbon (20 mg) was added to the system. In the atmosphere of hydrogen gas, the system was then stirred at room temperature and the reaction was carried out overnight. LC-MS detection showed that the reaction was finished. The reaction solution was filtrated, and the filtrate was concentrated. The residue was directly used in the next step.

(5) Preparation of N-(3-((2-((4-(6-acetyl-2,6-diazaspiro[3.3]heptan-2-yl)-2-methoxyphenyl)amino)-5-(trifluoromethyl)pyrimidin-4-yl)amino)phenyl)acrylamide

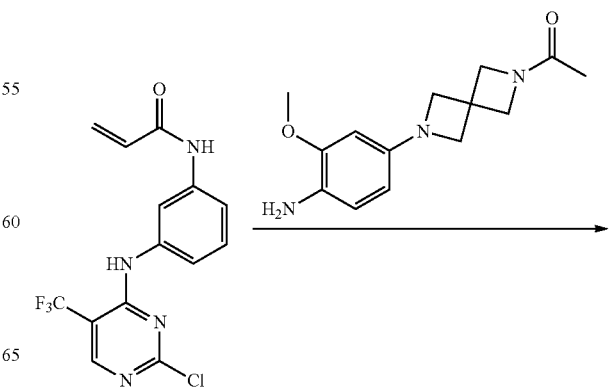

-continued

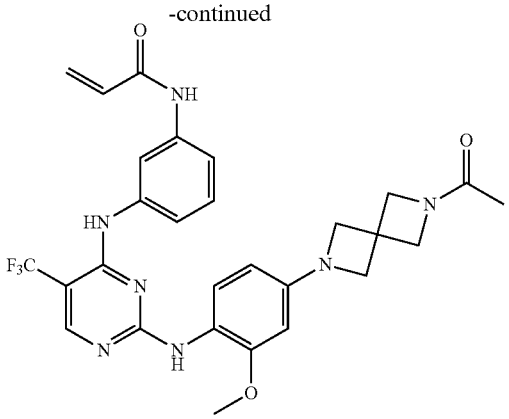

1-(6-(4-Amino-3-methoxyphenyl)-2,6-diazaspiro[3.3]heptan-2-yl)ethan-1-one (175 mg, 0.67 mmol) and N-(3-((2-chloro-5-(trifluoromethyl)pyrimidin-4-yl)amino)phenyl)acrylamide (229 mg, 0.67 mmol) were dissolved in 1,4-dioxane (15 mL), and tris(dibenzylideneacetone)dipalladium (61 mg, 0.067 mmol), 2-dicyclohexylphosphino-2',4',6'-triisopropylbiphenyl (64 mg, 0.134 mmol) and cesium carbonate (436 mg, 1.34 mmol) were added. The mixture was heated to 110° C., and the reaction was carried out overnight. LC-MS detection showed that the reaction was finished. The reaction solution was filtrated, and the filtrate was concentrated. The residue was purified by silica gel column chromatography (dichloromethane:methanol=15:1) to get the title compound (15 mg, yield: 3.95%).

Molecular formula: C28H28F3N7O3 Molecular weight: 567.6 LC-MS (m/z): 568.3 (M+H+)

1H-NMR (400 MHz, DMSO-d6) δ: 10.10 (s, 1H), 8.41-8.52 (m, 1H), 8.24 (s, 1H), 8.07 (s, 1H), 7.75-7.84 (m, 1H), 7.48 (d, J=7.2 Hz, 1H), 7.36 (d, J=8.4 Hz, 1H), 7.17-7.24 (m, 2H), 6.40 (dd, J1=16.8 Hz, J2=10.0 Hz, 1H), 6.25 (dd, J1=2.0 Hz, J2=17.2 Hz, 1H), 6.04 (s, 1H), 5.77 (s, 1H), 4.26 (s, 2H), 3.98 (s, 2H), 3.86 (s, 4H), 3.71 (s, 3H), 1.75 (s, 3H).

Example 31 Preparation of N-(3-((2-((2-methoxy-4-(6-methyl-2,6-diazaspiro[3.3]heptan-2-yl)phenyl)amino)-5-(trifluoromethyl)pyrimidin-4-yl)amino)phenyl)acrylamide (Compound 33)

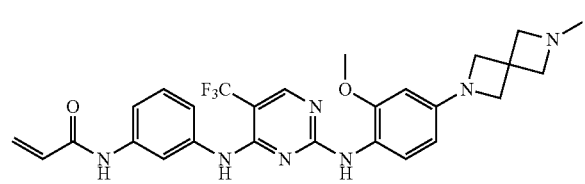 [SMILES: C=CC(=O)Nc1cccc(Nc2nc(Nc3ccc(N4CC5(CN(C)C5)C4)cc3OC)ncc2C(F)(F)F)c1]

(1) Preparation of tert-butyl 6-(3-methoxy-4-nitrophenyl)-2,6-diazaspiro[3.3]heptan-2-carboxylate

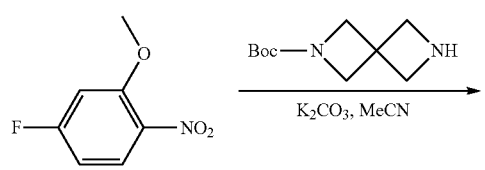

-continued

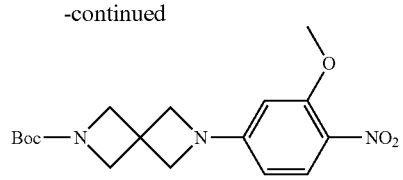

4-Fluoro-2-methoxy-1-nitrobenzene (0.2 g, 1.17 mmol), tert-butyl 2,6-diazaspiro[3.3]heptan-2-carboxylate (0.23 g, 1.17 mmol) and potassium carbonate (0.32 g, 2.34 mmol) were added to acetonitrile (4 mL). The mixture was heated to 80° C. and reacted for 16 h. After the reaction, the mixture was filtrated. The filtrate was distilled under reduced pressure to remove the solvent and get the title compound (0.3 g, yield: 73.47%).

(2) Preparation of 2-(3-methoxy-4-nitrophenyl)-2,6-diazaspiro[3.3]heptane

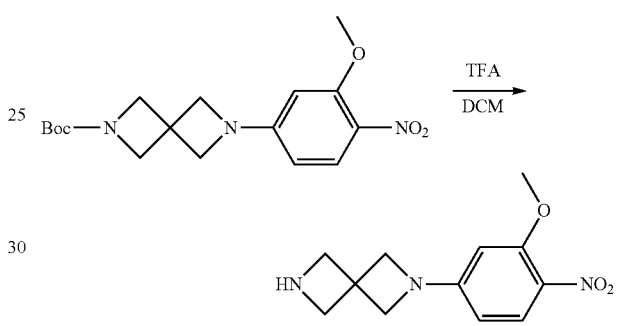

Tert-butyl 6-(3-methoxy-4-nitrophenyl)-2,6-diazaspiro[3.3]heptan-2-carboxylate (0.3 g, 0.86 mmol) was dissolved in dichloromethane (5 mL), and trifluoroacetic acid (5 mL) was added. The mixture was stirred at 25° C. for 1 h. After the reaction, the reaction solution was concentrated, and methanol (20 mL) was added. The solvent was removed under reduced pressure to get the title compound (0.2 g, yield: 93.4%).

(3) Preparation of 2-(3-methoxy-4-nitrophenyl)-6-methyl-2,6-diazaspiro[3.3]heptane

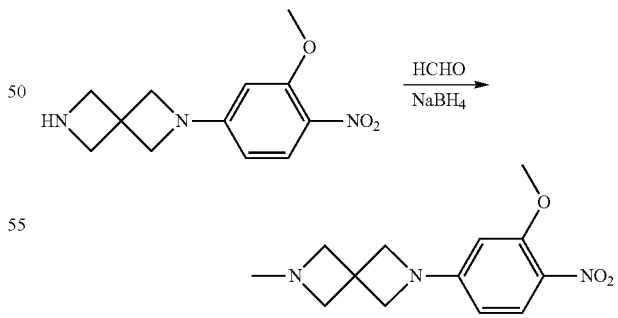

2-(3-Methoxy-4-nitrophenyl)-2,6-diazaspiro[3.3]heptane (0.2 g, 0.8 mmol) and formaldehyde (0.19 g, 2.41 mmol, 37% aqueous solution) were added to methanol (5 mL), and stirred at room temperature for 1 h. Sodium borohydride (0.12 g, 3.21 mmol) was then added in batches to the reaction solution, and the reaction was further carried out for 2 h. After the reaction, the reaction solution was dried by distillation under reduced pressure, and the residue was purified by silica gel column chromatography (dichloromethane:methanol=20:1-3:1) to get the title compound (0.15 g, yield: 71%).

(4) Preparation of 2-methoxy-4-(6-methyl-2,6-diazaspiro[3.3]heptan-2-yl)aniline

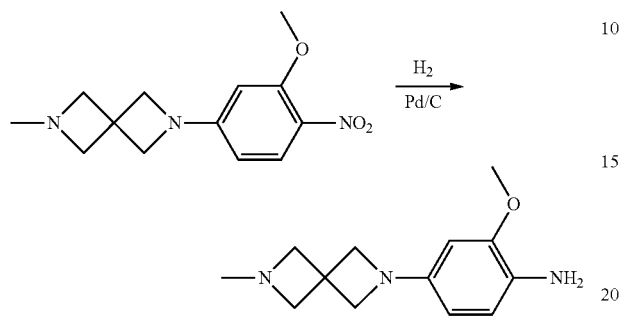

2-(3-Methoxy-4-nitrophenyl)-6-methyl-2,6-diazaspiro [3.3]heptane (0.15 g, 0.57 mmol) and Pd/C (50 mg, 10%) were added to methanol (30 mL). In the atmosphere of hydrogen gas, the system was then stirred and reacted at room temperature for 1 h. After the reaction, the system was filtered, and concentrated to get the title compound (90 mg, yield: 67.7%).

(5) Preparation of N-(3-((2-((2-methoxy-4-(6-methyl-2,6-diazaspiro[3.3]heptan-2-yl)phenyl) amino)-5-(trifluoromethyl)pyrimidin-4-yl)amino) phenyl)acrylamide

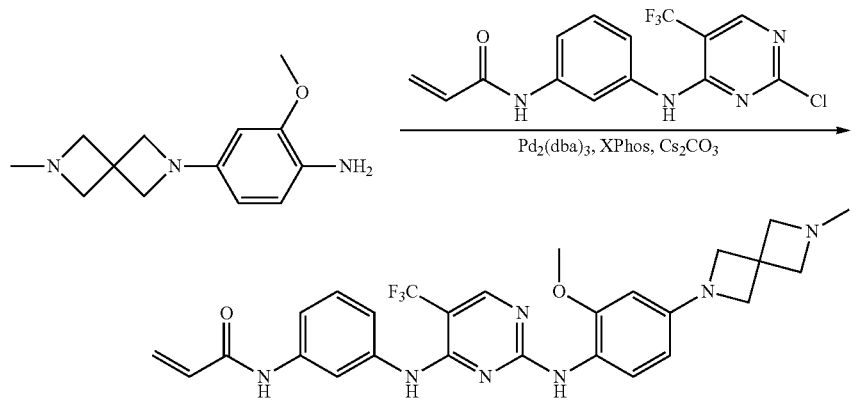

2-Methoxy-4-(6-methyl-2,6-diazaspiro[3.3]heptan-2-yl) aniline (90 mg, 0.39 mmol), N-(3-((2-chloro-5-(trifluoromethyl)pyrimidin-4-yl)amino)phenyl)acrylamide (159 mg, 0.46 mmol), cesium carbonate (377 mg, 1.16 mmol), tris (dibenzylideneacetone)dipalladium (38 mg, 0.04 mmol), and 2-dicyclohexylphosphino-2',4',6'-triisopropylbiphenyl (35 mg, 0.073 mmol) were added to dioxane (5 mL) one after another. Under the protection of nitrogen gas, the reaction was carried out at 100° C. for 16 h. After the reaction, the mixture was concentrated, and the residue was purified by silica gel column chromatography (dichloromethane:methanol=30:1) to get the title compound (17 mg, yield: 8.1%).

Molecular formula: C27H28F3N7O2 Molecular weight: 539.6 LC-MS (m/z): 540.3 (M+H+)

1H-NMR (400 MHz, MeOD) δ: 8.45 (s, 1H), 8.08 (s, 1H), 7.46 (d, J=8.8 Hz, 1H), 7.40 (t, J=8.0 Hz, 1H), 7.19 (d, J=8.0 Hz, 1H), 6.70 (s, 1H), 6.46-6.53 (m, 1H), 6.34-6.39 (m, 1H), 6.15 (s, 2H), 5.78 (dd, J1=1.6 Hz, J2=10.0 Hz, 1H), 4.39 (s, 2H), 3.82 (s, 2H), 3.30-3.35 (m, 7H), 3.12 (s, 3H).

Example 32 Preparation of N-(3-((2-((7-methoxy-1, 2,3,4-tetrahydroisoquinolin-6-yl)amino)-5-(trifluoromethyl)pyrimidin-4-yl)amino)phenyl)acrylamide (Compound 34)

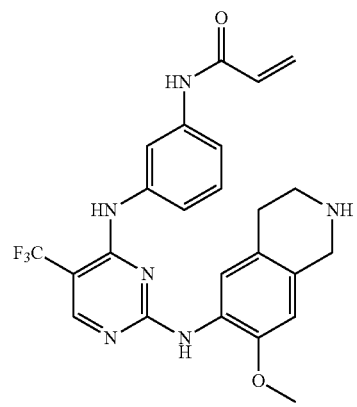 [SMILES: C=CC(=O)Nc1cccc(Nc2nc(Nc3cc4c(cc3OC)CNCC4)ncc2C(F)(F)F)c1]

(1) Preparation of tert-butyl 6-amino-7-methoxy-3, 4-dihydroisoquinolin-2(1H)-carboxylate

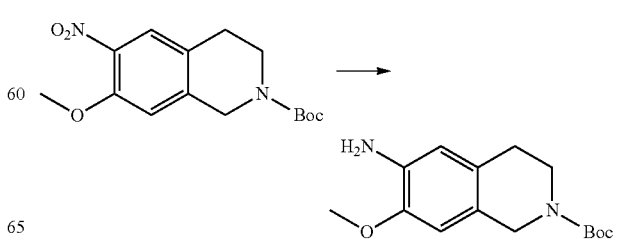

Tert-butyl 7-methoxy-6-nitro-3,4-dihydroisoquinolin-2 (1H)-carboxylate (300 mg, 0.97 mmol) and palladium-carbon (30 mg) were suspended in methanol (50 mL). The system was vacuumized, and hydrogen gas was introduced. The mixture was reacted at room temperature for 16 h and filtrated through diatomaceous earth. The solvent was removed under reduced pressure, and the crude product was purified by silica gel column chromatography (methanol:dichloromethane=0-1:10) to get the title compound as a white solid (257 mg, yield: 95%).

(2) Preparation of tert-butyl 6-((4-((3-acrylamidophenyl)amino)-5-(trifluoromethyl)pyrimidin-2-yl)amino)-7-methoxy-3,4-dihydroisoquinolin-2(1H)-carboxylate

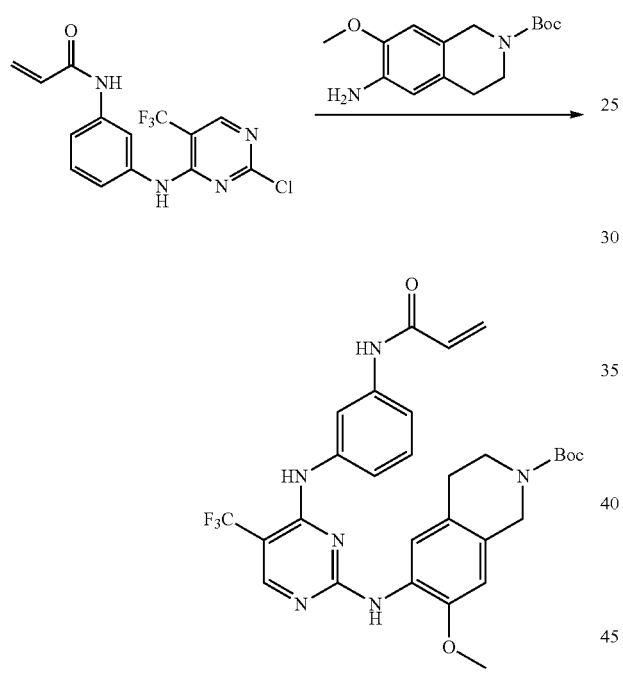

N-(3-((2-chloro-5-(trifluoromethyl)pyrimidin-4-yl)amino)phenyl)acrylamide (316 mg, 0.925 mmol) and tert-butyl 6-amino-7-methoxy-3,4-dihydroisoquinolin-2(1H)-carboxylate (257 mg, 0.925 mmol) were dissolved in isopropanol (40 mL), and trifluoroacetic acid (32 mg, 0.28 mmol) was added. Under the protection of nitrogen gas, The mixture was reacted at 70° C. for 16 h. The resultant mixture was cooled to room temperature, and concentrated. Saturated sodium bicarbonate solution was added, and the mixture was extracted with ethyl acetate (100 mL×3). The organic phases were combined, washed with saturated saline solution, dried with anhydrous sodium sulfate, and concentrated. The crude product was purified by silica gel column chromatography (methanol:dichloromethane=0-1:10) to get the title compound as a greyish-white solid (150 mg, yield: 27.7%).

(3) Preparation of N-(3-((2-((7-methoxy-1,2,3,4-tetrahydroisoquinolin-6-yl)amino)-5-(trifluoromethyl)pyrimidin-4-yl)amino)phenyl)acrylamide

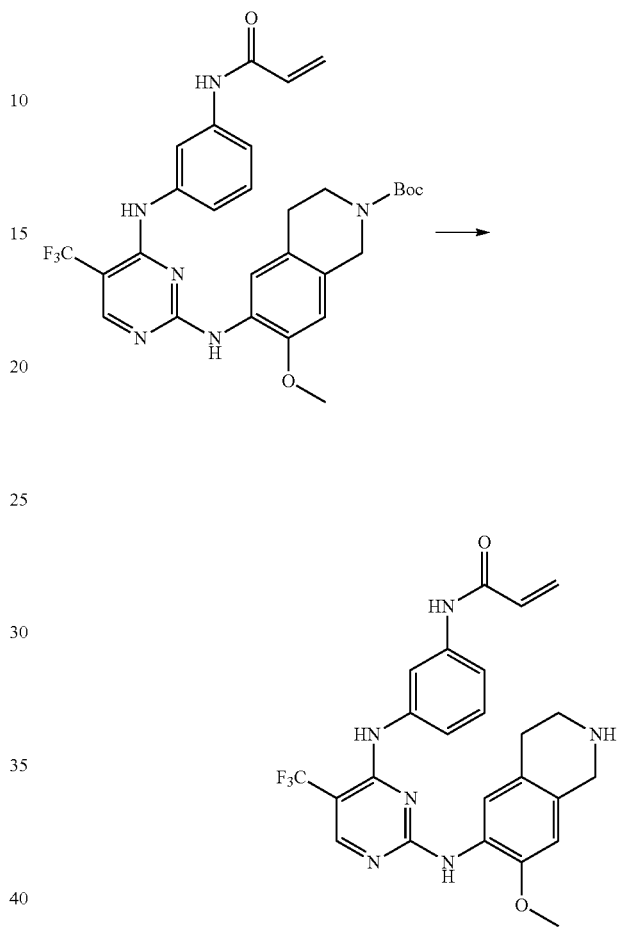

Tert-butyl 6-((4-((3-acrylamidophenyl)amino)-5-(trifluoromethyl)pyrimidin-2-yl)amino)-7-methoxy-3,4-dihydroisoquinolin-2(1H)-carboxylate (150 mg, 0.256 mmol) was dissolved in dichloromethane (10 mL), and trifluoroacetic acid (10 mL) was added. The mixture was stirred at room temperature for 3 h. The solvent was removed under reduced pressure, and saturated sodium bicarbonate solution was added. The mixture was extracted with ethyl acetate (50 mL×3). The organic phases were combined, washed with saturated saline solution, and dried with anhydrous sodium sulfate. The solvent was removed under reduced pressure, to get the title compound as a light yellow oil (88 mg, yield: 70.9%).

Molecular formula: $C_{24}H_{23}F_3N_6O_2$ Molecular weight: 484.5 LC-MS (m/z): 485 (M+H+)

1H-NMR (400 MHz, MeOD-d4) δ: 8.38 (s, 1H), 7.76 (d, J=8.0 Hz, 1H), 7.67 (s, 2H), 7.44 (t, J=8.0 Hz, 1H), 7.18-7.17 (m, 1H), 6.80 (s, 1H), 6.46-6.38 (m, 2H), 5.81-5.78 (m, 1H), 4.23 (s, 2H), 3.88 (s, 3H), 3.38-3.35 (m, 2H), 2.65-2.58 (m, 2H).

Example 33 Preparation of N-(3-((2-((2-acetyl-8-methoxy-1,2,3,4-tetrahydroisoquinoline-5-yl)amino)-5-(trifluoromethyl)pyrimidin-4-yl)amino)phenyl)acrylamide (Compound 35)

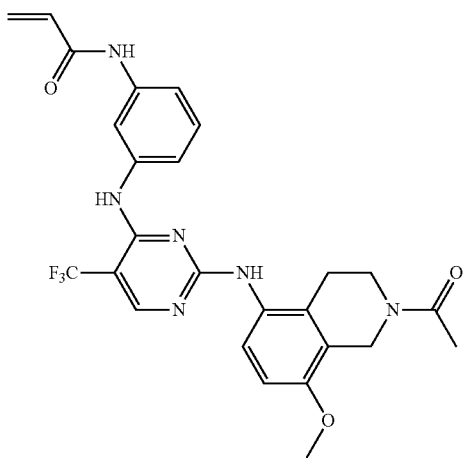 [SMILES: C=CC(=O)Nc1cccc(Nc2nc(Nc3ccc(OC)c4c3CCN(C(C)=O)C4)ncc2C(F)(F)F)c1]

(1) Preparation of 1-(8-methoxy-5-nitro-3,4-dihydroisoquinolin-2(1H)-yl)ethanone

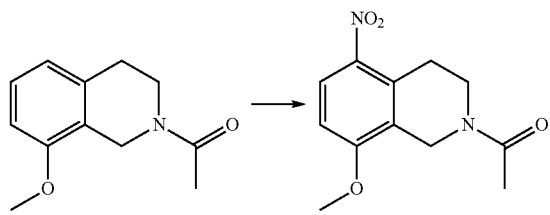 [SMILES: COc1cccc2c1CN(C(C)=O)CC2 ; COc1ccc([N+](=O)[O-])c2c1CN(C(C)=O)CC2]

At 0° C., 1-(8-methoxy-3,4-dihydroisoquinolin-2(1H)-yl)ethanone (1.0 g, 4.87 mmol) was dissolved in a mixed solution of acetic acid and acetic anhydride (10 mL, at a volume ratio of 1:1), and fuming nitric acid (337 mg, 5.36 mL) was added dropwisely. After the addition, the mixture was warmed to room temperature and reacted for 30 min, and then cooled to 0° C. Water (40 mL) was added to the reaction solution, and the mixture was extracted with ethyl acetate (100 mL×2). The organic phase and the water phase were separated. The organic phase was dried with anhydrous sodium sulfate, and purified by silica gel column chromatography (petroleum ether: ethyl acetate=1:1) to get the title compound (0.33 g, yield: 27%).

(2) Preparation of 1-(5-amino-8-methoxy-3,4-dihydroisoquinolin-2(1H)-yl)ethanone

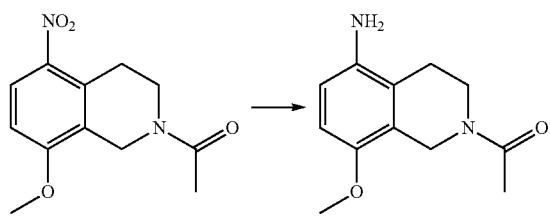 [SMILES: COc1ccc([N+](=O)[O-])c2c1CN(C(C)=O)CC2 ; COc1ccc(N)c2c1CN(C(C)=O)CC2]

1-(8-Methoxy-5-nitro-3,4-dihydroisoquinolin-2(1H)-yl)ethanone (0.3 g, 1.2 mmol) and palladium-carbon (10%, 30 mg) were suspended in methanol (20 mL). The system was vacuumized, and hydrogen gas was introduced. The mixture was reacted at room temperature for 6 h, filtrated, concentrated, and purified by silica gel column chromatography (dichloromethane:methanol=10:1) to get the title compound (0.24 g, yield: 91%).

(3) Preparation of N-(3-((2-((2-acetyl-8-methoxy-1,2,3,4-tetrahydroisoquinoline-5-yl)amino)-5-(trifluoromethyl)pyrimidin-4-yl)amino)phenyl)acrylamide

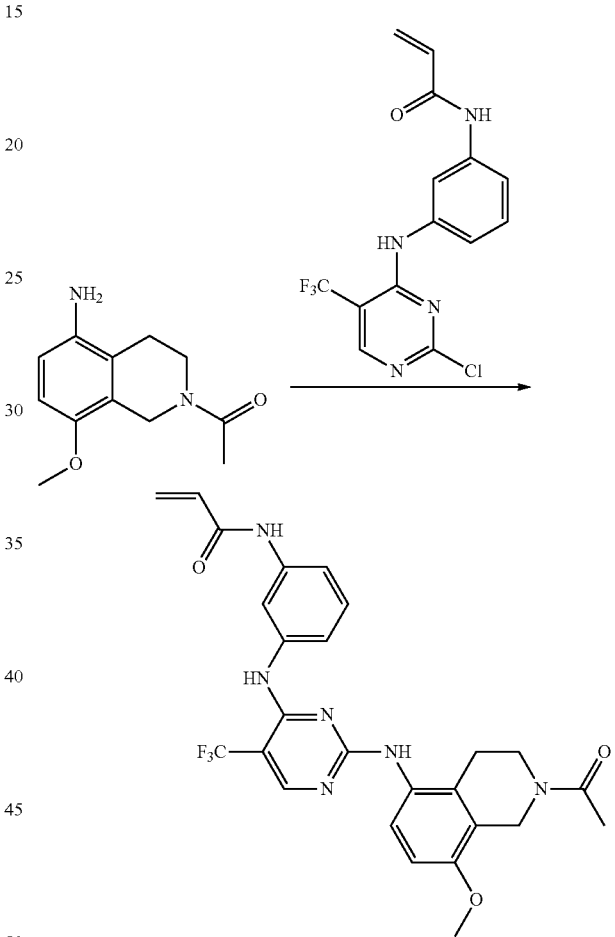

1-(5-Amino-8-methoxy-3,4-dihydroisoquinolin-2(1H)-yl)ethanone (100 mg, 0.45 mmol) and N-(3-((2-chloro-5-(trifluoromethyl)pyrimidin-4-yl)amino)phenyl)acrylamide (154 mg, 0.45 mmol) were dissolved in isopropanol (10 mL), and a catalytic amount of trifluoroacetic acid was added dropwisely. The mixture was heated to 70° C. and reacted for 12 h. After the reaction, the solution was concentrated and purified by silica gel column chromatography (dichloromethane:methanol=10:1) to get the title compound (93.2 mg, yield: 39%).

Molecular formula: C26H25F3N6O3 Molecular weight: 526.52 LC-MS (m/z): 527.2 (M+H+)

1H-NMR (400 MHz, DMSO-d6) δ: 10.06 (s, 1H), 8.92 (brs, 1H), 8.45 (s, 1H), 8.25 (s, 1H), 7.67-7.71 (d, J=16.0 Hz, 1H), 7.07-7.38 (m, 4H), 6.71 (s, 1H), 6.40-6.47 (m, 1H), 6.24 (d., J=16.8 Hz, 1H), 5.73-5.77 (m, 1H), 4.41 (s, 2H), 3.75-3.80 (m, 3H), 3.48 (d, J=5.2 Hz, 2H), 2.60 (t, J=5.6 Hz, 1H), 2.04 (s, 1H), 1.98 (s, 2H).

Example 34 Preparation of N-(3-((2-((2-acetyl-7-methoxyisoindolin-4-yl)amino)-5-(trifluoromethyl)pyrimidin-4-yl)amino)phenyl)acrylamide (Compound 36)

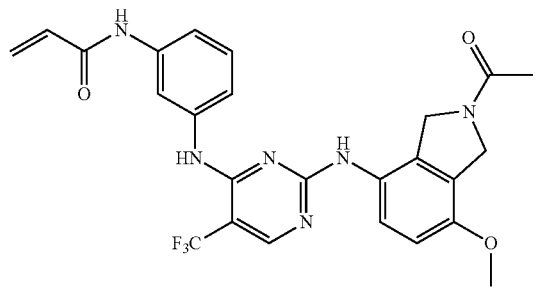 [SMILES: C=CC(=O)Nc1cccc(Nc2nc(Nc3ccc(OC)c4c3CN(C(C)=O)C4)ncc2C(F)(F)F)c1]

(1) 1-(4-methoxy-7-nitroisoindolin-2-yl)ethan-1-one

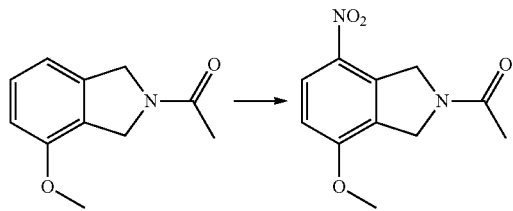 [SMILES: COc1cccc2c1CN(C(C)=O)C2 ; COc1ccc([N+](=O)[O-])c2c1CN(C(C)=O)C2]

At −20° C., 1-(4-methoxyisoindolin-2-yl)ethan-1-one (1.3 g, 6.8 mmol) was dissolved in a mixed solution of acetic acid and acetic anhydride (7 mL, at a volume ratio of 1:1), and fuming nitric acid (471 mg, 7.48 mmol) was added dropwisely. After the addition, the mixture was warmed to room temperature and reacted for 30 min, and then cooled to 0° C. Water (30 mL) was added to the reaction solution, and the reaction solution was extracted with ethyl acetate (50 mL×2). The organic phases were combined, dried with anhydrous sodium sulfate, and purified by silica gel column chromatography (petroleum ether: ethyl acetate=1:1) to get the title compound (0.53 g, yield: 33%).

(2) Preparation of 1-(4-amino-7-methoxyisoindolin-2-yl)ethan-1-one

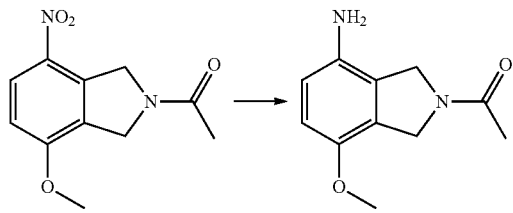 [SMILES: COc1ccc([N+](=O)[O-])c2c1CN(C(C)=O)C2 ; COc1ccc(N)c2c1CN(C(C)=O)C2]

1-(4-Methoxy-7-nitroisoindolin-2-yl)ethan-1-one (0.4 g, 1.69 mmol) and palladium-carbon (10%, 60 mg) were suspended in methanol (50 mL). The system was vacuumized, and hydrogen gas was introduced. The mixture was reacted at room temperature for 3 h, and filtrated. The filtrate was concentrated, and purified by silica gel column chromatography (dichloromethane:methanol=20:1) to get the title compound (0.32 g, yield: 91%).

(3) Preparation of N-(3-((2-((2-acetyl-7-methoxyisoindolin-4-yl)amino)-5-(trifluoromethyl)pyrimidin-4-yl)amino)phenyl)acrylamide

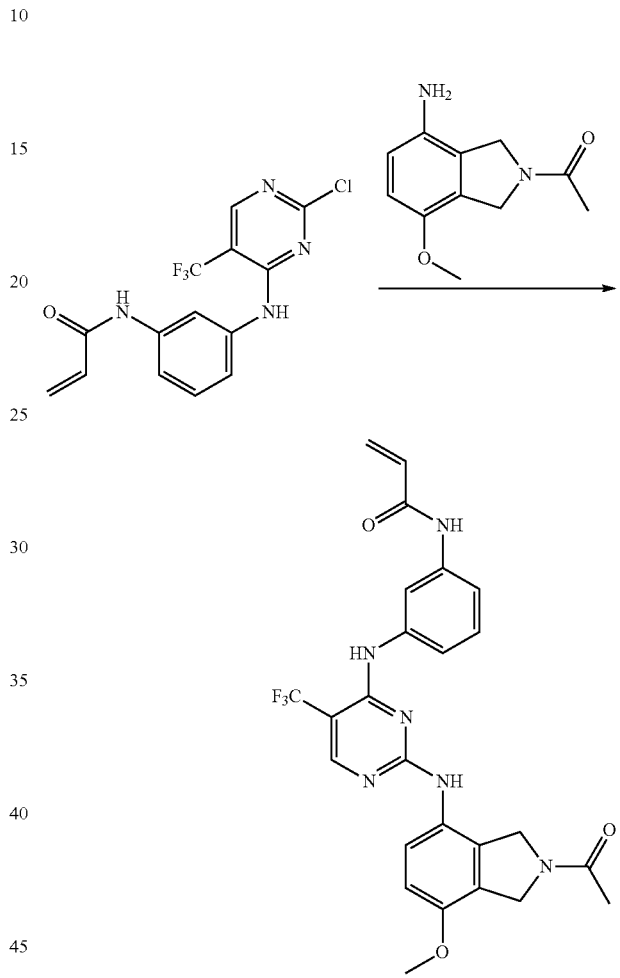

1-(4-Amino-7-methoxyisoindolin-2-yl)ethan-1-one (100 mg, 0.48 mmol) and N-(3-((2-chloro-5-(trifluoromethyl)pyrimidin-4-yl)amino)phenyl)acrylamide (164.5 mg, 0.48 mmol) were dissolved in isopropanol (10 mL), and a catalytic amount of trifluoroacetic acid was added dropwisely. The mixture was heated to 70° C. and reacted for 12 h. After the reaction, the solution was dried by distillation, and purified by silica gel column chromatography (dichloromethane:methanol=10:1) to get the title compound (76 mg, yield: 31%).

Molecular formula: C25H23F3N6O3 Molecular weight: 512.48 LC-MS (m/z): 513.2 (M+H+)

1H-NMR (400 MHz, DMSO-d6) δ: 10.05 (s, 1H), 9.12 (s, 1H), 8.63 (d, 1H, J=20.0 Hz), 8.29 (s, 1H), 7.73 (s, 1H), 7.47-7.62 (m, 1H), 7.15-7.26 (m, 3H), 6.68 (brs, 1H), 6.36-6.44 (m, 1H), 6.19-6.26 (m, 1H), 5.72-5.76 (m, 1H), 4.57-4.63 (m, 2H), 4.40 (s, 2H), 3.72-3.76 (m, 3H), 2.03 (s, 3H).

Example 35 Preparation of N-(3-((2-((2-acetyl-1,2,3,4-tetrahydroisoquinoline-5-yl)amino)-5-(trifluoromethyl)pyrimidin-4-yl)amino)phenyl)acrylamide (Compound 37)

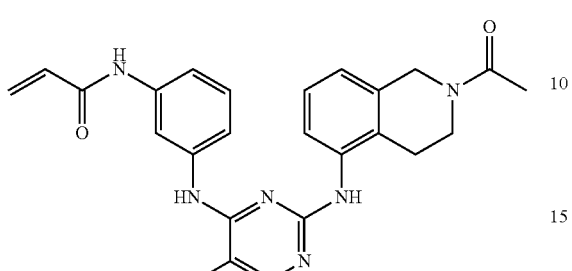

(1) Preparation of 1-(5-nitro-3,4-dihydroisoquinolin-2(1H)-yl)ethan-1-one

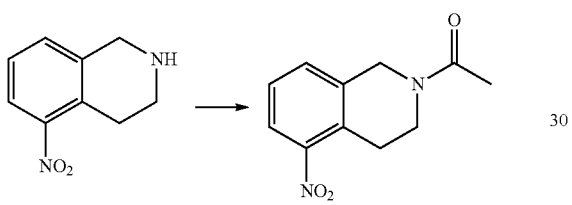

In an ice-water bath, 5-nitro-1,2,3,4-tetrahydroisoquinoline (1.2 g, 6.73 mmol), and triethylamine (1.02 g, 10.1 mmol) were dissolved in dichloromethane (40 mL), and acetyl chloride (0.64 g, 8.1 mmol) was slowly added dropwisely. After the addition, the mixture was warmed to room temperature and reacted for 2 h. After the reaction, the filtrate was dried by distillation, and purified by silica gel column chromatography (petroleum ether: ethyl acetate=5:1) to get the title compound (1.1 g, yield: 74%).

(2) Preparation of 1-(5-amino-3,4-dihydroisoquinolin-2(1H)-yl)ethan-1-one

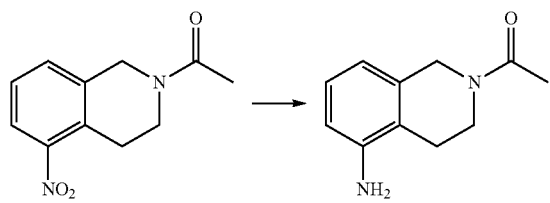 [SMILES: CC(=O)N1CCc2c(cccc2[N+](=O)[O-])C1 ; CC(=O)N1CCc2c(N)cccc2C1]

1-(5-Nitro-3,4-dihydroisoquinolin-2(1H)-yl)ethan-1-one (1.0 g, 4.54 mmol) and palladium-carbon (10%, 100 mg) were suspended in methanol (30 mL). The system was vacuumized, and hydrogen gas was introduced. The mixture was reacted at room temperature for 6 h, filtrated, concentrated, and purified by silica gel column chromatography (dichloromethane:methanol=10:1) to get the title compound (0.77 g, yield: 89%).

(3) Preparation of N-(3-((2-((2-acetyl-1,2,3,4-tetrahydroisoquinoline-5-yl)amino)-5-(trifluoromethyl)pyrimidin-4-yl)amino)phenyl)acrylamide

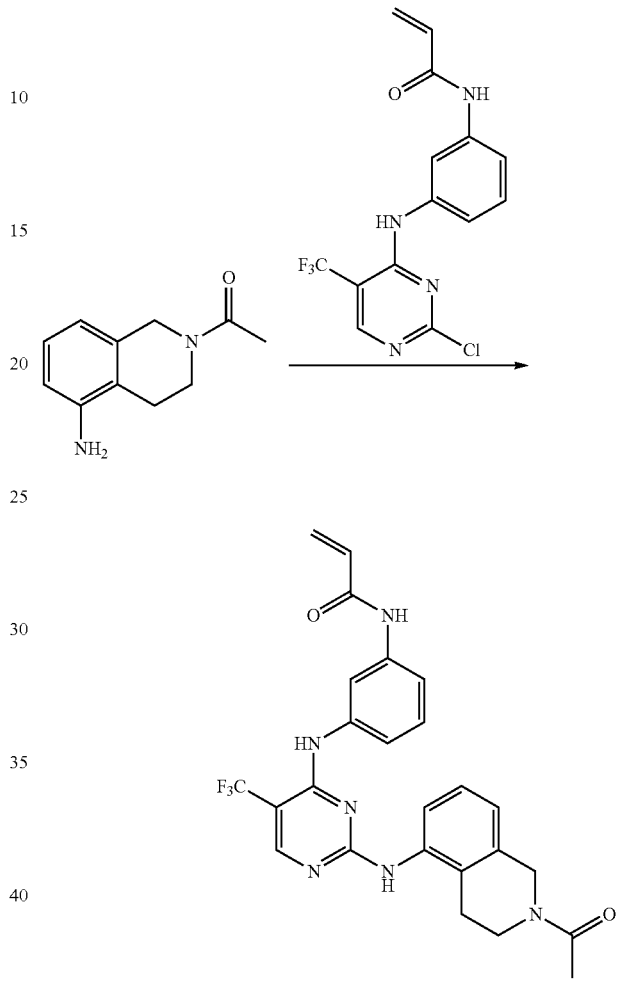

1-(5-Amino-3,4-dihydroisoquinolin-2(1H)-yl)ethan-1-one (100 mg, 0.53 mmol) and N-(3-((2-chloro-5-(trifluoromethyl)pyrimidin-4-yl)amino)phenyl)acrylamide (182 mg, 0.53 mmol) were dissolved in isopropanol (10 mL), and a catalytic amount of trifluoroacetic acid was added dropwisely. The mixture was heated to 70° C. and reacted for 12 h. After the reaction, the solution was dried by distillation, and purified by silica gel column chromatography (dichloromethane:methanol=10:1) to get the title compound (95 mg, yield: 36%).

Molecular formula: $C_{25}H_{23}F_3N_6O_2$ Molecular weight: 496.48 LC-MS (m/z): 497.2 (M+H+)

1H-NMR (400 MHz, DMSO-d6) δ: 10.07 (s, 1H), 9.02 (s, 1H), 8.53 (s, 1H), 8.28 (s, 1H), 7.71 (d, 1H, J=17.2 Hz), 6.93-7.39 (m, 6H), 6.43 (dd, 1H, J1=10.4 Hz, J2=17.2 Hz), 6.23 (dd, 1H, J1=2.0 Hz, J2=17.2 Hz), 5.73-5.76 (m, 1H), 4.51-4.56 (m, 2H), 3.48-3.50 (m, 2H), 2.64 (t, 1H, J=5.6 Hz), 2.53-2.56 (m, 1H), 1.98-2.03 (d, 3H).

Example 36 Preparation of N-(3-(2-(1,2,3,4-tetrahydroisoquinoline-5-ylamino)-5-(trifluoromethyl)pyrimidin-4-ylamino)phenyl)acrylamide (Compound 38)

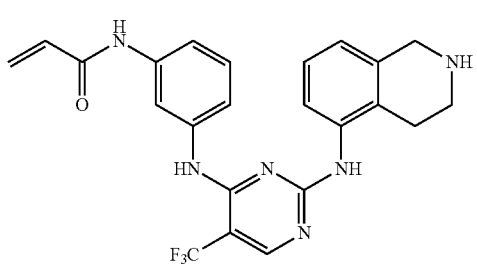 [SMILES: C=CC(=O)Nc1cccc(Nc2nc(Nc3cccc4c3CCNC4)ncc2C(F)(F)F)c1]

(1) Preparation of tert-butyl 5-nitro-3,4-dihydroisoquinolin-2(1H)-carboxylate

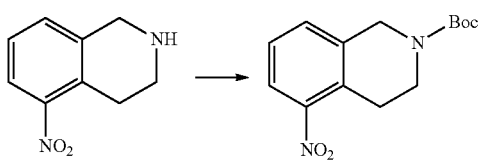 [SMILES: O=[N+]([O-])c1cccc2c1CCNC2 ; CC(C)(C)OC(=O)N1CCc2c(cccc2[N+](=O)[O-])C1]

5-Nitro-1,2,3,4-tetrahydroisoquinoline (2.0 g, 11.2 mmol), 4-dimethylaminopyridine (13.4 mg, 0.11 mmol), and triethylamine (1.70 g, 16.8 mmol) were dissolved in tetrahydrofuran (40 mL), and di-tert-butyl dicarbonate (2.92 g, 13.4 mmol) was added dropwisely. The reaction was carried out at room temperature for 6 h. After the reaction, the reaction liquid was concentrated, and purified by silica gel column chromatography (petroleum ether: ethyl acetate=10:1) to get the title compound (2.65 g, yield: 85%).

(2) Preparation of tert-butyl 5-amino-3,4-dihydroisoquinolin-2(1H)-carboxylate

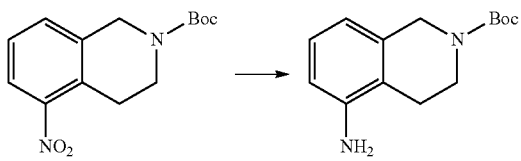 [SMILES: CC(C)(C)OC(=O)N1CCc2c(cccc2[N+](=O)[O-])C1 ; CC(C)(C)OC(=O)N1CCc2c(N)cccc2C1]

Tert-butyl 5-nitro-3,4-dihydroisoquinolin-2(1H)-carboxylate (2.0 g, 7.2 mmol) and palladium-carbon (10%, 200 mg) were suspended in methanol (100 mL). The system was vacuumized, and hydrogen gas was introduced. The mixture was reacted at room temperature for 6 h, filtrated, concentrated, and purified by silica gel column chromatography (petroleum ether: ethyl acetate=1:1) to get the title compound (1.57 g, yield: 88%).

(3) Preparation of tert-butyl 5-((4-((3-acrylamidophenyl)amino)-5-(trifluoromethyl)pyrimidin-2-yl)amino)-3,4-dihydroisoquinolin-2(1H)-carboxylate

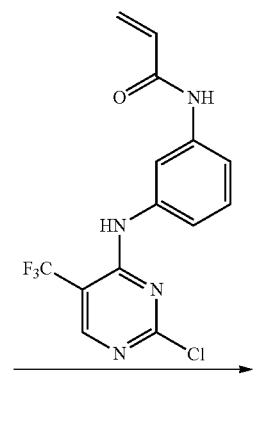

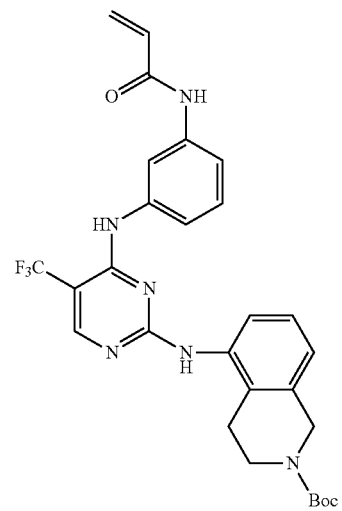

Tert-butyl 5-amino-3,4-dihydroisoquinolin-2(1H)-carboxylate (150 mg, 0.60 mmol) and N-(3-((2-chloro-5-(trifluoromethyl)pyrimidin-4-yl)amino)phenyl)acrylamide (206 mg, 0.60 mmol) were dissolved in isopropanol (10 mL), and a catalytic amount of trifluoroacetic acid was added dropwisely. The mixture was heated to 70° C. and reacted for 12 h. After the reaction, the solution was concentrated, and purified by silica gel column chromatography (dichloromethane:methanol=30:1) to get the title compound (133 mg, yield: 40%).

(4) Preparation of N-(3-(2-(1,2,3,4-tetrahydroisoquinoline-5-ylamino)-5-(trifluoromethyl)pyrimidin-4-ylamino)phenyl)acrylamide

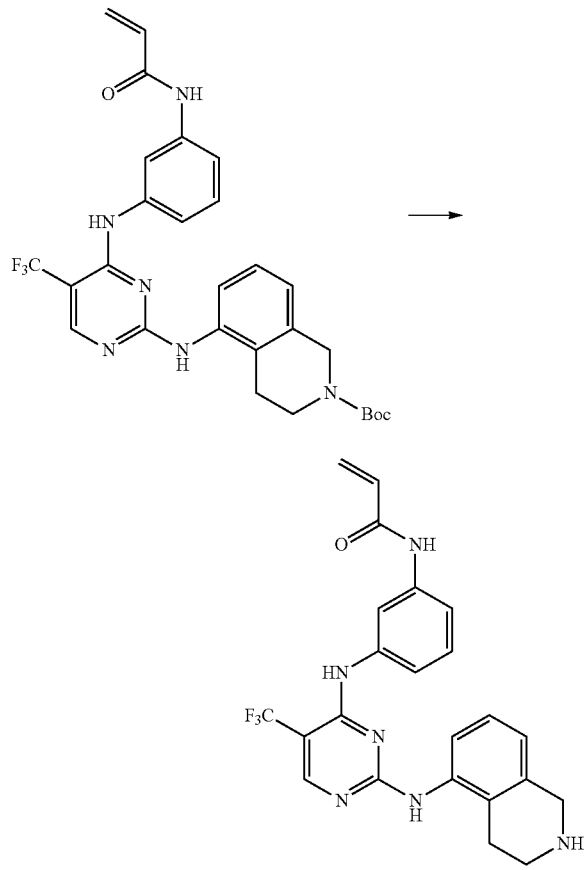

Tert-butyl 5-((4-((3-acrylamidophenyl)amino)-5-(trifluoromethyl)pyrimidin-2-yl)amino)-3,4-dihydroisoquinolin-2(1H)-carboxylate (130 mg, 0.23 mmol) was dissolved in dichloromethane (10 mL), and trifluoroacetic acid (5 mL) was added dropwisely. The reaction was carried out at room temperature for 2 h. After the reaction, the solution was concentrated, and saturated sodium bicarbonate solution was added dropwisely to adjust pH of the mixture to 8. The mixture was extracted with ethyl acetate (100 mL×2). The organic phase was dried with anhydrous sodium sulfate, concentrated, and purified by silica gel column chromatography (dichloromethane:methanol=10:1) to get the title compound (92 mg, yield: 88%).

Molecular formula: C23H21F3N6O Molecular weight: 454.45 LC-MS (m/z): 455.2 (M+H+)

1H-NMR (400 MHz, DMSO-d6) δ: 10.28 (s, 1H), 9.06 (s, 1H), 8.53 (s, 1H), 8.28 (s, 1H), 7.83 (s, 1H), 7.43 (d, J=7.6 Hz, 1H), 7.31-7.33 (m, 1H), 7.12-7.18 (m, 1H), 7.02-7.06 (m, 1H), 6.89 (d, J=7.6 Hz, 1H), 6.47-6.54 (m, 1H), 6.24 (dd, J1=2.0 Hz, J2=17.2 Hz, 1H), 5.72-5.76 (m, 1H), 4.07 (s, 2H), 3.12-3.16 (m, 2H), 2.76-2.79 (m, 2H).

Example 37 Preparation of N-(3-((2-(1-methyl-1H-indol-3-yl)-5-(trifluoromethyl)pyrimidin-4-yl)amino)phenyl)acrylamide (Compound 39)

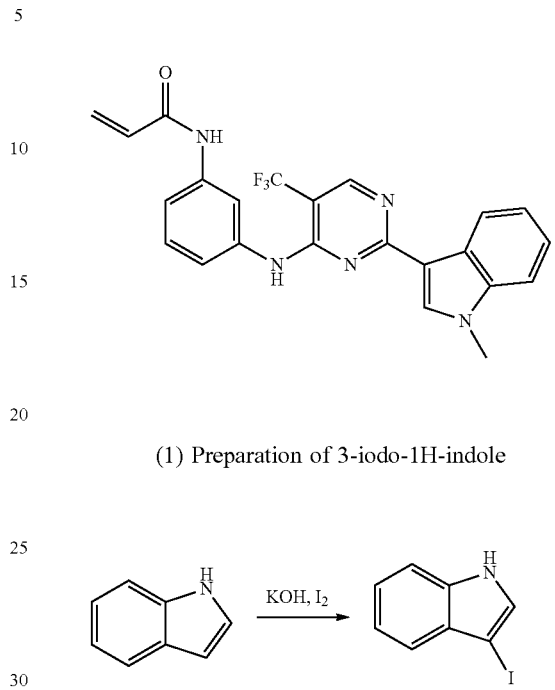

(1) Preparation of 3-iodo-1H-indole

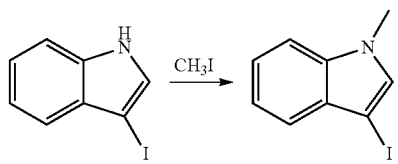

Indole (11.72 g, 100 mmol) and potassium hydroxide (6.73 g, 119.9 mmol) were dissolved in N,N-dimethylformamide (200 mL), and iodine (25.4 g, 100 mmol) dissolved in N,N-dimethylformamide (50 mL) was added to the reaction solution dropwisely. After the reaction for 1 h, TLC detection showed that raw materials were completely reacted. Water was added, and the mixture was extracted with ethyl acetate twice. The organic phases were combined, dried with anhydrous sodium sulfate, and concentrated in vacuum to get the title compound as a yellow solid (23.1 g, yield: 95%).

(2) Preparation of 3-iodo-1-methyl-1H-indole

3-Iodo-1H-indole (2.43 g, 10 mmol) was dissolved in tetrahydrofuran (50 mL), sodium hydride (mass percentage 60%, 800 mg, 20 mmol) was added, and iodomethane (2.84 g, 20 mmol) was added dropwisely. The mixture was stirred at room temperature for 12 h, and TLC detection showed that raw materials disappeared. Water was added, and the mixture was extracted with ethyl acetate twice. The organic phases were combined, dried with anhydrous sodium sulfate, and concentrated in vacuum to get the title compound (1.88 g, yield: 73%).

(3) Preparation of (1-methyl-1H-indol-3-yl)boronic acid

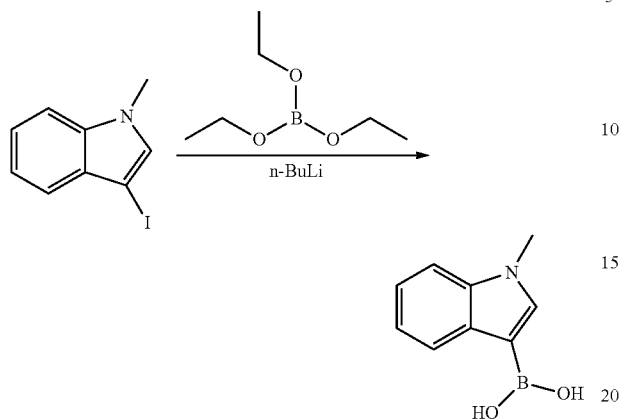

Triethyl borate (2.56 g, 17.53 mmol) was dissolved in tetrahydrofuran (20 mL), and cooled to −78° C. N-butyl lithium (2.4 mol/L, 7.3 mL, 17.53 mmol) was added, and stirred for 0.5 h. 3-Iodo-1-methyl-1H-indole (1.5 g, 5.84 mmol) was added, and the mixture was slowly warmed to room temperature and stirred for 2 h. TLC detection showed that raw materials disappeared. Water was added, and the mixture was extracted with ethyl acetate twice. The organic phases were combined, dried with anhydrous sodium sulfate, and concentrated in vacuum to get the title compound (500 mg), which was directly used in the next step without purification.

(4) Preparation of N-(3-((2-(1-methyl-1H-indol-3-yl)-5-(trifluoromethyl)pyrimidin-4-yl)amino)phenyl) acrylamide

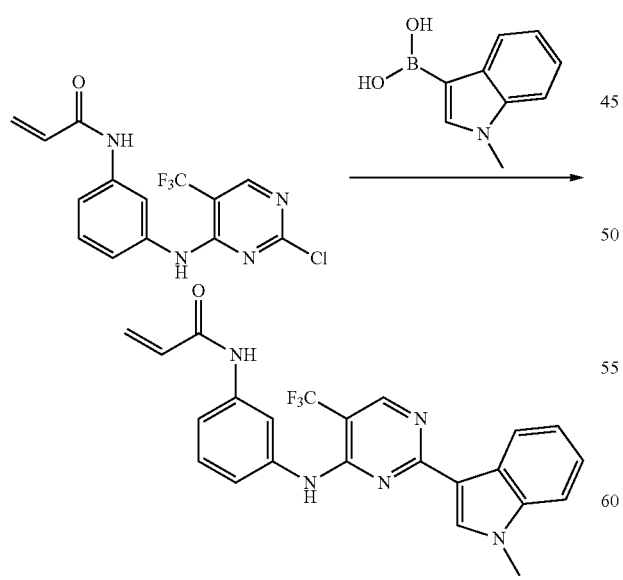

(1-Methyl-1H-indol-3-yl)boronic acid (500 mg, crude product) was dissolved in 1,4-dioxane (20 mL), and N-(3-((2-chloro-5-(trifluoromethyl)pyrimidin-4-yl)amino)phenyl)acrylamide (490 mg, 1.43 mmol), [1,1'-bis(diphenylphosphino)ferrocene]dichloropalladium (II) (50 mg, a mass ratio of 10%) and cesium carbonate (1.4 g, 4.29 mmol) were added. The mixture was heated to 90° C. and reacted overnight. After the reaction, the undissolved substance was filtrated out. Water was added, and the mixture was extracted with ethyl acetate twice. The organic phases were combined, dried with anhydrous sodium sulfate, and concentrated. The crude product was purified by silica gel column chromatography (methanol:dichloromethane=1:50) to get the title compound as a yellow solid (50 mg, yield: 8%).

Molecular formula: C23H18F3N5O Molecular weight: 437.42 LC-MS (m/z): 438.2 (M+H+)

1H-NMR (400 MHz, DMSO-d6) δ: 10.25 (s, 1H), 8.87 (s, 1H), 8.60 (s, 1H), 8.29 (s, 1H), 8.08-8.02 (m, 2H), 7.54 (d, J=8.4 Hz, 1H), 7.45 (d, J=8.4 Hz, 1H), 7.41-7.37 (m, 1H), 7.21-7.14 (m, 2H), 6.95-6.91 (m, 1H), 6.47-6.41 (m, 1H), 6.25 (dd, J1=2.0 Hz, J2=17.2 Hz, 1H), 5.74 (dd, J1=2.0 Hz, J2=10.0 Hz, 1H), 3.84 (s, 3H).

Example 38 Preparation of N-(3-((2-((8-methoxy-2-methyl-1,2,3,4-tetrahydroisoquinoline-5-yl)amino)-5-(trifluoromethyl)pyrimidin-4-yl)amino)phenyl) acrylamide (Compound 40)

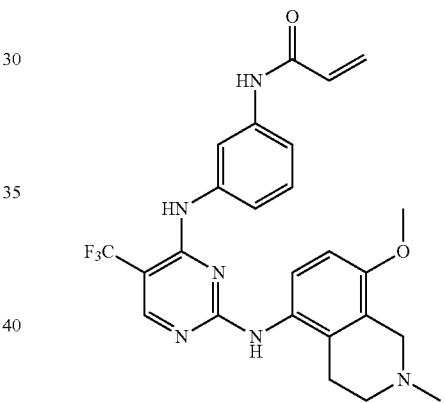

(1) Preparation of ethyl (3-methoxyphenylethyl)amino carboxylate

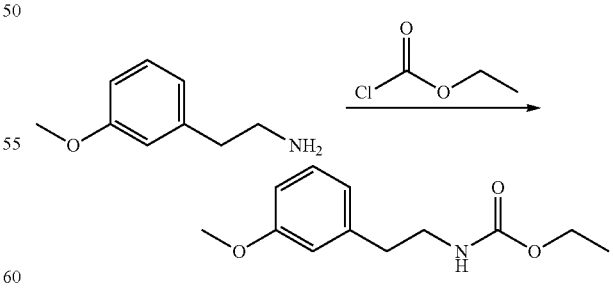

2-(3-Methoxyphenyl)ethan-1-amine (30.24 g, 200 mmol) was dissolved in dichloromethane (500 mL), and triethylamine (60.6 g, 600 mmol) was added. The mixture was cooled in an ice-water bath, and ethyl chlorocarbonate (49 g, 451 mmol) was added dropwisely. The mixture was stirred at 25° C. for 16 h, and diluted with water (500 mL). The water phase was extracted with dichloromethane (300 mL×2). The organic phases were combined, washed with saturated saline solution, dried with anhydrous sodium sulfate, and concentrated in vacuum, to get the title compound (32.2 g, yield: 72%).

(2) Preparation of 8-methoxy-3,4-dihydroisoquinolin-1(2H)-one

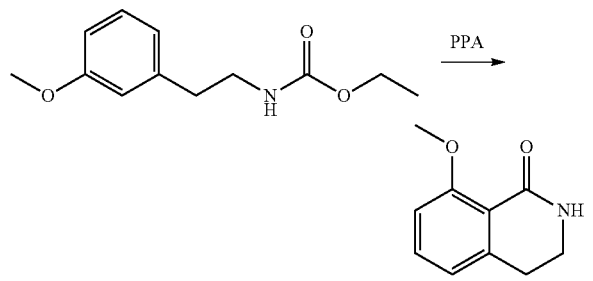

Ethyl (3-methoxyphenylethyl)amino carboxylate (32 g, 143.3 mmol) was dissolved in polyphosphoric acid (300 mL). The mixture was heated to 140° C. and reacted for 30 min. Water (1 L) was added. The mixture was extracted with ethyl acetate (400 mL×2). The organic phases were combined, dried with anhydrous sodium sulfate, and concentrated in vacuum. The crude product was purified by silica gel column chromatography (ethyl acetate:methanol=20:1) to get the title compound (2.54 g, yield: 10%).

(3) Preparation of 8-methoxy-1,2,3,4-tetrahydroisoquinoline

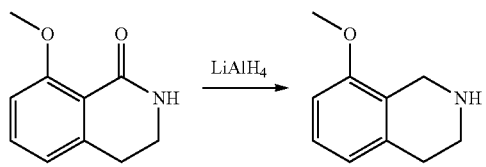

8-Methoxy-3,4-dihydroisoquinolin-1(2H)-one (2.5 g, 14.1 mmol) was dissolved in tetrahydrofuran (50 mL). The mixture was cooled in an ice-water bath, and lithium aluminum hydride (1.07 g, 28.2 mmol) was added slowly. After the addition, the mixture was heated to reflux. The reaction was carried out for 4 h. Water (1 g), aqueous NaOH solution (mass percentage 15%, 1 mL) and water (1 g) were added sequentially. The mixture was filtrated under suction. The filtrate was concentrated in vacuum to get the title compound (1.4 g, yield: 61%).

(4) Preparation of 8-methoxy-2-methyl-1,2,3,4-tetrahydroisoquinoline

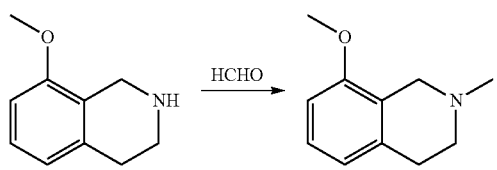

8-Methoxy-1,2,3,4-tetrahydroisoquinoline (1.4 g, 8.6 mmol) was dissolved in methanol (50 mL), and aqueous formaldehyde solution (mass percentage 35%, 3.69 g, 43 mmol) was added. The mixture was stirred for 0.5 h, and sodium cyanoborohydride (1.62 g, 25.8 mmol) was added. The reaction was carried out at 25° C. for 16 h. Water (100 mL) was added. The mixture was extracted with dichloromethane (200 mL×2), dried with anhydrous sodium sulfate, and concentrated in vacuum to get the title compound (1.1 g, yield: 72.4%).

(5) Preparation of 8-methoxy-2-methyl-5-nitro-1,2,3,4-tetrahydroisoquinoline

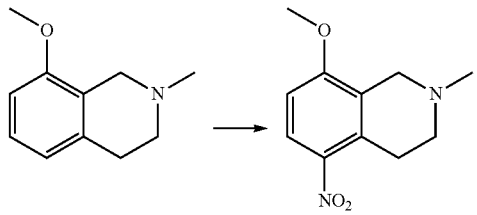 [SMILES: COc1cccc2c1CN(C)CC2 ; COc1ccc([N+](=O)[O-])c2c1CN(C)CC2]

8-Methoxy-2-methyl-1,2,3,4-tetrahydroisoquinoline (1.1 g, 6.2 mmol) was dissolved in trifluoroacetic anhydride (20 mL), and potassium nitrate (3.13 g, 31 mmol) was added. The mixture was stirred for 0.5 h, heated to 60° C. and reacted for 16 h. Undissolved substance was removed by filtration, and the filtrate was concentrated in vacuum. The crude product was purified by silica gel column chromatography (eluting with ethyl acetate) to get the title compound (300 mg, yield: 21.7%).

(6) Preparation of 8-methoxy-2-methyl-1,2,3,4-tetrahydroisoquinoline-5-amine

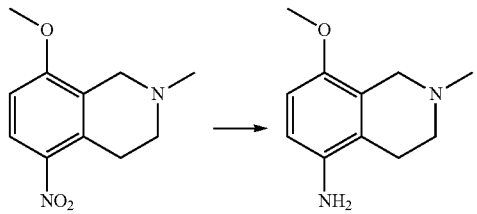 [SMILES: COc1ccc([N+](=O)[O-])c2c1CN(C)CC2 ; COc1ccc(N)c2c1CN(C)CC2]

8-Methoxy-2-methyl-5-nitro-1,2,3,4-tetrahydroisoquinoline (300 mg, 1.35 mmol) was dissolved in methanol (20 mL), and palladium-carbon (30 mg) was added. Hydrogen gas was introduced at 25° C., and the reaction was carried out for 16 h. The mixture was filtrated, and the filtrate was concentrated in vacuum to get the title compound (220 mg, yield: 84.7%).

185

(7) Preparation of N-(3-((2-((8-methoxy-2-methyl-1,2,3,4-tetrahydroisoquinolin-5-yl)amino)-5-(trifluoromethyl)pyrimidin-4-yl)amino)phenyl)acrylamide

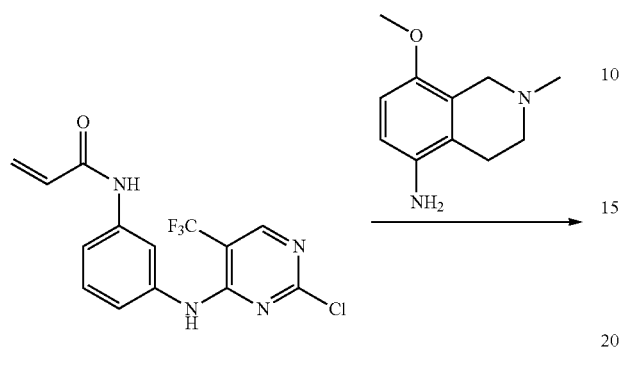

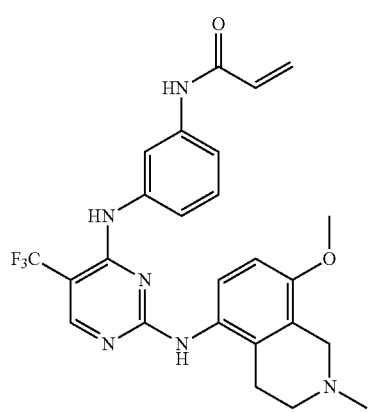

8-Methoxy-2-methyl-1,2,3,4-tetrahydroisoquinolin-5-amine (100 mg, 0.52 mmol) and N-(3-((2-chloro-5-(trifluoromethyl)pyrimidin-4-yl)amino)phenyl)acrylamide (178.2 mg, 0.52 mmol) were dissolved in isopropanol (10 mL), and trifluoroacetic acid (0.05 mL) was added. The reaction was carried out under reflux for 16 h. The mixture was diluted with water (10 mL), and extracted with ethyl acetate (20 mL×3). The organic phases were combined, dried with anhydrous sodium sulfate, and concentrated. The crude product was purified by silica gel column chromatography (methanol:dichloromethane=1:50) to get the title compound as a yellow solid (120 mg, yield: 46.3%).

Molecular formula: C25H25F3N6O2 Molecular weight: 498.5 LC-MS (m/z): 250.2 (M/2+H+)

1H-NMR (400 MHz, DMSO-d6) δ: 10.08 (s, 1H), 8.75 (s, 1H), 8.40 (s, 1H), 8.22 (s, 1H), 7.71 (s, 1H), 7.35 (s, 1H), 7.13-7.10 (m, 3H), 6.60 (s, 1H), 6.47-6.40 (m, 1H), 6.26-6.21 (m, 1H), 5.75-5.72 (m, 1H), 3.70 (s, 3H), 2.60 (t, J=5.4 Hz, 2H), 2.41 (t, J=5.6 Hz, 2H), 2.28 (s, 3H).

186

Example 39 Preparation of N-(3-((2-((2-methoxy-4-(1-(oxetan-3-yl)piperidin-4-yl)phenyl)amino)-5-(trifluoromethyl)pyrimidin-4-yl)amino)phenyl)acrylamide (Compound 41)

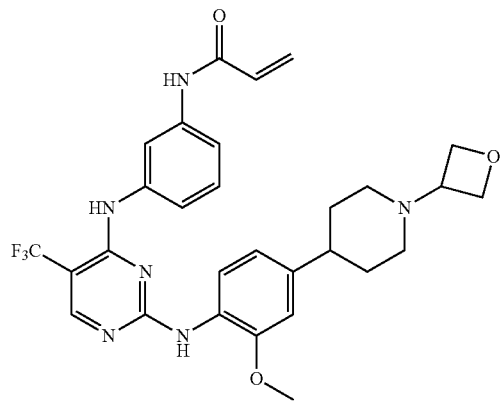 [SMILES: C=CC(=O)Nc1cccc(Nc2nc(Nc3ccc(C4CCN(C5COC5)CC4)cc3OC)ncc2C(F)(F)F)c1]

(1) Preparation of benzyl (4-bromo-2-methoxyphenyl)carbamate

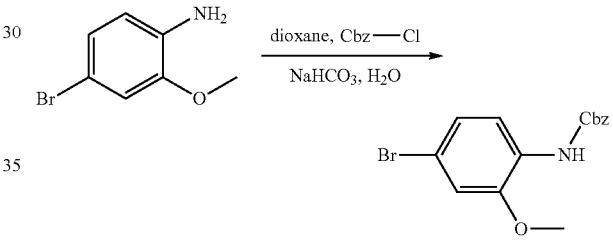

Under the protection of nitrogen gas, 4-bromo-2-methoxyaniline (15 g, 74.24 mmol) was dissolved in 1,4-dioxane (250 mL), and a solution of sodium bicarbonate (15.8 g, 188.07 mmol) in water (150 mL) was added. At 0° C., carbobenzoxy chloride (19.1 g, 111.96 mmol) was added dropwisely to the reaction system. After the addition, the reaction was carried out at room temperature for 20 min. TLC detection showed that raw materials disappeared. The mixture was extracted with ethyl acetate (100 mL×3). The organic phases were combined, washed with saturated saline solution (100 mL×2), dried with anhydrous sodium sulfate, and concentrated in vacuum. The crude product was purified by silica gel column chromatography (ethyl acetate: petroleum ether=1:5) to get the title compound as a white solid (15 g, yield: 60%).

(2) Preparation of tert-butyl 4-(4-(((benzyloxy)carbonyl)amino)-3-methoxyphenyl)-5,6-dihydropyridin-1(2H)-carboxylate

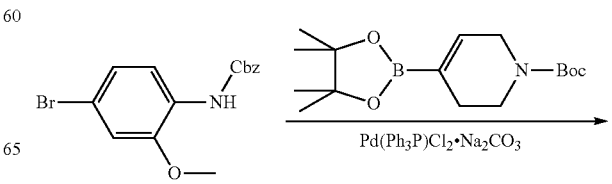

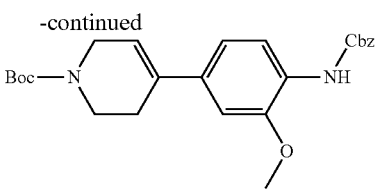
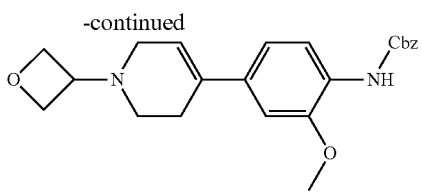

Benzyl (4-bromo-2-methoxyphenyl)carbamate (9 g, 26.77 mmol) was dissolved in 1,4-dioxane and water (2:1, 210 mL), and sodium carbonate (8.5 g, 80.20 mmol), tert-butyl 4-(4,4,5,5-tetramethyl-1,3,2-dioxaborolan-2-yl)-5,6-dihydropyridin-1(2H)-carboxylate (9.9 g, 32.00 mmol) and bis(triphenylphosphine)dichloropalladium (II) (1.1 g, 1.6 mmol) were added. Under the protection of nitrogen gas, the reaction was carried out at 100° C. for 5 h. The resultant mixture was cooled to room temperature, and extracted with ethyl acetate (100 mL×3). The organic phases were combined, washed with saturated saline solution (100 mL×2), dried with anhydrous sodium sulfate, and concentrated in vacuum. The crude product was purified by silica gel column chromatography (ethyl acetate: petroleum ether=1: 5) to get the title compound as a yellow solid (10 g, yield: 85%).

(3) Preparation of benzyl (2-methoxy-4-(1,2,3,6-tetrahydropyridin-4-yl)phenyl)carbamate trifluoroacetate

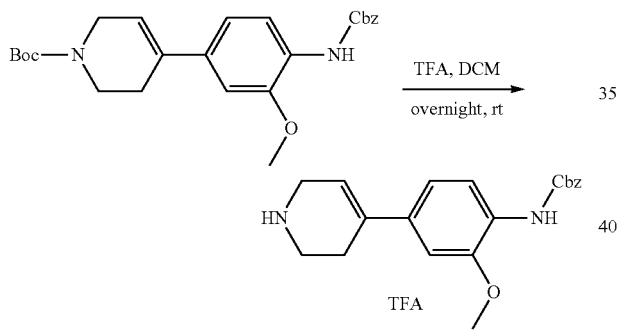

Tert-butyl 4-(4-(((benzyloxy)carbonyl)amino)-3-methoxyphenyl)-5,6-dihydropyridin-1(2H)-carboxylate (10 g, 22.80 mmol) was dissolved in dichloromethane (100 mL). At 0° C., trifluoroacetic acid (26 g, 230.01 mmol) was added dropwisely. After the addition, the mixture was warmed to room temperature and reacted overnight. The reaction solution was concentrated in vacuum to get the title compound as a yellow solid (11 g crude product).

(4) Preparation of benzyl (2-methoxy-4-(1-(oxetan-3-yl)-1,2,3,6-tetrahydropyridin-4-yl)phenyl)carbamate

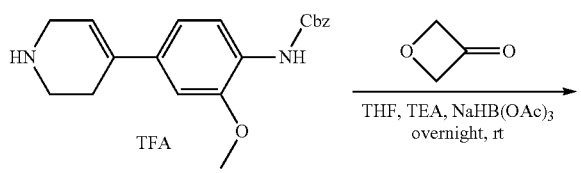

To benzyl (2-methoxy-4-(1,2,3,6-tetrahydropyridin-4-yl)phenyl)carbamate trifluoroacetate (11 g crude product) in tetrahydrofuran (110 mL), triethylamine (4.9 g, 48.42 mmol) was added dropwisely under stirring. After the addition, the mixture was stirred for 10 min. Oxetan-3-one (2.1 g, 29.14 mmol) was added. Sodium triacetoxyborohydride (12.9 g, 61.00 mmol) was added in batches. After the addition, the reaction was carried out at room temperature overnight. The mixture was extracted with ethyl acetate (50 mL×3). The organic phases were combined, washed with saturated saline solution (50 mL), dried with anhydrous sodium sulfate, and concentrated in vacuum. To the crude product, ethyl acetate (5 mL) was added. Solids were precipitated, and filtrated under suction to get the title compound as a greyish-white solid (5 g, yield: 52%).

(5) Preparation of 2-methoxy-4-(1-(oxetan-3-yl)piperidin-4-yl)aniline

Benzyl (2-methoxy-4-(1-(oxetan-3-yl)-1,2,3,6-tetrahydropyridin-4-yl)phenyl)carbamate (5 g, 12.68 mmol) was dissolved in tetrahydrofuran and methanol (5:3, 80 mL). Under the protection of nitrogen gas, dry palladium-carbon (1 g) was added. The system was vacuumized and hydrogen gas was introduced. The reaction was carried out at room temperature overnight. The mixture was filtrated. The filtrate was concentrated in vacuum to get the title compound as a brown solid (2 g, yield: 60%).

(6) Preparation of N-(3-((2-((2-methoxy-4-(1-(oxetan-3-yl)piperidin-4-yl)phenyl)amino)-5-(trifluoromethyl)pyrimidin-4-yl)amino)phenyl)acrylamide

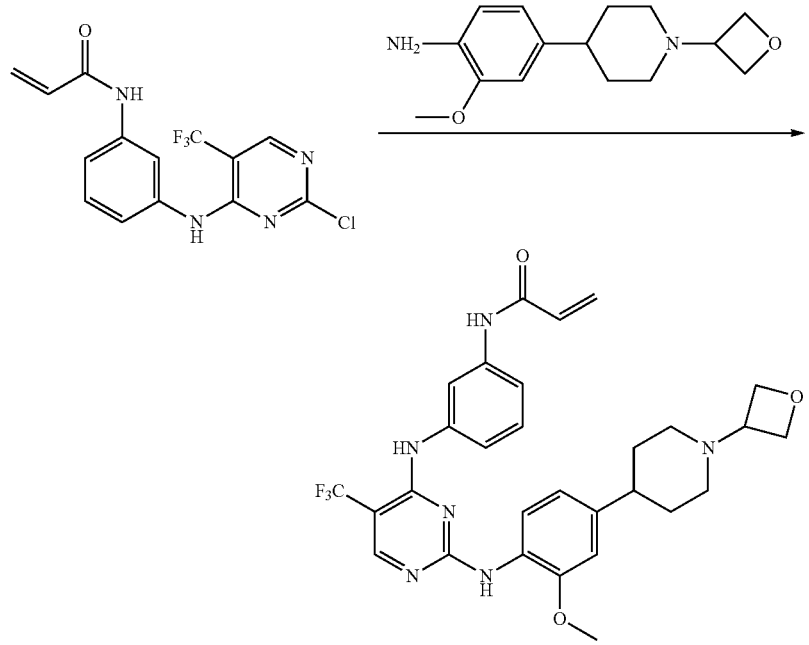

2-Methoxy-4-(1-(oxetan-3-yl)piperidin-4-yl)aniline (262.3 mg, 1.0 mmol) and N-(3-((2-chloro-5-(trifluoromethyl)pyrimidin-4-yl)amino)phenyl)acrylamide (343 mg, 1.0 mmol) were dissolved in isopropanol (10 mL), and a catalytic amount of trifluoroacetic acid was added. The reaction was carried out under reflux for 12 h. TLC detection showed that raw materials disappeared. The mixture was concentrated. The crude product was purified by silica gel column chromatography (methanol:dichloromethane=1: 100) to get the title compound as a white solid (50 mg, yield: 8.8%).

Molecular formula: C29H31F3N6O3 Molecular weight: 568.59 LC-MS (m/z): 285.2 (M/2+H+)

1H-NMR (400 MHz, DMSO-d6) δ: 10.15 (s, 1H), 8.76 (s, 1H), 8.31 (s, 1H), 8.06 (s, 1H), 7.77 (s, 1H), 7.64 (d, J=8.0 Hz, 1H), 7.55 (d, J=7.6 Hz, 1H), 7.29 (t, J=8.0 Hz, 1H), 7.13 (d, J=7.6 Hz, 1H), 6.84 (s, 1H), 6.52-6.38 (m, 2H), 6.25 (dd, J1=2.0 Hz, J2=16.8 Hz, 1H), 5.76-5.72 (m, 1H), 4.54 (t, J=6.6 Hz, 2H), 4.43 (t, J=6.0 Hz, 2H), 3.79 (s, 3H), 3.42-3.27 (m, 2H), 2.77 (d, J=10.8 Hz, 2H), 1.83-1.77 (m, 2H), 1.69-1.60 (m, 4H).

Example 40 Preparation of N-(3-((2-((2-methoxy-4-(3-(methylsulfonyl)propoxy)phenyl)amino)-5-(trifluoromethyl)pyrimidin-4-yl)amino)phenyl)acrylamide (Compound 43)

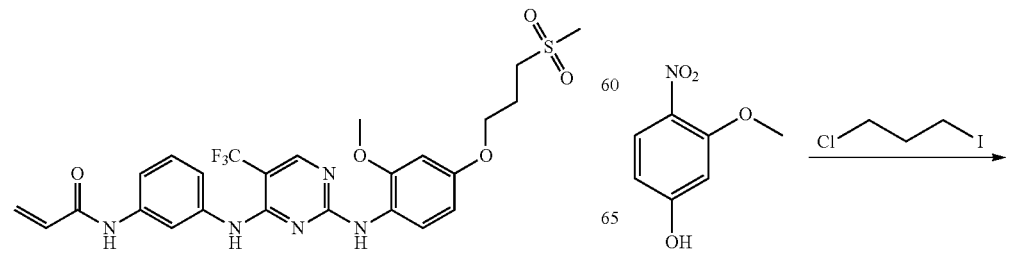

(1) Preparation of 3-methoxy-4-nitrophenol

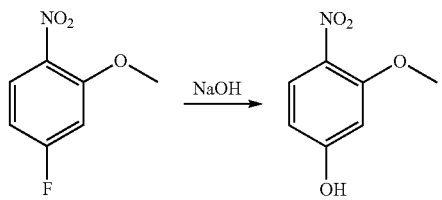

2-Methoxy-4-fluoronitrobenzene (3.4 g, 19.88 mmol) was dissolved in dimethyl sulfoxide (30 mL), and NaOH solution (1 N, 40 mL, 40 mmol) was added. The mixture was heated to 50° C., and reacted for 3 h. After the reaction, water (100 mL) was added. The mixture was extracted with ethyl acetate (50 mL×3). The organic phases were combined, and concentrated. The residue was purified by silica gel column chromatography (petroleum ether: ethyl acetate=5:1) to get the title compound (2.5 g, yield: 74.4%).

(2) Preparation of 4-(3-chloropropoxy)-2-methoxy-1-nitrobenzene

-continued

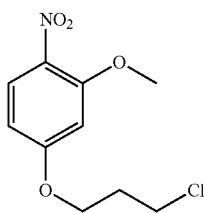

3-Methoxy-4-nitrophenol (2.5 g, 14.79 mmol) was dissolved in N,N-dimethylformamide (30 mL), and 3-iodo-1-chloropropane (3.62 g, 17.74 mmol) and potassium carbonate (3.1 g, 22.30 mmol) were added. The reaction was carried out at room temperature overnight. After the reaction, water (100 mL) was added. The mixture was extracted with ethyl acetate (3×50 mL). The organic phases were combined, and concentrated. The residue was purified by silica gel column chromatography (petroleum ether: ethyl acetate=4:1) to get the title compound (2.3 g, yield: 63.5%).

(3) Preparation of (3-(3-methoxy-4-nitrobenzeneoxy)propyl)(methyl)sulfane

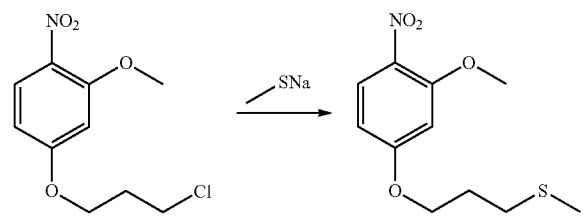

4-(3-Chloropropoxy)-2-methoxy-1-nitrobenzene (2.3 g, 9.39 mmol) was dissolved in methanol (30 mL), and aqueous sodium methanethiolate solution (2 N, 5.6 mL, 11.2 mmol) was added. The reaction was carried out at room temperature overnight. After the reaction, water (100 mL) was added. The mixture was extracted with ethyl acetate (3×50 mL). The organic phases were combined, and concentrated. The residue was purified by silica gel column chromatography (petroleum ether: ethyl acetate=3:1) to get the title compound (2.0 g, yield: 83%).

(4) Preparation of 2-methoxy-4-(3-(methylsulfonyl)propoxy)-1-nitrobenzene

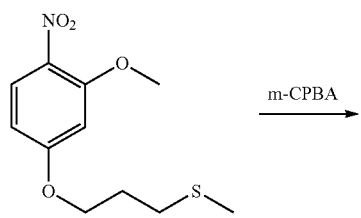

-continued

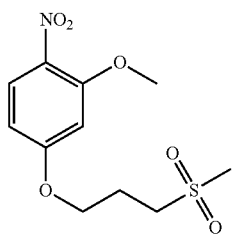

(3-(3-Methoxy-4-nitrobenzeneoxy)propyl)(methyl)sulfane (2.0 g, 7.78 mmol) was dissolved in dichloromethane (30 mL), and 3-chloroperbenzoic acid (2.0 g, 11.7 mmol) was added. The reaction was carried out at room temperature for 3 h. After the reaction, water (100 mL) was added. The mixture was extracted with dichloromethane (3×50 mL). The organic phases were combined, and concentrated. The residue was purified by silica gel column chromatography (petroleum ether: ethyl acetate=3:1) to get the title compound (1.5 g, yield: 66.7%).

(5) Preparation of 2-methoxy-4-(3-(methylsulfonyl)propoxy)aniline

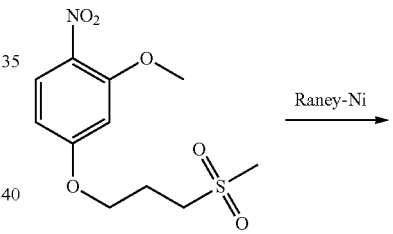

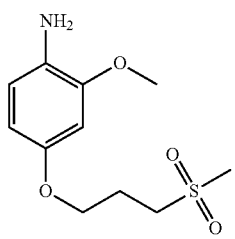

2-Methoxy-4-(3-(methylsulfonyl)propoxy)-1-nitrobenzene (1.5 g, 5.19 mmol) was dissolved in methanol (30 mL), and Raney Nickel was added. Hydrogen was introduced. The reaction was carried out at room temperature overnight. After the reaction, the mixture was filtrated and concentrated. The residue was directly used in the next step (1.0 g, yield: 74.6%).

(6) Preparation of N-(3-((2-((2-methoxy-4-(3-(methylsulfonyl)propoxy)phenyl)amino)-5-(trifluoromethyl)pyrimidin-4-yl)amino)phenyl)acrylamide

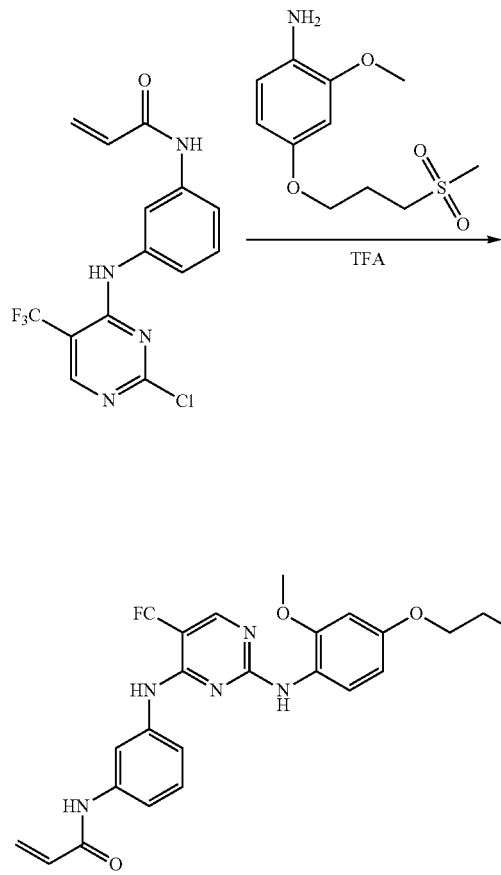

2-Methoxy-4-(3-(methylsulfonyl)propoxy)aniline (120 mg, 0.463 mmol) was dissolved in isopropanol (10 mL), and N-(3-((2-chloro-5-trifluoromethyl)pyrimidin-4-yl)amino)phenyl)acrylamide (158 mg, 0.462 mmol) and a catalytic amount of trifluoroacetic acid were added. The mixture was heated to 70° C. and reacted overnight. After the reaction, the system was concentrated, and ethyl acetate (50 mL) was added. The mixture was washed with saturated sodium bicarbonate solution, and the water phase was extracted with ethyl acetate (2×20 mL). The organic phases were combined and concentrated. The residue was purified by silica gel column chromatography (dichloromethane:methanol=20:1) to get the title compound (50 mg, yield: 19.1%).

Molecular formula: C25H26F3N5O5S Molecular weight: 565.1 LC-MS (m/z): 566.2 (M+H+)

1H-NMR (400 MHz, DMSO-d6) δ: 10.12 (s, 1H), 8.62 (brs, 1H), 8.27 (s, 1H), 8.15 (s, 1H), 7.75 (brs, 1H), 7.46-7.75 (m, 2H), 7.24 (t, J=8.0 Hz, 1H), 7.17 (brs, 1H), 6.57 (d, J=2.4 Hz, 1H), 6.42 (dd, J=16.8 Hz, 10.4 Hz, 1H), 6.24 (dd, J=16.8 Hz, 2.0 Hz, 2H), 5.74 (dd, J=10.0 Hz, 2.0 Hz, 1H), 4.00-4.04 (m, 2H), 3.75 (s, 3H), 3.23-3.27 (m, 2H), 3.01 (s, 3H), 2.07-2.14 (m, 2H).

Example 41 Preparation of N-(3-(2-(2-(3-(methylsulfonyl)propoxy)phenyl amino)-5-(trifluoromethyl)pyrimidin-4-ylamino)phenyl)acrylamide (Compound 44)

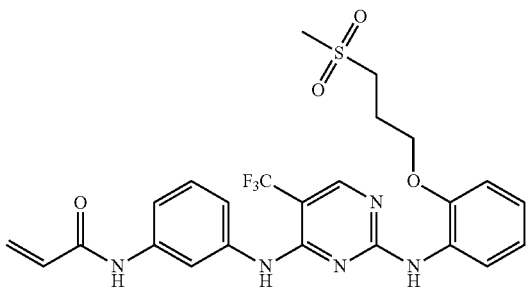 [SMILES: C=CC(=O)Nc1cccc(Nc2nc(Nc3ccccc3OCCCS(C)(=O)=O)ncc2C(F)(F)F)c1]

(1) Preparation of 1-(3-chloropropoxy)-2-nitrobenzene

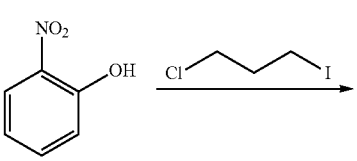

2-Nitrophenol (2.0 g, 14.39 mmol) was dissolved in N,N-dimethylformamide (30 mL), and 3-iodo-1-chloropropane (3.52 g, 17.25 mmol) and potassium carbonate (3.0 g, 21.58 mmol) were added. The reaction was carried out at room temperature overnight. After the reaction, water (100 mL) was added. The mixture was extracted with ethyl acetate (50 mL×3). The organic phases were combined, and concentrated. The residue was purified by silica gel column chromatography (petroleum ether: ethyl acetate=4:1) to get the title compound (2.0 g, yield: 64.7%).

(2) Preparation of methyl (3-(2-nitrobenzeneoxy)propyl)sulfane

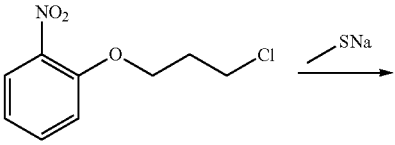

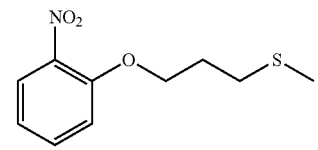

1-(3-Chloropropoxy)-2-nitrobenzene (2.0 g, 9.30 mmol) was dissolved in methanol (30 mL), and aqueous sodium methanethiolate solution (2 N, 5.6 mL, 11.2 mmol) was added. The reaction was carried out at room temperature overnight. After the reaction, water (100 mL) was added. The mixture was extracted with ethyl acetate (50 mL×3). The organic phases were combined, and concentrated. The residue was purified by silica gel column chromatography (petroleum ether: ethyl acetate=3:1) to get the title compound (1.8 g, yield: 85.7%).

(3) Preparation of 1-(3-(methylsulfonyl)propoxy)-2-nitrobenzene

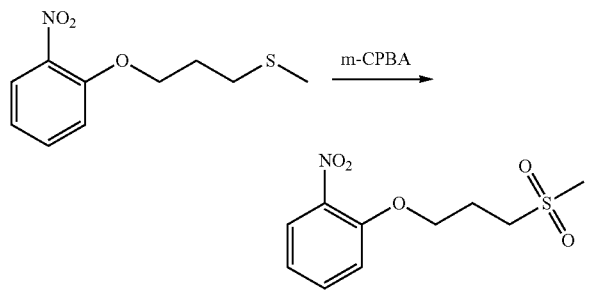

Methyl (3-(2-nitrobenzeneoxy)propyl)sulfane (1.8 g, 7.93 mmol) was dissolved in dichloromethane (30 mL), and 3-chloroperbenzoic acid (2.03 g, 11.87 mmol) was added. The reaction was carried out at room temperature for 3 h. After the reaction, water (100 mL) was added. The mixture was extracted with dichloromethane (50 mL×3). The organic phases were combined, and concentrated. The residue was purified by silica gel column chromatography (petroleum ether: ethyl acetate=3:1) to get the title compound (1.2 g, yield: 58.5%).

(4) Preparation of 2-(3-(methyl sulfonyl)propoxy)aniline

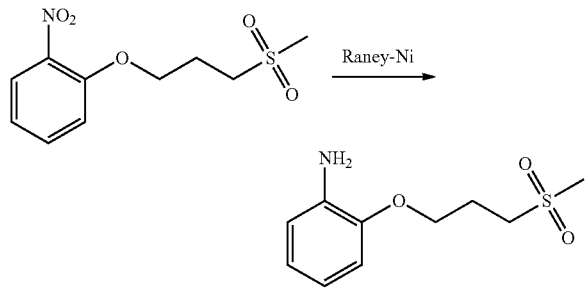

1-(3-(Methylsulfonyl)propoxy)-2-nitrobenzene (1.2 g, 4.63 mmol) was dissolved in methanol (30 mL), and Raney Nickel was added. Hydrogen gas was introduced, and the reaction was carried out at room temperature overnight. After the reaction, the mixture was filtrated and concentrated. The residue was directly used in the next step (0.8 g, yield: 75.5%).

(5) Preparation of N-(3-(2-(2-(3-(methyl sulfonyl) propoxy)phenyl amino)-5-(trifluoromethyl)pyrimidin-4-ylamino)phenyl)acrylamide

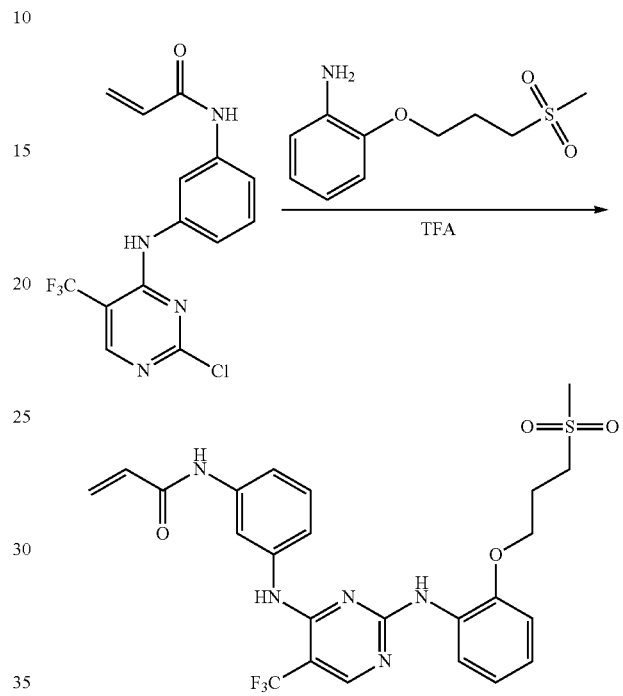

2-(3-(Methylsulfonyl)propoxy)aniline (100 mg, 0.437 mmol) was dissolved in isopropanol (10 mL), and N-(3-((2-chloro-5-trifluoromethyl)pyrimidin-4-yl)amino)phenyl) acrylamide (170 mg, 0.497 mmol) and a catalytic amount of trifluoroacetic acid were added. The mixture was heated to 70° C. and reacted overnight. After the reaction, the system was concentrated, and ethyl acetate (50 mL) was added. The mixture was washed with saturated sodium bicarbonate solution, and the water phase was extracted with ethyl acetate (20 mL×2). The organic phases were combined and concentrated. The residue was purified by silica gel column chromatography (dichloromethane:methanol=20:1) to get the title compound (120 mg, yield: 51.5%).

Molecular formula: $C_{24}H_{24}F_3N_5O_4S$ Molecular weight: 535.1 LC-MS (m/z): 536.2 (M+H+)

1H-NMR (400 MHz, DMSO-d6) δ: 10.13 (s, 1H), 8.78 (s, 1H), 8.36 (s, 1H), 8.33 (s, 1H), 7.77 (s, 1H), 7.72 (d, J=7.6 Hz, 1H), 7.48 (d, J=8.4 Hz, 1H), 7.27 (t, J=8.0 Hz, 1H), 7.13 (d, J=8.0 Hz, 1H), 6.89-6.94 (m, 2H), 6.62 (br, 1H), 6.42 (dd, J=16.8 Hz, 10.0 Hz, 1H), 6.23 (dd, J=16.8 Hz, 2.0 Hz, 1H), 5.74 (dd, J=10.0 Hz, 2.0 Hz, 1H), 4.06 (t, J=6.4 Hz, 2H), 3.25-3.29 (m, 2H), 2.96 (s, 3H), 2.11-2.16 (m, 2H).

The invention claimed is:
1. A compound of Formula (I), or a pharmaceutically acceptable salt, ester, or stereoisomer thereof:

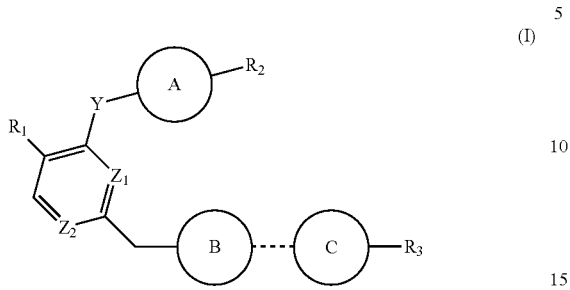

wherein
$Z_1$ is N; $Z_2$ is N;
X is $NR_5$ or absent;
Y is $NR_5$;
Ring A is phenyl optionally substituted by a substituent, wherein the substituent is selected from hydrogen atom, halogen atom, cyano, $C_{1-4}$alkyl, $C_{1-4}$alkoxy or halo-$C_{1-4}$alkyl;
Ring B is phenyl optionally substituted by a substituent, wherein the substituent is hydrogen atom, halogen atom, cyano, $C_{1-4}$alkyl, $C_{1-4}$alkoxy, halo-$C_{1-4}$alkyl, halo-$C_{1-4}$alkoxy, $C_{1-4}$alkylsulfonyl, $C_{1-4}$alkylsulfonyloxy, or $C_{1-4}$alkylsulfonyl$C_{1-4}$alkoxy;
Ring C is 7-10 membered N-containing fused heterocyclyl, 7-9 membered spiroheterocyclyl or 8 membered bridged heterocyclyl, each of which is optionally substituted by a substituent, wherein the substituent is hydrogen atom, halogen atom, cyano, $C_{1-4}$alkyl, $C_{1-4}$alkoxy, halo-$C_{1-4}$alkyl, halo-$C_{1-4}$alkoxy, $C_{1-4}$alkylsulfonyl, $C_{1-4}$alkylsulfonyloxy, $C_{1-4}$alkylsulfonyl $C_{1-4}$alkoxy or 3-6 membered O-containing heterocyclyl; or Ring C is 5-6 membered N-containing heterocyclyl which is substituted by 3-6 membered O-containing heterocyclyl, and when Ring A is phenyl and Ring B is phenyl, Ring C is not piperazinyl or morpholinyl;
$R_1$ is selected from halo-methyl or halo-ethyl;
$R_2$ is selected from hydrogen atom, —$N(R_6)(R_7)$, —$N(R_6)C(O)(R_7)$, $C_{1-4}$alkyl or 3-6 membered cycloalkyl;
$R_3$ is hydrogen atom; or $R_3$ is $C_{1-4}$alkyl, $C_{1-4}$alkoxy or —C(O)—$R_8$, each of which is optionally substituted by a substituent, wherein the substituent is selected from hydrogen atom, halogen atom or $C_{1-4}$alkyl or $C_{1-4}$alkylsulfonyl;
$R_5$ is selected from hydrogen atom, halogen atom or $C_{1-4}$alkyl;
$R_6$ and $R_7$ are independently selected from hydrogen atom, $C_{1-4}$alkyl, halo-$C_{1-4}$alkyl or $C_{2-4}$alkenyl;
$R_8$ is selected from hydrogen atom, methyl, ethyl or methoxyl.

2. The compound or a pharmaceutically acceptable salt, ester, or stereoisomer thereof according to claim 1, wherein
$Z_1$ is N; $Z_2$ is N;
X and Y are independently NH;
Ring A is phenyl optionally substituted by a substituent, wherein the substituent is selected from fluorine atom, chlorine atom, methyl, ethyl or trifluoromethyl;
Ring B is phenyl optionally substituted by a substituent, wherein the substituent is selected from fluorine atom, chlorine atom, methyl, ethyl, methoxyl, ethoxyl, trifluoromethyl, trifluoromethoxyl, methylsulfonylpropoxy or ethyl sulfonylpropoxy;
Ring C is 2-azaspiro[3.5]nonyl, 8-azabicyclo[3.2.1]octyl, octahydrocyclopenta[c]pyrrolyl, 2,7-diazaspiro[3.5]nonyl, 2,6-diazaspiro[3.3]heptyl, 2-azaspiro[3.3]heptyl, 3,8-diazabicyclo[3.2.1]octyl or hexahydropyrrolo[3,4-c]pyrrolyl, each of which is optionally substituted by a substituent, wherein the substituent is selected from fluorine atom, chlorine atom, methyl, ethyl, methoxyl, trifluoromethyl, methylsulfonyl, oxetanyl, tetrahydrofuranyl, piperidyl, piperazinyl or morpholinyl; or Ring C is azetidinyl, pyrrolidinyl, dihydropyrrolyl, imidazolidinyl, thiazolidinyl, oxazolidinyl, piperidyl, piperidin-one-yl, tetrahydropyridyl, tetrahydropyridin-one-yl, dihydropiperidin-one-yl, each of which is substituted by a substituent, wherein the substituent is oxetanyl, tetrahydrofuranyl, piperidyl, piperazinyl or morpholinyl;
$R_1$ is trifluoromethyl;
$R_2$ is —NHC(O)CH=$CH_2$;
$R_3$ is selected from hydrogen atom, methyl, ethyl, trifluoromethyl, methoxyl, 2-fluoroethyl, acetyl, propionyl, 3-fluoropropionyl or 3-methylsulfonylpropoxy.

3. The compound or a pharmaceutically acceptable salt, ester, or stereoisomer thereof according to claim 2, wherein
Ring A is phenyl optionally substituted by a substituent, wherein the substituent is selected from fluorine atom, chlorine atom, methyl, ethyl or trifluoromethyl;
Ring B is phenyl optionally substituted by a substituent, wherein the substituent is selected from fluorine atom, chlorine atom, methyl, ethyl, methoxyl, ethoxyl, trifluoromethyl, trifluoromethoxyl, methylsulfonylpropoxy or ethyl sulfonylpropoxy;
Ring C is azetidinyl, pyrrolidinyl, dihydropyrrolyl, imidazolidinyl, thiazolidinyl, oxazolidinyl, piperidyl, piperidin-one-yl, tetrahydropyridyl, tetrahydropyridin-one-yl or dihydropiperidin-one-yl, each of which is optionally substituted by a substituent, wherein the substituent is oxetanyl, tetrahydrofuranyl or morpholinyl.

4. The compound or a pharmaceutically acceptable salt, ester, or stereoisomer thereof wherein the compound d is selected from:

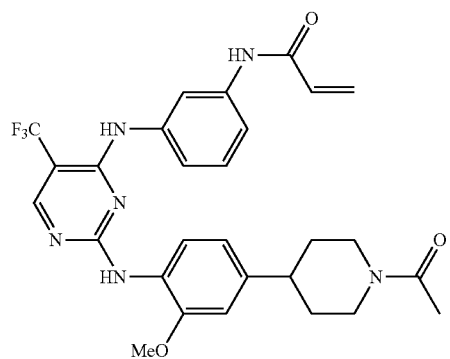

205
-continued
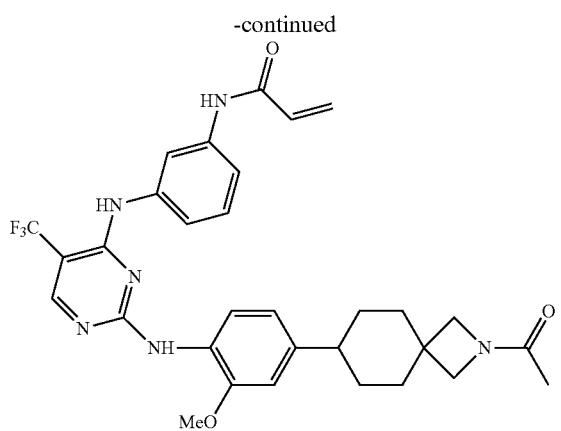
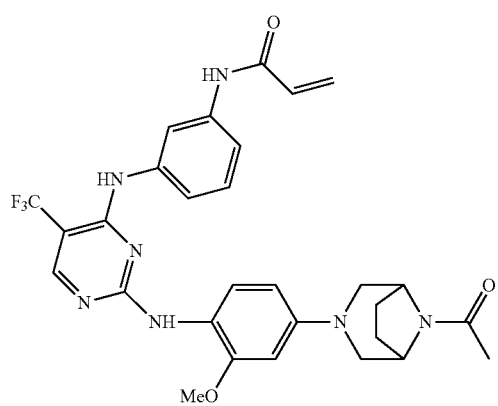
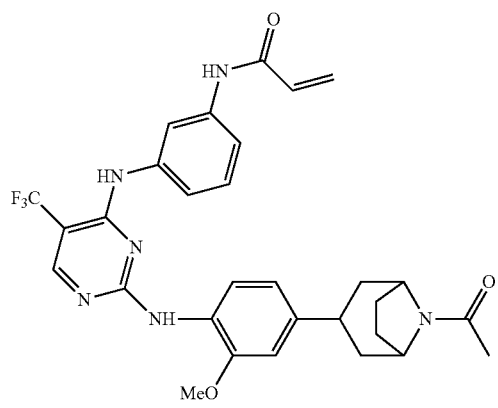
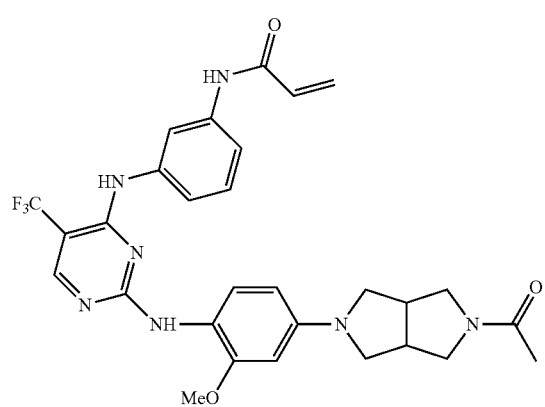
206
-continued
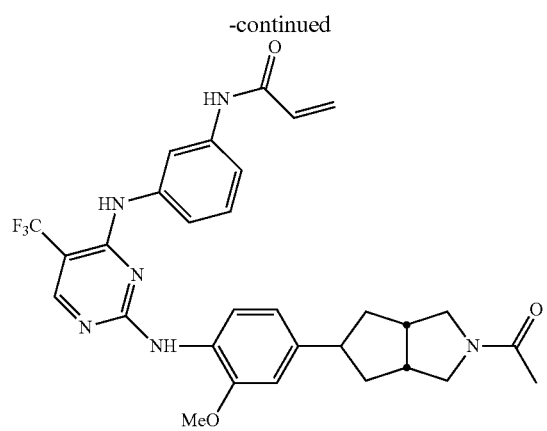
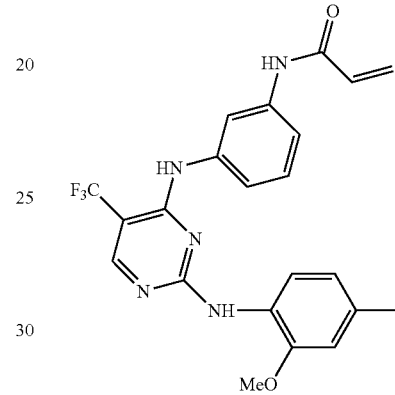
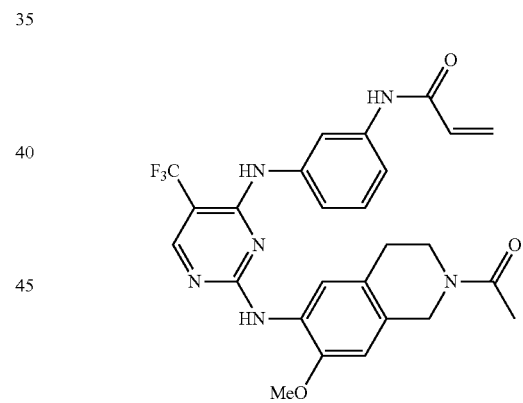
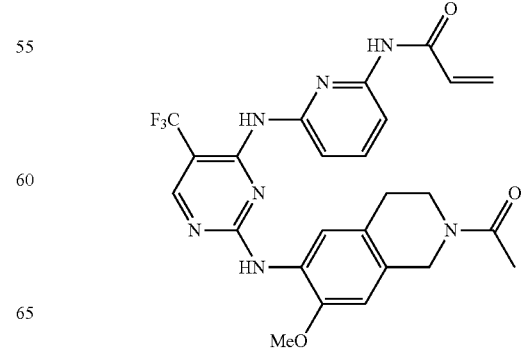

207
-continued
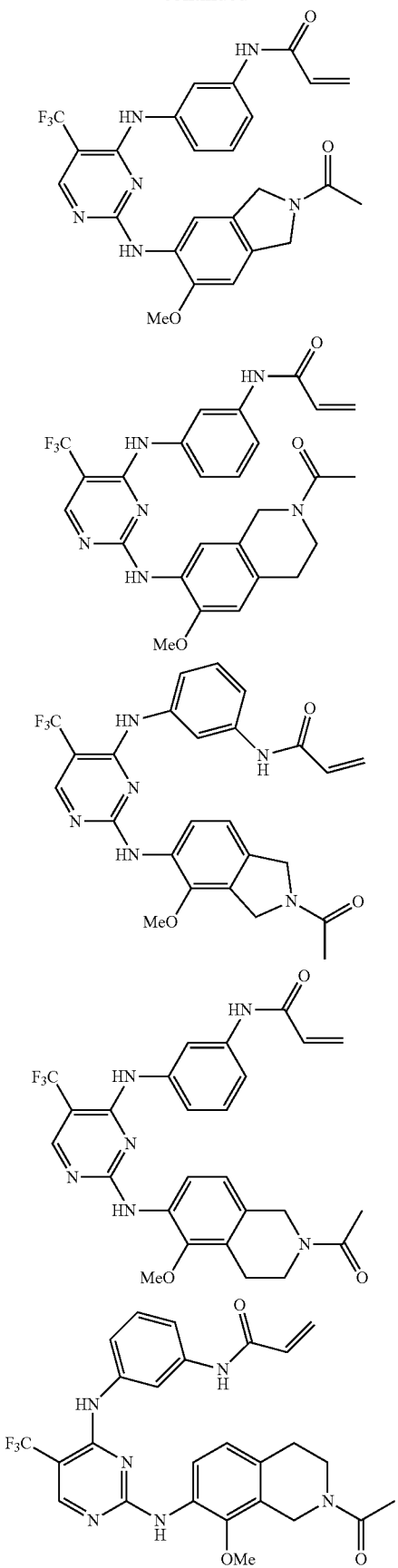
208
-continued
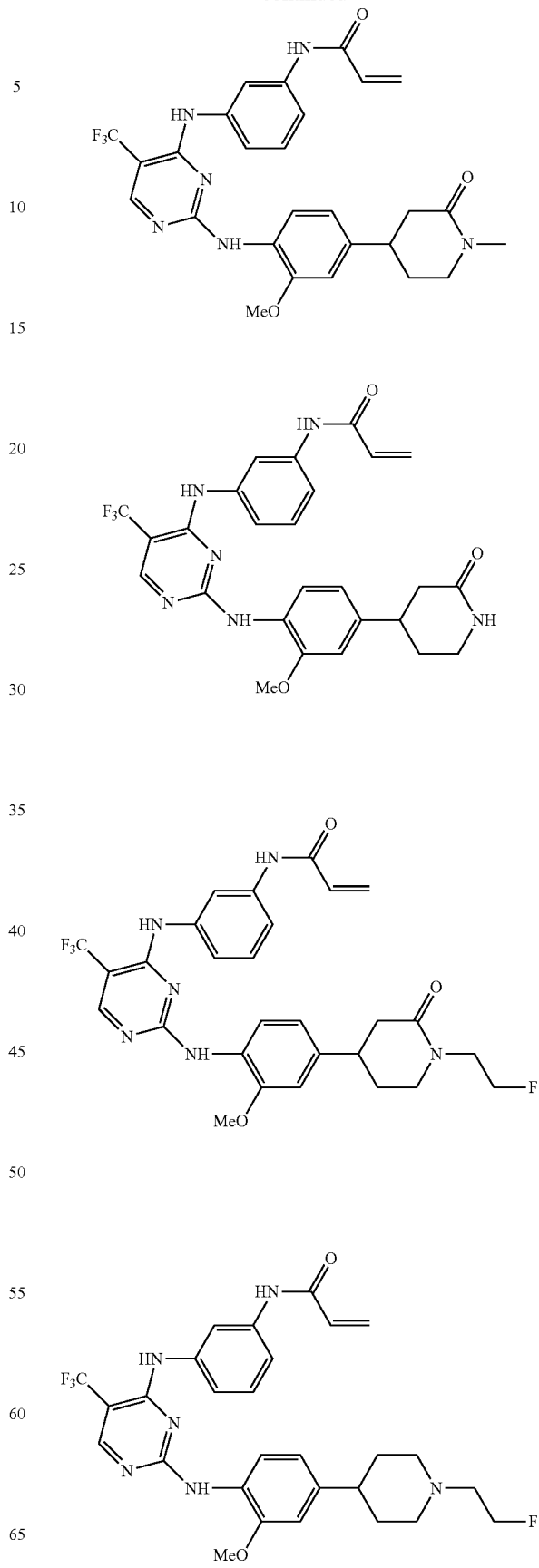

-continued
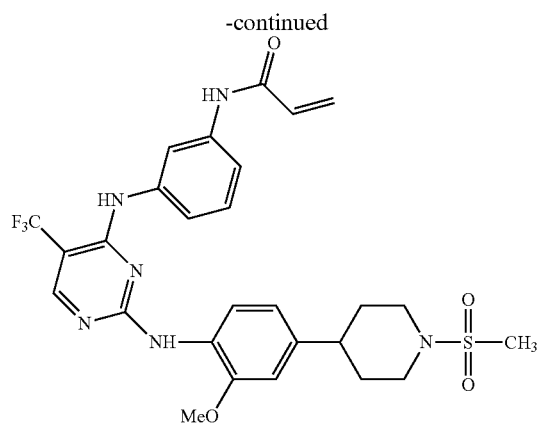
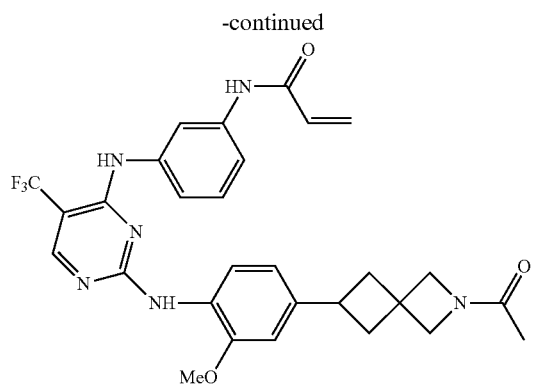
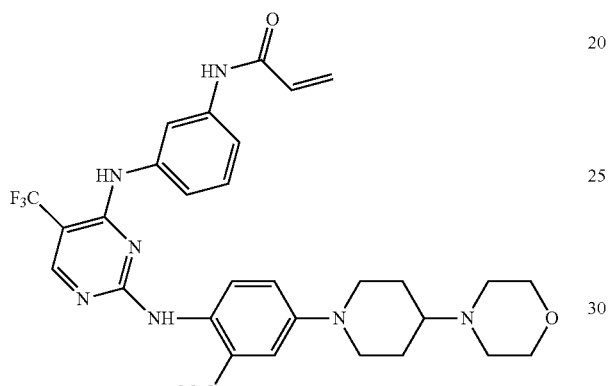
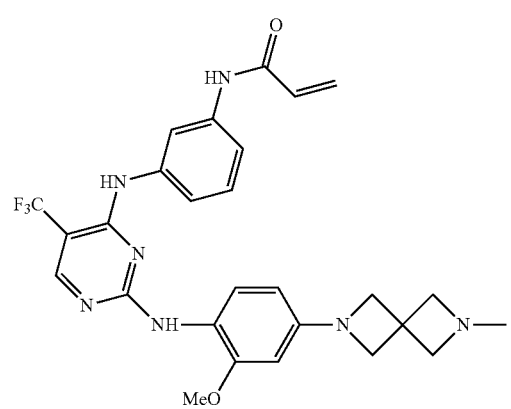
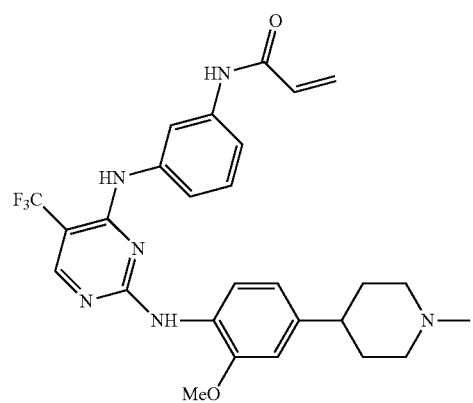
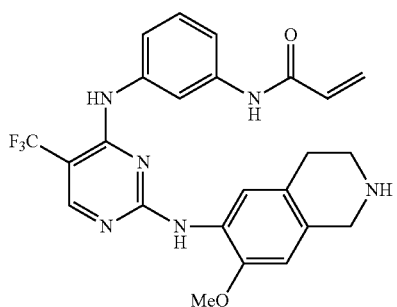
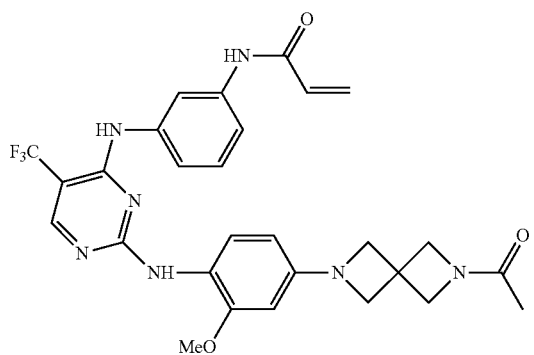
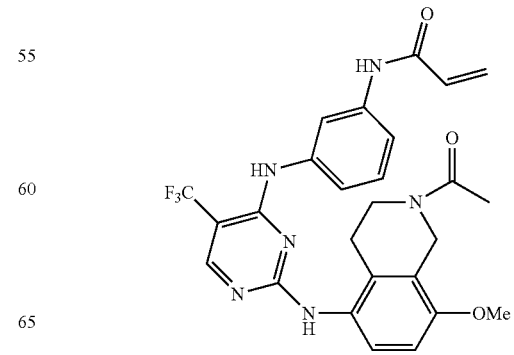

211
-continued
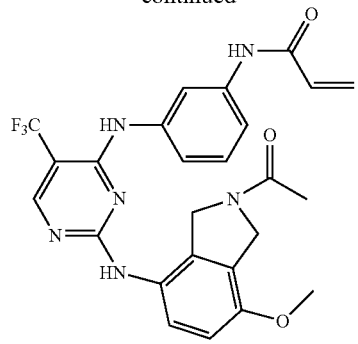
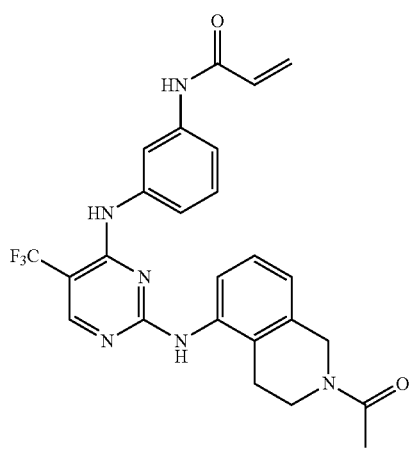
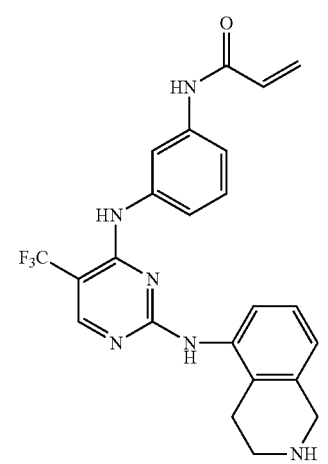
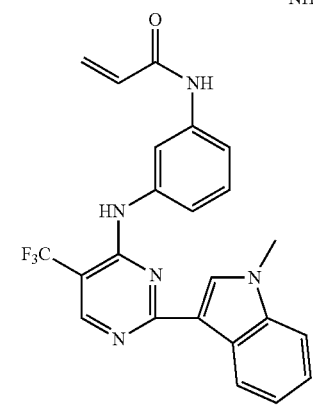
212
-continued
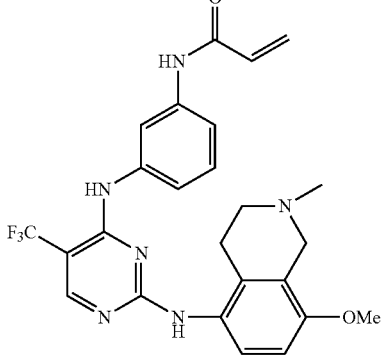
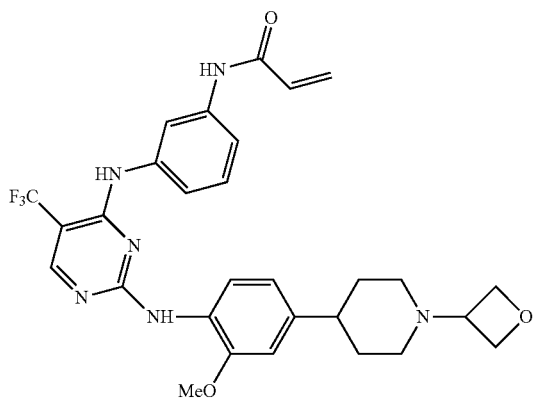
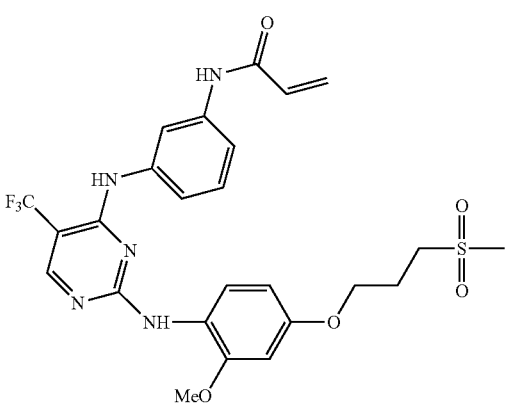

-continued

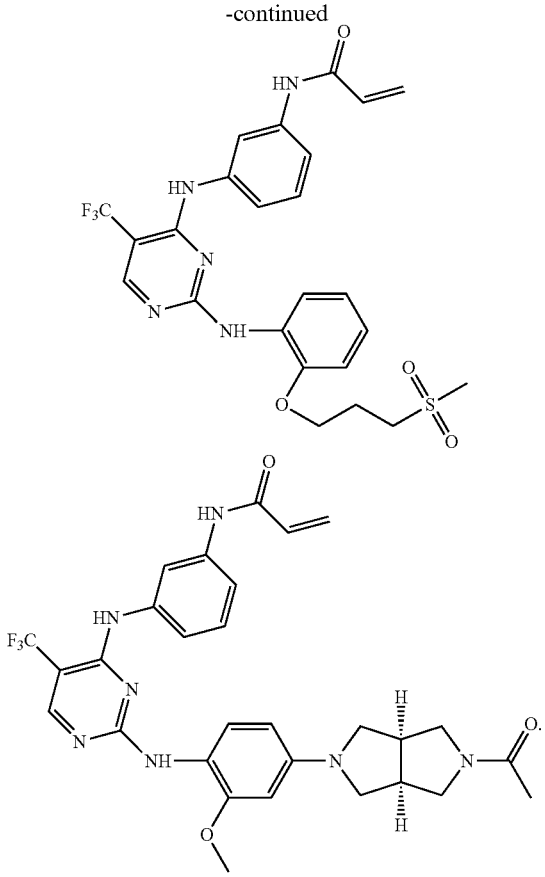

5. A pharmaceutical composition, comprising the compound, or a pharmaceutically acceptable salt, ester, or stereoisomer thereof according claim 1;
optionally, the pharmaceutical composition further comprises one or more second therapeutic agents; and
optionally, the pharmaceutical composition further comprises one or more pharmaceutically acceptable carrier and/or diluent.

6. A method for reducing or inhibiting activity of EGFR or mutant thereof in a cell, comprising administering to the cell an effective amount of the compound, or a pharmaceutically acceptable salt, ester, or stereoisomer thereof according to claim 1.

7. The method of claim 6, wherein the cell is in a subject and wherein the subject has a disease associated with overactivity of EGFR.

8. A kit comprising the compound, or a pharmaceutically acceptable salt, ester, or stereoisomer thereof according to claim 1, and optionally, instructions.

9. The pharmaceutical composition of claim 5, wherein the second therapeutic agent is selected from: DNA replication inhibitors, mitotic inhibitors, angiogenesis inhibitors, growth factor inhibitors, antibodies, antimetabolites, antitumor hormone drugs, platinum drugs, immunosuppressors, additional tyrosine kinase inhibitors.

10. The pharmaceutical composition of claim 5, wherein the second therapeutic agent is selected from: methotrexate, capecitabine, gemcitabine, doxifluridine, pemetrexed disodium, pazopanib, imatinib, erlotinib, lapatinib, gefitinib, vandetanib, herceptin, bevacizumab, rituximab, trastuzumab, paclitaxel, vinorelbine, docetaxel, doxorubicin, hydroxycamptothecine, mitomycin, epirubicin, pirarubicin, bleomycin, letrozole, tamoxifen, fulvestrant, triptorelin, flutamide, leuprorelin, anastrozole, ifosfamide, busulfan, cyclophosphamide, carmustine, nimustine, semustine, mechlorethamine, melphalan, chlorambucil, carboplatin, cisplatin, oxaliplatin, lobaplatin, topotecan, camptothecin, everolimus, sirolimus, temsirolimus, 6-mercaptopurine, 6-thioguanine, azathioprine, actinomycin D, daunorubicin, adriamycin, mitoxantrone, mithramycin or aminoglutethimide.

11. The method of claim 7, wherein the disease is hyperproliferative disease or is chronic obstructive pulmonary disease.

12. The method of claim 11, wherein the hyperproliferative disease is cancer or noncancerous disease.

13. The method of claim 12, wherein the cancer is selected from: esophageal cancer, brain tumor, lung cancer, squamous cell cancer, bladder cancer, gastric cancer, ovarian cancer, peritoneal cancer, pancreatic cancer, breast cancer, head and neck cancer, cervical cancer, endometrial cancer, colorectal cancer, liver cancer, renal cancer, solid tumor, non-Hodgkin's lymphoma, central nervous system tumor, prostatic cancer and thyroid cancer.

14. The method of claim 12, wherein the noncancerous disease is benign hyperplasia of skin or prostate.

15. The method of claim 7, wherein the disease has drug resistance caused by EGFR mutant; wherein, the EGFR mutant comprises one or more of the following mutations: T790M mutation, L858R mutation, and d746-750 mutation.

16. The method of claim 6, wherein the EGFR mutant comprises one or more of the following mutations: T790M mutation, L858R mutation, and d746-750 mutation.

* * * * *

SEQUENCE LISTING

```
<160> NUMBER OF SEQ ID NOS: 1

<210> SEQ ID NO 1
<211> LENGTH: 1210
<212> TYPE: PRT
```

```
<213> ORGANISM: Homo sapiens

<400> SEQUENCE: 1

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
370                 375                 380

Pro Pro Leu Asp Pro Gln Glu Leu Asp Ile Leu Lys Thr Val Lys Glu
385                 390                 395                 400
```

```
Ile Thr Gly Phe Leu Leu Ile Gln Ala Trp Pro Glu Asn Arg Thr Asp
            405                 410                 415

Leu His Ala Phe Glu Asn Leu Glu Ile Ile Arg Gly Arg Thr Lys Gln
        420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
        485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
            565                 570                 575

Asp Asn Cys Ile Gln Cys Ala His Tyr Ile Asp Gly Pro His Cys Val
        580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
            645                 650                 655

Leu Leu Val Val Ala Leu Gly Ile Gly Leu Phe Met Arg Arg Arg His
        660                 665                 670

Ile Val Arg Lys Arg Thr Leu Arg Arg Leu Leu Gln Glu Arg Glu Leu
    675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
            725                 730                 735

Lys Val Lys Ile Pro Val Ala Ile Lys Glu Leu Arg Glu Ala Thr Ser
        740                 745                 750

Pro Lys Ala Asn Lys Glu Ile Leu Asp Glu Ala Tyr Val Met Ala Ser
    755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
            805                 810                 815

Trp Cys Val Gln Ile Ala Lys Gly Met Asn Tyr Leu Glu Asp Arg Arg
```

```
                    820                 825                 830
Leu Val His Arg Asp Leu Ala Ala Arg Asn Val Leu Val Lys Thr Pro
                835                 840                 845
Gln His Val Lys Ile Thr Asp Phe Gly Leu Ala Lys Leu Leu Gly Ala
                850                 855                 860
Glu Lys Glu Tyr His Ala Glu Gly Gly Lys Val Pro Ile Lys Trp
865                 870                 875                 880
Met Ala Leu Glu Ser Ile Leu His Arg Ile Tyr Thr His Gln Ser Asp
                885                 890                 895
Val Trp Ser Tyr Gly Val Thr Val Trp Glu Leu Met Thr Phe Gly Ser
                900                 905                 910
Lys Pro Tyr Asp Gly Ile Pro Ala Ser Glu Ile Ser Ser Ile Leu Glu
                915                 920                 925
Lys Gly Glu Arg Leu Pro Gln Pro Pro Ile Cys Thr Ile Asp Val Tyr
                930                 935                 940
Met Ile Met Val Lys Cys Trp Met Ile Asp Ala Asp Ser Arg Pro Lys
945                 950                 955                 960
Phe Arg Glu Leu Ile Ile Glu Phe Ser Lys Met Ala Arg Asp Pro Gln
                965                 970                 975
Arg Tyr Leu Val Ile Gln Gly Asp Glu Arg Met His Leu Pro Ser Pro
                980                 985                 990
Thr Asp Ser Asn Phe Tyr Arg Ala Leu Met Asp Glu Glu Asp Met Asp
                995                1000                1005
Asp Val Val Asp Ala Asp Glu Tyr Leu Ile Pro Gln Gln Gly Phe
               1010                1015                1020
Phe Ser Ser Pro Ser Thr Ser Arg Thr Pro Leu Leu Ser Ser Leu
               1025                1030                1035
Ser Ala Thr Ser Asn Asn Ser Thr Val Ala Cys Ile Asp Arg Asn
               1040                1045                1050
Gly Leu Gln Ser Cys Pro Ile Lys Glu Asp Ser Phe Leu Gln Arg
               1055                1060                1065
Tyr Ser Ser Asp Pro Thr Gly Ala Leu Thr Glu Asp Ser Ile Asp
               1070                1075                1080
Asp Thr Phe Leu Pro Val Pro Glu Tyr Ile Asn Gln Ser Val Pro
               1085                1090                1095
Lys Arg Pro Ala Gly Ser Val Gln Asn Pro Val Tyr His Asn Gln
               1100                1105                1110
Pro Leu Asn Pro Ala Pro Ser Arg Asp Pro His Tyr Gln Asp Pro
               1115                1120                1125
His Ser Thr Ala Val Gly Asn Pro Glu Tyr Leu Asn Thr Val Gln
               1130                1135                1140
Pro Thr Cys Val Asn Ser Thr Phe Asp Ser Pro Ala His Trp Ala
               1145                1150                1155
Gln Lys Gly Ser His Gln Ile Ser Leu Asp Asn Pro Asp Tyr Gln
               1160                1165                1170
Gln Asp Phe Phe Pro Lys Glu Ala Lys Pro Asn Gly Ile Phe Lys
               1175                1180                1185
Gly Ser Thr Ala Glu Asn Ala Glu Tyr Leu Arg Val Ala Pro Gln
               1190                1195                1200
Ser Ser Glu Phe Ile Gly Ala
               1205                1210
```